United States Patent
Oh et al.

(10) Patent No.: US 10,797,243 B2
(45) Date of Patent: *Oct. 6, 2020

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Cheonan (KR)

(72) Inventors: Hong-Se Oh, Hwaseong (KR); Young-Kwang Kim, Hwaseong (KR)

(73) Assignee: Rohm and Haas Electronic Materials Korea Ltd, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/093,695

(22) PCT Filed: Mar. 20, 2017

(86) PCT No.: PCT/KR2017/002959
§ 371 (c)(1),
(2) Date: Oct. 15, 2018

(87) PCT Pub. No.: WO2017/191896
PCT Pub. Date: Nov. 9, 2017

(65) Prior Publication Data
US 2019/0131526 A1 May 2, 2019

(30) Foreign Application Priority Data

May 3, 2016 (KR) .................. 10-2016-0054769
Feb. 23, 2017 (KR) .................. 10-2017-0024353

(51) Int. Cl.
C07C 211/61 (2006.01)
H01L 51/00 (2006.01)
C09K 11/06 (2006.01)
C07D 333/76 (2006.01)
H05B 33/14 (2006.01)
C07D 307/91 (2006.01)
H01L 51/50 (2006.01)

(52) U.S. Cl.
CPC .......... *H01L 51/006* (2013.01); *C07C 211/61* (2013.01); *C07D 307/91* (2013.01); *C07D 333/76* (2013.01); *C09K 11/06* (2013.01); *H01L 51/0058* (2013.01); *H05B 33/14* (2013.01); *C07C 2603/18* (2017.05); *C07C 2603/40* (2017.05); *C07C 2603/94* (2017.05); *C09K 2211/1011* (2013.01); *C09K 2211/1014* (2013.01); *H01L 51/0054* (2013.01); *H01L 51/0067* (2013.01); *H01L 51/0072* (2013.01); *H01L 51/0077* (2013.01); *H01L 51/0085* (2013.01); *H01L 51/5016* (2013.01); *H01L 51/5064* (2013.01); *H01L 2251/5384* (2013.01); *H01L 2251/552* (2013.01)

(58) Field of Classification Search
None
See application file for complete search history.

(56) References Cited

U.S. PATENT DOCUMENTS

| | | |
|---|---|---|
| 9,698,355 B2 | 7/2017 | Kang et al. |
| 9,711,731 B2 | 7/2017 | Herron et al. |
| 9,732,099 B1 | 8/2017 | Jun et al. |

FOREIGN PATENT DOCUMENTS

| | | |
|---|---|---|
| KR | 2016-0111559 A | 9/2016 |
| WO | 2012/039561 A1 | 3/2012 |
| WO | 2013/012298 A1 | 1/2013 |
| WO | 2014/129846 A1 | 8/2014 |
| WO | 2015/037965 A1 | 3/2015 |
| WO | 2015/084114 A1 | 6/2015 |

*Primary Examiner* — Ana Z Muresan
(74) *Attorney, Agent, or Firm* — S. Matthew Cairns

(57) ABSTRACT

The present disclosure relates to an organic electroluminescent compound and an organic electroluminescent device comprising the same. By using the organic electroluminescent compound of the present disclosure, an organic electroluminescent device having excellent luminous properties can be produced.

10 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

In order to enhance the efficiency and stability of an organic EL device, it has a structure of a multilayer comprising a hole injection layer, a hole transport layer, a light-emitting layer, an electron transport layer, and an electron injection layer. The selection of a compound comprised in the hole transport layer is known as a method for improving the characteristics of a device such as hole transport efficiency to the light-emitting layer, luminous efficiency, lifespan, etc.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4''-tris(3-methylphenylphenylamino)triphenylamine (MTDATA), etc., were used as a hole injection and transport material. However, an organic EL device using these materials is problematic in quantum efficiency and operational lifespan. It is because, when an organic EL device is driven under high current, thermal stress occurs between an anode and the hole injection layer. Thermal stress significantly reduces the operational lifespan of the device. Further, since the organic material used in the hole injection layer has very high hole mobility, the hole-electron charge balance may be broken and quantum yield (cd/A) may decrease.

Therefore, a hole transport layer for improving performance of an organic EL device still needs to be developed.

Korean Patent Appln. Laying-Open No. KR 10-2015-0066202 discloses a benzo[b]fluorene substituted with an arylamino, etc. However, the reference does not specifically disclose a compound in which an arylamino, etc., is substituted at the fifth carbon position of a benzo[b]fluorene.

International Publication No. WO 2015/061198 A also discloses a benzo[b]fluorene substituted with an arylamino, etc. However, the reference does not specifically disclose an example of using the compound in a hole transport layer. Also, the reference does not disclose a compound in which an arylamino, etc., is substituted at the fifth carbon position of a benzo[b]fluorene.

DISCLOSURE OF THE INVENTION

Problems to be Solved

The objective of the present disclosure is to provide an organic electroluminescent compound which can be used to produce an organic electroluminescent device having excellent lifespan properties, improved luminous efficiency due to an increase of triplet energy, and/or excellent thermal stability due to a decrease of deposition temperature.

Solution to Problems

The present inventors found that luminous efficiency is improved due to an increase of triplet energy and/or thermal stability is improved due to a decrease of deposition temperature by having a substituent at the fifth carbon position of an organic electroluminescent compound having a structure of benzo[b]fluorene. More specifically, the above objective can be achieved by an organic electroluminescent compound represented by the following formula 1:

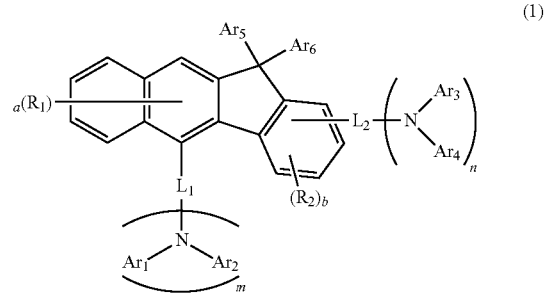

(1)

wherein $Ar_1$ to $Ar_6$ each independently represent a substituted or unsubstituted (C1-C30)alkyl, a substituted or unsubstituted (C6-C30)aryl, a substituted or unsubstituted 5- to 30-membered heteroaryl, or a substituted or unsubstituted spiro[fluorene-(C3-C30)cycloalkane]yl; or $Ar_1$ and $Ar_2$, $Ar_3$ and $Ar_4$, and $Ar_5$ and $Ar_6$ may be linked to each other to form a mono- or polycyclic, 3- to 30-membered alicyclic or aromatic ring, whose carbon atom(s) may be replaced with at least one hetero atom selected from nitrogen, oxygen, and sulfur;

$L_1$ represents a single bond, a substituted or unsubstituted (C6-C30)arylene, or a substituted or unsubstituted 5- to 30-membered heteroarylene;

$L_2$ represents a single bond, a substituted or unsubstituted (C1-C30)alkylene, a substituted or unsubstituted (C6-C30)arylene, or a substituted or unsubstituted 5- to 30-membered heteroarylene, with a proviso that where n is 0, $L_2$ does not exist;

$R_1$ and $R_2$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted 3- to 7-membered heterocycloalkyl, a substituted or unsubstituted (C6-C30)aryl(C1-C30)alkyl, $-NR_{11}R_{12}$, $-SiR_{13}R_{14}R_{15}$, $-SR_{16}$, $-OR_{17}$, a cyano, a nitro, or a hydroxyl; or are linked to an adjacent substituent(s) to form a mono- or polycyclic, 3- to 30-membered alicyclic or aromatic ring, whose carbon atom(s) may be replaced with at least one hetero atom selected from nitrogen, oxygen, and sulfur;

$R_{11}$ to $R_{17}$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted 3- to 7-membered heterocycloalkyl, or a substituted or unsubstituted (C3-C30)cycloalkyl; or are linked to an adjacent substituent(s) to form a mono- or polycyclic, 3- to 30-membered alicyclic or aromatic ring, whose carbon atom(s) may be replaced with at least one hetero atom selected from nitrogen, oxygen, and sulfur;

m represents an integer of 1 to 2, where m is 2, each of $NAr_1Ar_2$ may be the same or different;

n represents an integer of 0 to 2, where n is 2, each of $NAr_3Ar_4$ may be the same or different;

a represents an integer of 1 to 5, where a is an integer of 2 or more, each of $R_1$ may be the same or different;

b represents an integer of 1 to 4, where b is an integer of 2 or more, each of $R_2$ may be the same or different;

the heteroaryl(ene) contains at least one hetero atom selected from B, N, O, S, Si, and P; and the heterocycloalkyl contains at least one hetero atom selected from O, S, and N.

Effects of the Invention

By using the organic electroluminescent compound of the present disclosure, an organic electroluminescent device having excellent luminous efficiency and/or thermal stability can be produced. In addition, since the luminous efficiency and/or thermal stability of the organic electroluminescent device is excellent, a relatively long lifespan of the device can be achieved.

EMBODIMENTS OF THE INVENTION

Hereinafter, the present disclosure will be described in detail. However, the following description is intended to explain the disclosure, and is not meant in any way to restrict the scope of the disclosure.

The present disclosure relates to an organic electroluminescent compound of formula 1, an organic electroluminescent material comprising the compound, and an organic electroluminescent device comprising the material.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, and may be comprised in a light-emitting layer as a phosphorescent host material and/or a hole transport layer as a hole transport material, but is not limited thereto.

Hereinafter, the organic electroluminescent compound represented by formula 1 will be described in detail.

Herein, "(C1-C30)alkyl(ene)" is meant to be a linear or branched alkyl having 1 to 30 carbon atoms constituting the chain, in which the number of carbon atoms is preferably 1 to 10, more preferably 1 to 6, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "(C6-C30)aryl(ene)" is a monocyclic or fused ring derived from an aromatic hydrocarbon having 6 to 30 ring backbone carbon atoms, in which the number of ring backbone carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. "5- to 30-membered heteroaryl(ene)" is an aryl group having at least one, preferably 1 to 4 heteroatoms selected from the group consisting of B, N, O, S, Si, and P, and 5 to 30 ring backbone atoms, in which the number of ring backbone atoms is preferably 5 to 20, more preferably 5 to 15; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

The compound of formula 1 may be represented by the following formula 2 or 3:

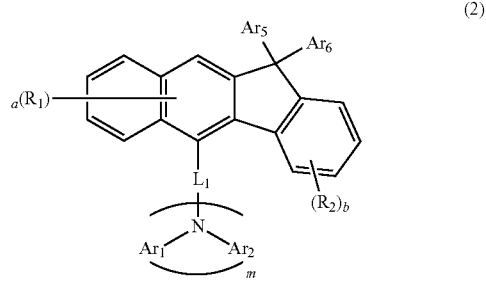

(2)

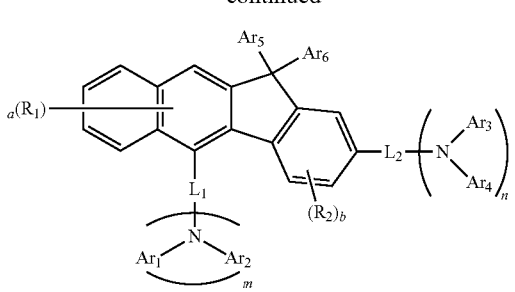

(3)

wherein Ar₁ to Ar₆, L₁, L₂, R₁, R₂, a, b, m, and n are as defined in formula 1.

Herein, "substituted" in the expression "substituted or unsubstituted" means that a hydrogen atom in a certain functional group is replaced with another atom or functional group, i.e., a substituent. The substituents of the substituted alkyl(ene), the substituted aryl(ene), the substituted heteroaryl(ene), the substituted cycloalkyl, the substituted heterocycloalkyl, the substituted arylalkyl, and the substituted spiro[fluorene-(C3-C30)cycloalkane]yl in Ar₁ to Ar₆, L₁, L₂, R₁, R₂, and R₁₁ to R₁₇ in formula 1 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; and preferably each independently are a (C1-C6)alkyl or a (C6-C20)aryl.

In formula 1 above, Ar₁ to Ar₆ each independently represent a substituted or unsubstituted (C1-C30)alkyl, a substituted or unsubstituted (C6-C30)aryl, a substituted or unsubstituted 5- to 30-membered heteroaryl, or a substituted or unsubstituted spiro[fluorene-(C3-C30)cycloalkane]yl; or Ar₁ and Ar₂, Ar₃ and Ar₄, and Ar₅ and Ar₆ may be linked to each other to form a mono- or polycyclic, 3- to 30-membered alicyclic or aromatic ring, whose carbon atom(s) may be replaced with at least one hetero atom selected from nitrogen, oxygen, and sulfur.

Preferably, Ar₁ to Ar₄ each independently represent a substituted or unsubstituted (C6-C25)aryl, a substituted or unsubstituted 5- to 15-membered heteroaryl, or a substituted or unsubstituted spiro[fluorene-(C5-C8)cycloalkane]yl, and more preferably, Ar₁ to Ar₄ each independently represent a (C6-C25)aryl unsubstituted or substituted with a (C1-C6)alkyl or a (C6-C20)aryl; a 5- to 15-membered heteroaryl unsubstituted or substituted with a (C1-C6)alkyl or a (C6-C12)aryl; an unsubstituted spiro[fluorene-cyclopentane]yl; or an unsubstituted spiro[fluorene-cyclohexane]yl. Specifically, Ar₁ to Ar₄ may each independently represent a phenyl, a biphenyl, a terphenyl, a fluorenyl substituted with a methyl(s), a fluorenyl substituted with a phenyl(s), a benzofluorenyl substituted with a methyl(s), a naphthylphenyl, a phenyl substituted with a fluorene, a pyridinyl substituted with a phenyl, a dibenzofuranyl, a dibenzothiophenyl, a dibenzosilolyl substituted with a methyl(s), a dibenzosilolyl substituted with a phenyl(s), a spiro[fluorene-cyclopentane]yl, a spiro[fluorene-cyclohexane]yl, etc.

Preferably, Ar₅ and Ar₆ each independently represent a substituted or unsubstituted (C1-C6)alkyl, or a substituted or unsubstituted (C6-C12)aryl; or may be linked to each other to form a mono- or polycyclic, 5- to 15-membered alicyclic or aromatic ring, and more preferably, Ar₅ and Ar₆ each independently represent an unsubstituted (C1-C6)alkyl, or an unsubstituted (C6-C12)aryl; or may be linked to each other to form a monocyclic, 5- to 15-membered alicyclic ring. Specifically, Ar₅ and Ar₆ may each independently represent a methyl, a phenyl, etc., or may be linked to each other to form a spirocyclopentane.

L₁ represents a single bond, a substituted or unsubstituted (C6-C30)arylene, or a substituted or unsubstituted 5- to 30-membered heteroarylene, preferably represents a single bond, a substituted or unsubstituted (C6-C20)arylene, or a substituted or unsubstituted 5- to 15-membered heteroarylene, and more preferably represents a single bond, an unsubstituted (C6-C20)arylene, or an unsubstituted 5- to 15-membered heteroarylene. Specifically, L₁ may represent a single bond, a phenylene, a naphthylene, a biphenylene, a naphthylphenylene, a pyridinephenylene, a pyridinylene, a phenylpyridinylene, a bipyridinylene, a dibenzofuranylene, a dibenzothiophenylene, etc.

L₂ represents a single bond, a substituted or unsubstituted (C1-C30)alkylene, a substituted or unsubstituted (C6-C30)arylene, or a substituted or unsubstituted 5- to 30-membered heteroarylene, with a proviso that where n is 0, L₂ does not exist. L₂ preferably represents a single bond, or a substituted or unsubstituted (C6-C12)arylene, and more preferably represents a single bond, or an unsubstituted (C6-C12)arylene. Specifically, L₂ may represent a single bond, a phenylene, etc.

R₁ and R₂ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted 3- to 7-membered heterocycloalkyl, a substituted or unsubstituted (C6-C30)aryl(C1-C30)alkyl, —NR₁₁R₁₂, —SiR₁₃R₁₄R₁₅, —SR₁₆, —OR₁₇, a cyano, a nitro, or a hydroxyl; or are linked to an adjacent substituent(s) to form a mono- or polycyclic, 3- to 30-membered alicyclic or aromatic ring, whose carbon atom(s) may be replaced with at least one hetero atom selected from nitrogen, oxygen, and sulfur, preferably each independently represent hydrogen, or a substituted or unsubstituted (C6-C15)aryl, and more preferably each independently represent hydrogen, or an unsubstituted (C6-C15)aryl. Specifically, R₁ and R₂ may each independently represent hydrogen, biphenyl, etc.

R₁₁ to R₁₇ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted 3- to 7-membered heterocycloalkyl, or a substituted or unsubstituted (C3-C30)cycloalkyl; or are linked to an adjacent substituent(s) to form a mono- or polycyclic, 3- to 30-membered alicyclic or aromatic ring, whose carbon atom(s) may be replaced with at least one hetero atom selected from nitrogen, oxygen, and sulfur.

According to one embodiment of the present disclosure, in formula 1 above, $Ar_1$ to $Ar_4$ each independently represent a substituted or unsubstituted (C6-C25)aryl, a substituted or unsubstituted 5- to 15-membered heteroaryl, or a substituted or unsubstituted spiro[fluorene-(C5-C8)cycloalkane]yl; $Ar_5$ and $Ar_6$ each independently represent a substituted or unsubstituted (C1-C6)alkyl, or a substituted or unsubstituted (C6-C12)aryl; or may be linked to each other to form a mono- or polycyclic, 5- to 15-membered alicyclic or aromatic ring; $L_1$ represents a single bond, a substituted or unsubstituted (C6-C20)arylene, or a substituted or unsubstituted 5- to 15-membered heteroarylene; $L_2$ represents a single bond, or a substituted or unsubstituted (C6-C12)arylene, with a proviso that where n is 0, $L_2$ does not exist; and $R_1$ and $R_2$ each independently represent hydrogen, or a substituted or unsubstituted (C6-C15)aryl.

According to another embodiment of the present disclosure, in formula 1 above, Ar to $Ar_4$ each independently represent a (C6-C25)aryl unsubstituted or substituted with a (C1-C6)alkyl or a (C6-C20)aryl; a 5- to 15-membered heteroaryl unsubstituted or substituted with a (C1-C6)alkyl or a (C6-C12)aryl; an unsubstituted spiro[fluorene-cyclopentane]yl; or an unsubstituted spiro[fluorene-cyclohexane]yl; $Ar_5$ and $Ar_6$ each independently represent an unsubstituted (C1-C6)alkyl, or an unsubstituted (C6-C12)aryl; or may be linked to each other to form a monocyclic, 5- to 15-membered alicyclic ring; $L_1$ represents a single bond, an unsubstituted (C6-C20)arylene, or an unsubstituted 5- to 15-membered heteroarylene; $L_2$ represents a single bond, or an unsubstituted (C6-C12)arylene, with a proviso that where n is 0, $L_2$ does not exist; and $R_1$ and $R_2$ each independently represent hydrogen, or an unsubstituted (C6-C15)aryl.

The organic electroluminescent compound represented by formula 1 includes the following compounds, but is not limited thereto:

C-1

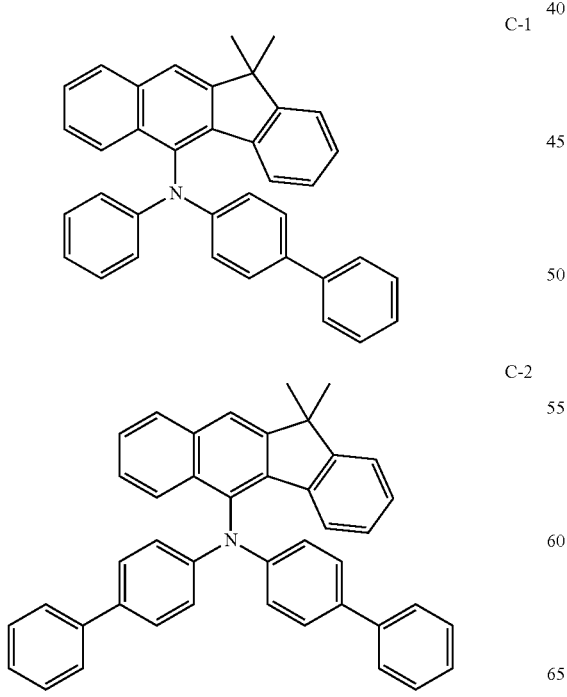

C-2

C-3

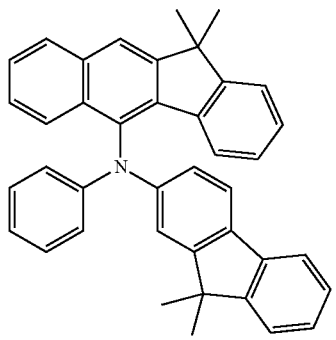

C-4

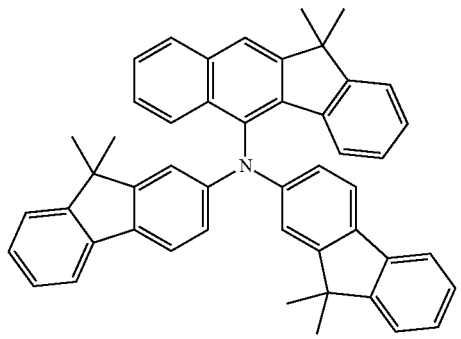

C-5

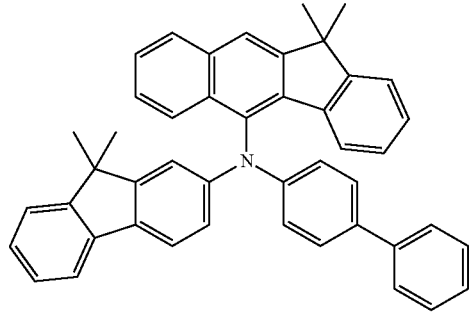

C-6

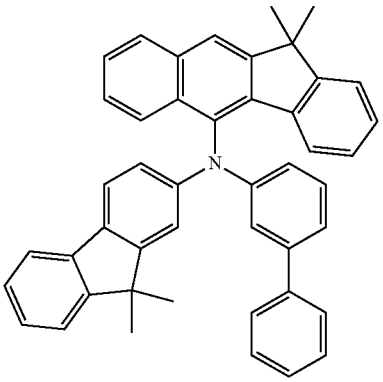

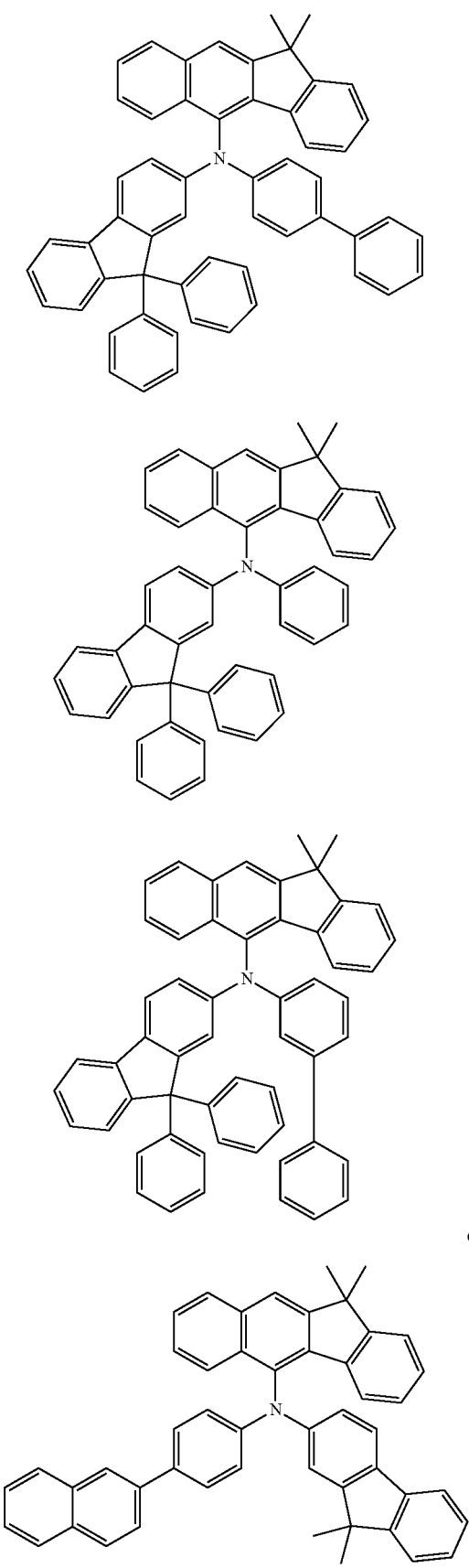
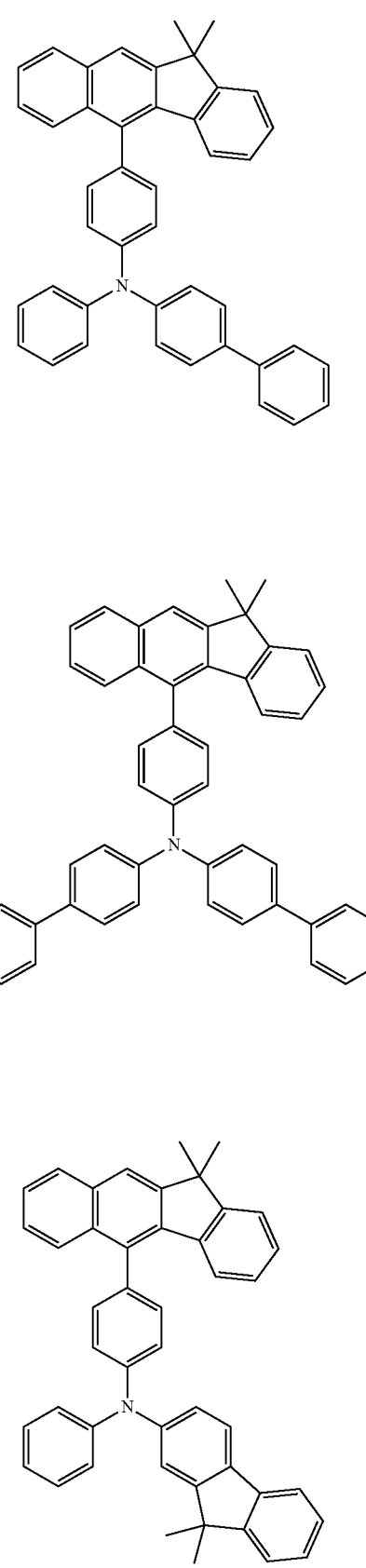

C-14
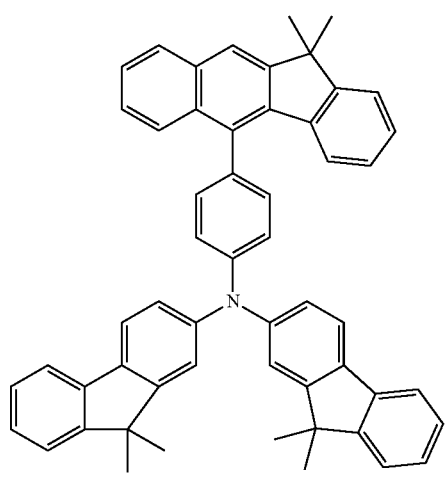
C-15
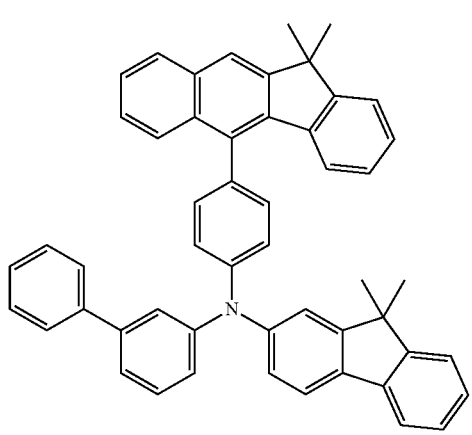
C-17
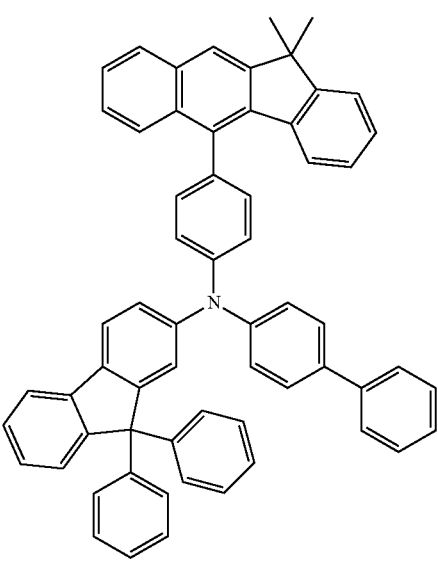
C-18
C-19
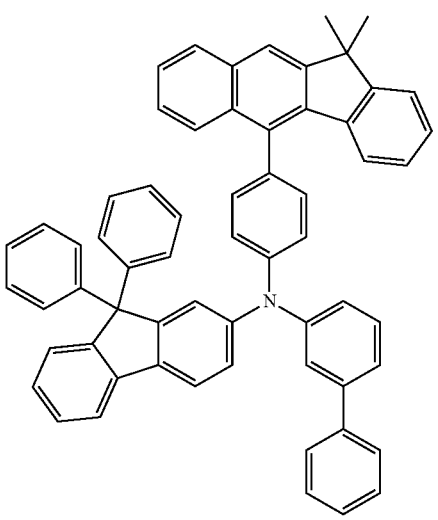
C-16

C-20
C-21
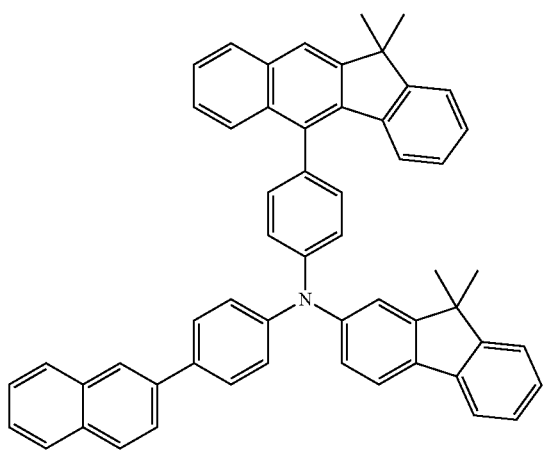
C-23
C-22
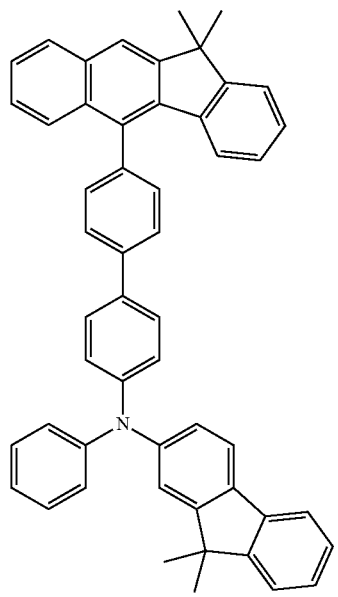
C-24
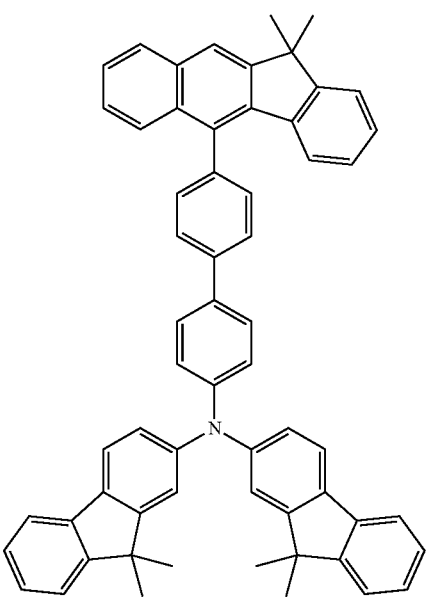

C-25
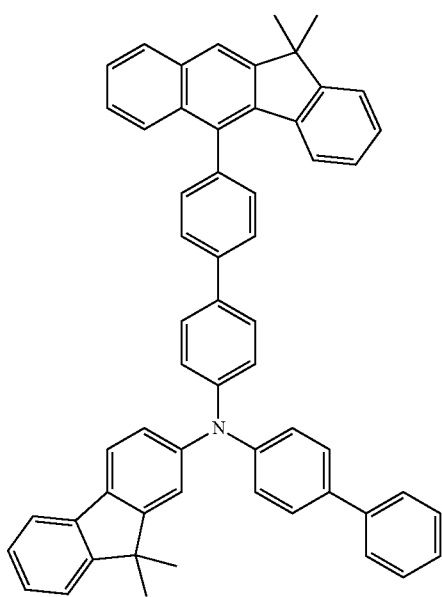
C-26
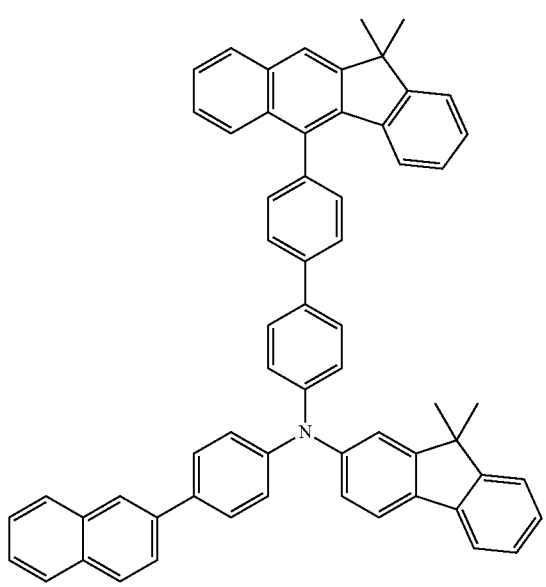
C-27
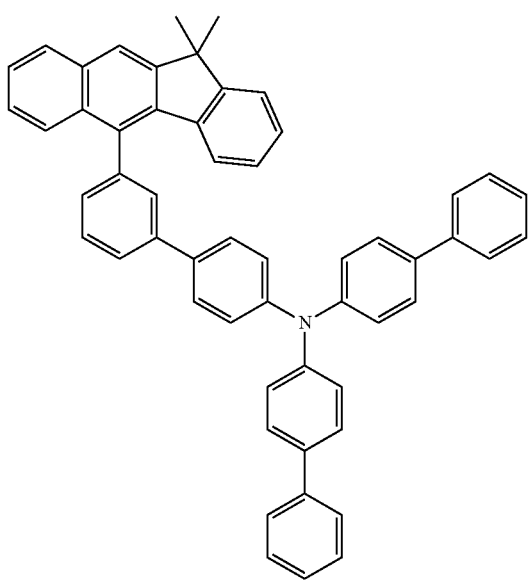
C-28
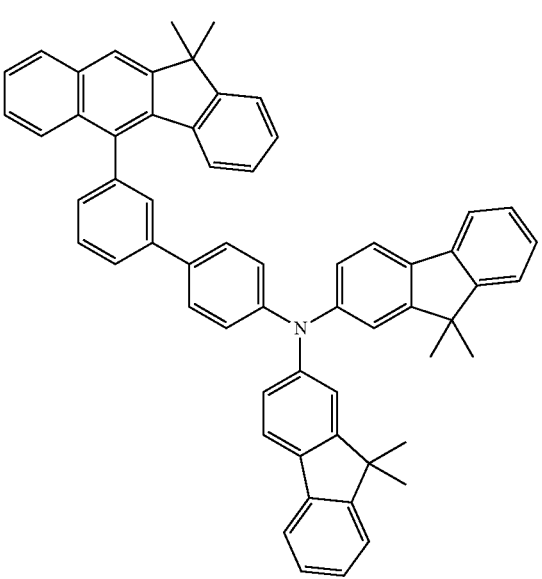

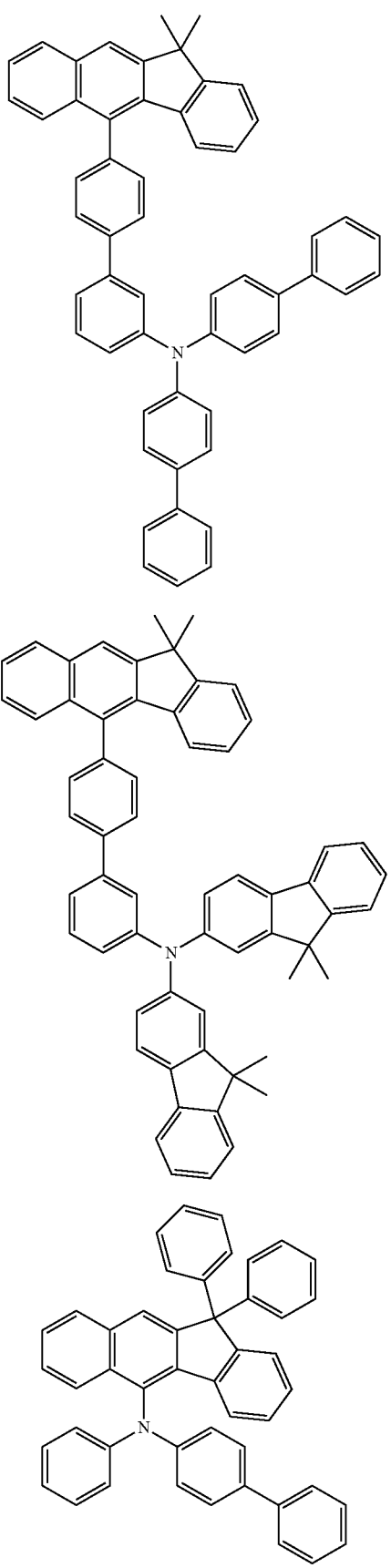
C-29
C-30
C-31
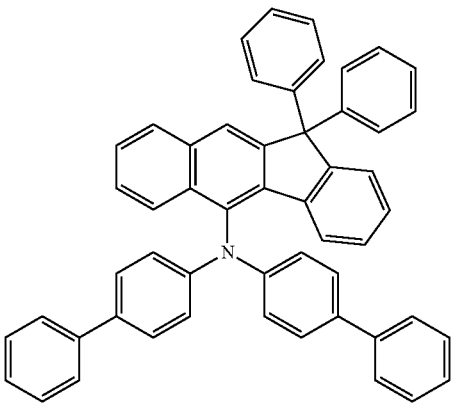
C-32
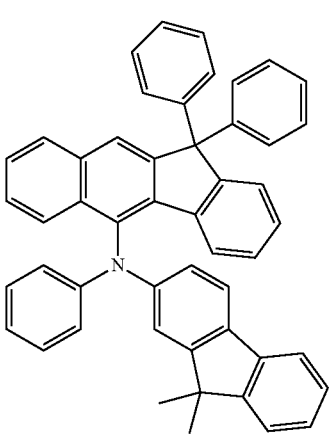
C-33
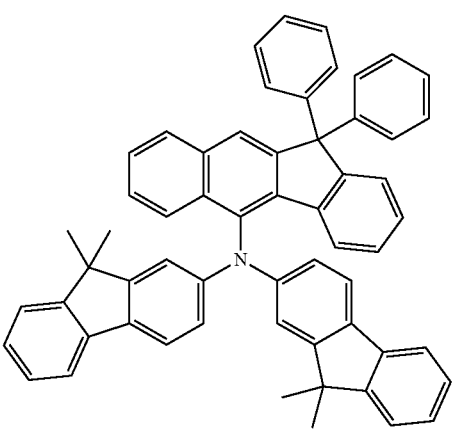
C-34

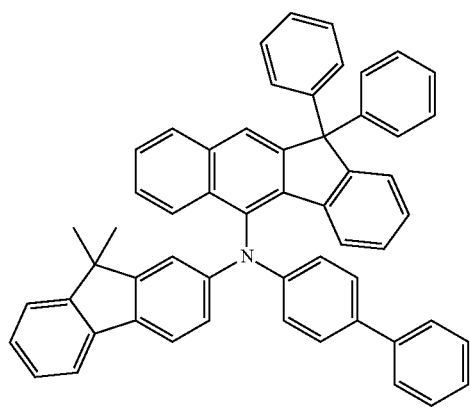
C-35
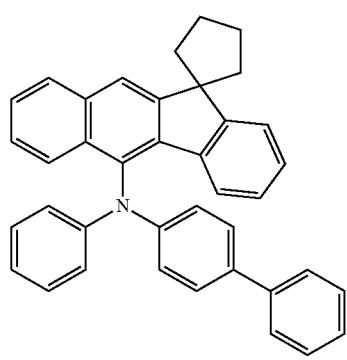
C-36
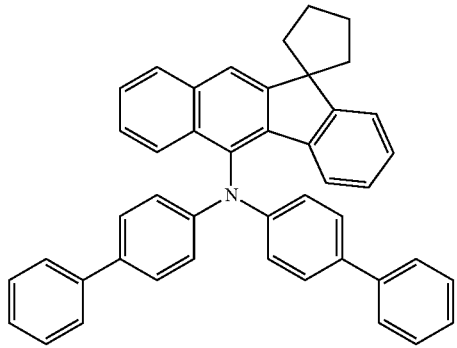
C-37
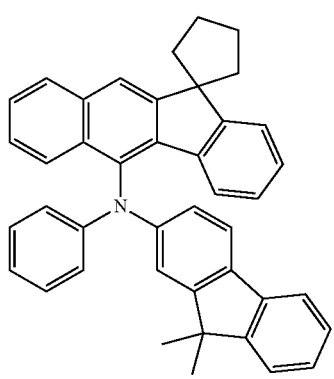
C-38
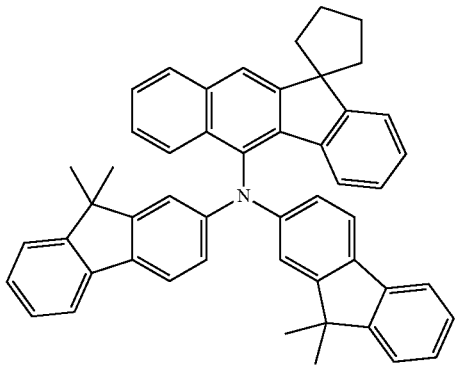
C-39
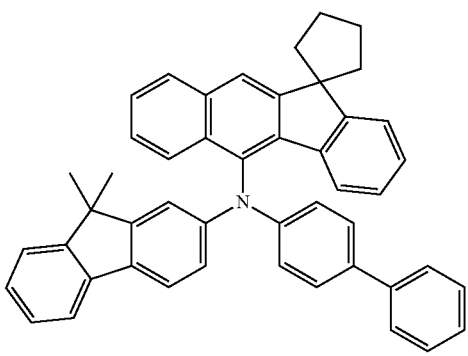
C-40
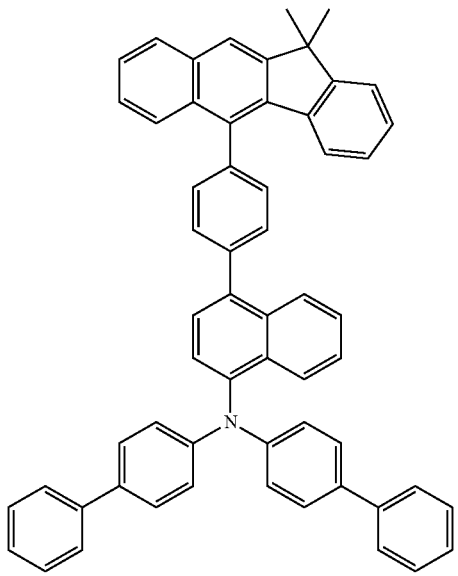
C-41

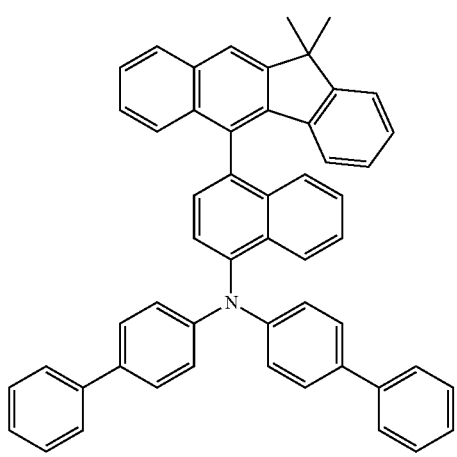
C-42
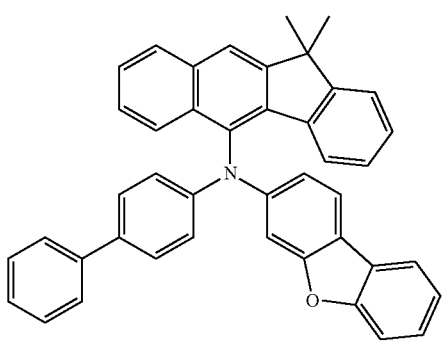
C-46
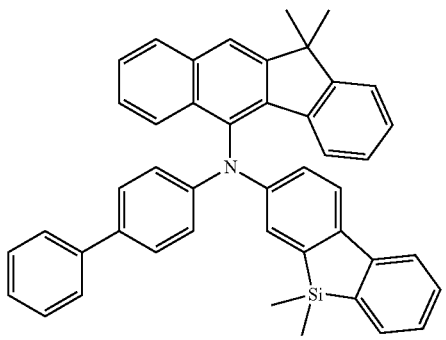
C-47
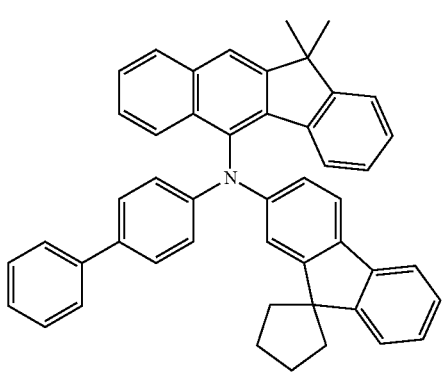
C-48
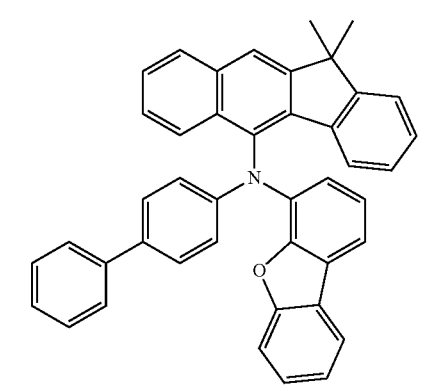
C-49

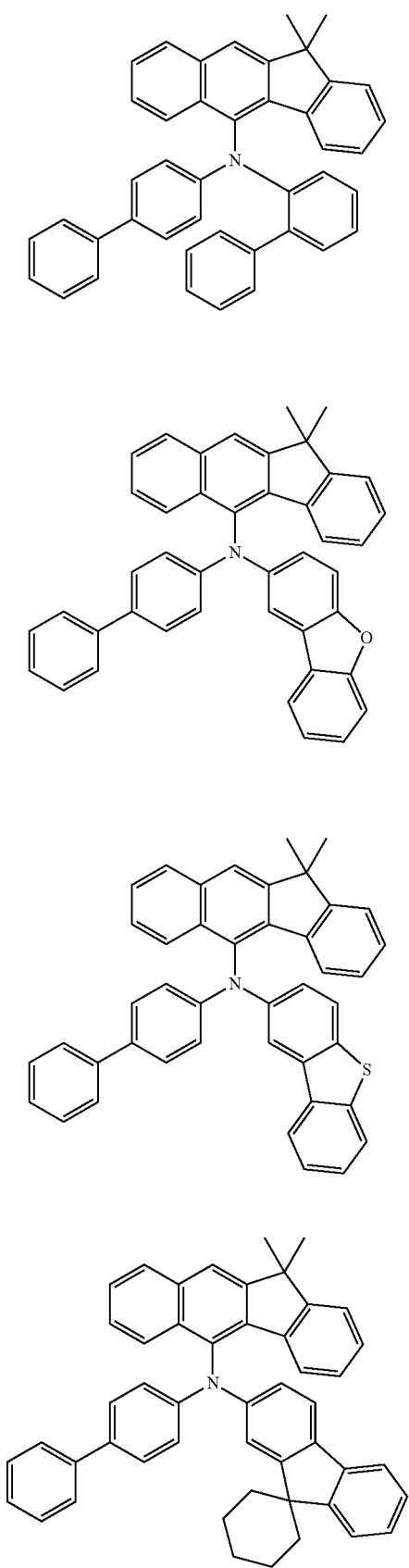
C-50
C-51
C-52
C-53
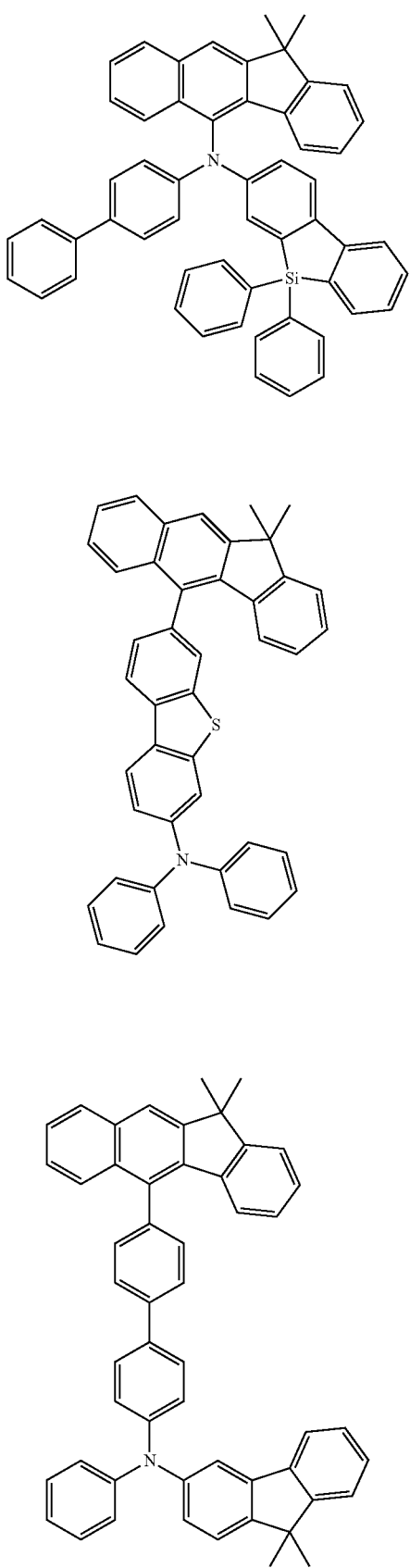
C-54
C-55
C-56

-continued
C-57
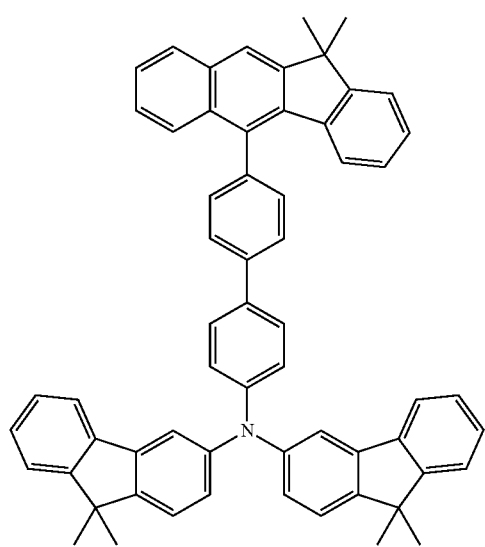
C-58
C-59
-continued
C-60
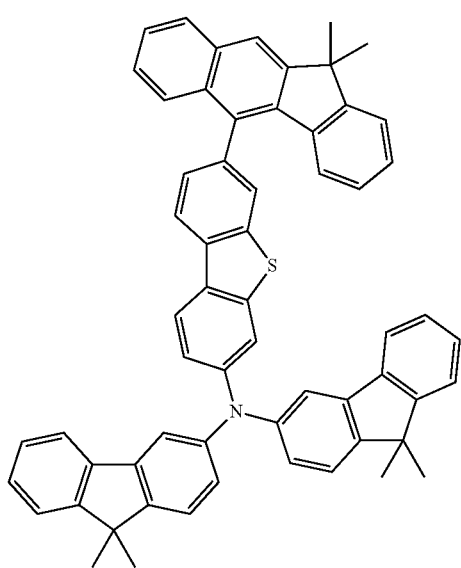
C-61
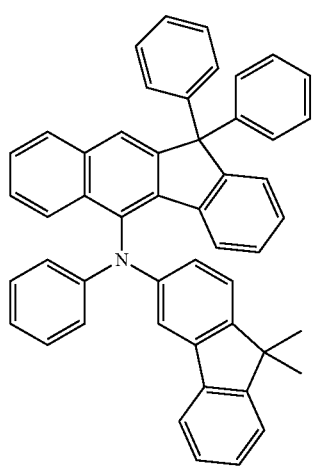
C-62
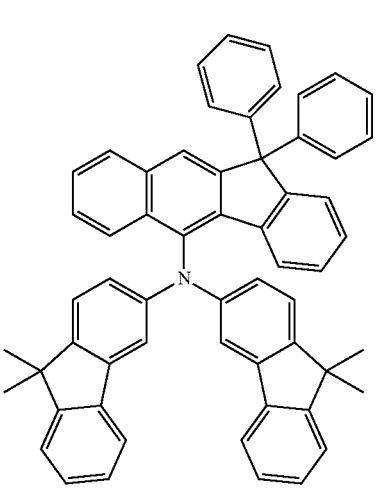

-continued
C-63
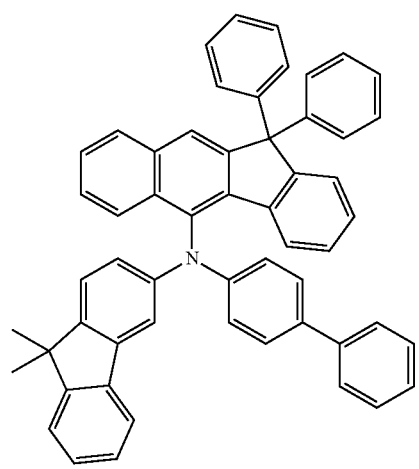
C-64
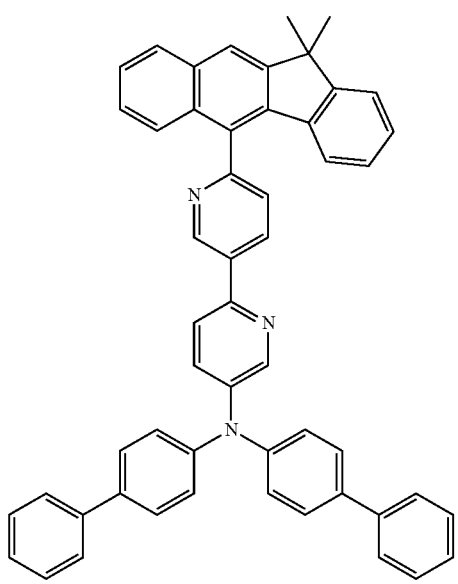
C-65
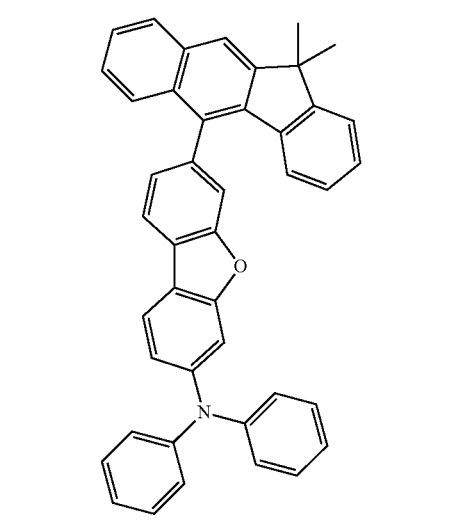
-continued
C-66
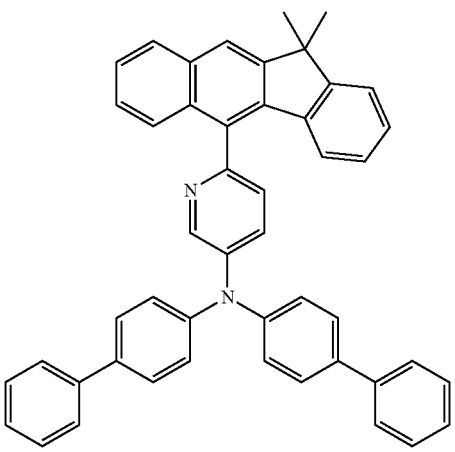
C-67
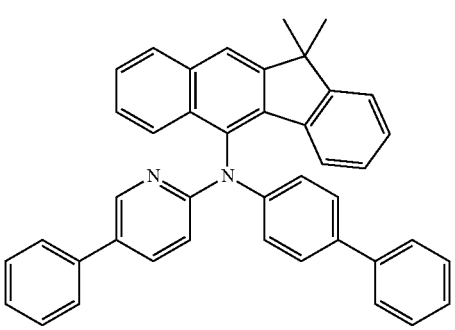
C-68
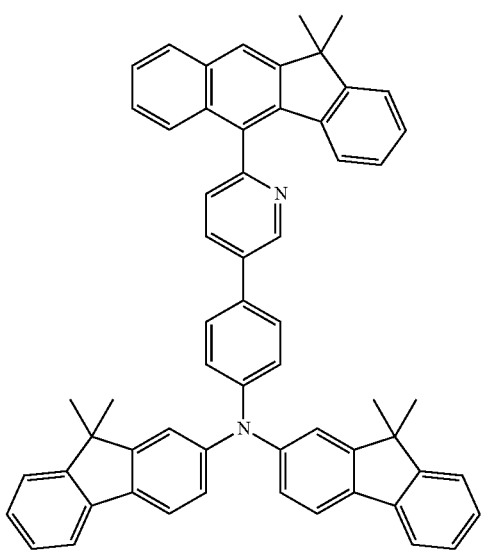

C-69
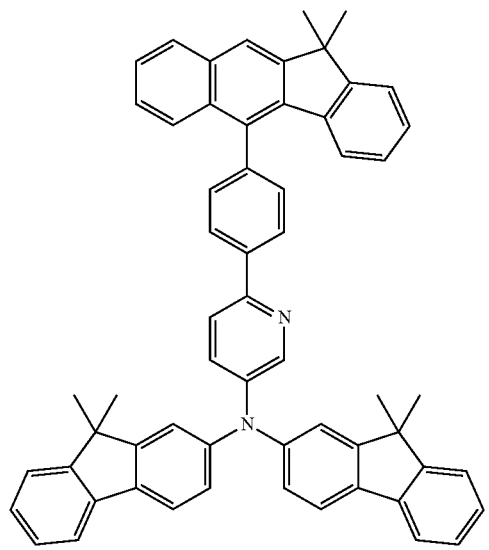
C-70
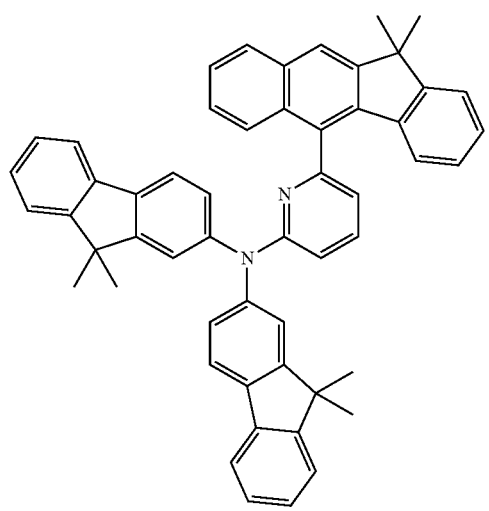
C-71
C-72
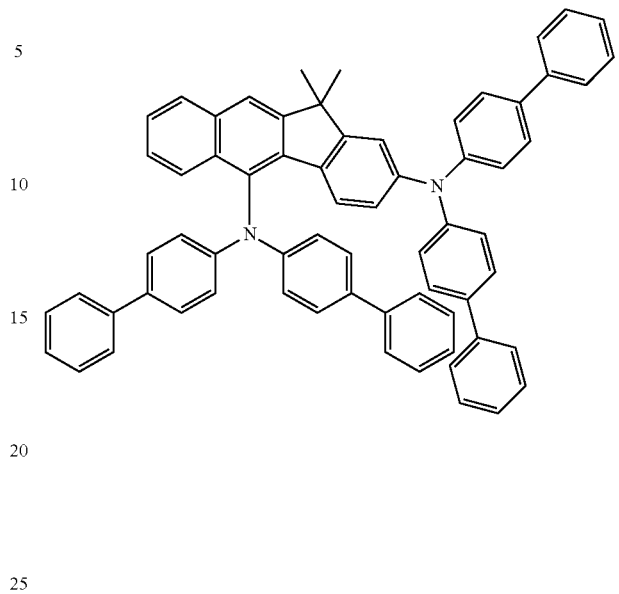
C-73
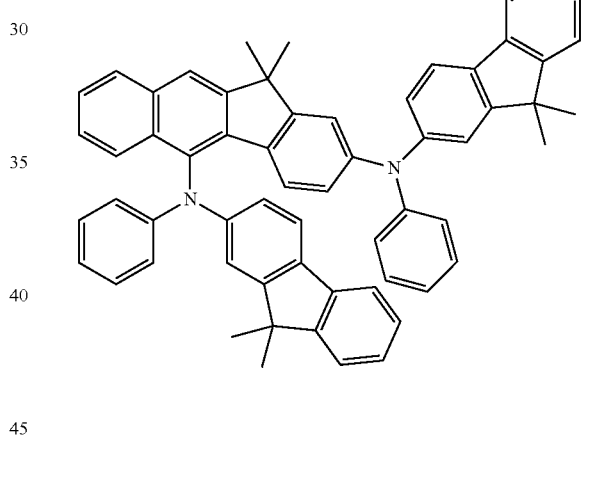
C-74
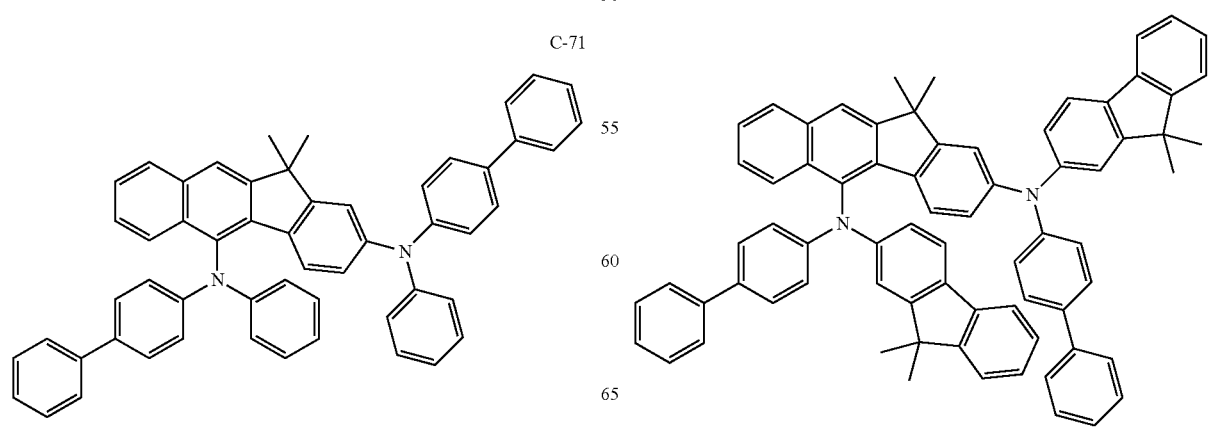

C-75
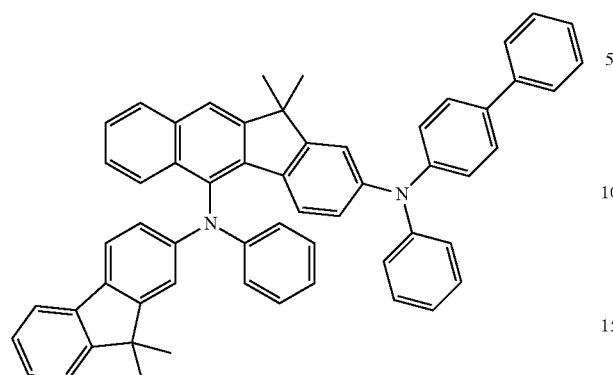
C-76
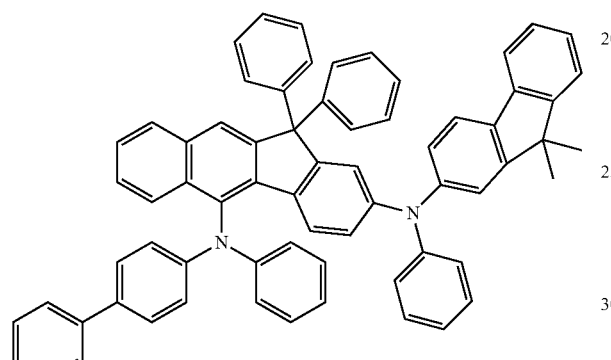
C-77
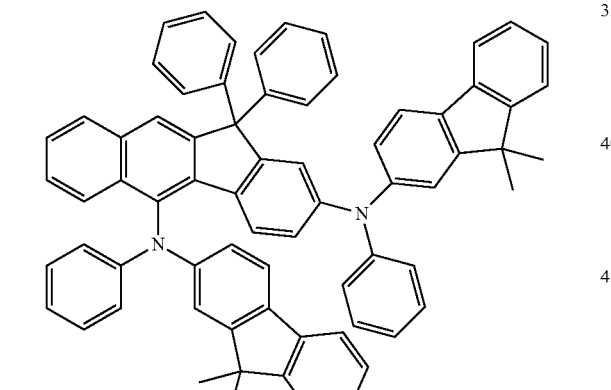
C-78
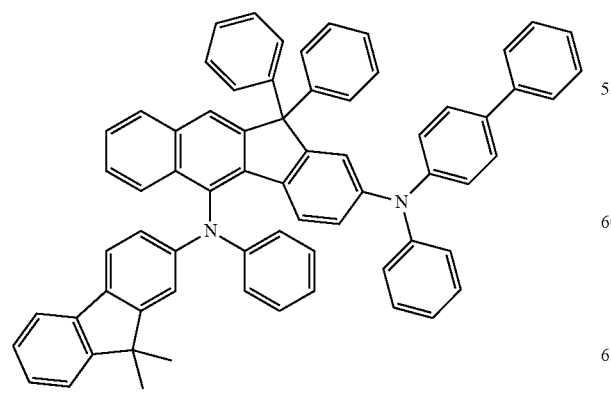
C-79
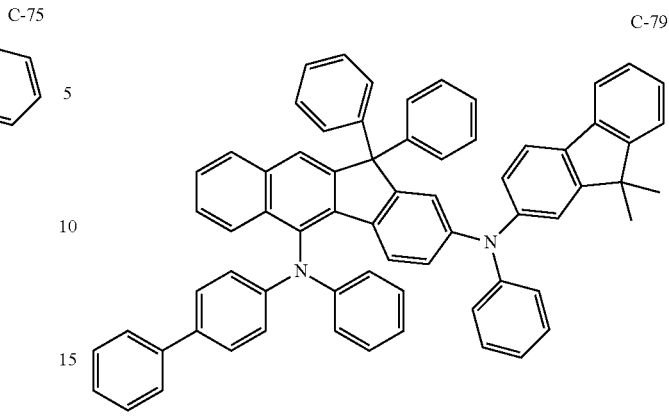
C-80
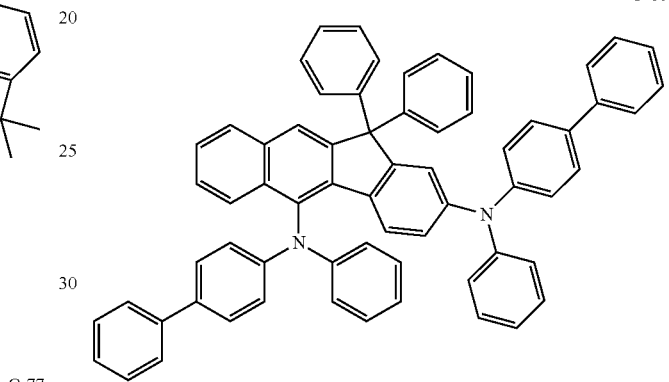
C-81
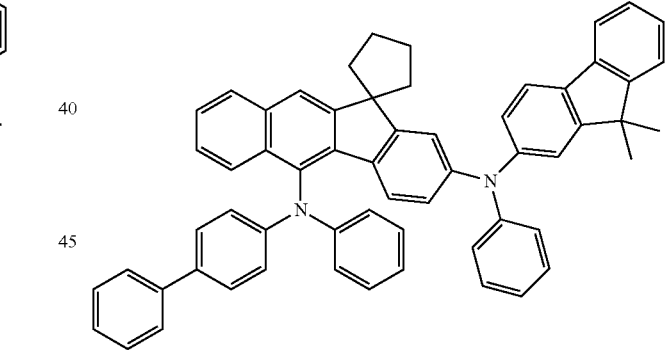
C-82
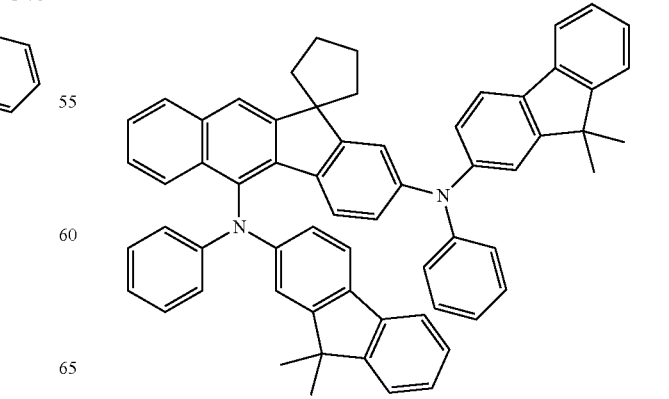

C-83
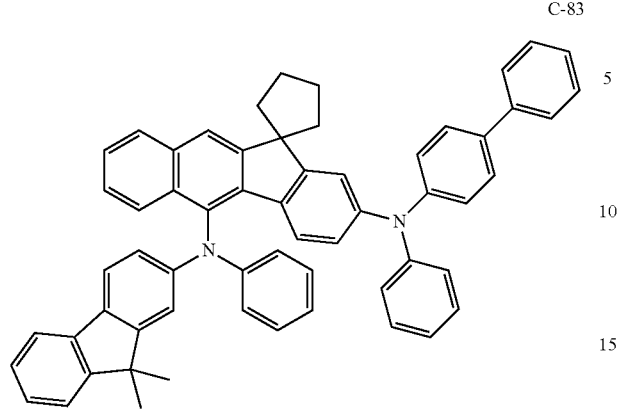
C-87
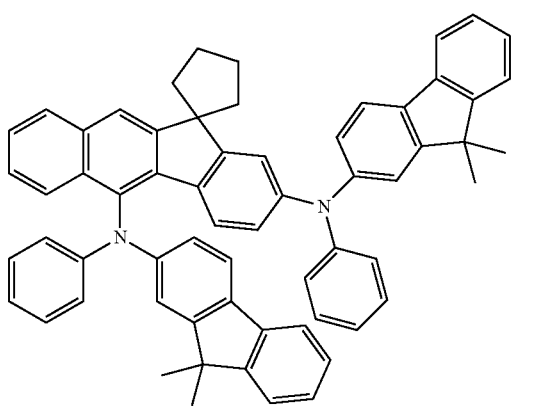
C-84
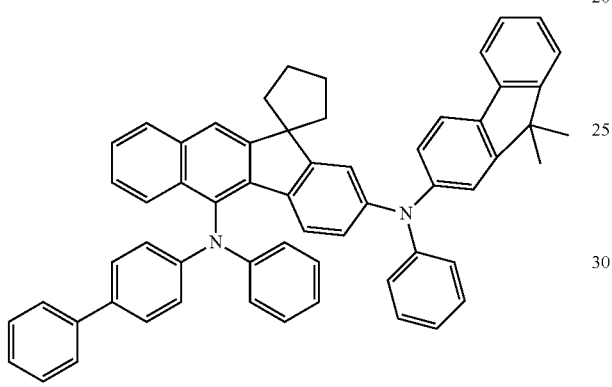
C-88
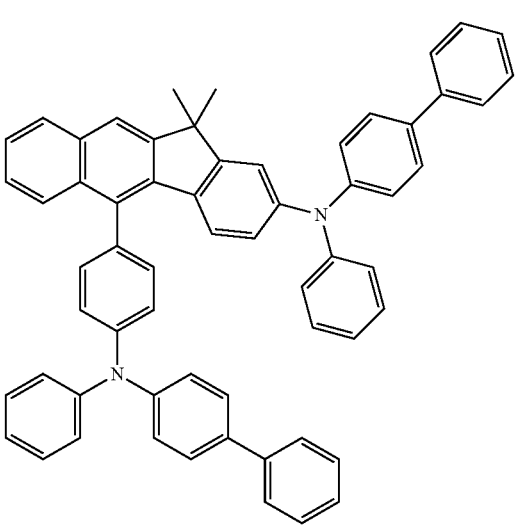
C-85
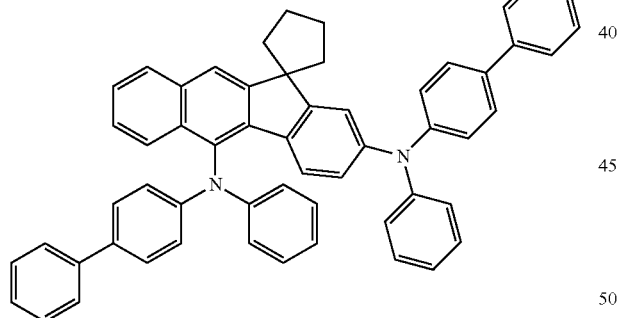
C-86
C-89
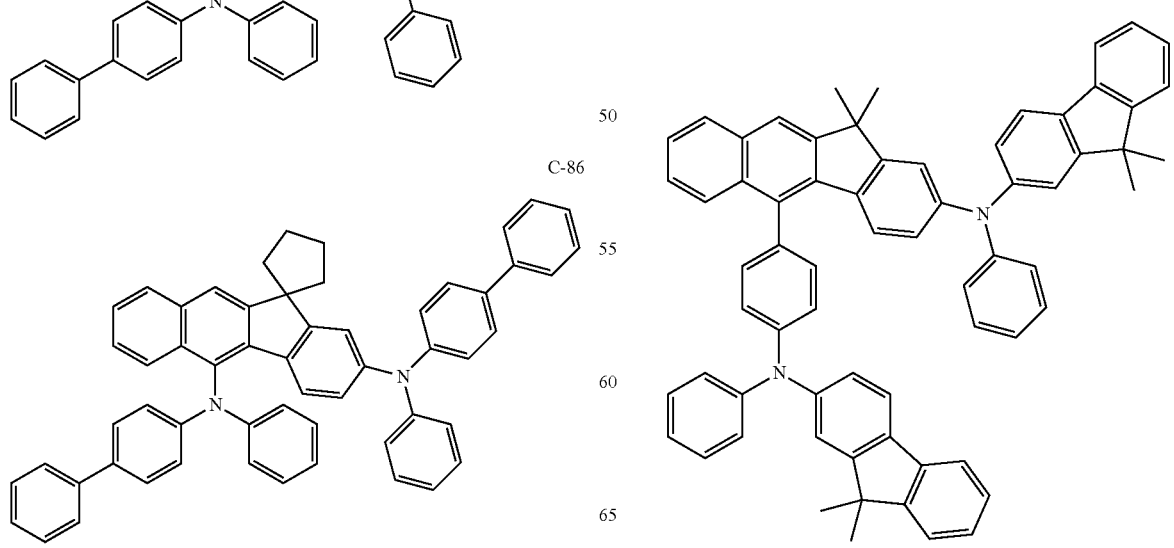

C-90
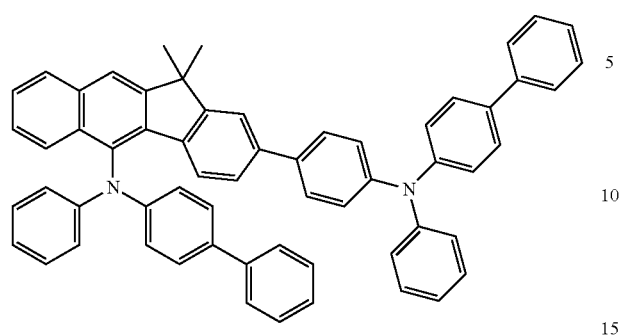
C-93
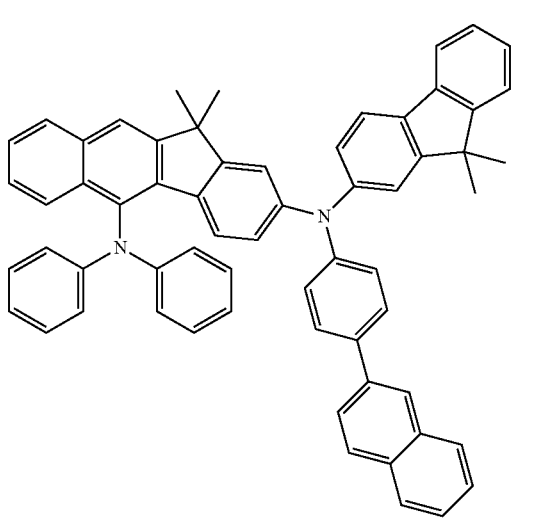
C-91
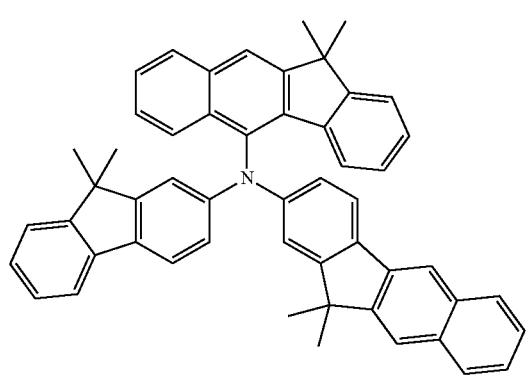
C-92
C-94
The organic electroluminescent compound of the present disclosure can be prepared by a synthetic method known to a person skilled in the art. For example, it can be prepared according to the following reaction schemes.
[Reaction Scheme 1]
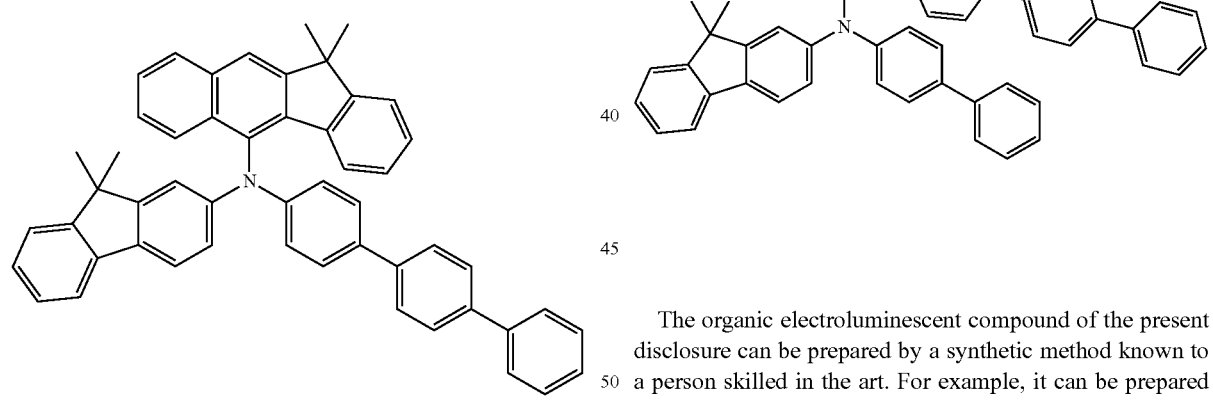

-continued
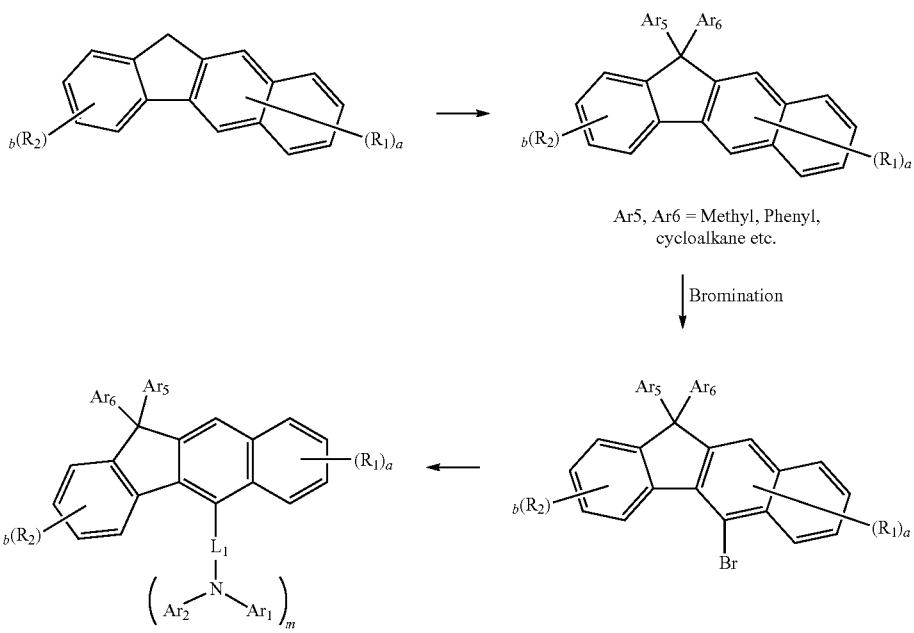
[Reaction Scheme 2]
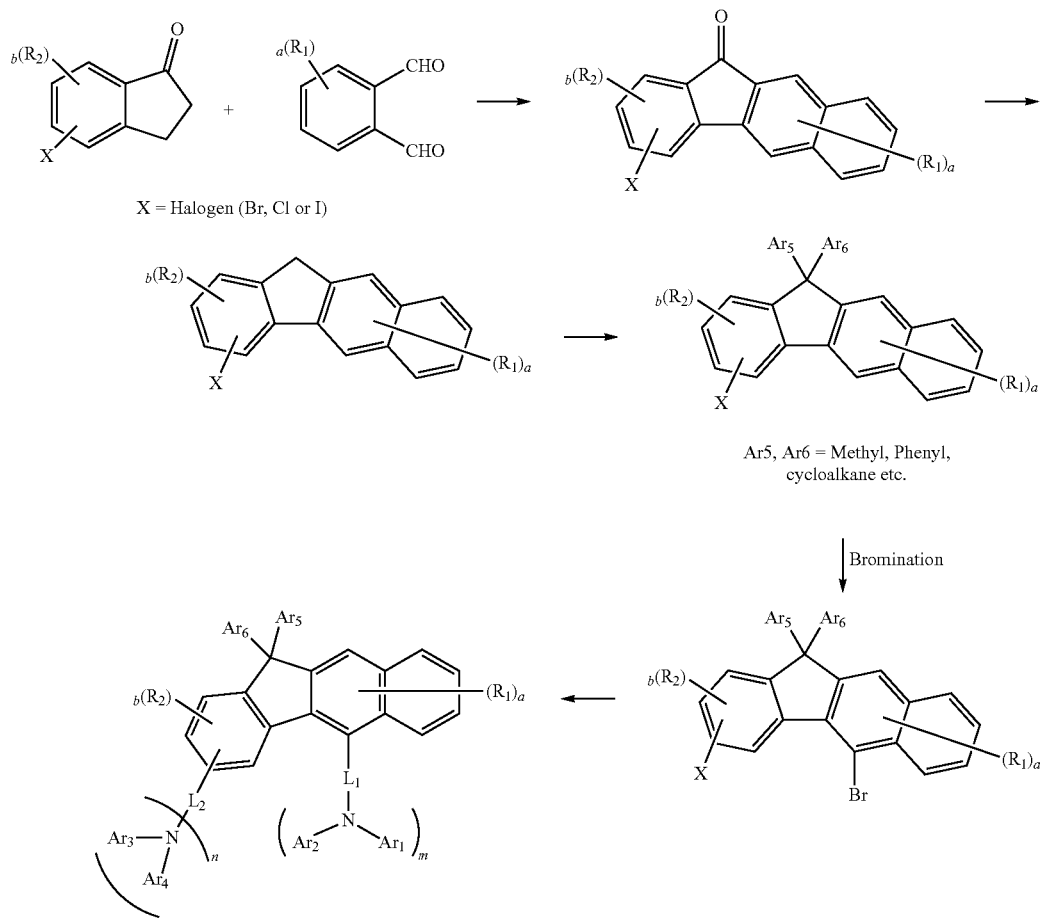

[Reaction Scheme 3]

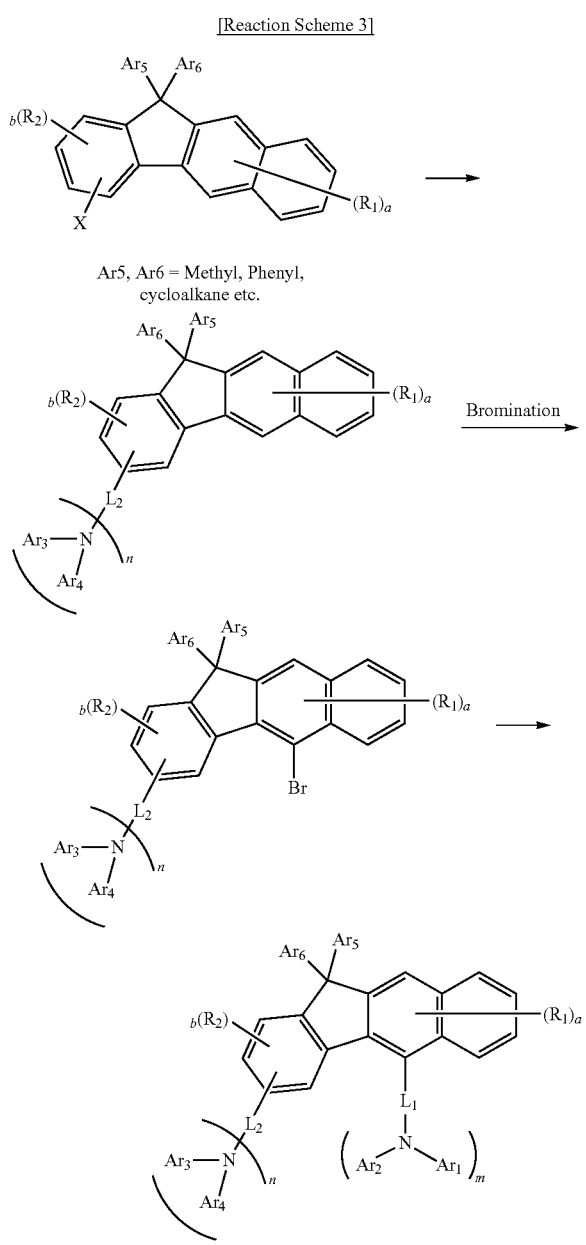

Ar5, Ar6 = Methyl, Phenyl, cycloalkane etc.

Bromination wherein $Ar_1$ to $Ar_6$, $L_1$, $L_2$, $R_1$, $R_2$, a, b, m, and n are as defined in formula 1, and X represents a halogen.

The present disclosure provides an organic electroluminescent material comprising the organic electroluminescent compound of formula 1, and an organic electroluminescent device comprising the material.

The above material may be a host material of a light-emitting layer, specifically a host material of an organic electroluminescent device emitting red light. The above material may be a hole transport material, specifically a hole transport material of an organic electroluminescent device emitting red light. When there are two or more hole transport layers, the material may be a hole transport material comprised in the hole transport layer adjacent to the light-emitting layer.

The above material can be comprised of the organic electroluminescent compound according to the present disclosure alone, or can further include conventional materials generally used in organic electroluminescent materials.

The organic electroluminescent device comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound of the present disclosure may be comprised in at least one layer of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer, preferably in at least one layer of the light-emitting layer and the hole transport layer. When there are two or more light-emitting layers or hole transport layers, the organic electroluminescent compound can be used in at least one of the layers. When used in the hole transport layer, the organic electroluminescent compound of the present disclosure may be comprised as a hole transport material. When there are two or more hole transport layers, the compound of the present disclosure may be comprised in the hole transport layer adjacent to the light-emitting layer. When used in the light-emitting layer, the organic electroluminescent compound of the present disclosure may be comprised as a host material.

According to one embodiment of the present disclosure, the organic electroluminescent compound of the present disclosure may be used as the hole transport material, and may provide an organic electroluminescent device having excellent lifespan properties, improved luminous efficiency due to an increase of triplet energy, and/or excellent thermal stability due to a decrease of deposition temperature.

The organic electroluminescent device comprising the organic electroluminescent compound of the present disclosure as a host material can further comprise one or more host compounds besides the organic electroluminescent compound of the present disclosure, and can further comprise one or more dopants.

When the organic electroluminescent compound of the present disclosure is comprised as a host material (first host material) of the light-emitting layer, another compound can be comprised as a second host material. Herein, the weight ratio of the first host material to the second host material is in the range of 1:99 to 99:1.

The host material of a compound other than the organic electroluminescent compound of the present disclosure can be any of the known hosts. The compound which can be comprised as a host material of a light-emitting layer where the compound of the present disclosure is used as a hole transport material, and the compound which can be comprised as a second host material where the compound of the present disclosure is used as a host material may be preferable in terms of luminous efficiency if they are selected from the group consisting of the compounds represented by the following formulas 11 to 16:

$$H\!-\!\!-\!(Cz\!-\!L_4)_h\!-\!\!-\!M \quad (11)$$

-continued

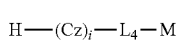  (12)

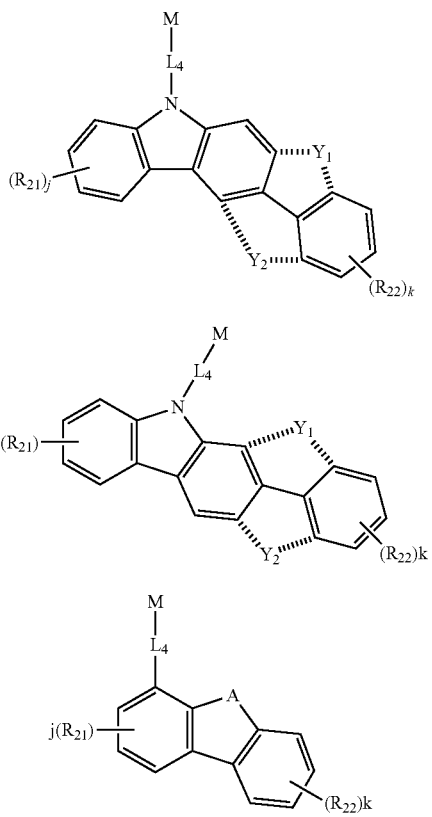

(13)

(14)

(15)

wherein
Cz represents the following structure:

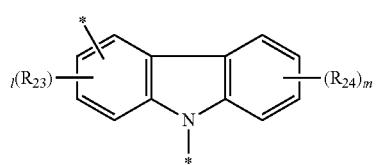

A represents —O— or —S—; and
$R_{21}$ to $R_{24}$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, or —$SiR_{25}R_{26}R_{27}$; in which $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; $Y_1$ and $Y_2$, each independently, represent —O—, —S—, —$NR_{31}$— or —$CR_{32}R_{33}$—, with the proviso that $Y_1$ and $Y_2$ are not present simultaneously; $R_{31}$ to $R_{33}$, each independently, represent a substituted or unsubstituted (C1-C30)alkyl, a substituted or unsubstituted (C6-C30)aryl, or a substituted or unsubstituted (5- to 30-membered)heteroaryl; $R_{32}$ and $R_{33}$ may be the same or different; h and i, each independently, represent an integer of 1 to 3; j, k, l, and m, each independently, represent an integer of 0 to 4; where if h, i, j, k, l, or m represents an integer of 2 or more, each (Cz-$L_4$), each (Cz), each $R_{21}$, each $R_{22}$, each $R_{23}$, or each $R_{24}$ may be the same or different;

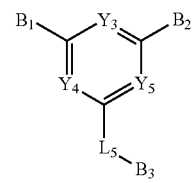  (16)

wherein
$Y_3$ to $Y_5$, each independently, represent $CR_{34}$ or N, preferably at least one of them are N;
$R_{34}$ represents hydrogen, a substituted or unsubstituted (C1-C30)alkyl, a substituted or unsubstituted (C6-C30)aryl, or a substituted or unsubstituted (5- to 30-membered)heteroaryl;
$B_1$ and $B_2$, each independently, represent hydrogen, a substituted or unsubstituted (C6-C30)aryl, or a substituted or unsubstituted (5- to 30-membered)heteroaryl;
$B_3$ represents a substituted or unsubstituted (C6-C30)aryl, or a substituted or unsubstituted (5- to 30-membered)heteroaryl; and
$L_5$ represents a single bond, a substituted or unsubstituted (C6-C30)arylene, or a substituted or unsubstituted (5- to 30-membered)heteroarylene.

Specifically, the examples of the second host material are as follows, but are not limited thereto.

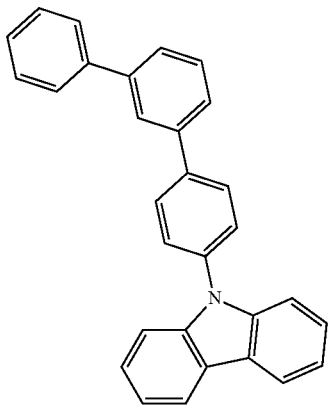

B-1

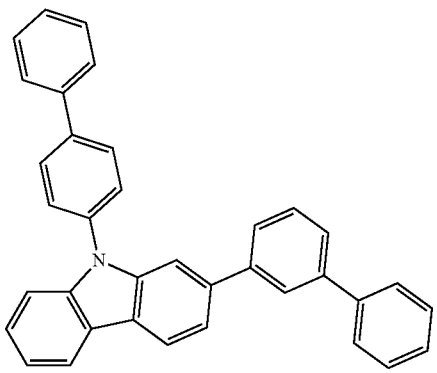

B-2

B-3
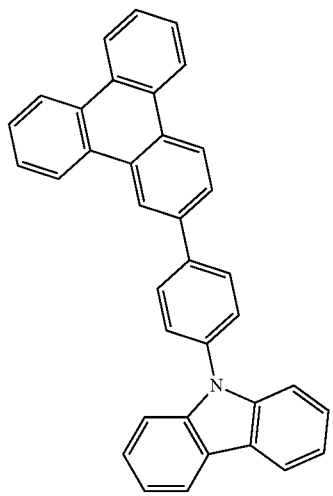
B-6
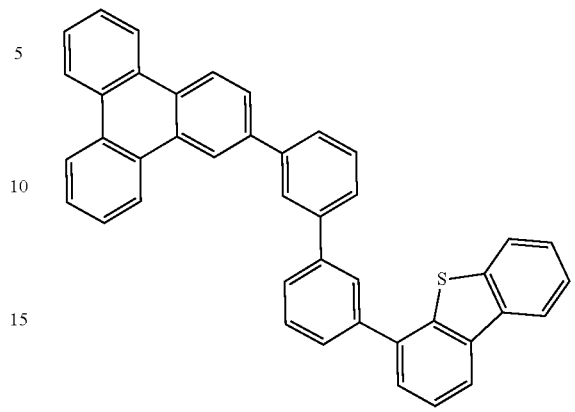
B-4
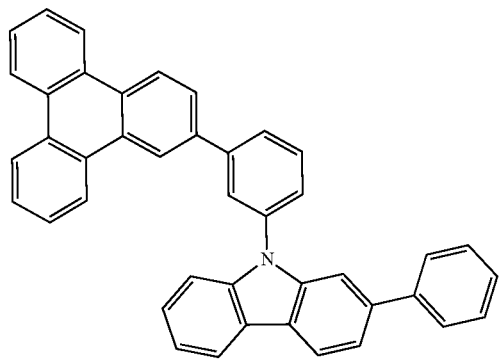
B-7
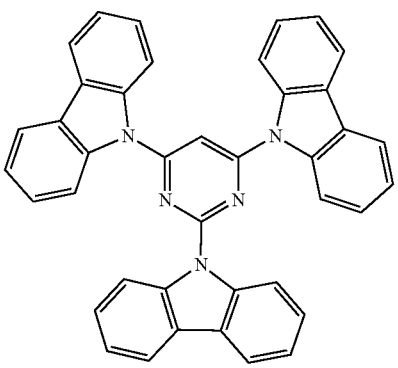
B-5
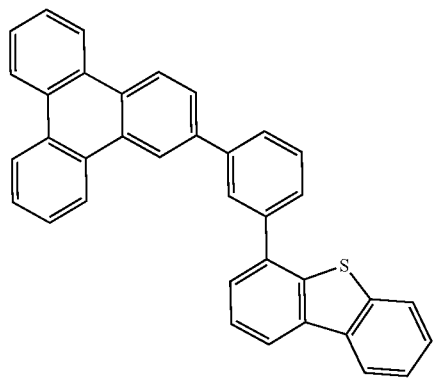
B-8
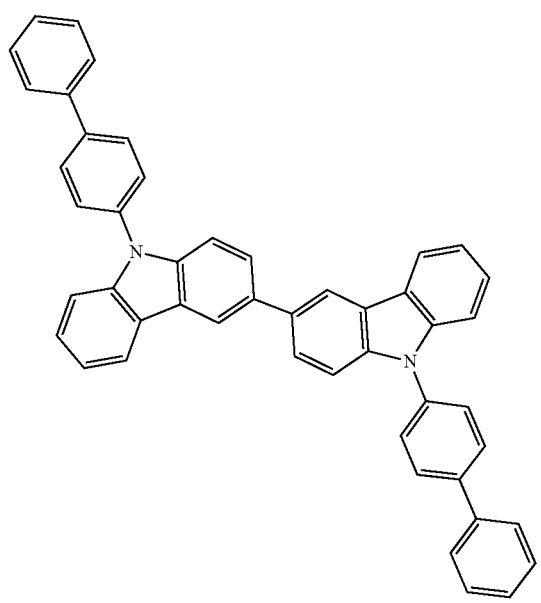

B-9
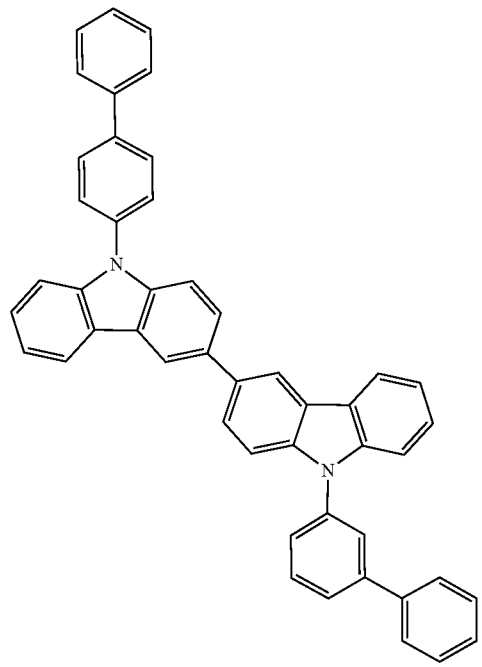
B-11
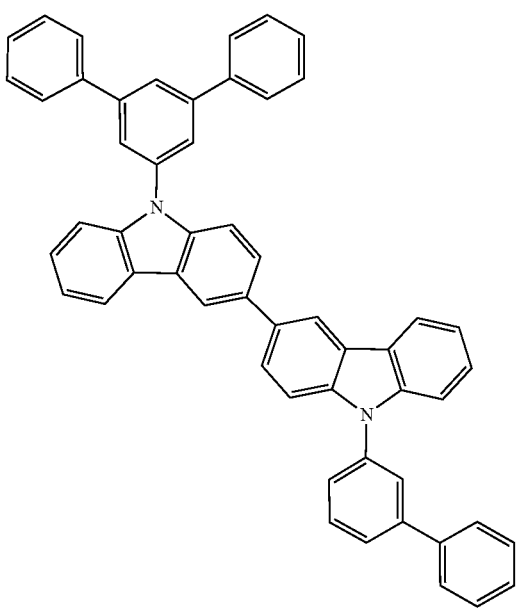
B-10
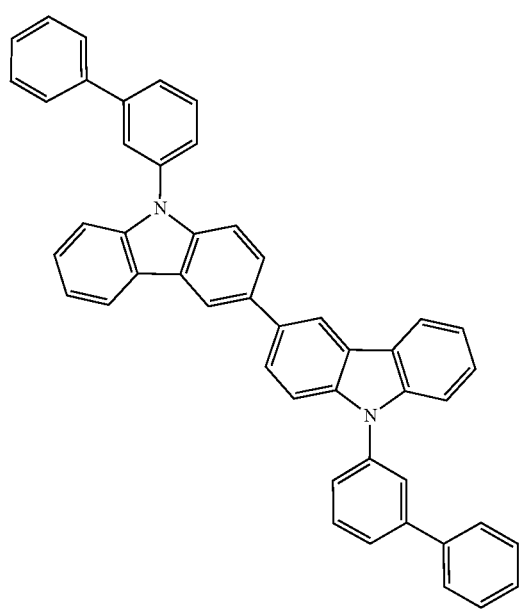
B-12
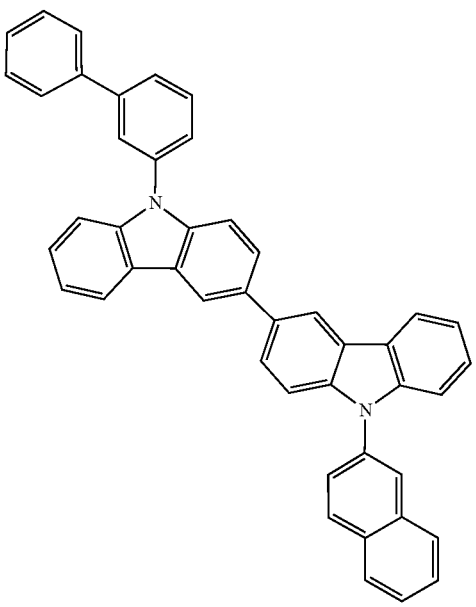

B-13
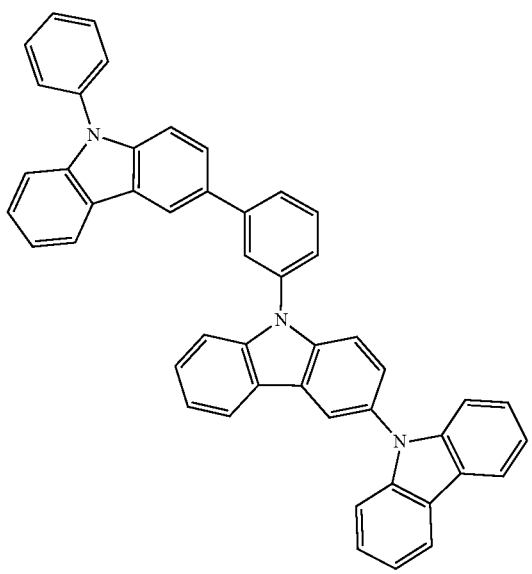
B-14
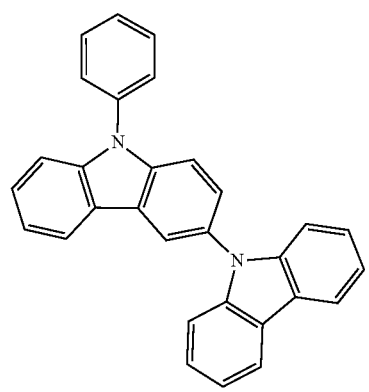
B-15
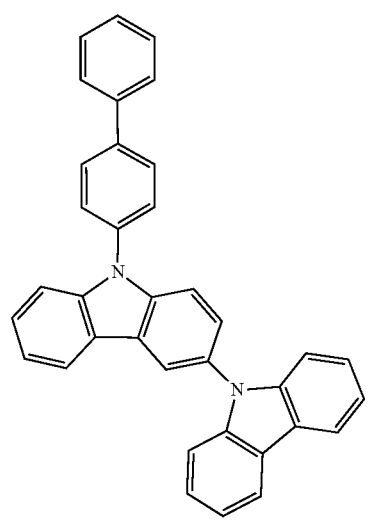
B-16
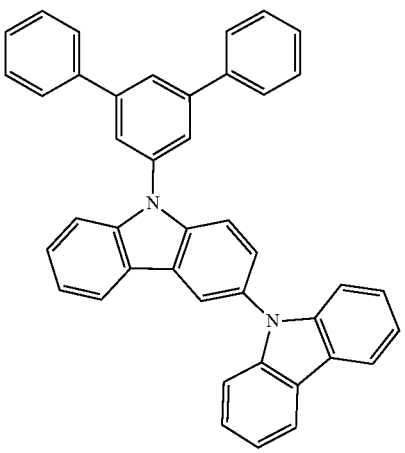
B-17
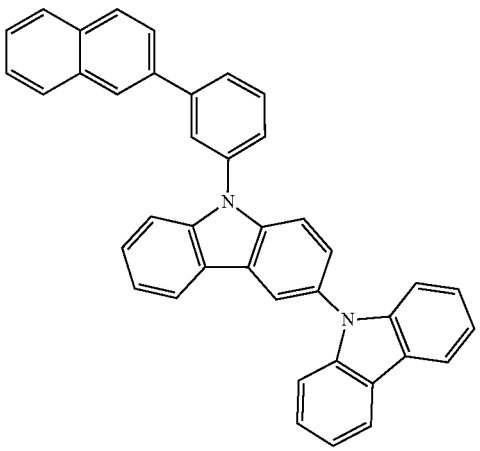
B-18
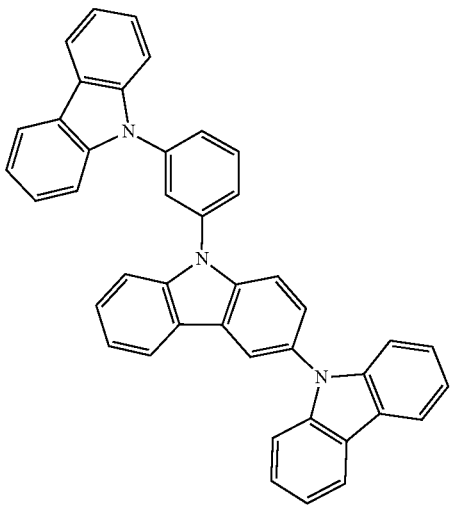

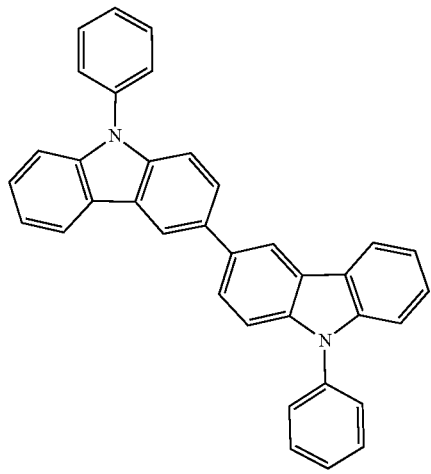
B-19
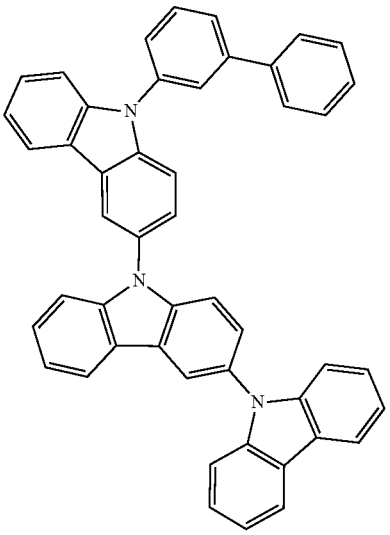
B-22
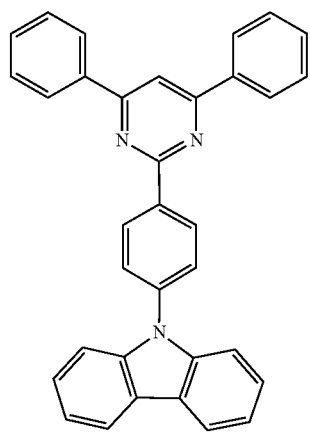
B-20
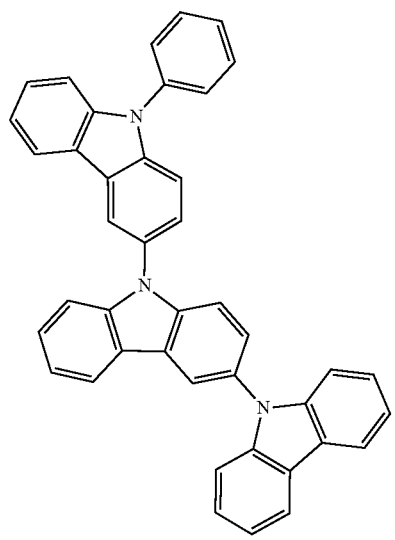
B-21
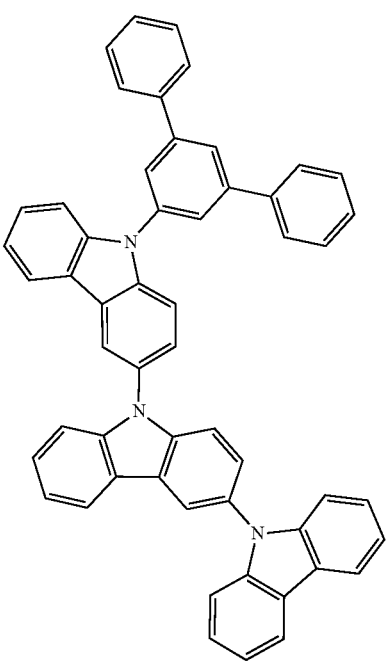
B-23

-continued
B-24
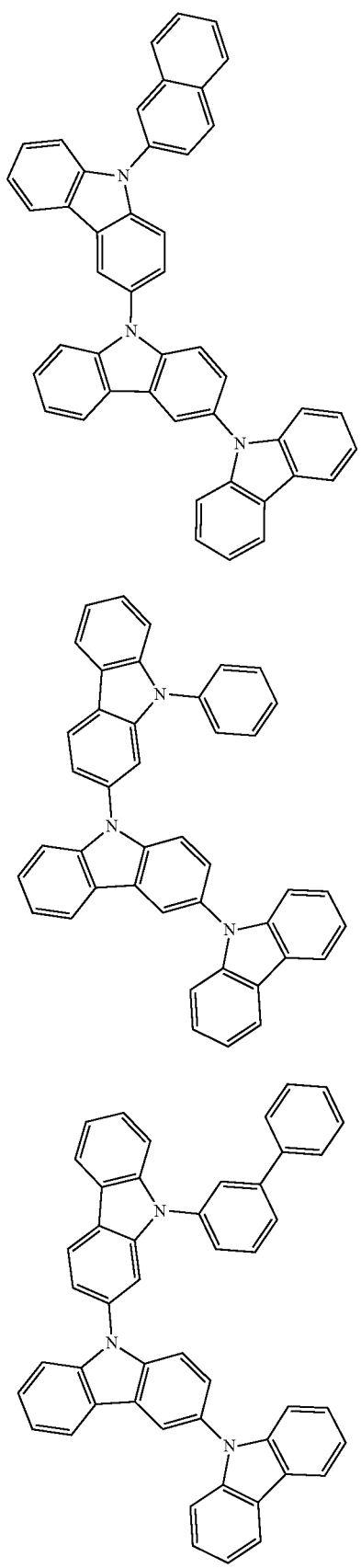
B-25
B-26
B-27
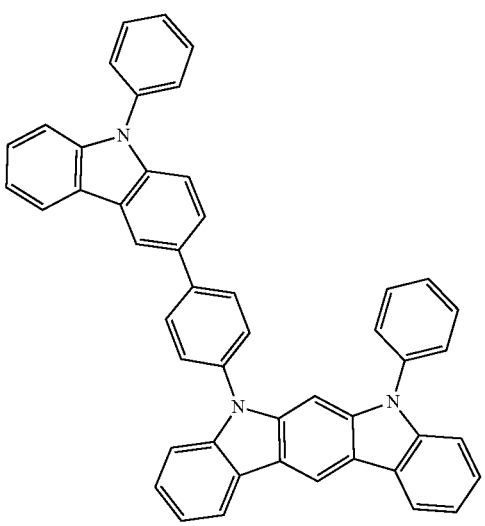
B-28
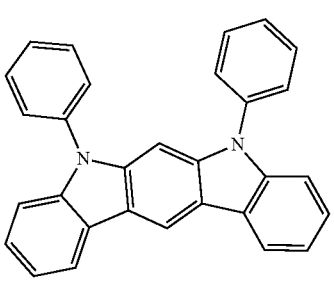
B-29
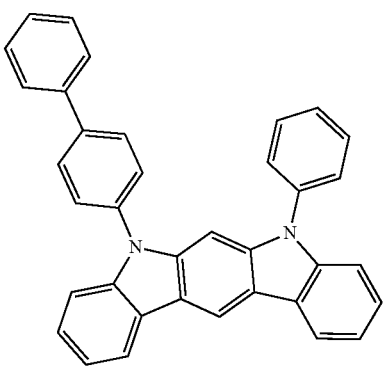
B-30
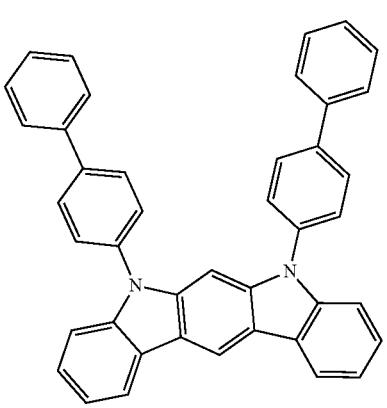

B-31
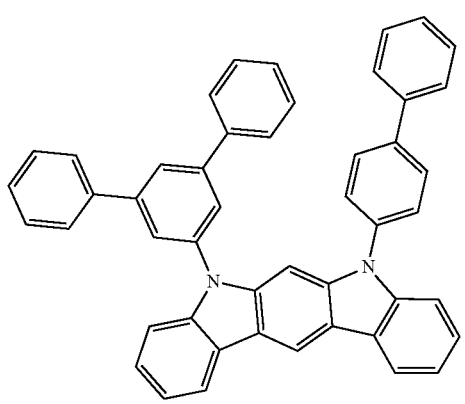
B-32
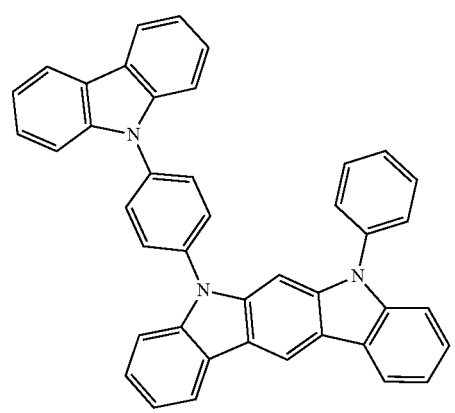
B-33
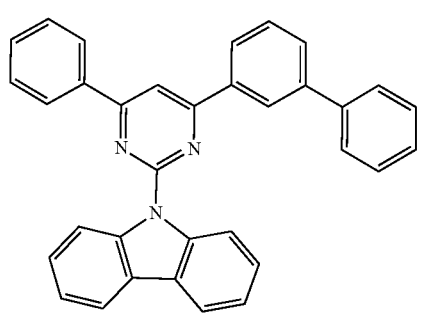
B-34
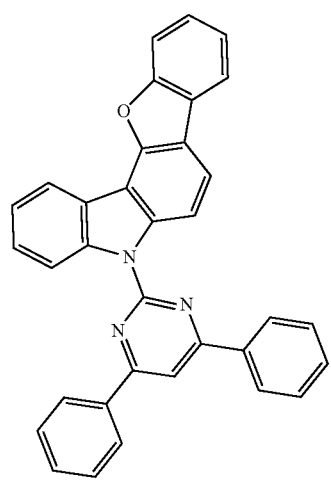
B-35
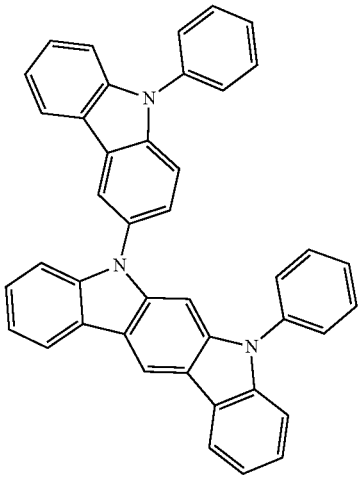
B-36
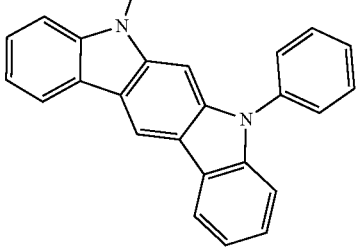
B-37
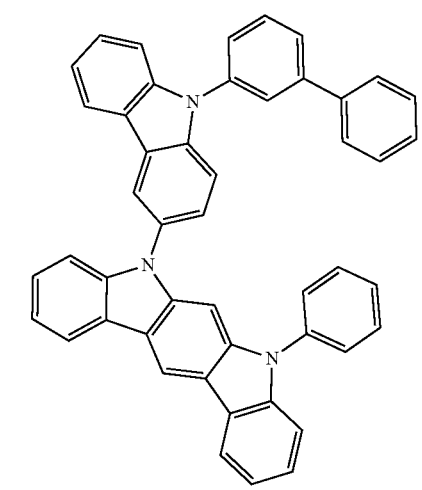

B-38
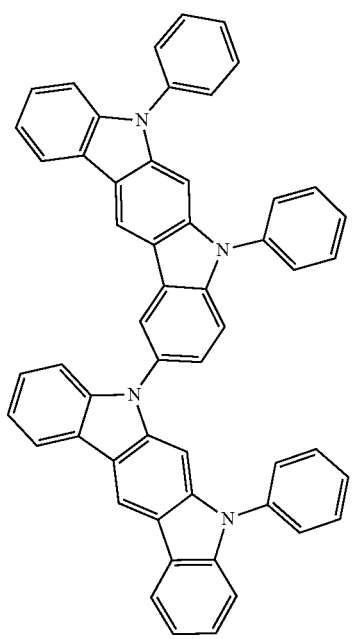
B-39
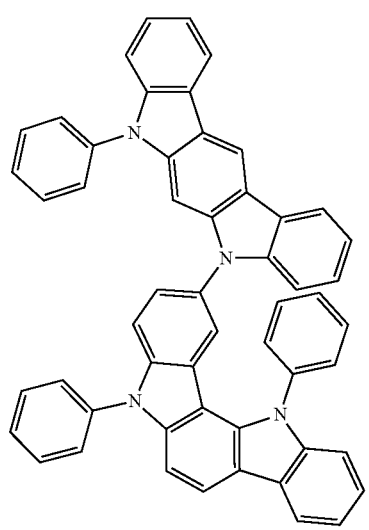
B-40
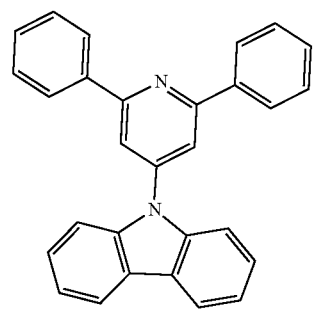
B-41
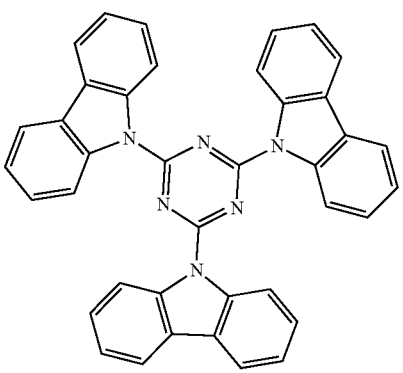
B-42
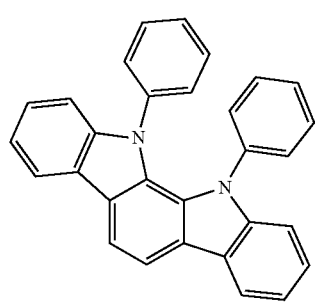
B-43
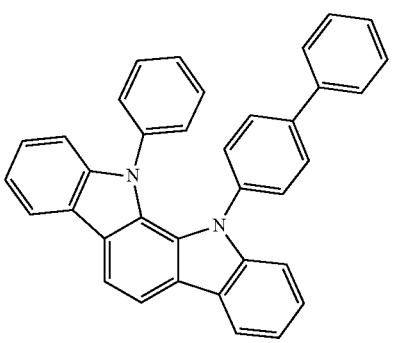
B-44
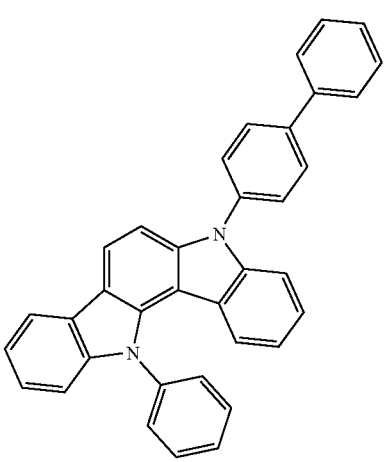

B-45
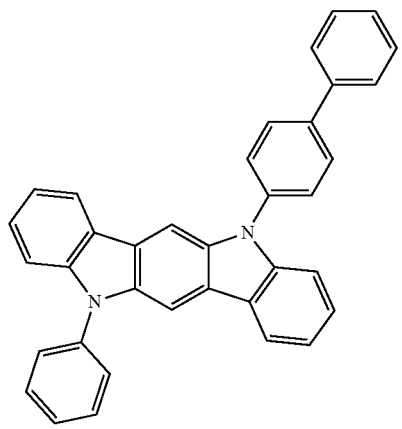
B-46
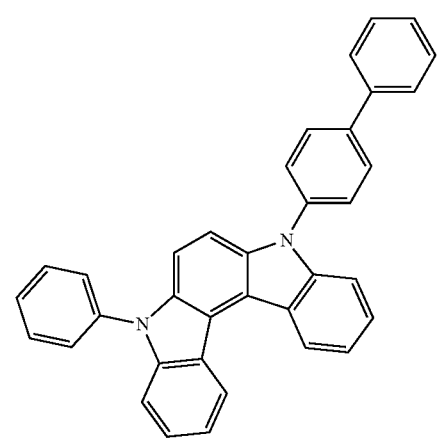
B-47
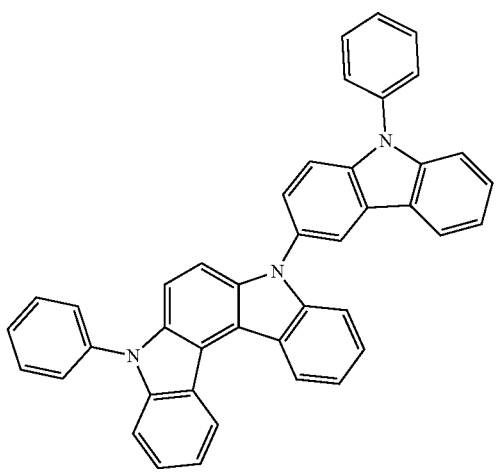
B-48
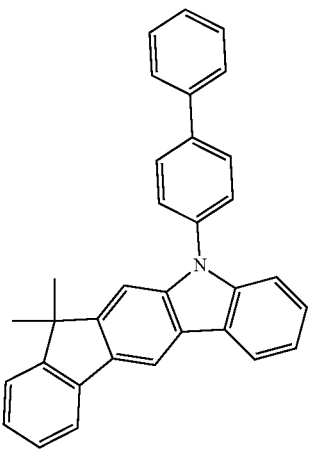
B-49
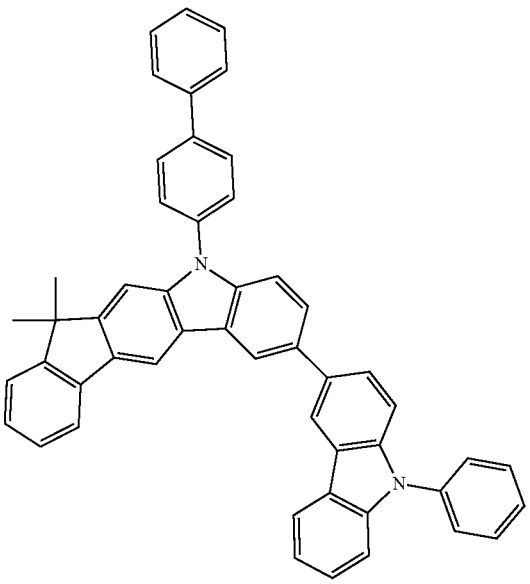
B-50
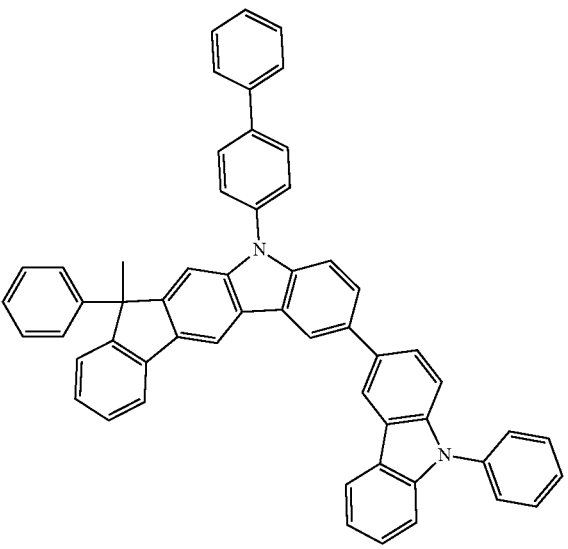

-continued
B-51
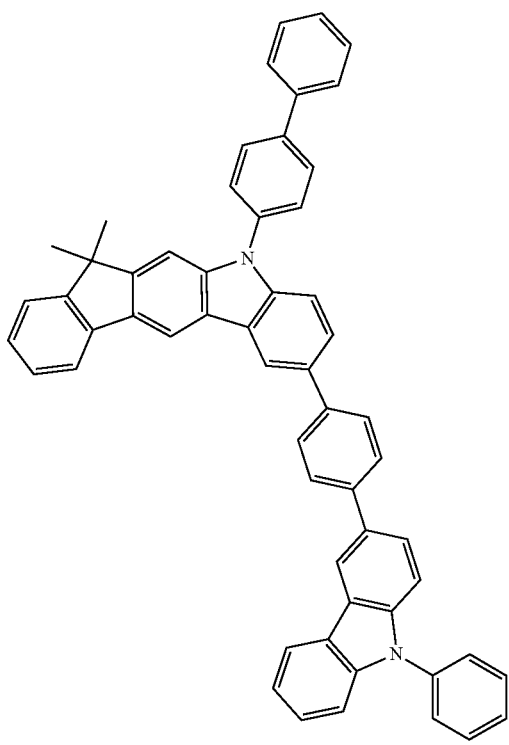
B-52
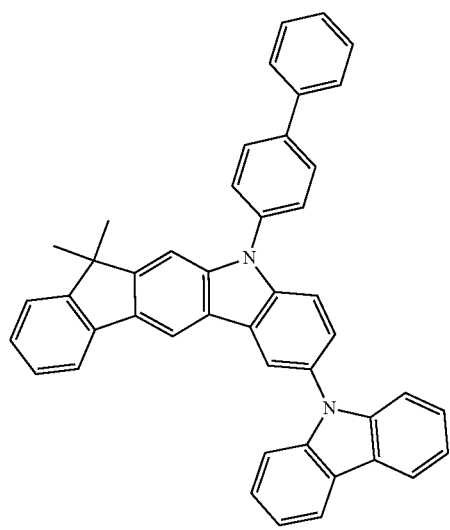
B-53
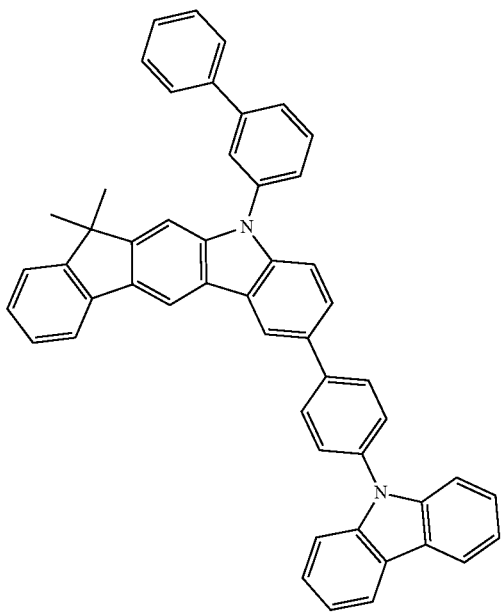
B-54
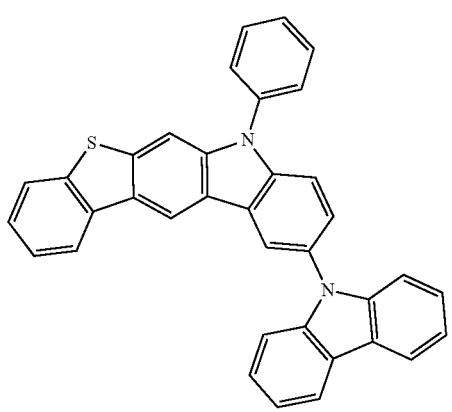
B-55
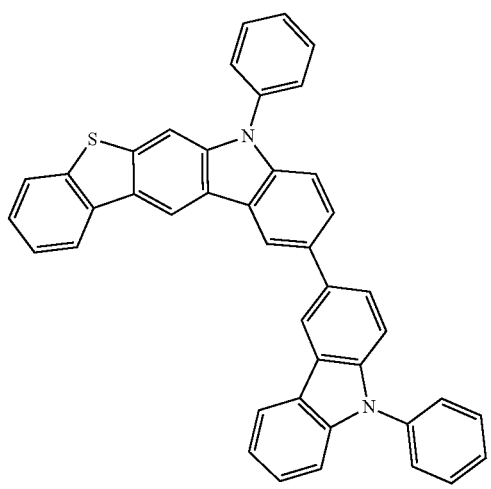

B-56
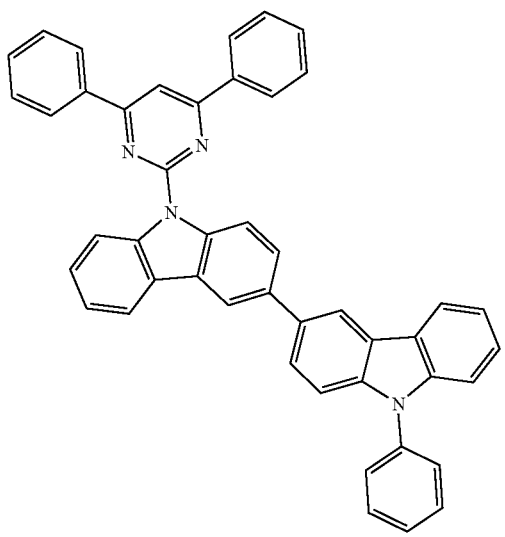
B-57
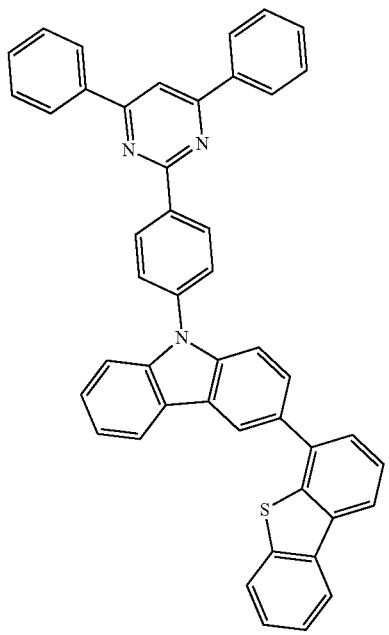
B-58
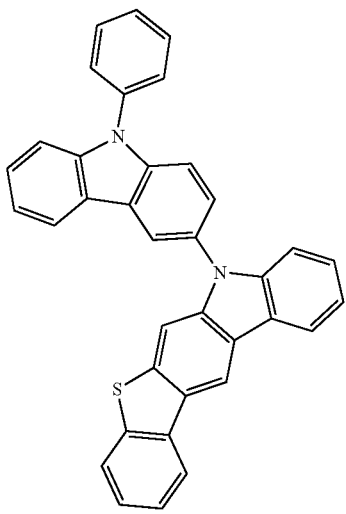
B-59
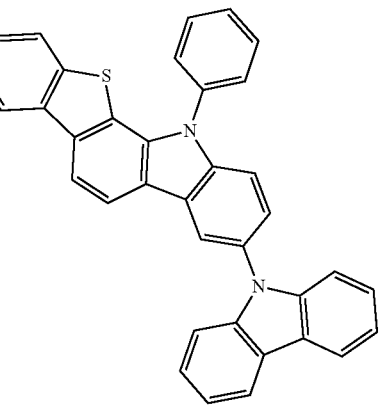
B-60
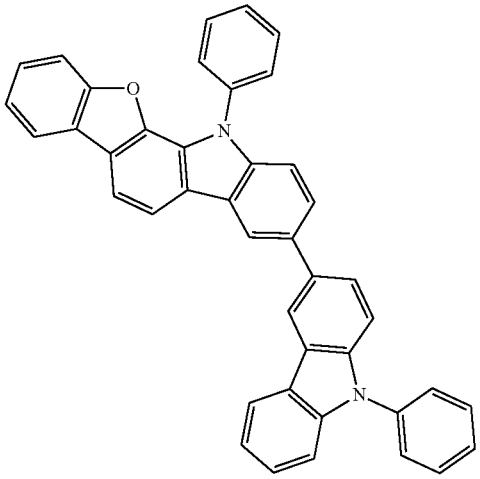

B-61
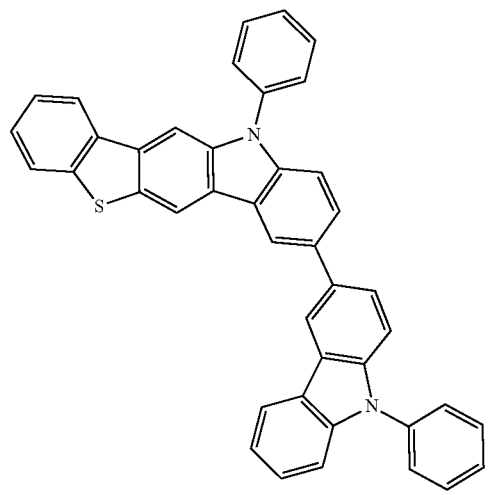
B-62
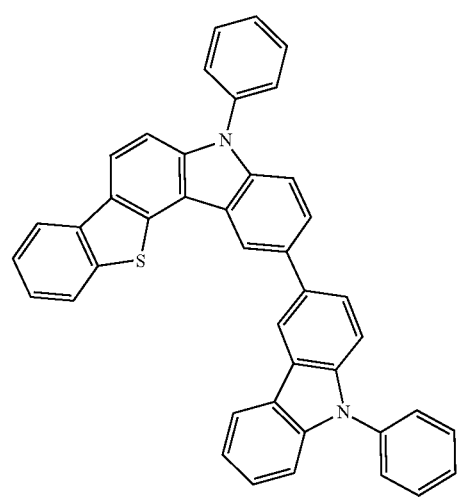
B-63
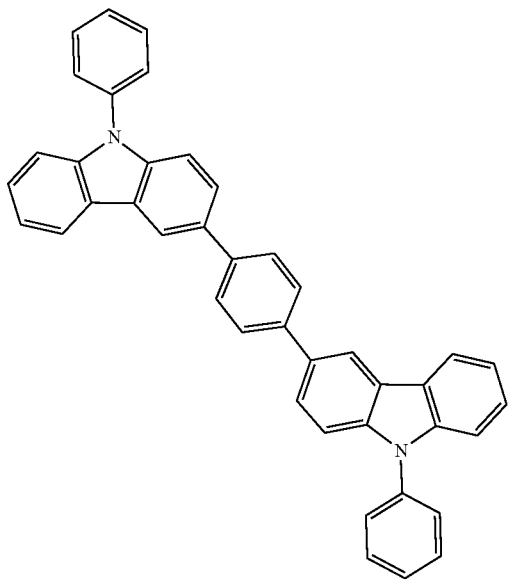
B-64
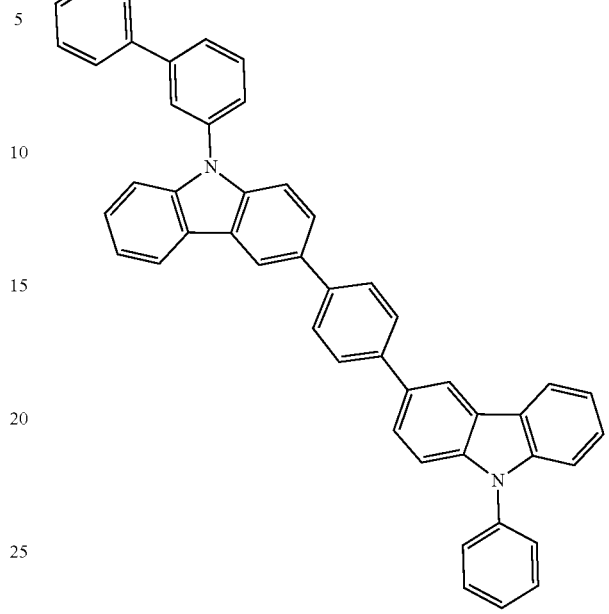
B-65
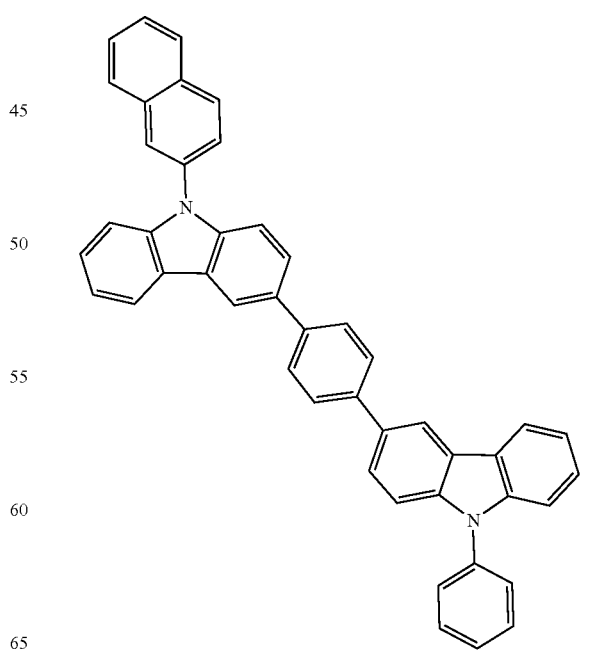

B-66
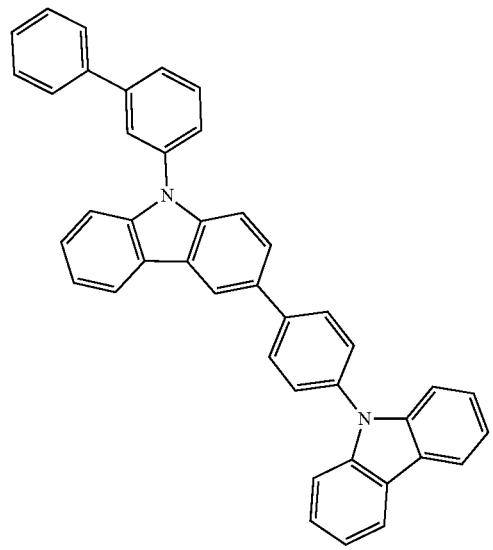
B-68
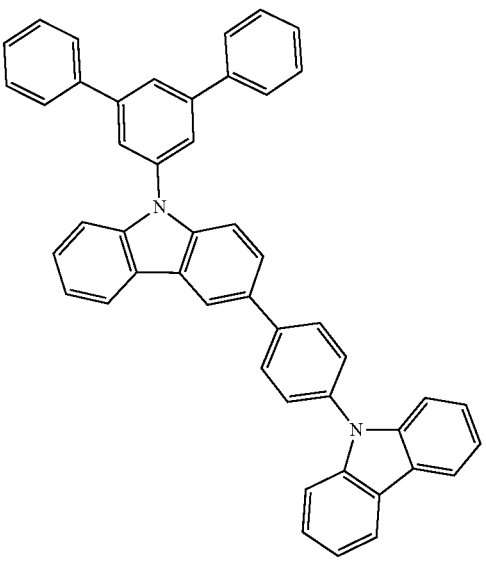
B-67
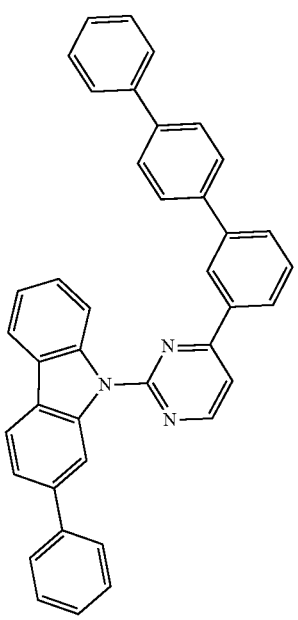
B-69

B-70
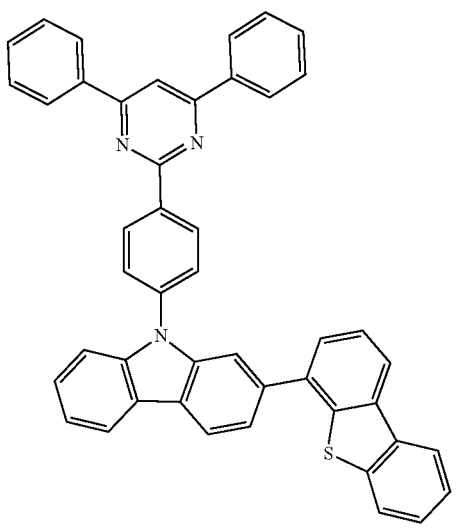
B-71
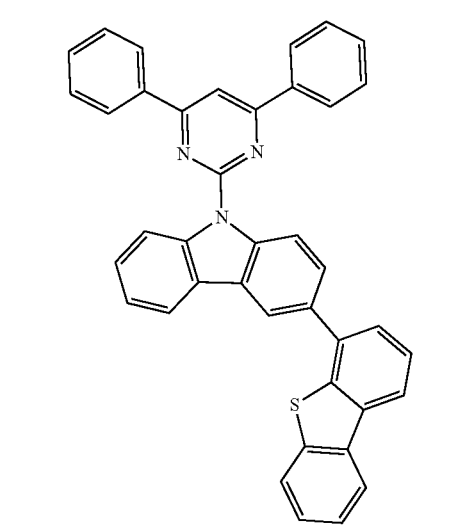
B-72
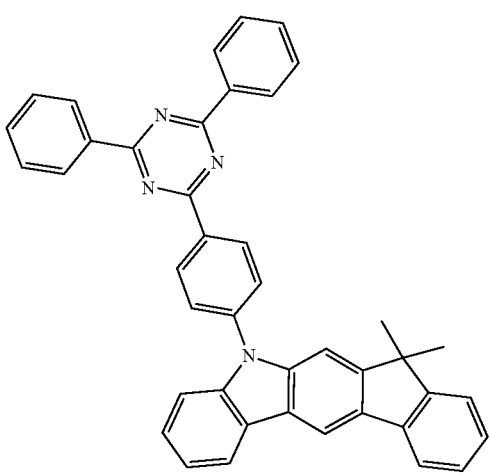
B-73
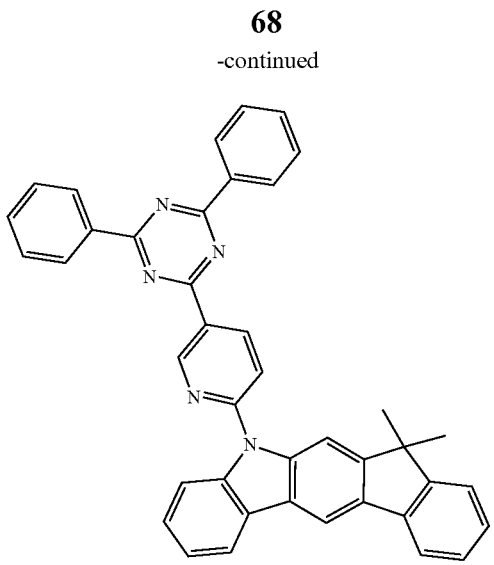
B-74
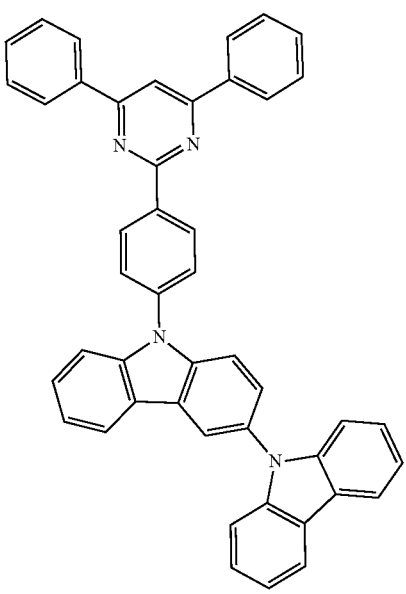
B-75
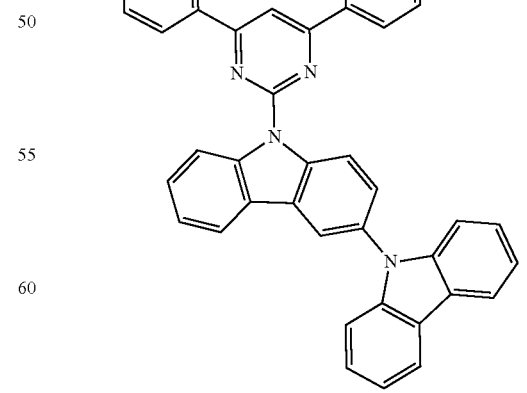

B-76
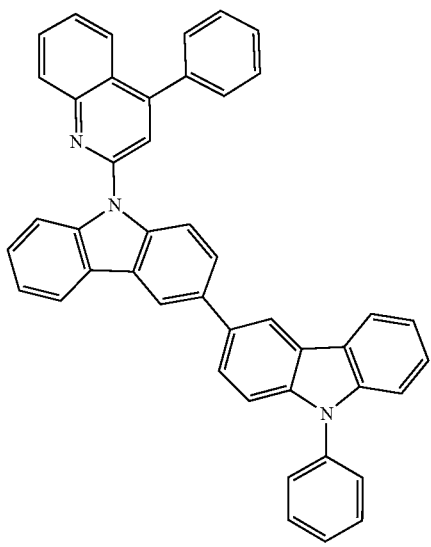
B-77
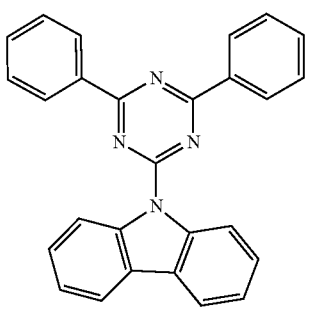
B-78
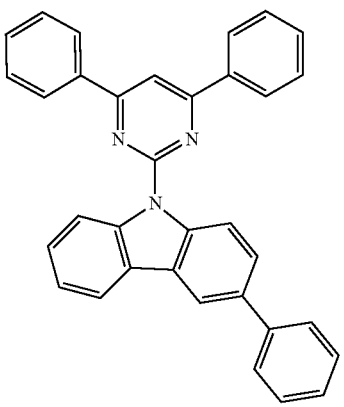
B-79
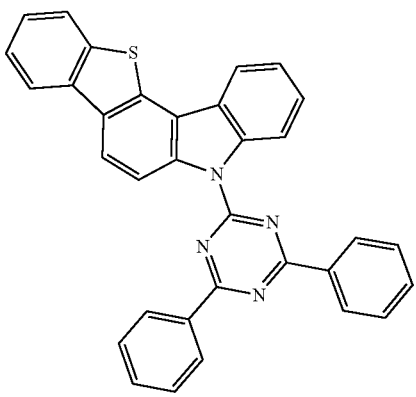
B-80
B-81
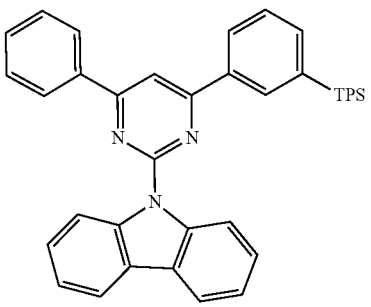
B-82

-continued
B-83
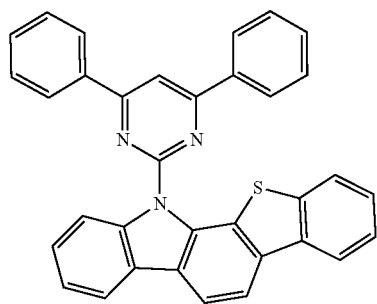
B-84
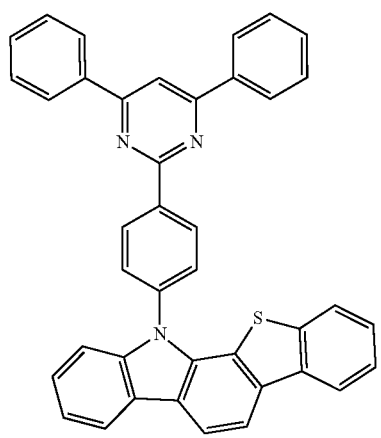
B-85
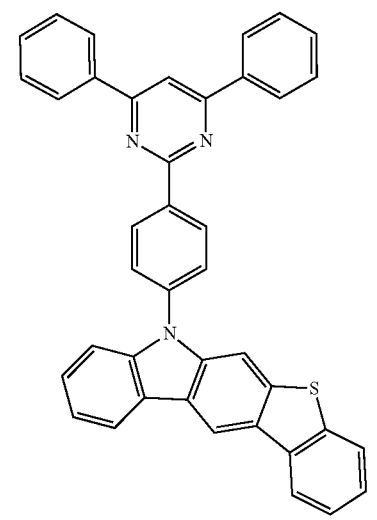
-continued
B-86
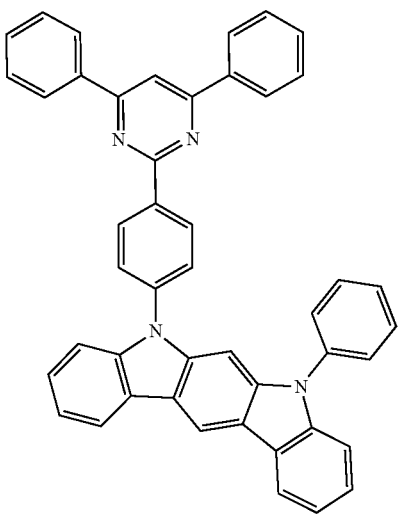
B-87
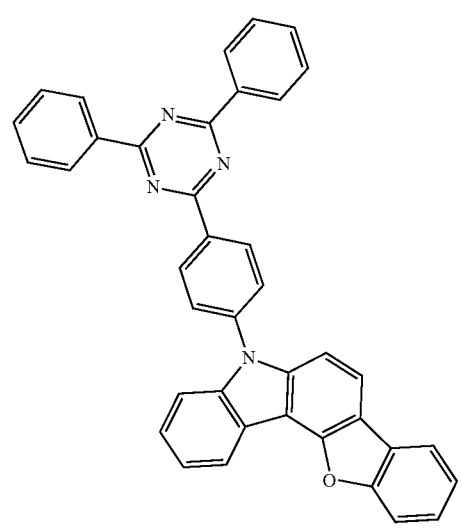
B-88
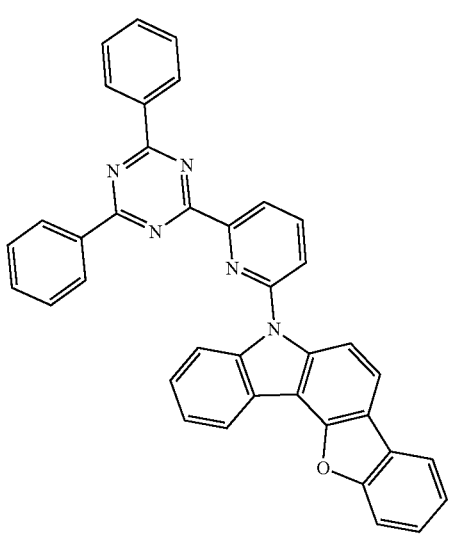

B-89
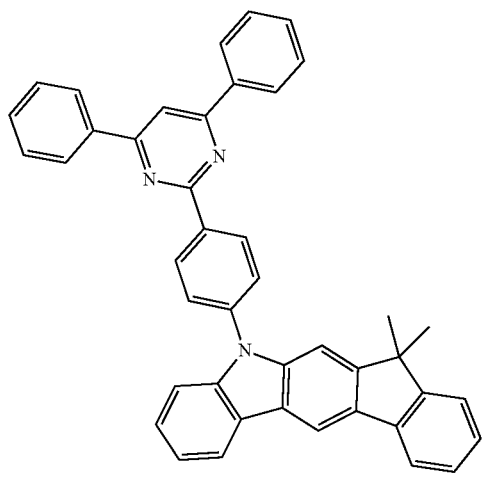
B-90
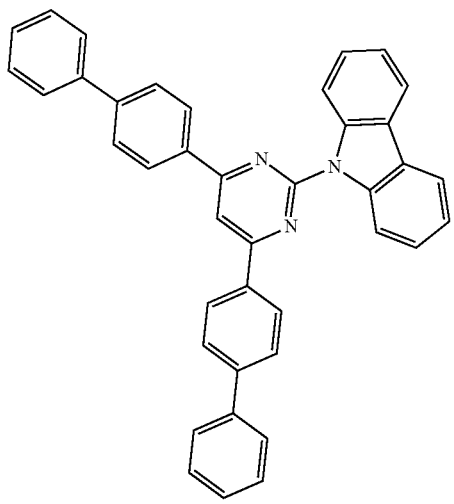
B-91
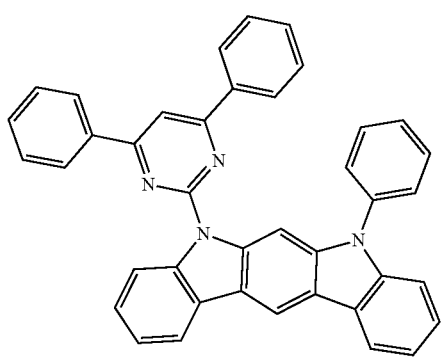
B-92
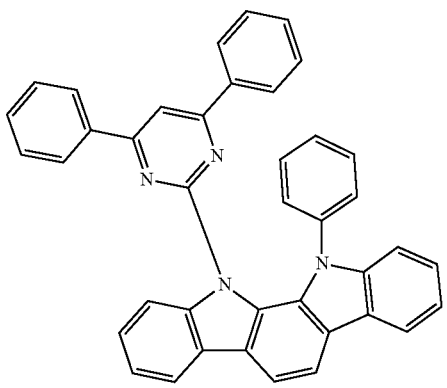
B-93
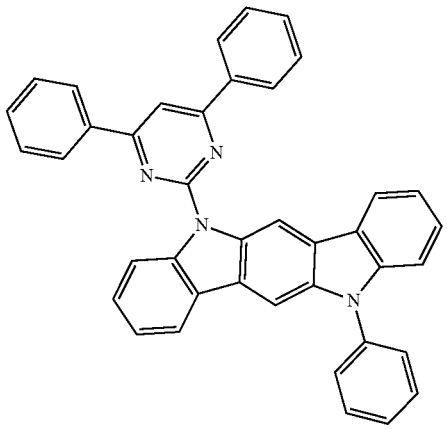
B-94
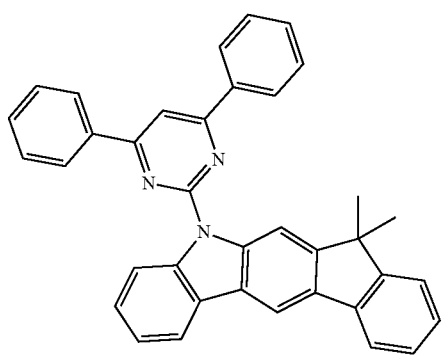

B-95
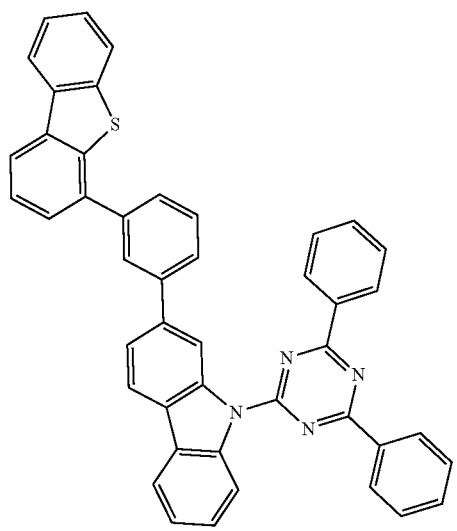
B-98
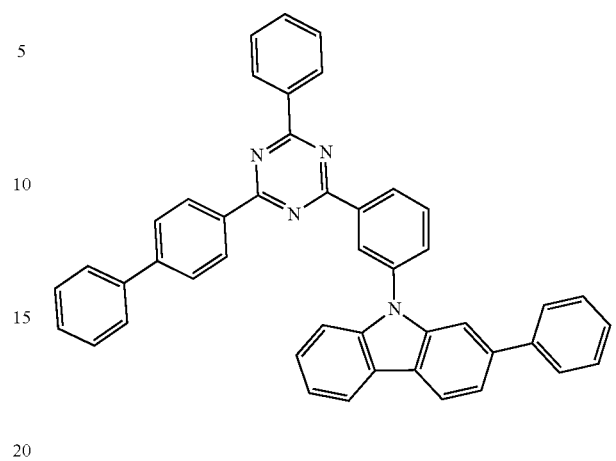
B-96
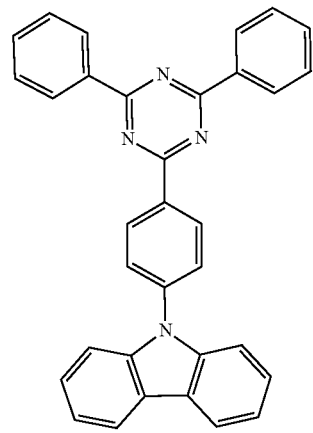
B-99
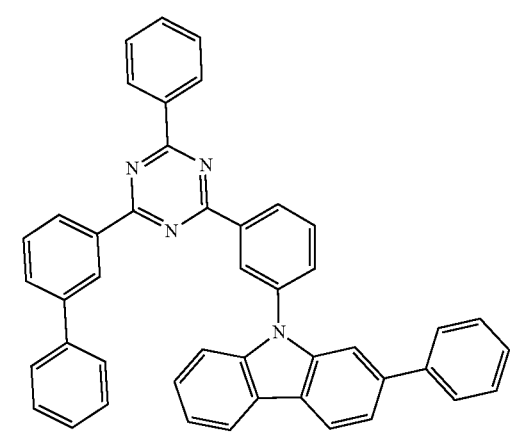
B-97
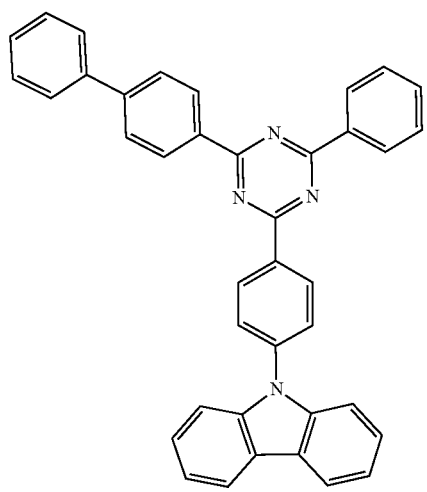
B-100
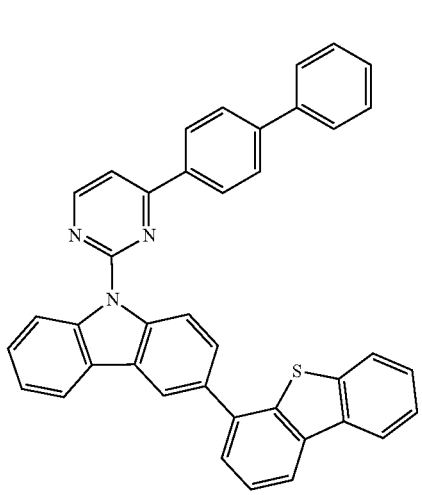

B-101
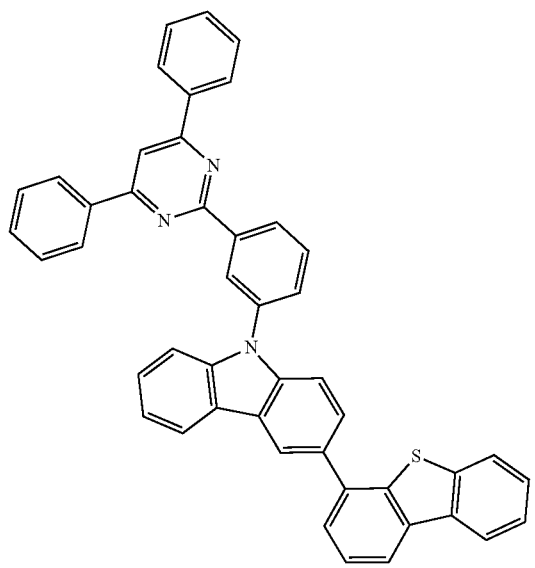
B-102
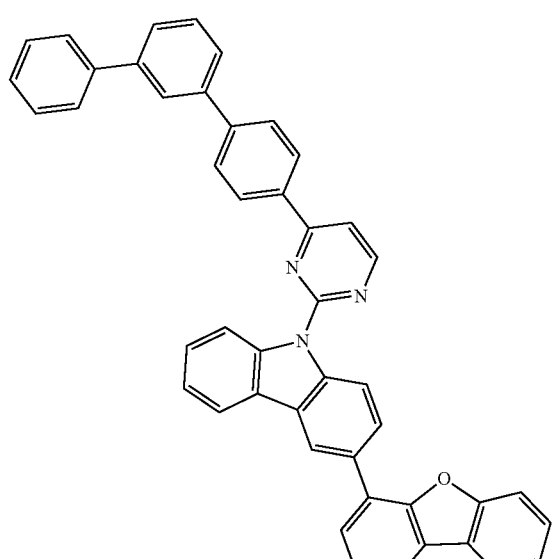
B-103
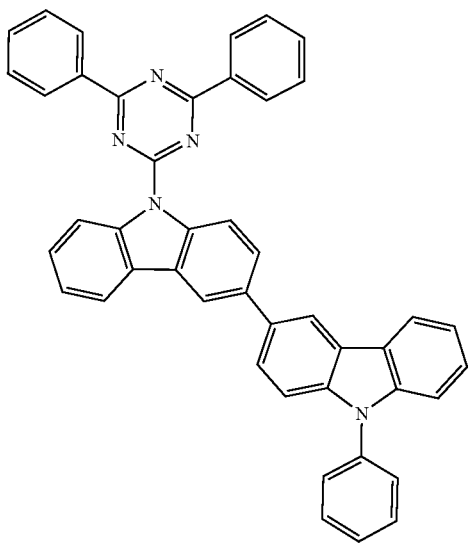
B-104
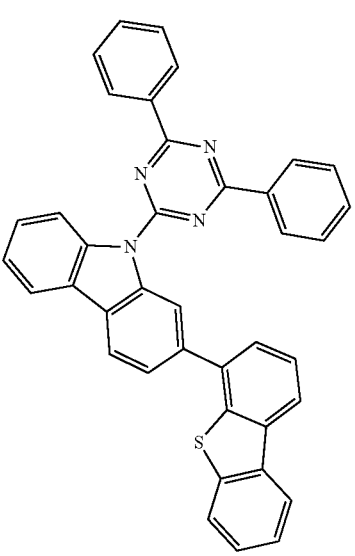
B-105
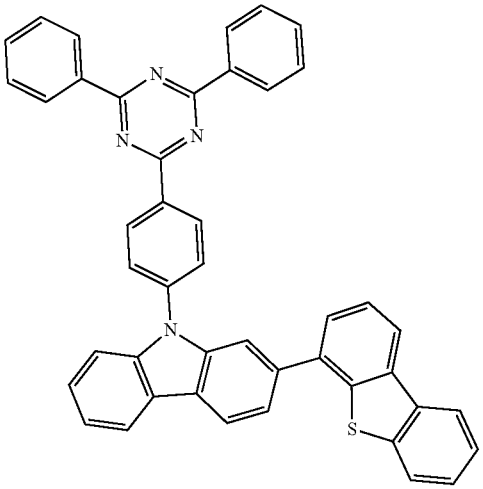

B-106
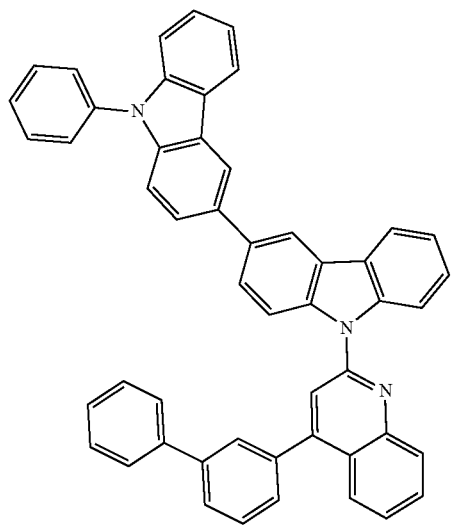
B-107
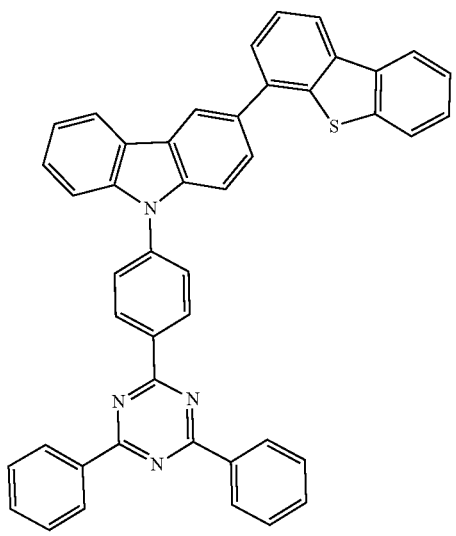
B-108
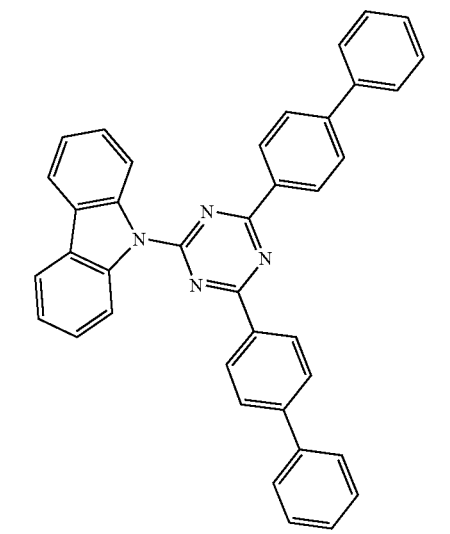
B-109
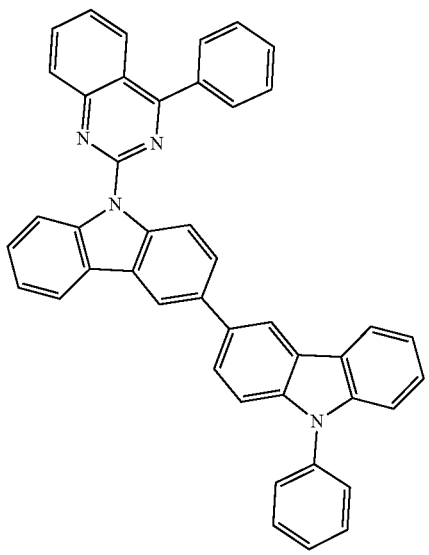
B-110
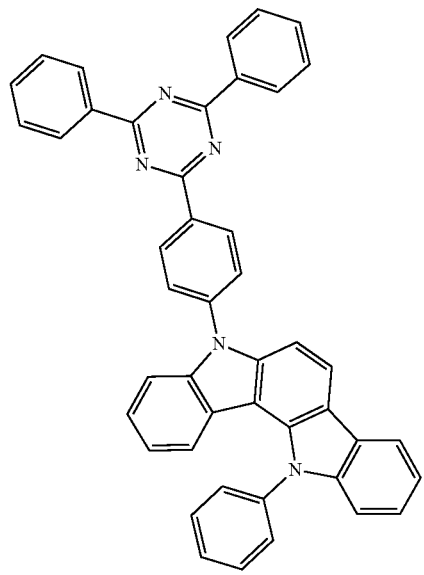
B-111
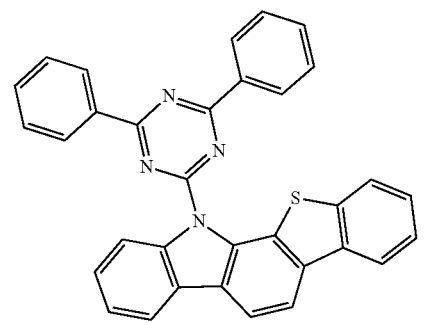

B-112
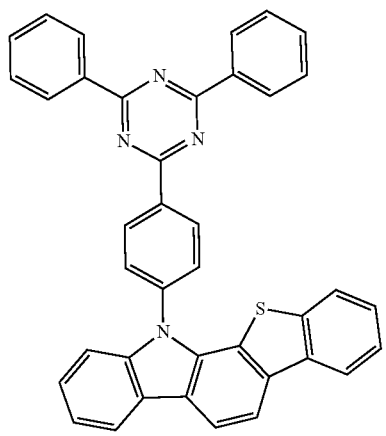
B-115
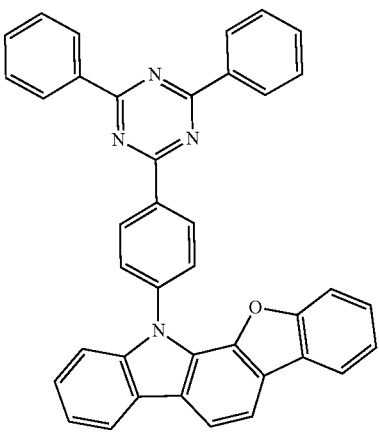
B-113
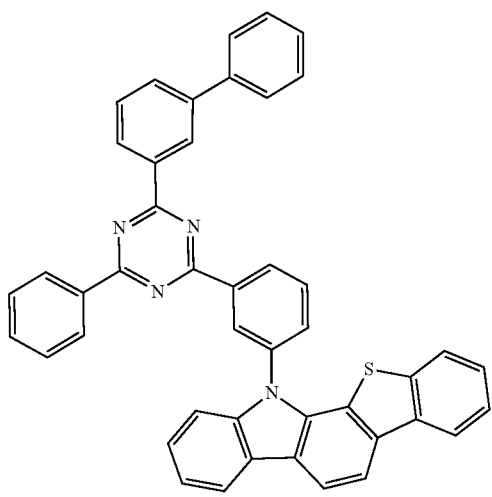
B-116
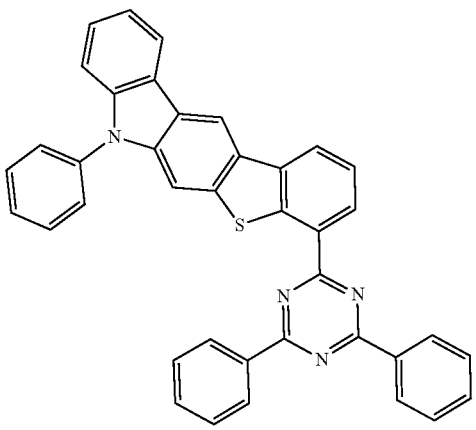
B-114
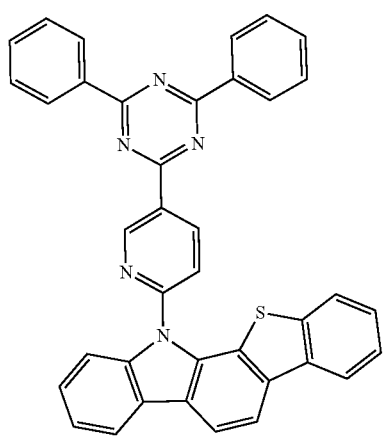
B-117
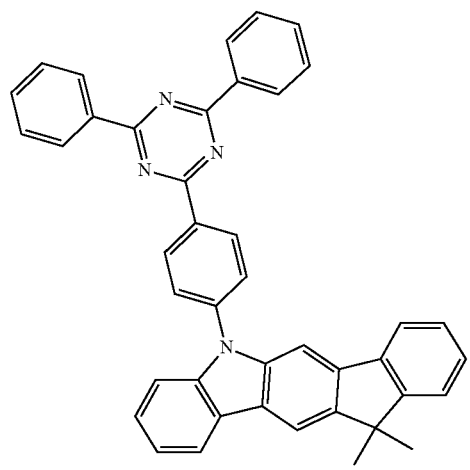

B-118
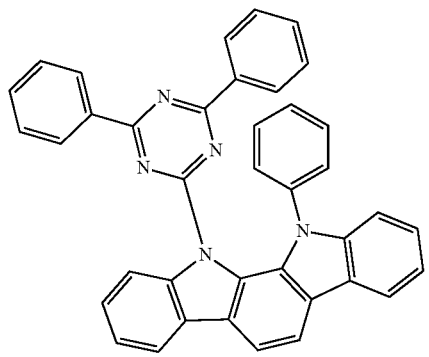
B-119
B-120
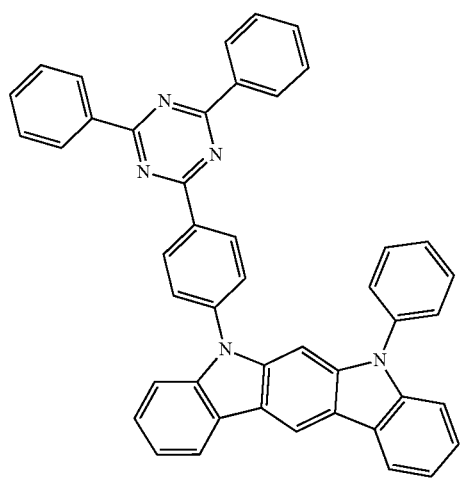
B-121
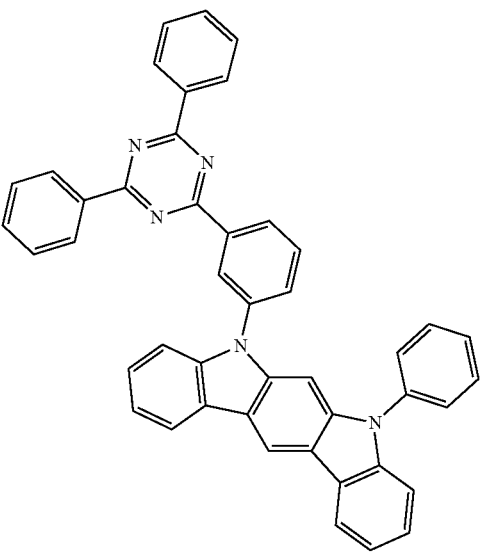
B-122
B-123
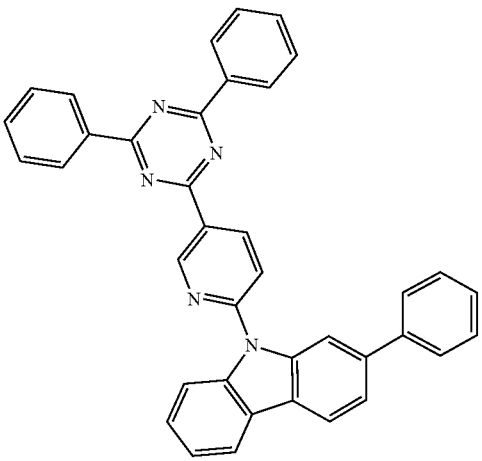

B-124
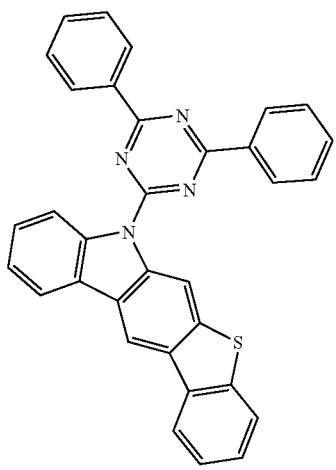
B-125
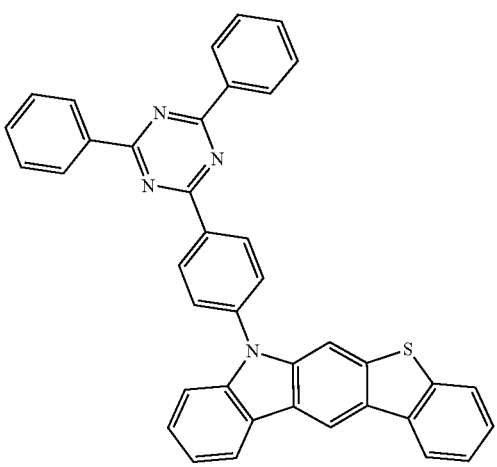
B-126
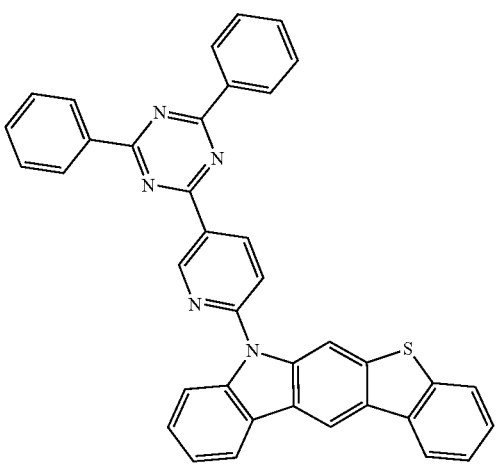
B-127
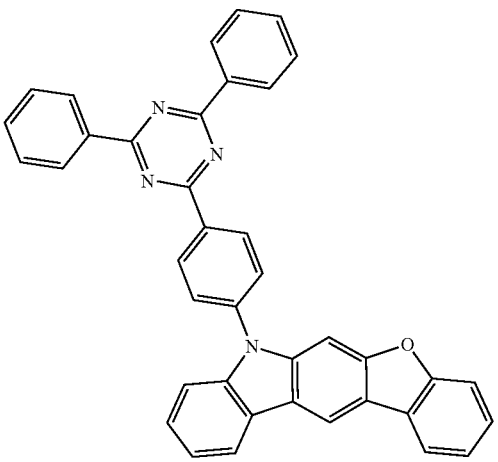
B-128
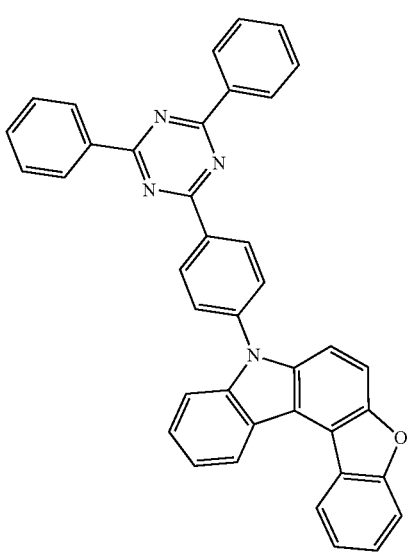
B-129
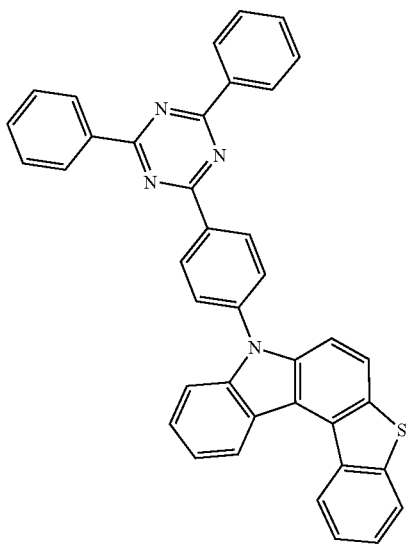

B-130
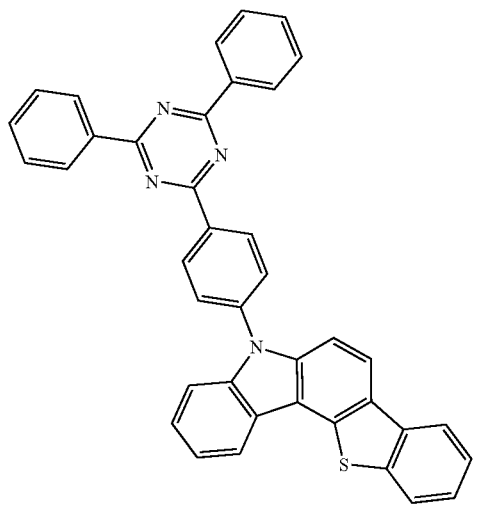
B-131
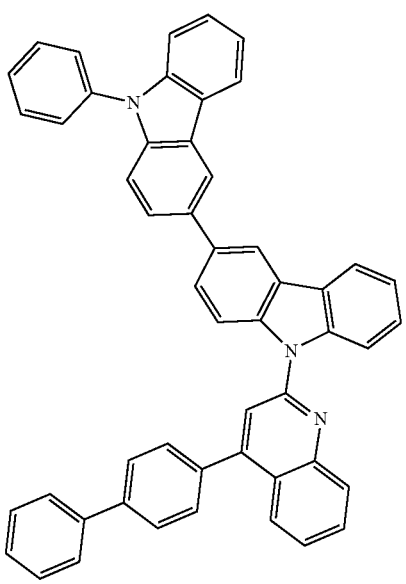
B-132
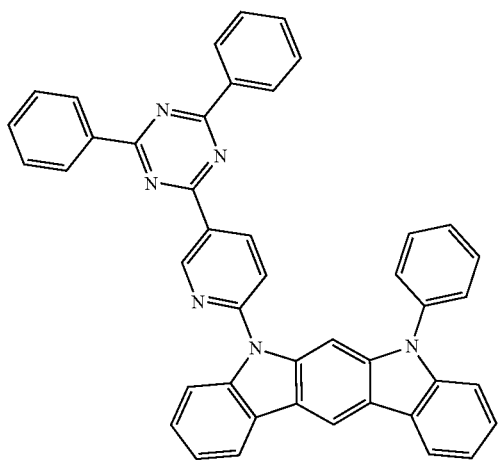
B-133
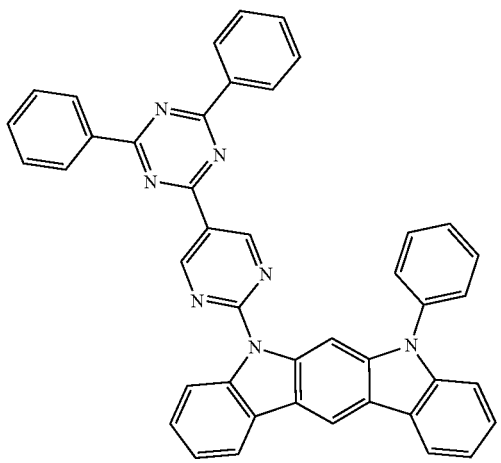
B-134
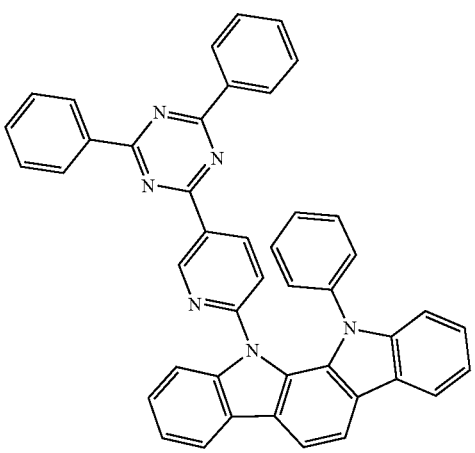
B-135
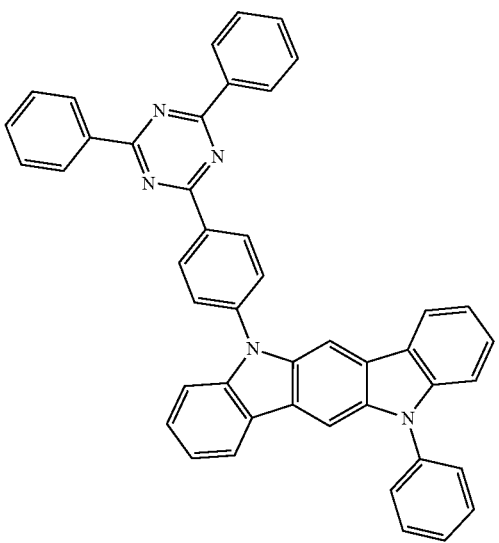

B-136
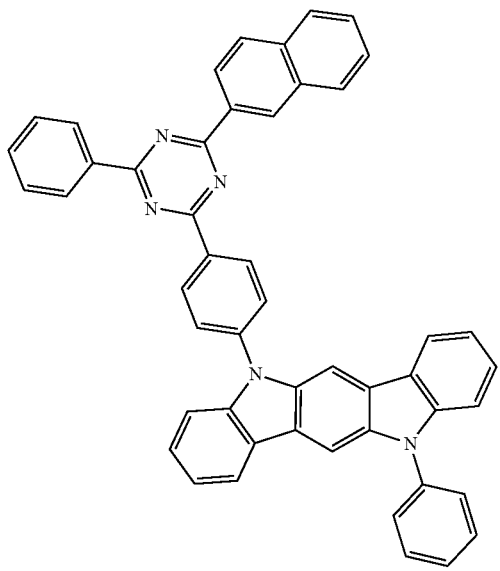
B-137
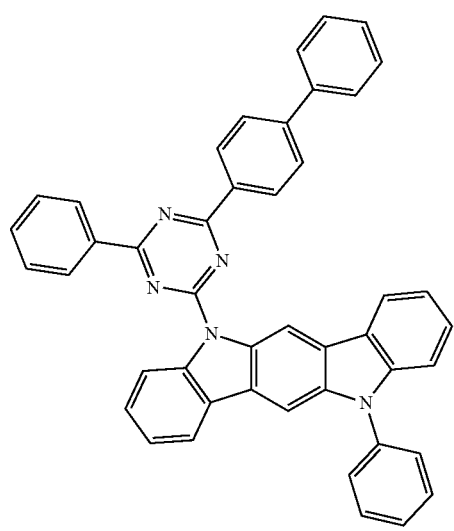
B-138
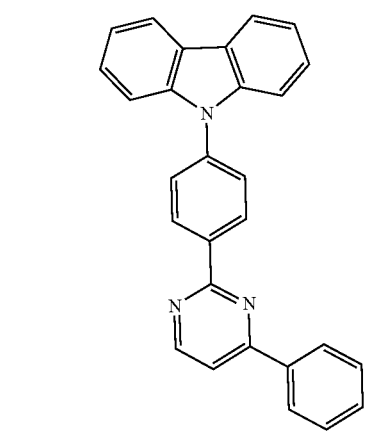
B-139
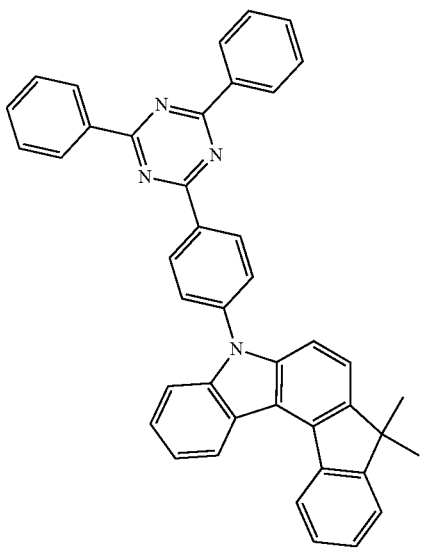
B-140
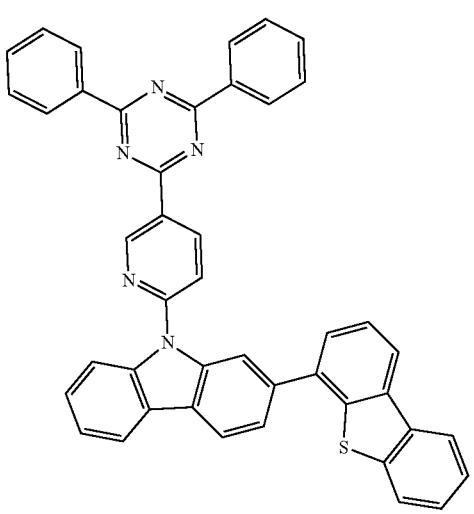
B-141
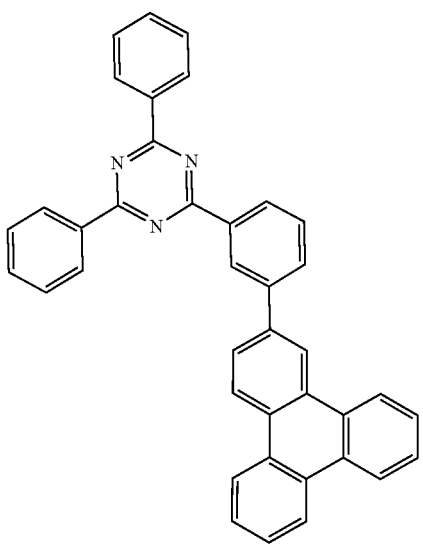

B-142
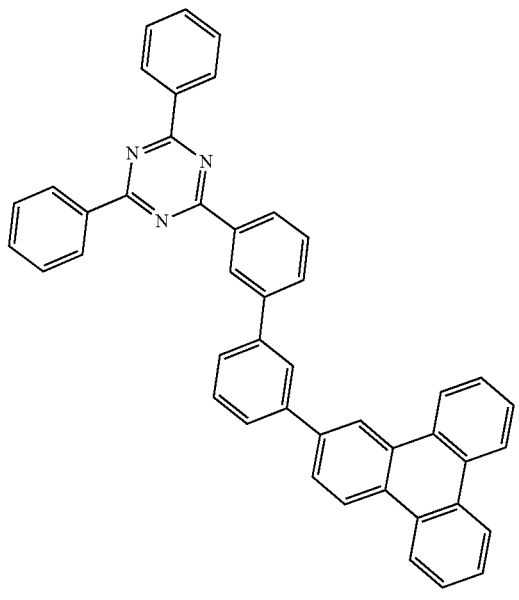
B-143
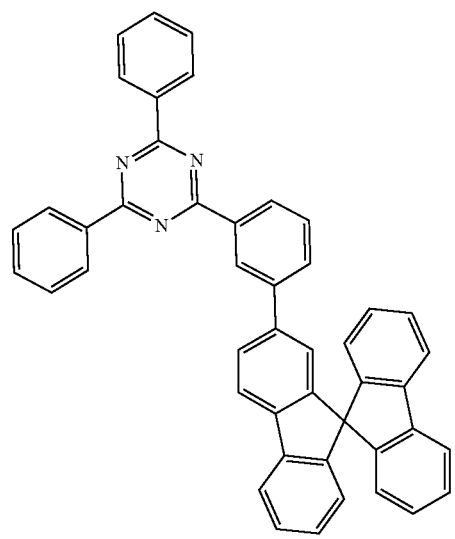
B-144
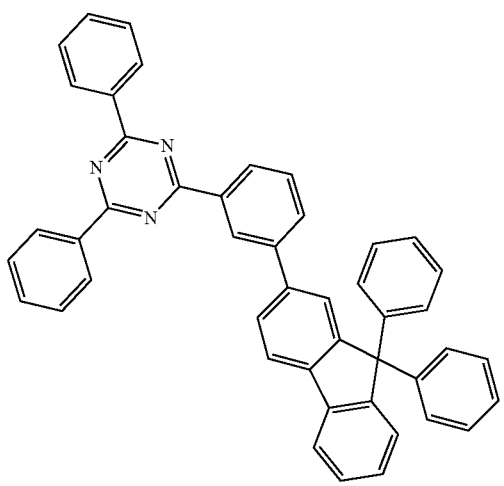
B-145
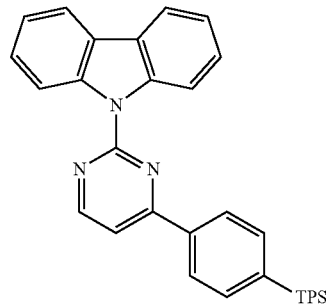
B-146
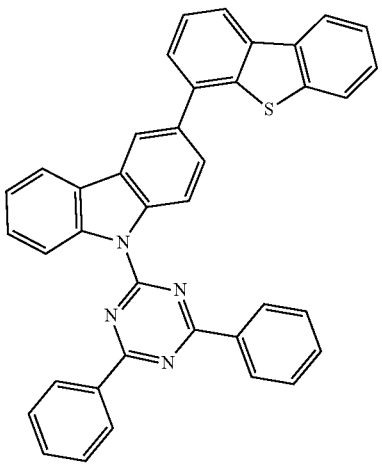
B-147
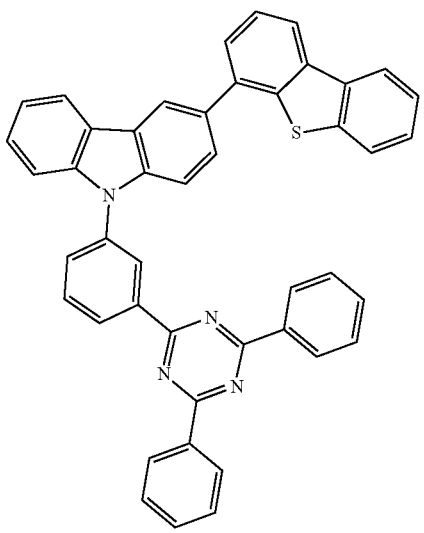

B-148
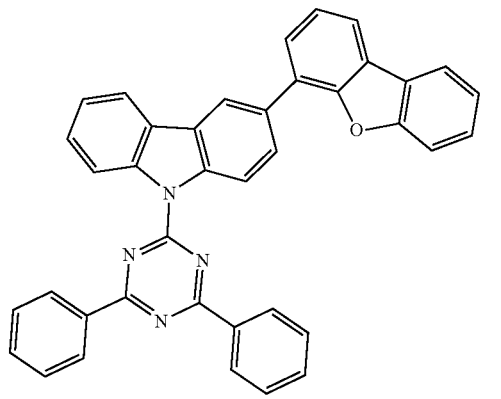
B-151
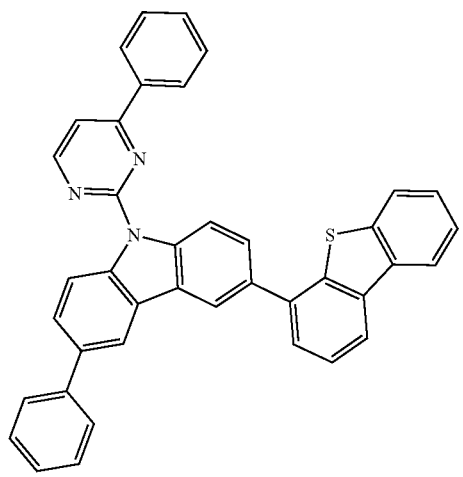
B-149
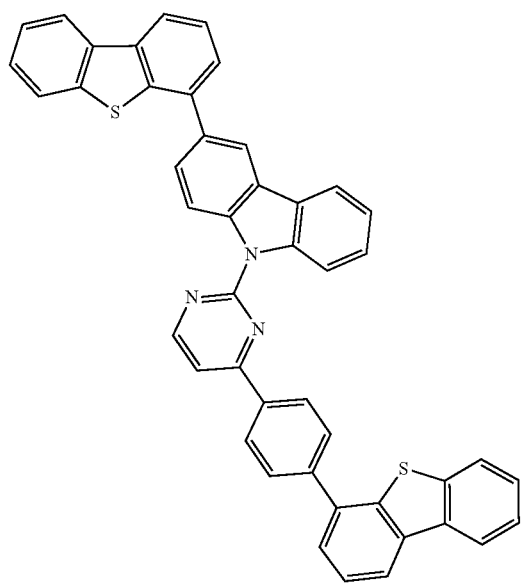
B-152
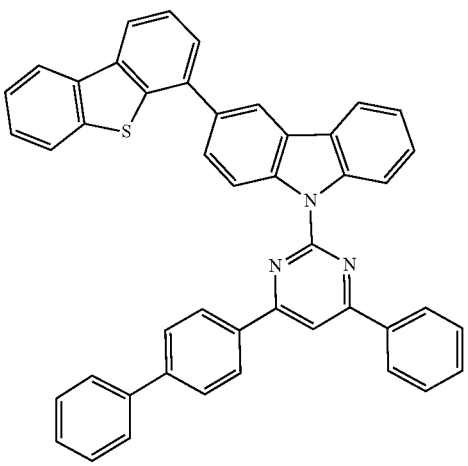
B-150
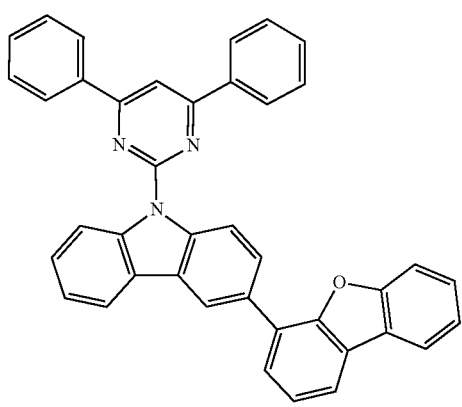
B-153

B-154
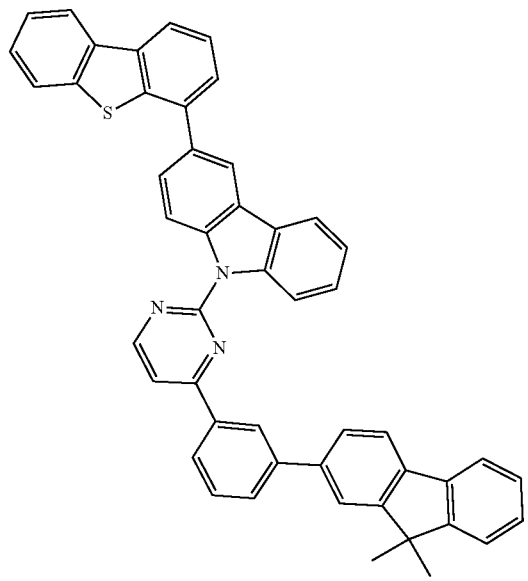
B-155
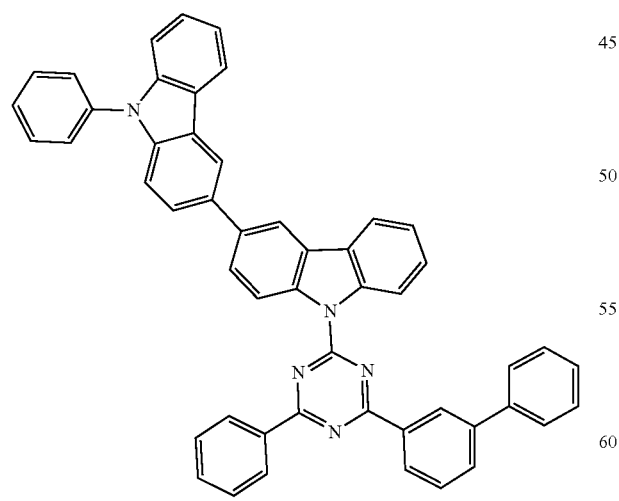
B-156
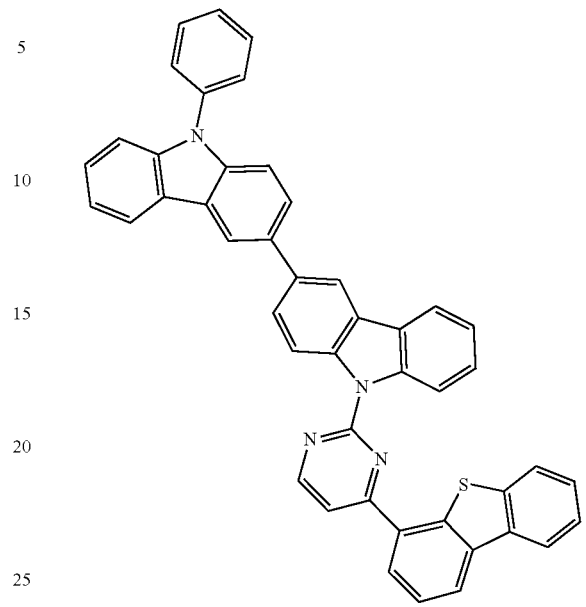
B-157
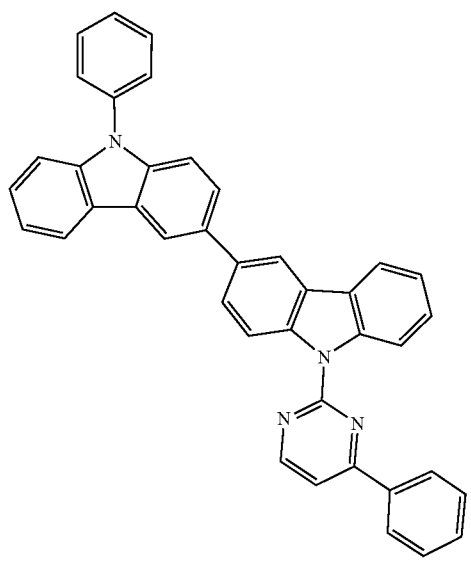

B-158
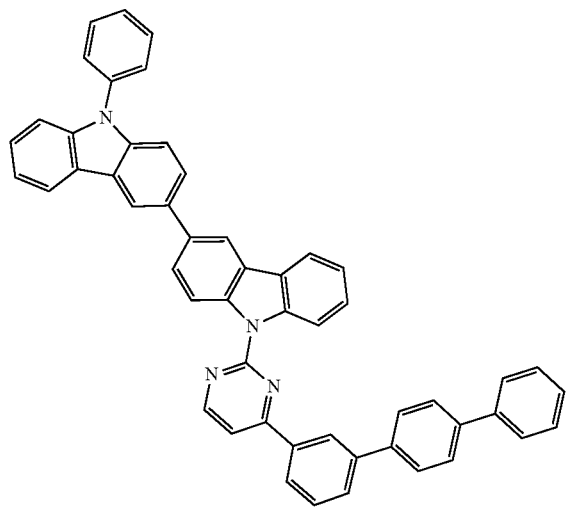
B-159
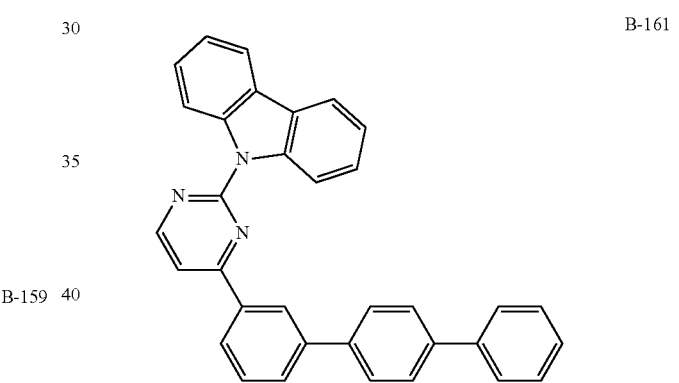
B-160
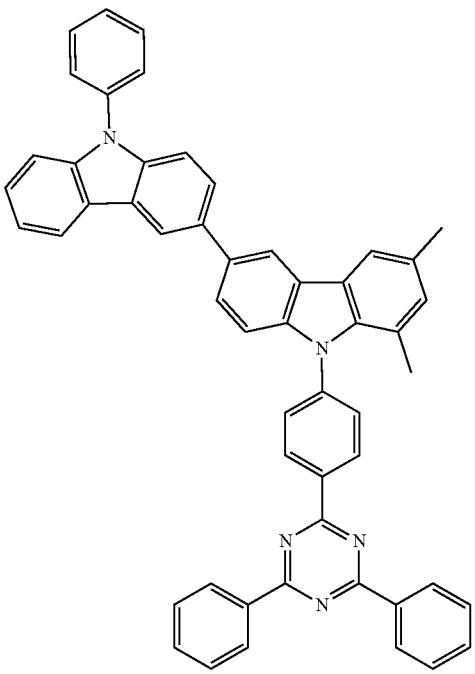
B-161
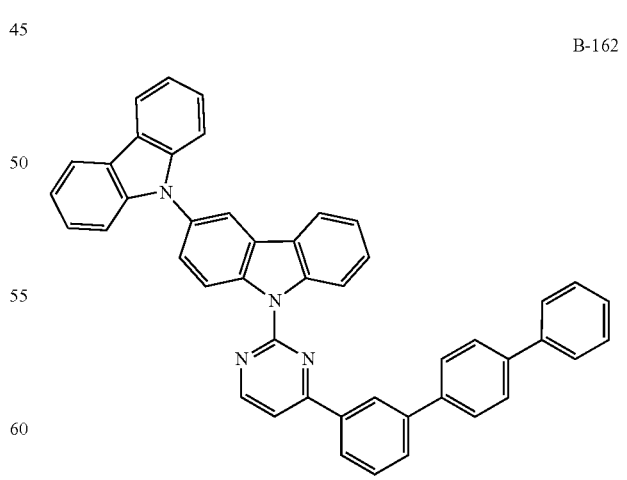
B-162

B-163
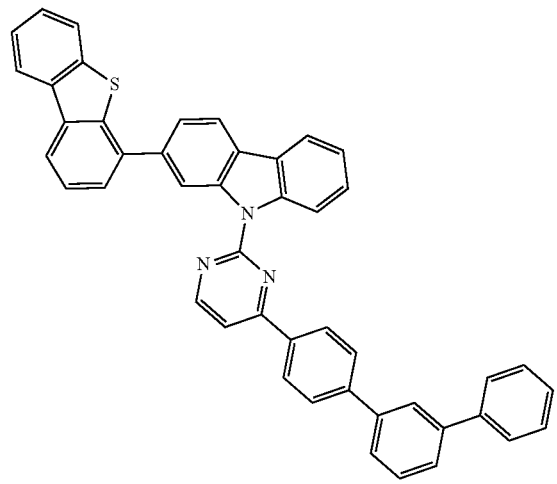
B-164
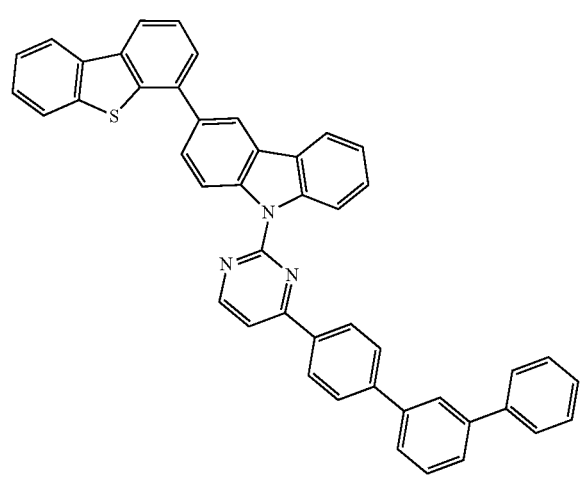
B-165
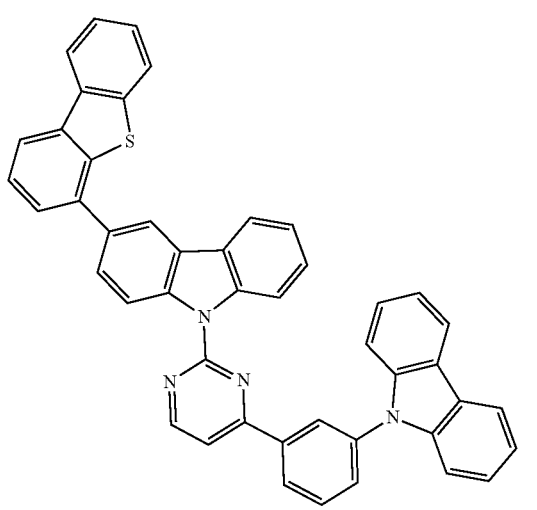
B-166
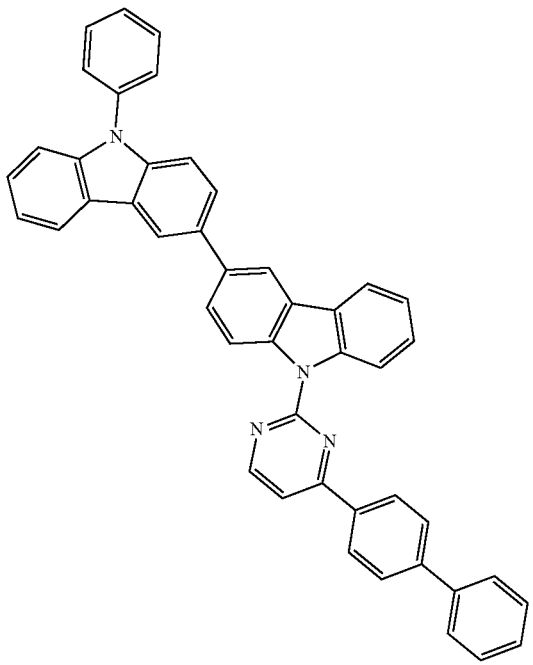
B-167
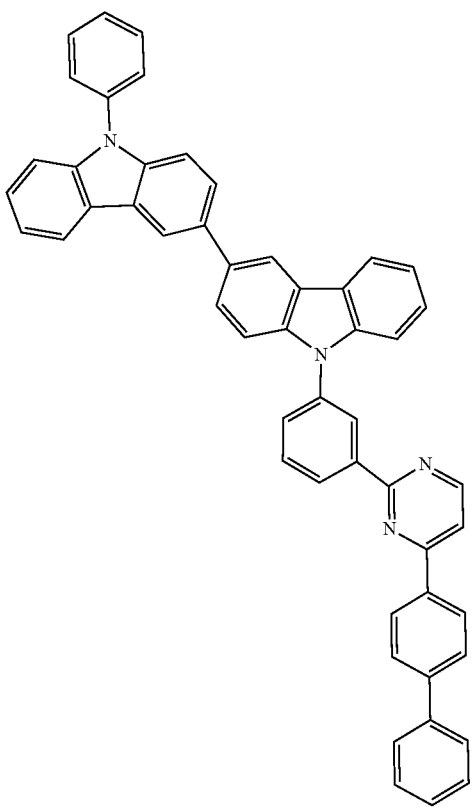

B-168
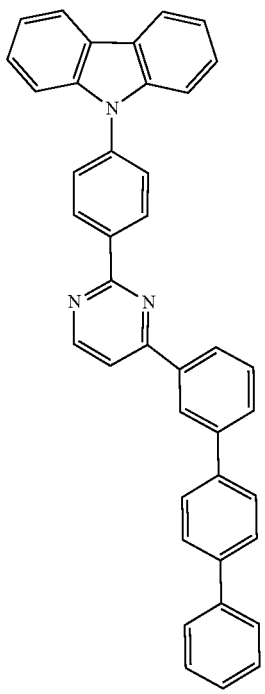
B-169
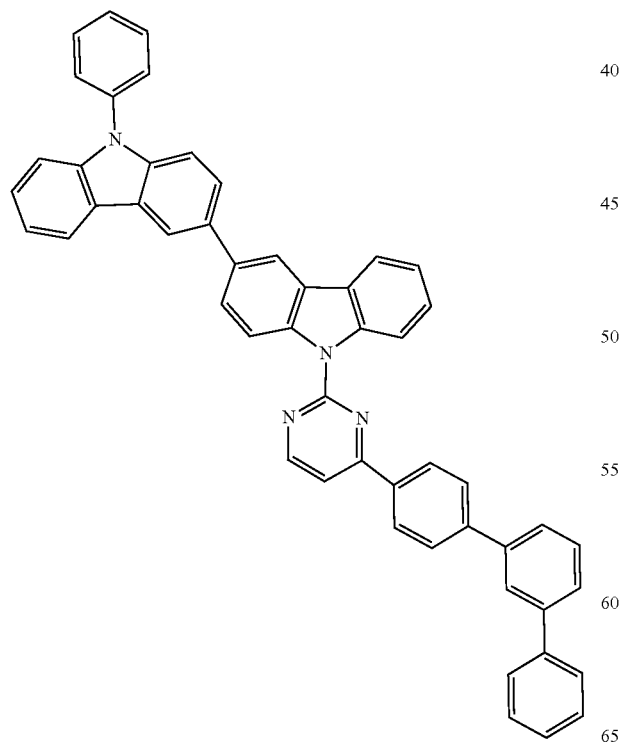
B-170
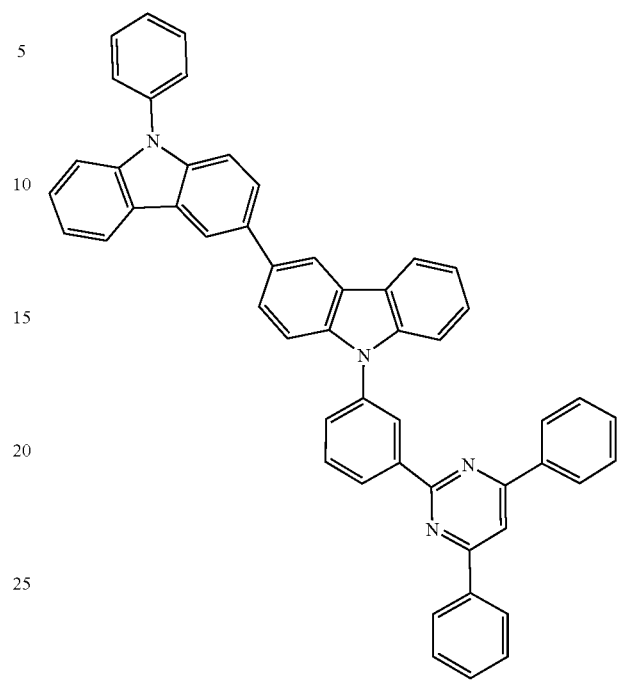
B-171
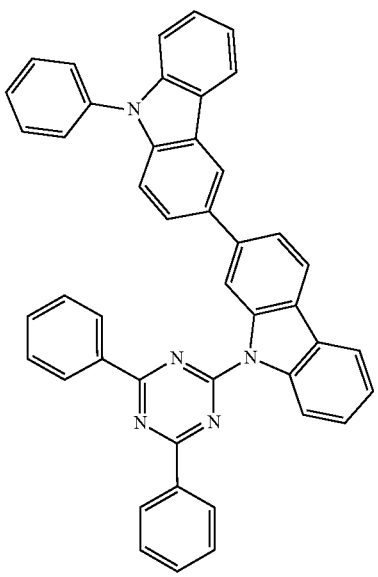

B-172
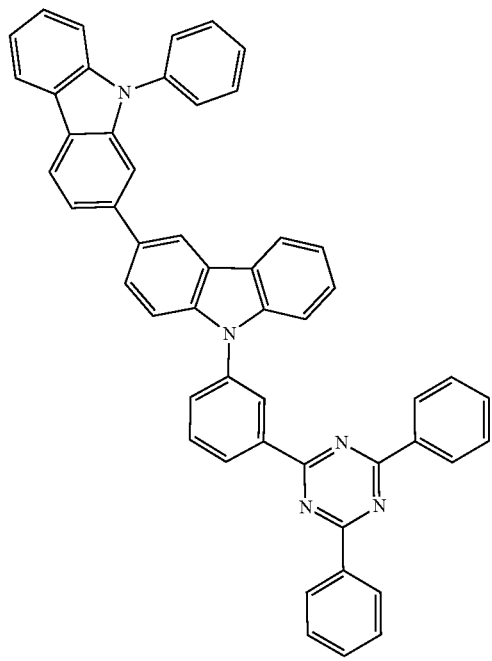
B-174
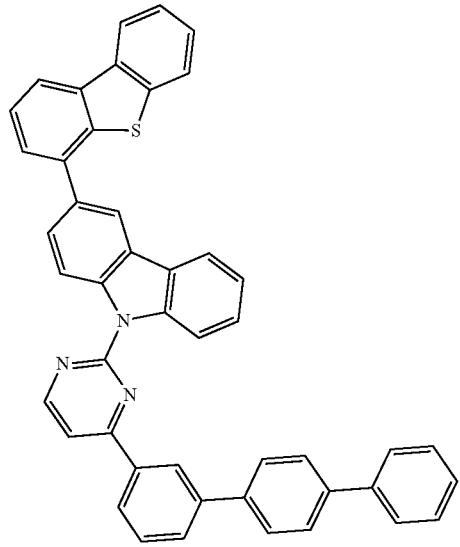
B-173
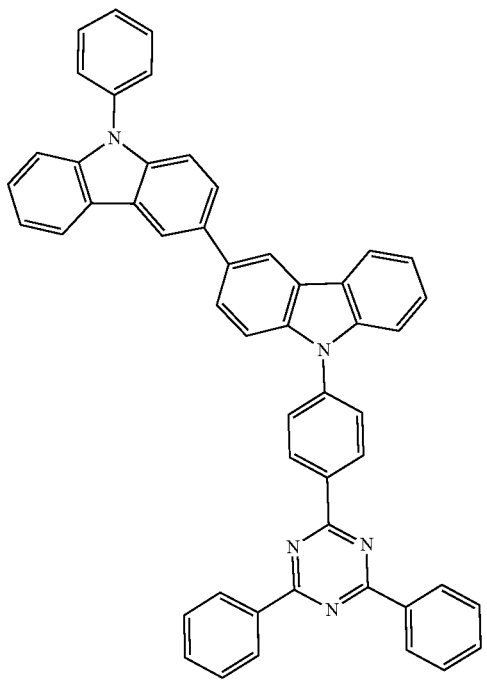
B-175
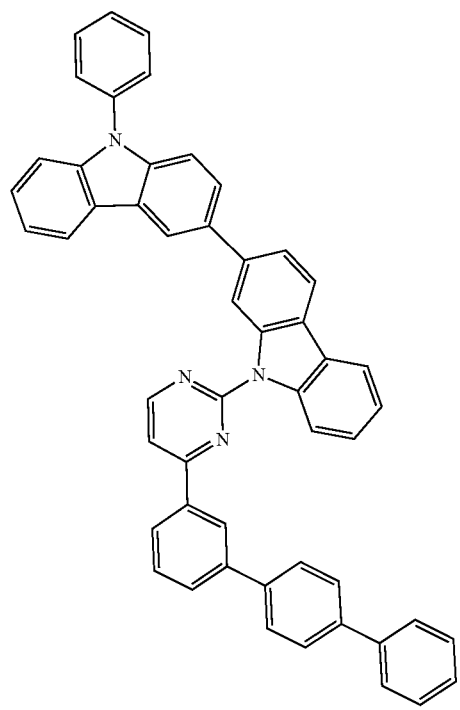

B-176
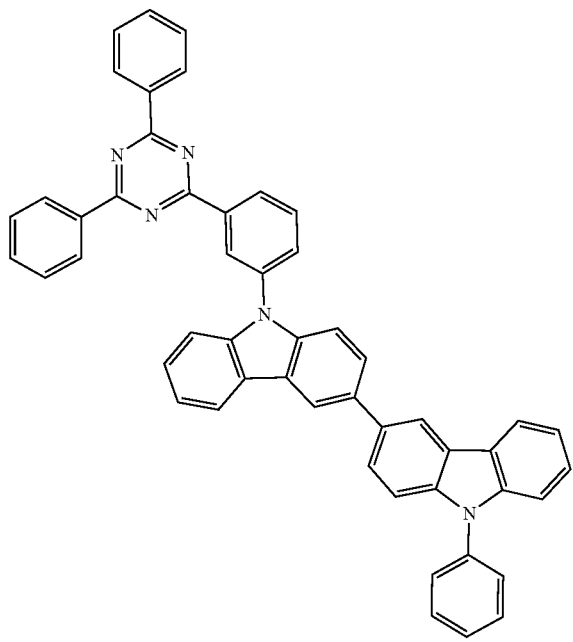
B-177
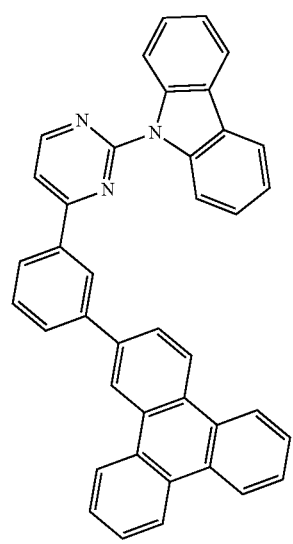
B-178
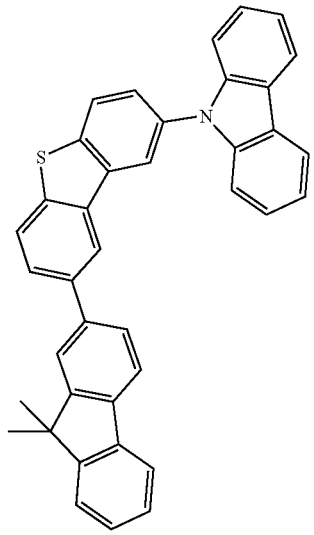
B-179
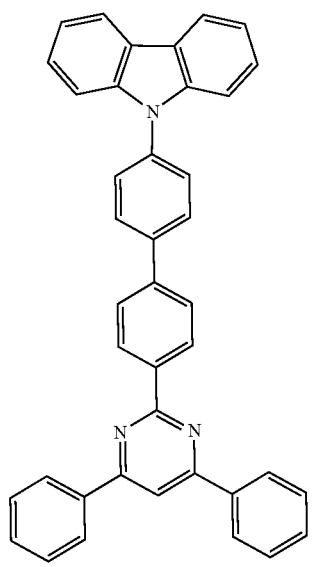

B-180
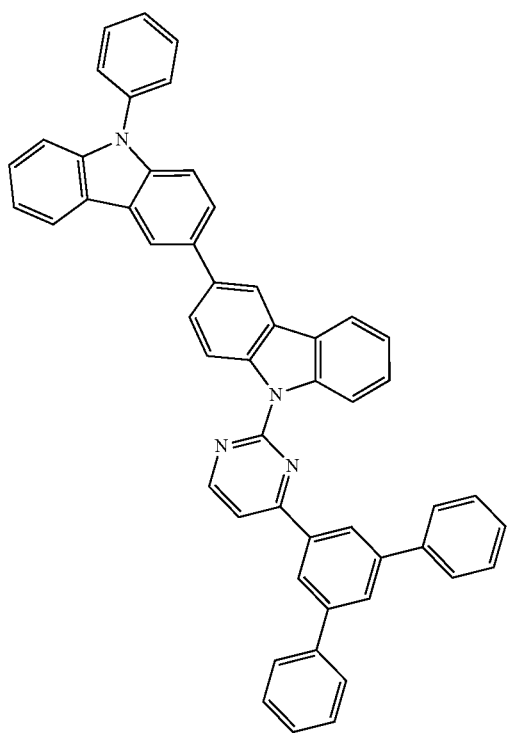
B-182
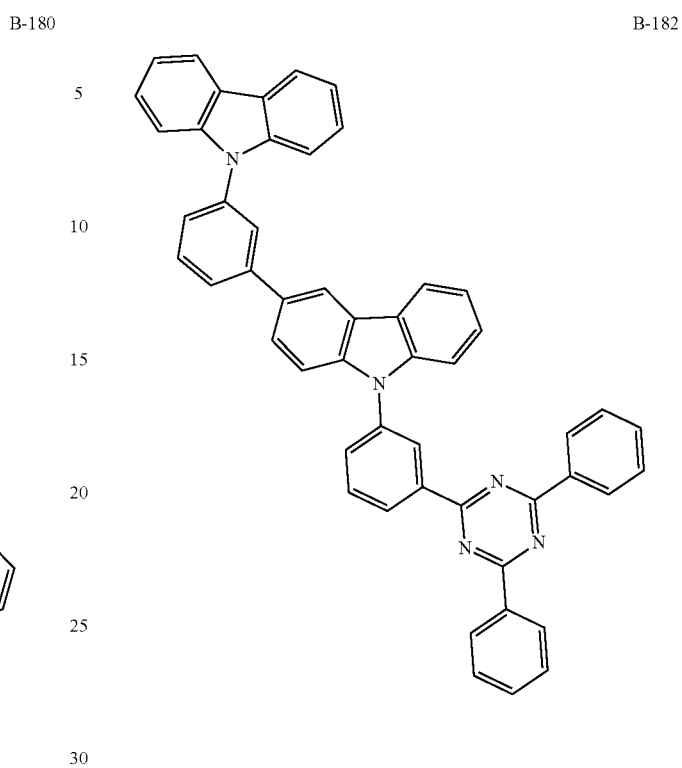
B-181
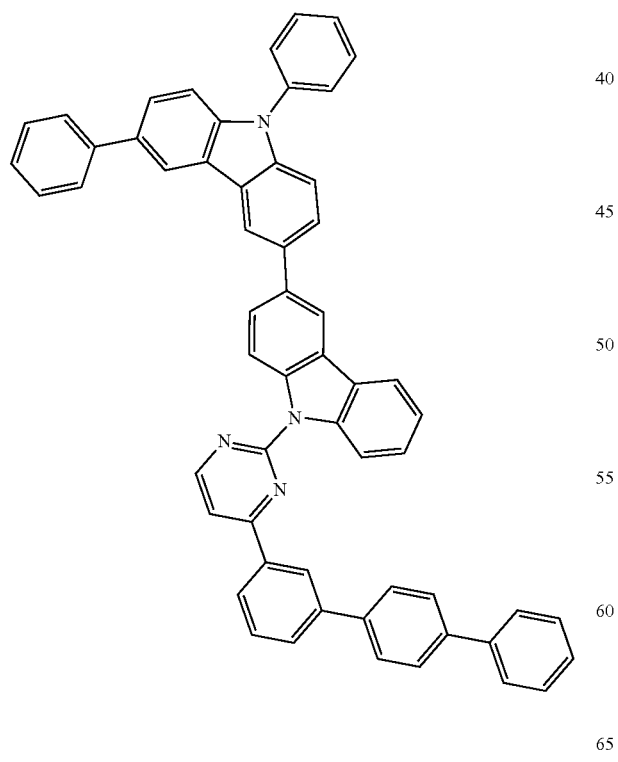
B-183
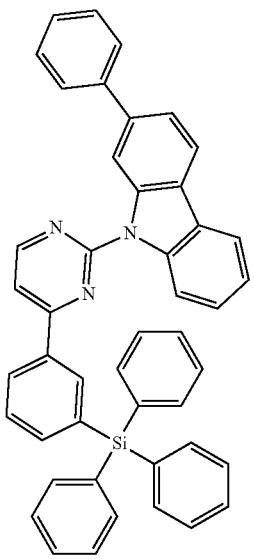

B-184
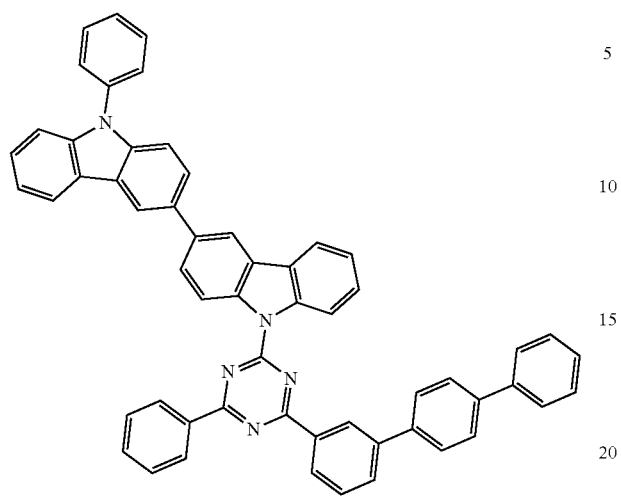
B-187
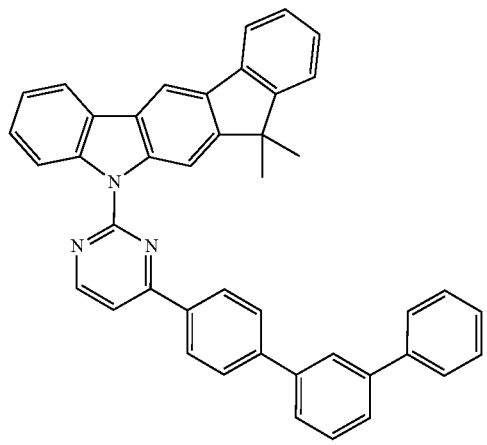
B-185
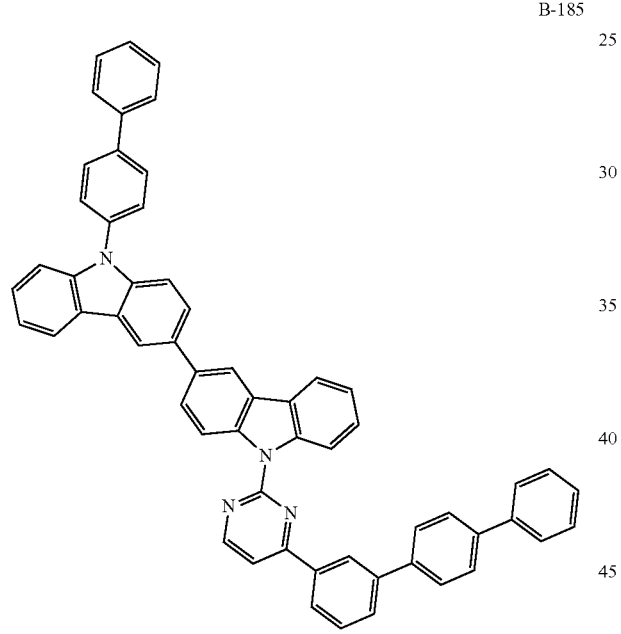
B-188
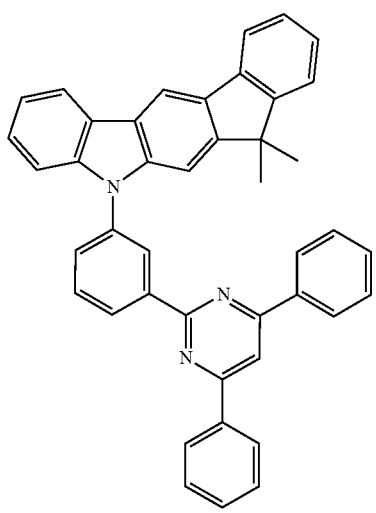
B-186
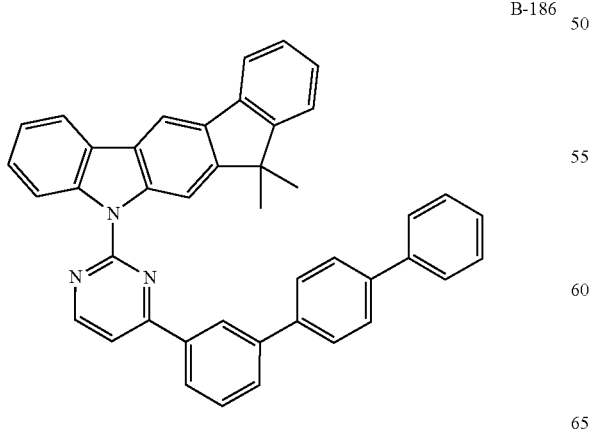
B-189
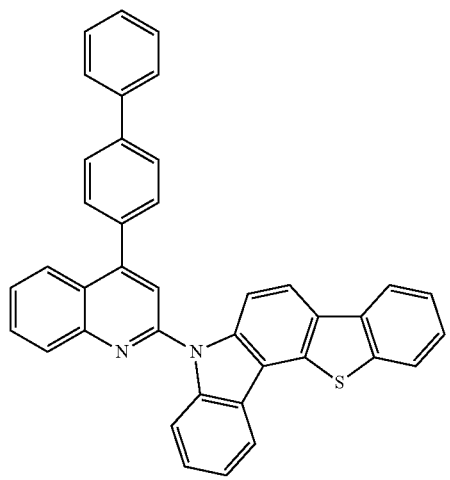

B-190
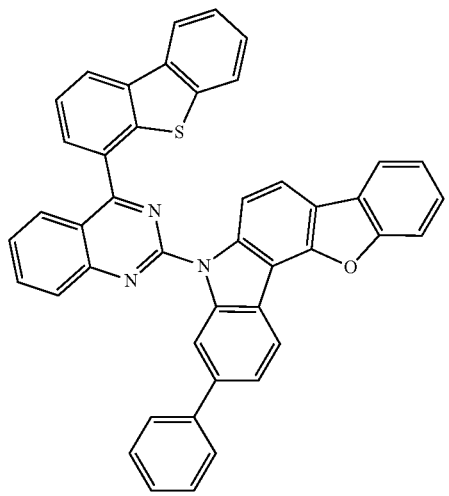
B-191
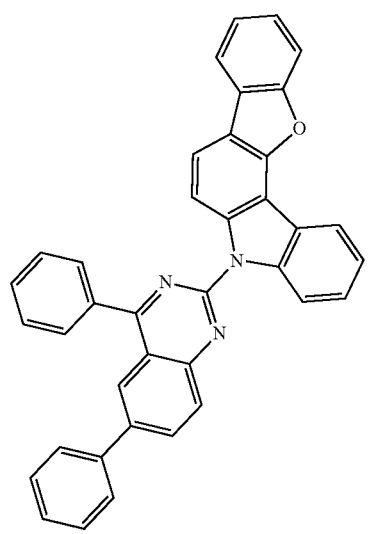
B-192
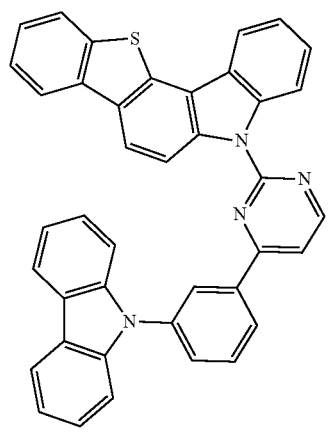
B-193
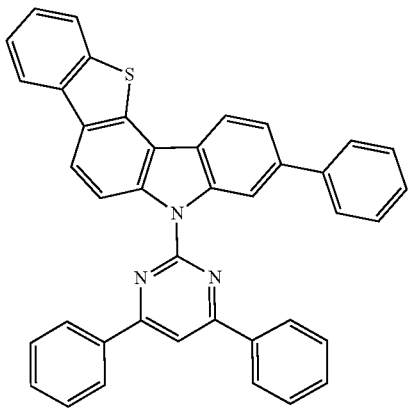
B-194
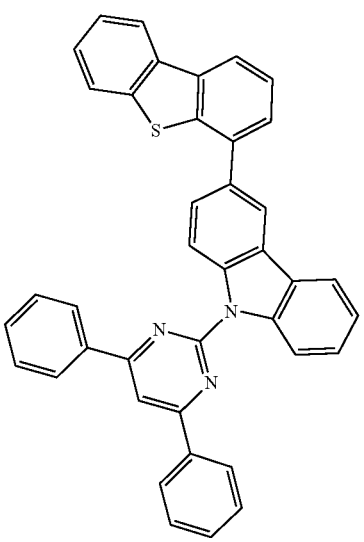
B-195
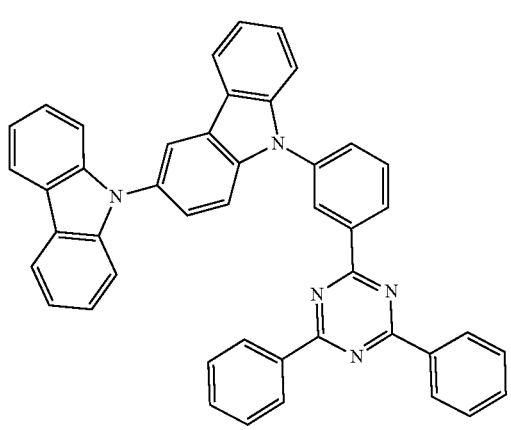

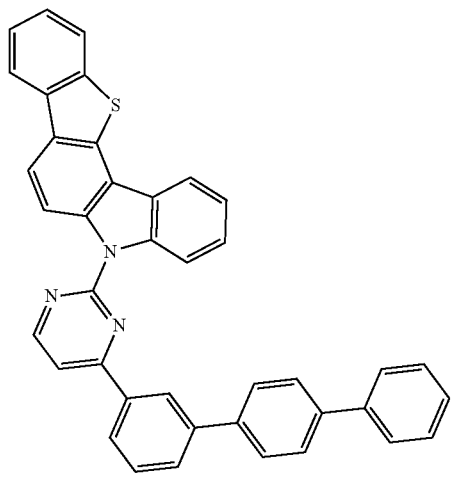

B-196

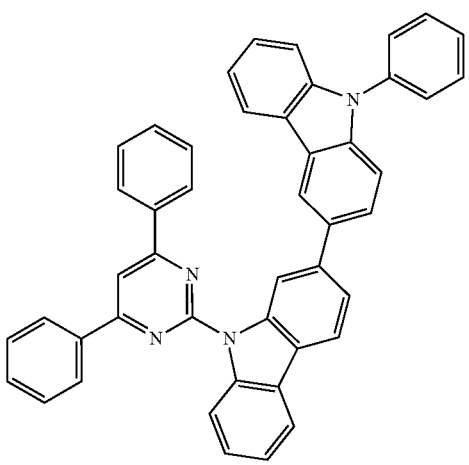

B-197

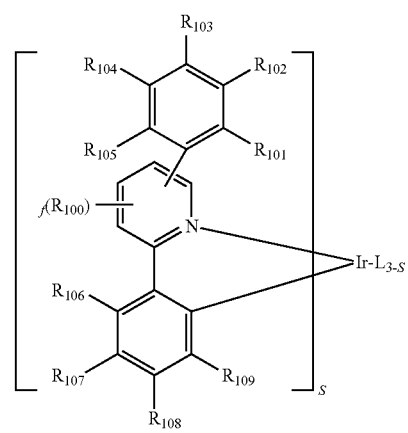

B-198

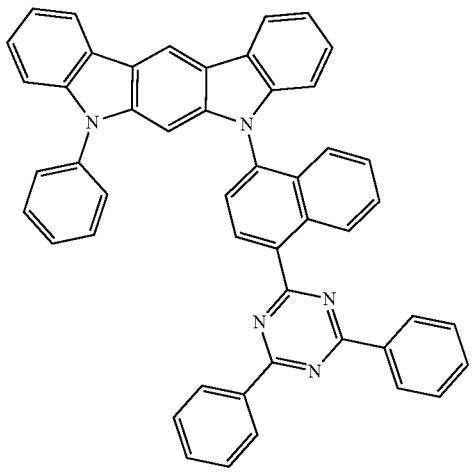

B-199

[wherein TPS represents a triphenylsilyl group]

The dopant comprised in the organic electroluminescent device according to the present disclosure may be preferably at least one phosphorescent dopant. The phosphorescent dopant materials applied to the organic electroluminescent device according to the present disclosure are not particularly limited, but may be preferably selected from metallated complex compounds of iridium (Ir), osmium (Os), copper (Cu), and platinum (Pt), may be more preferably selected from ortho-metallated complex compounds of iridium (Ir), osmium (Os), copper (Cu), and platinum (Pt), and may be even more preferably ortho-metallated iridium complex compounds.

The dopant comprised in the organic electroluminescent device of the present disclosure may be preferably selected from the group consisting of the compounds of formulas 101 to 104 below, but is not limited thereto.

(101)

-continued (102)

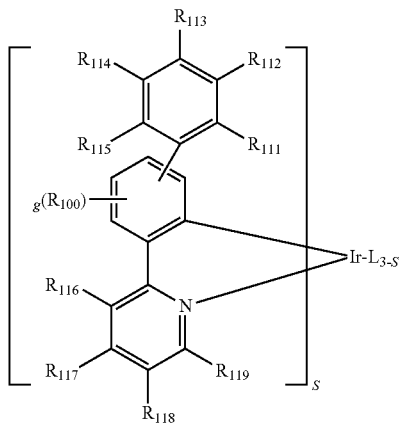

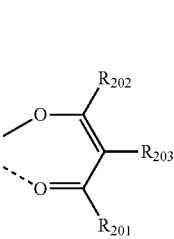

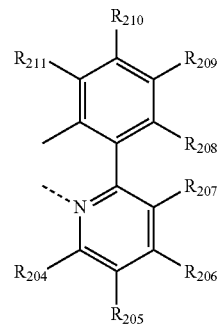

wherein L is selected from the following structures:

(103)

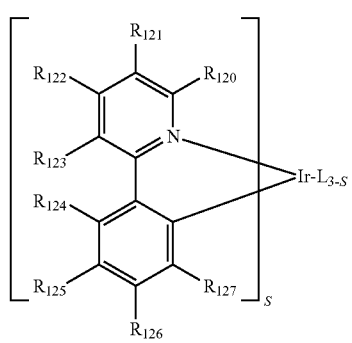

$R_{100}$, $R_{134}$, and $R_{135}$, each independently, represent hydrogen, deuterium, a substituted or unsubstituted (C1-C30)alkyl, or a substituted or unsubstituted (C3-C30)cycloalkyl;

$R_{100}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, or a substituted or unsubstituted (C1-C30)alkoxy; adjacent substituents of $R_{106}$ to $R_{109}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and adjacent substituents of $R_{120}$ to $R_{123}$ may be linked to each other to form a substituted or unsubstituted fused ring, e.g., a quinoline unsubstituted or substituted with an alkyl or an aryl;

$R_{124}$ to $R_{133}$ and $R_{136}$ to $R_{139}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

(104)

X represents $CR_{11}R_{12}$, O, or S;

$R_{11}$ and $R_{12}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; and adjacent substituents of $R_{208}$ to $R_{211}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where f or g is an integer of 2 or more, each $R_{100}$ may be the same or different; and s represents an integer of 1 to 3.

The specific examples of the dopant compound are as follows:

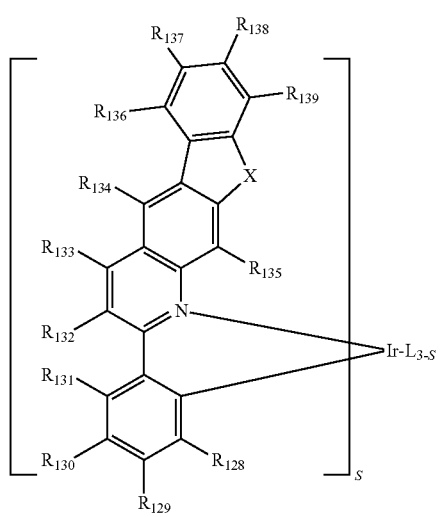

D-1 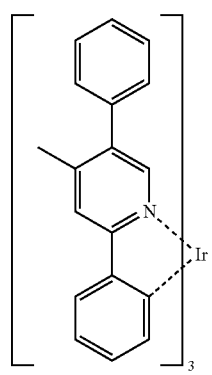
D-2 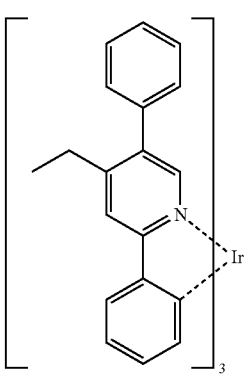
D-3 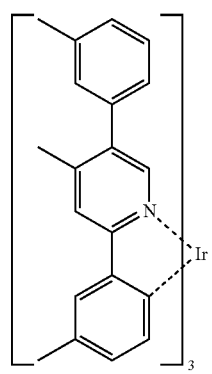
D-4 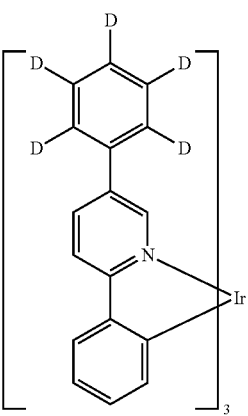
-continued
D-5 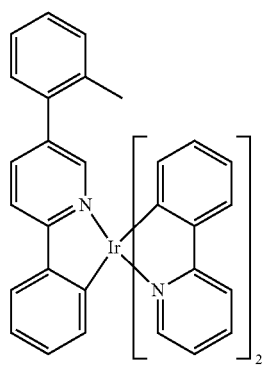
D-6 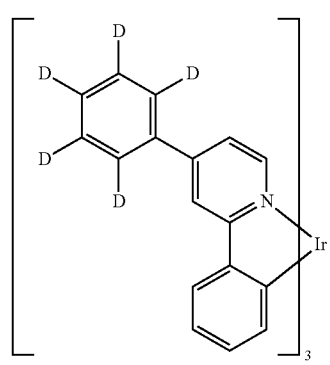
D-7 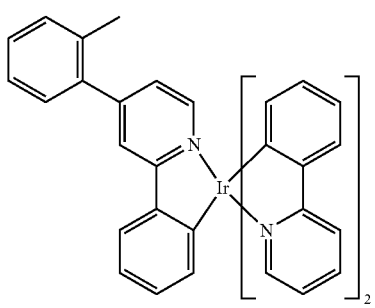
D-8 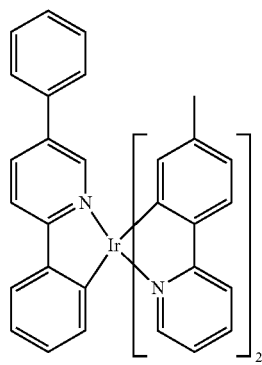

D-9
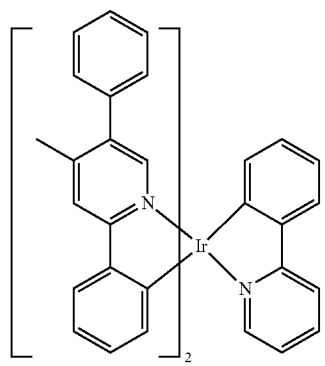
D-10
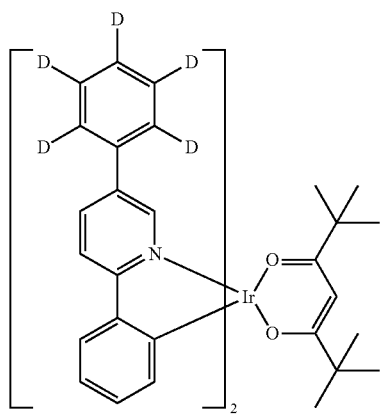
D-11
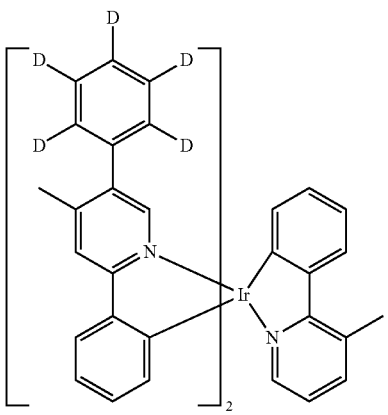
D-12
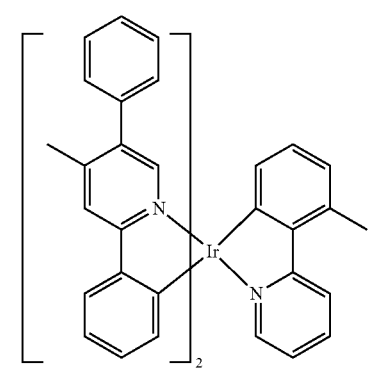
D-13
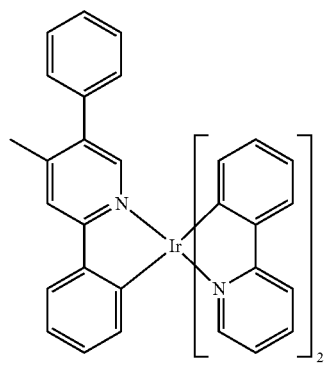
D-14
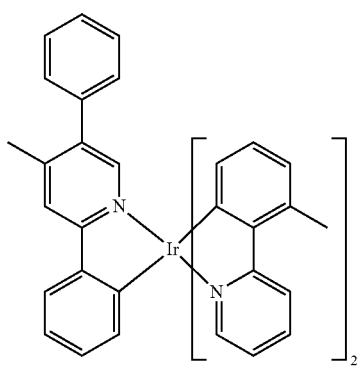
D-15
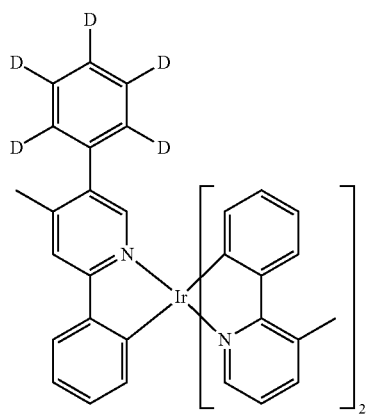
D-16
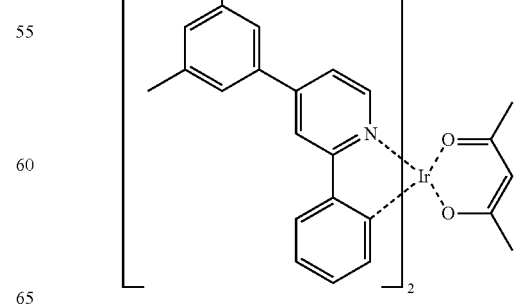

-continued
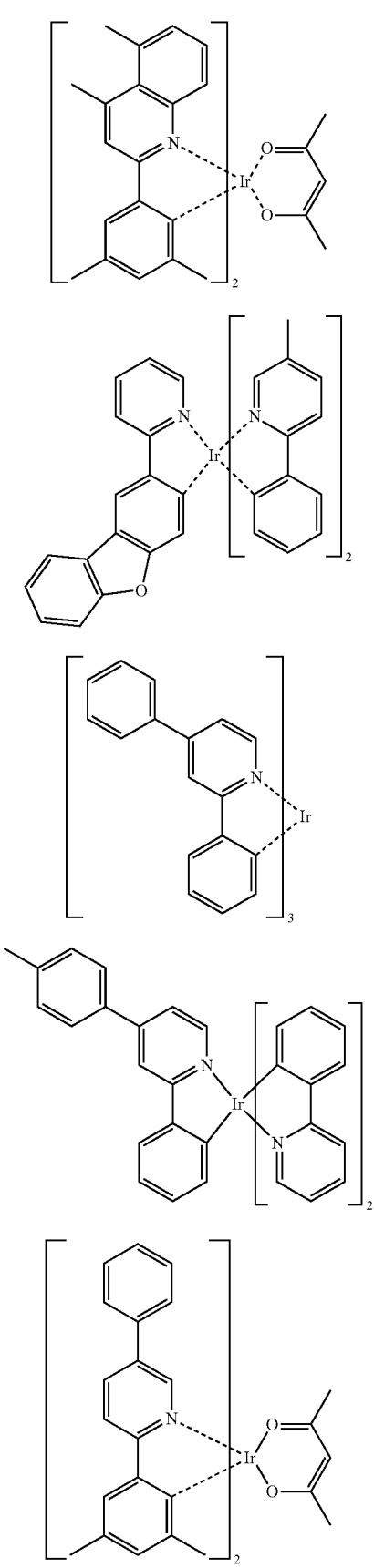
D-17
D-18
D-19
D-20
D-21
-continued
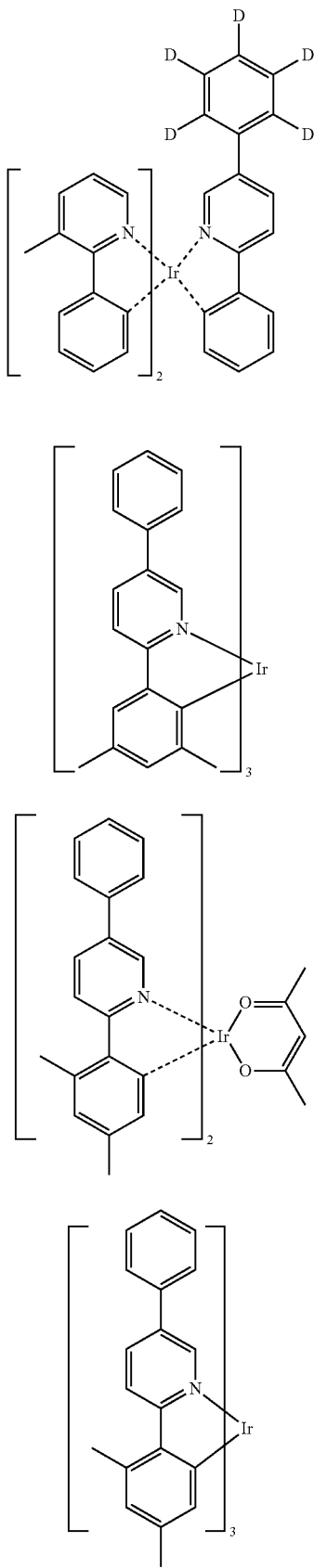
D-22
D-23
D-24
D-25

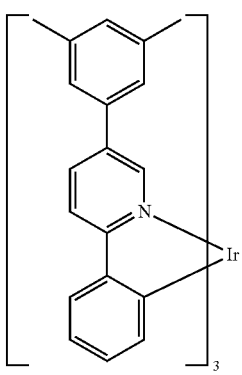
D-26
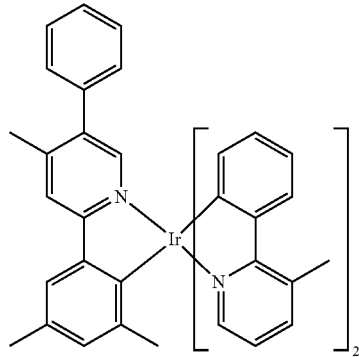
D-30
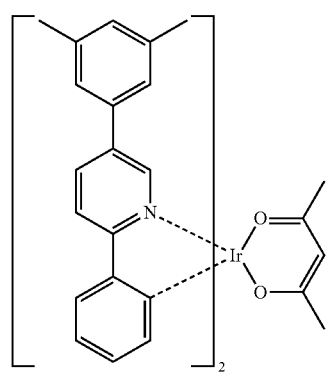
D-27
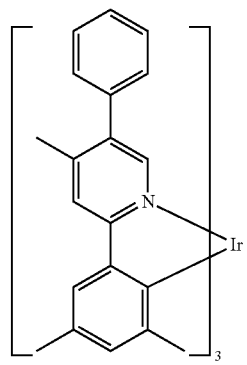
D-31
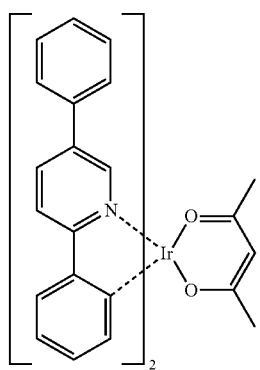
D-28
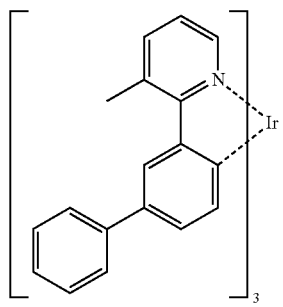
D-32
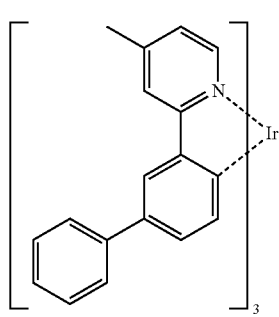
D-33
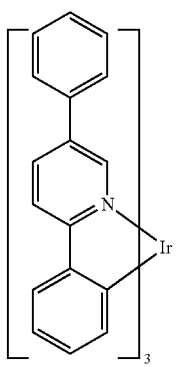
D-29
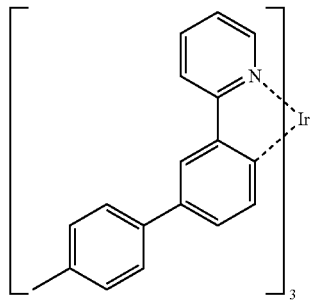
D-34

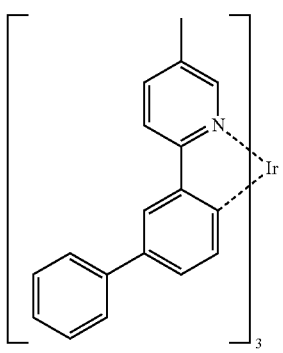
D-35
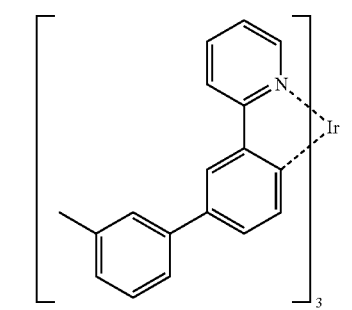
D-36
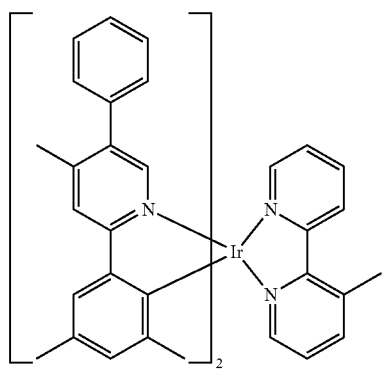
D-37
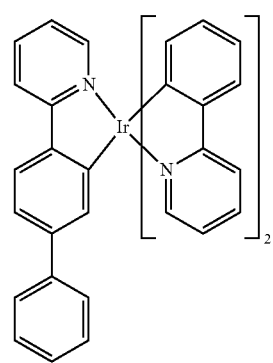
D-38
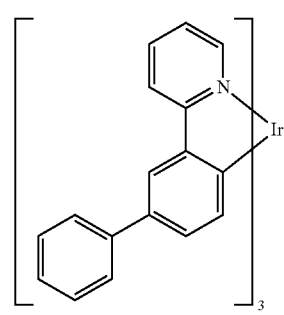
D-39
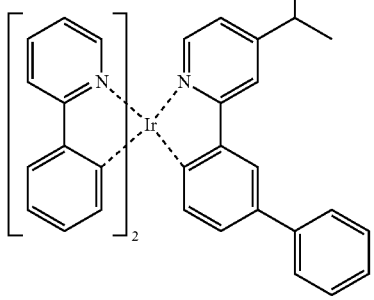
D-40
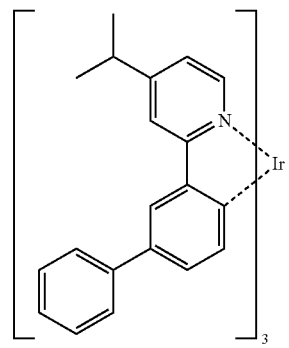
D-41
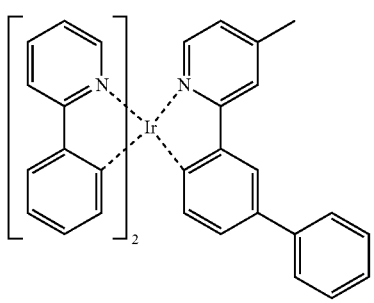
D-42
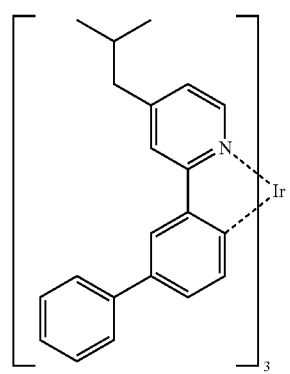
D-43

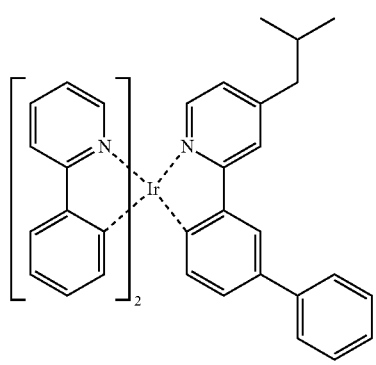
D-44
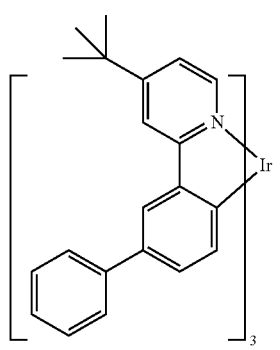
D-48
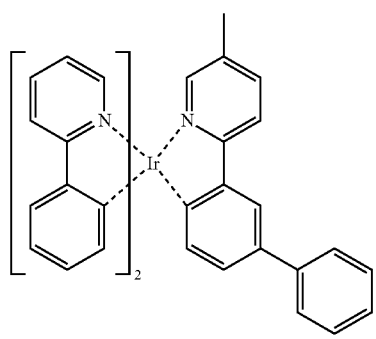
D-45
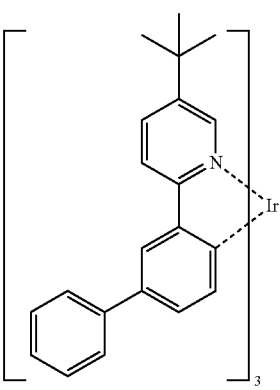
D-49
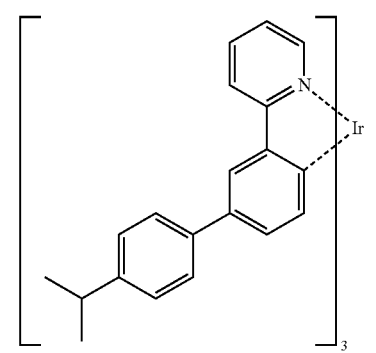
D-46
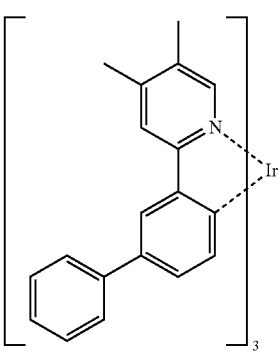
D-50
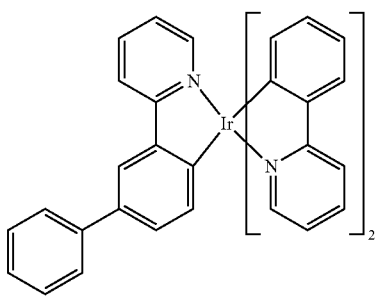
D-47
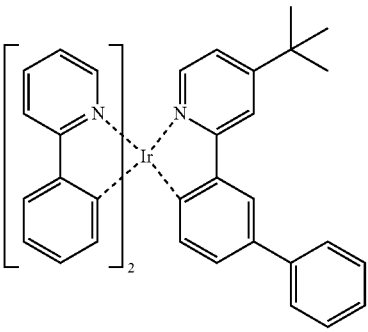
D-51

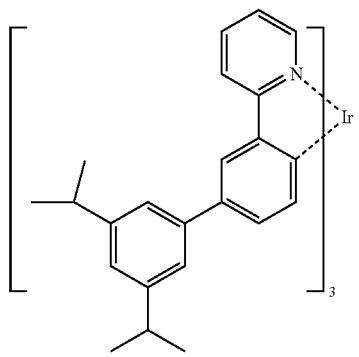 D-52
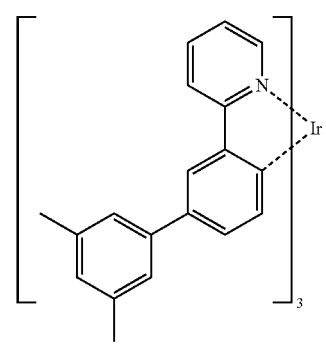 D-53
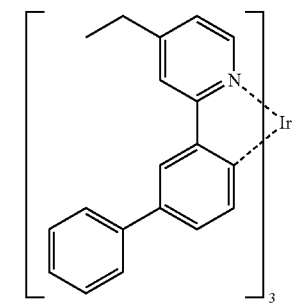 D-54
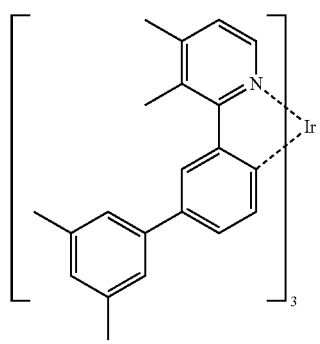 D-55
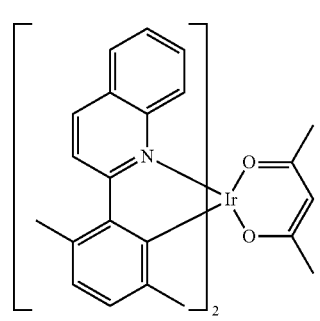 D-56
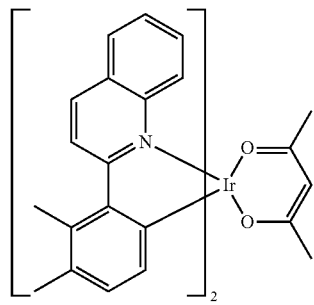 D-57
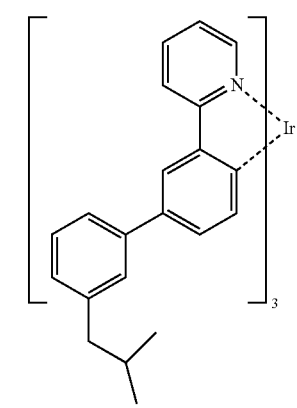 D-58
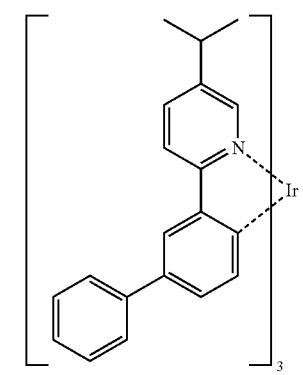 D-59
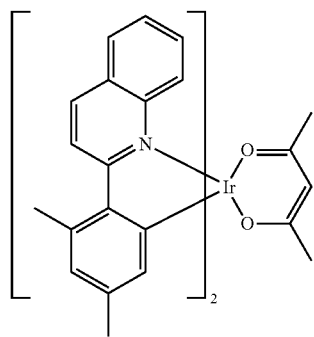 D-60

-continued
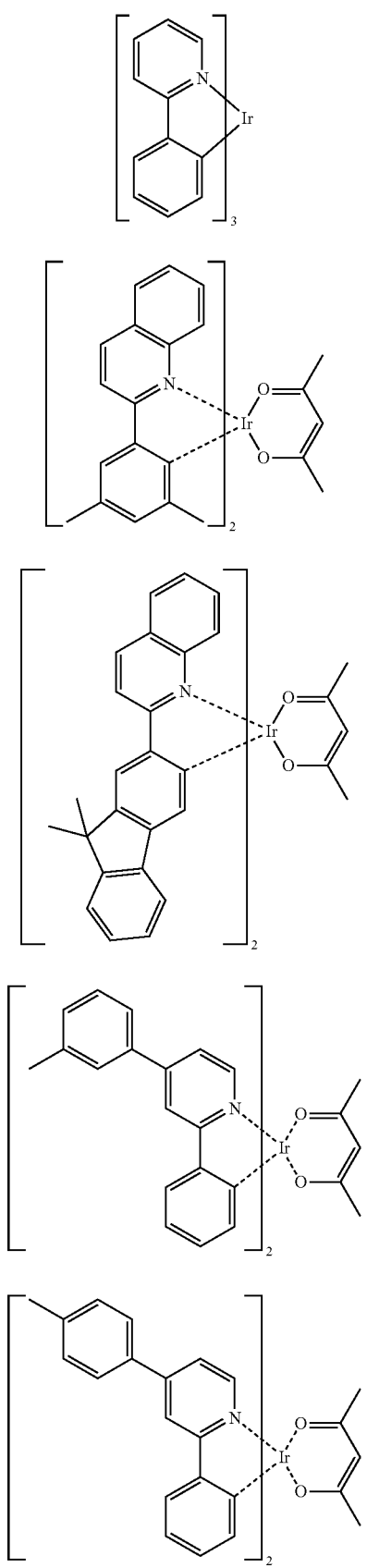
D-61
D-62
D-63
D-64
D-65
-continued
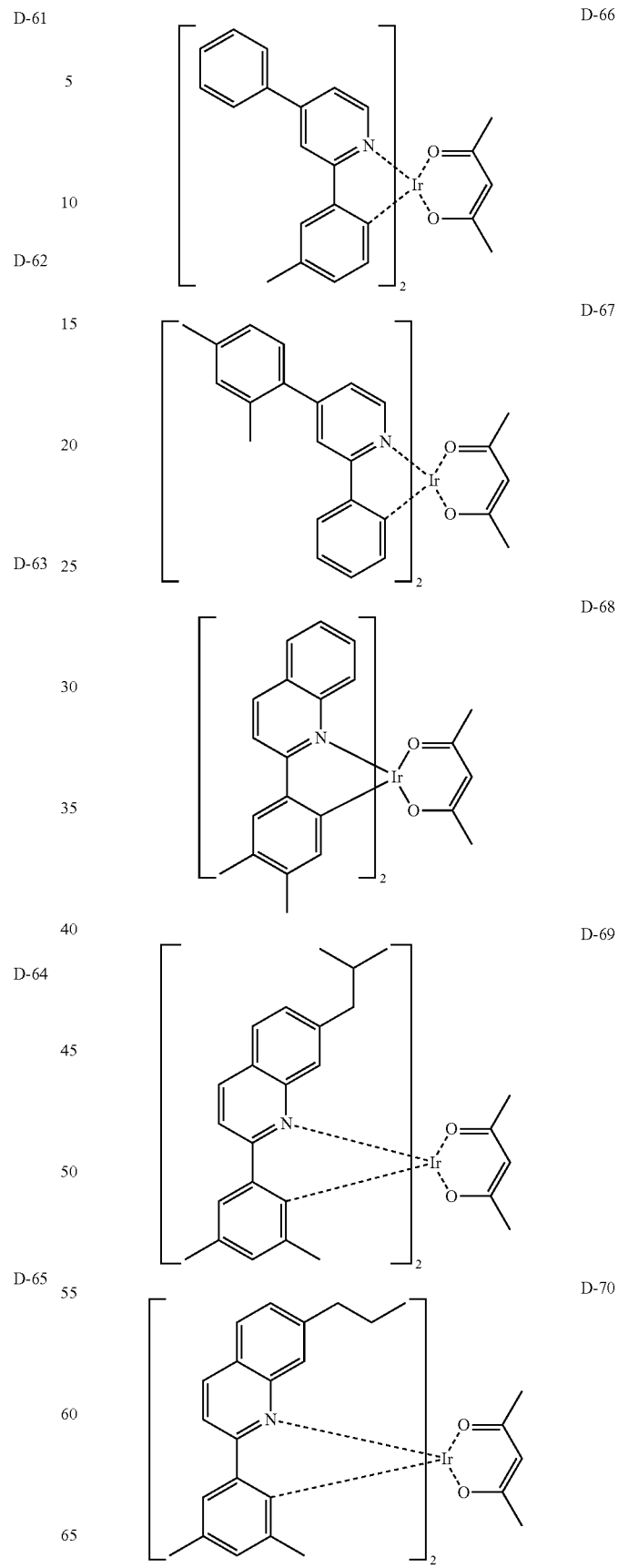
D-66
D-67
D-68
D-69
D-70

D-71 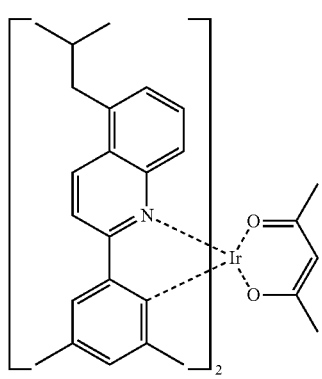
D-72 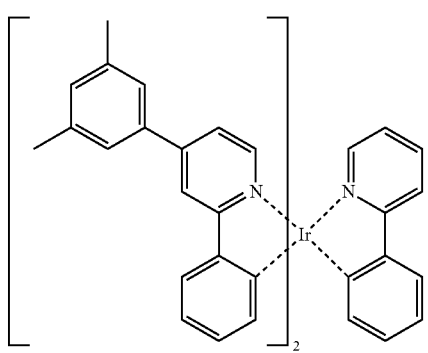
D-73 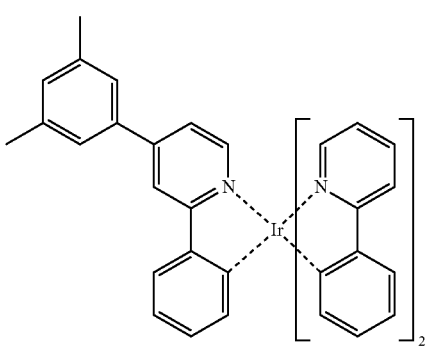
D-74 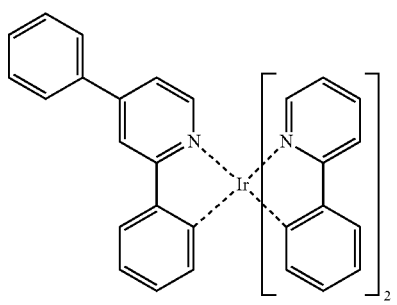
D-75 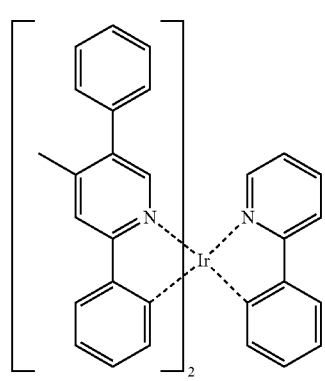
D-76 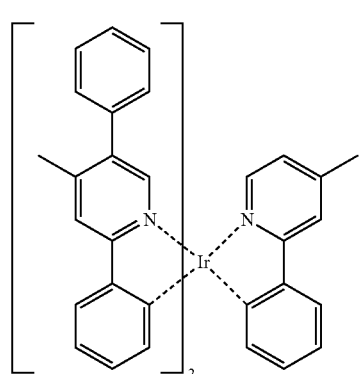
D-77 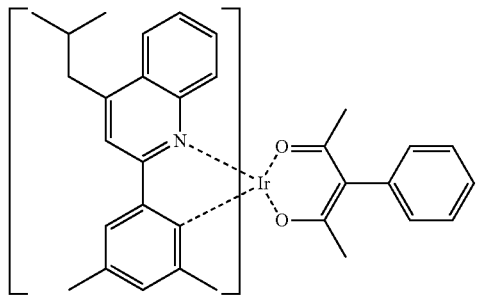
D-78 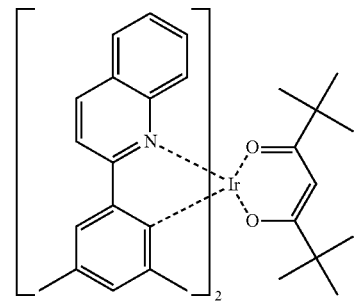

-continued
D-79
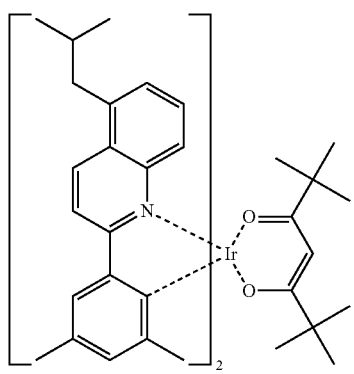
D-80
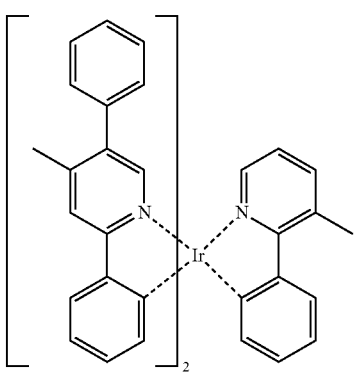
D-81
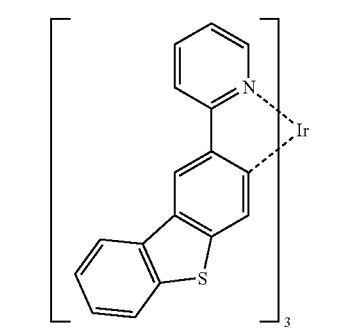
D-82
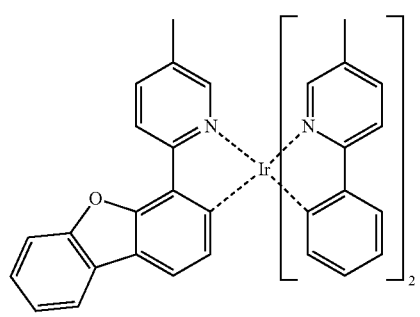
-continued
D-83
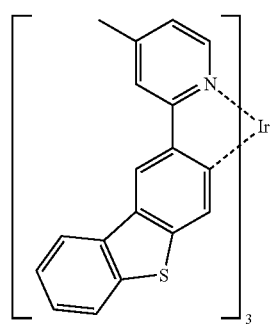
D-84
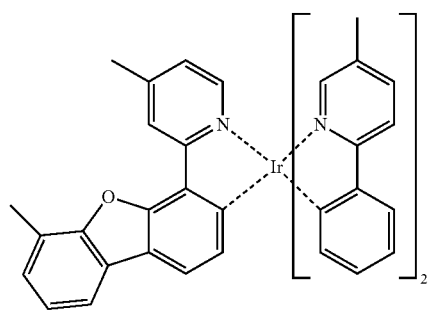
D-85
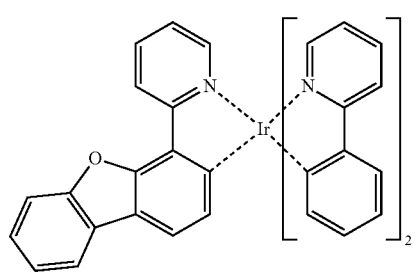
D-86
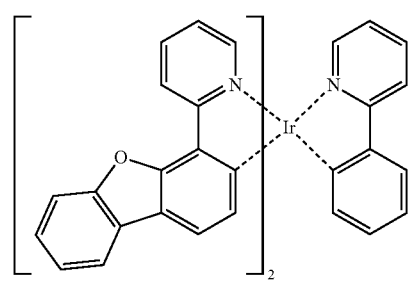
D-87
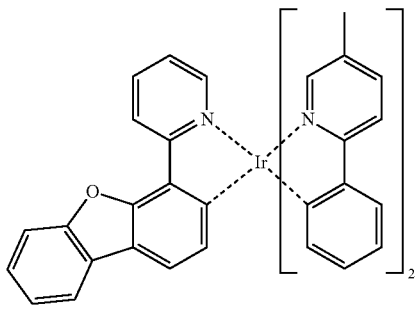

D-88
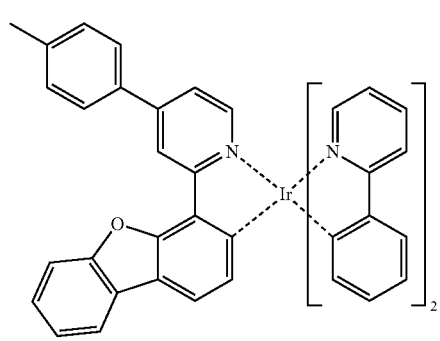
D-89
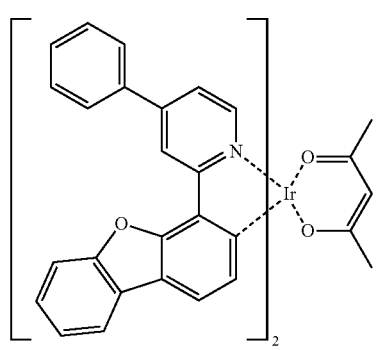
D-90
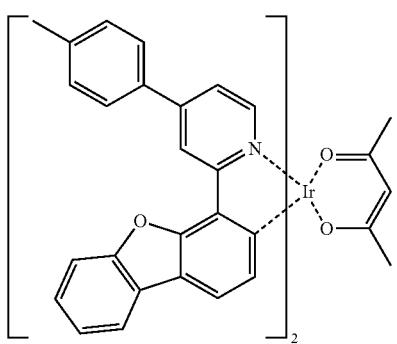
D-91
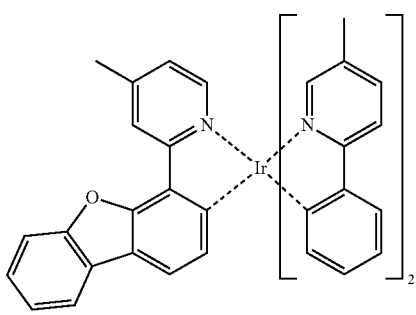
D-92
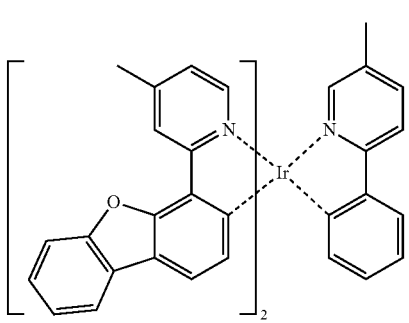
D-93
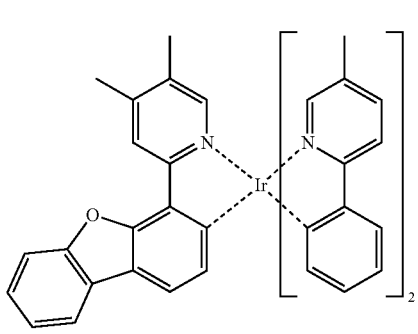
D-94
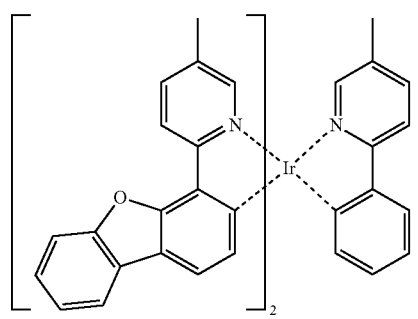
D-95
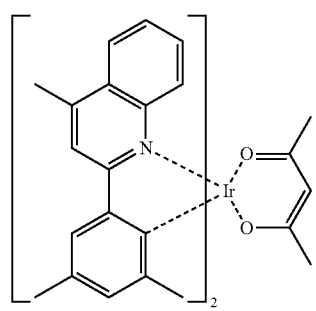
D-96
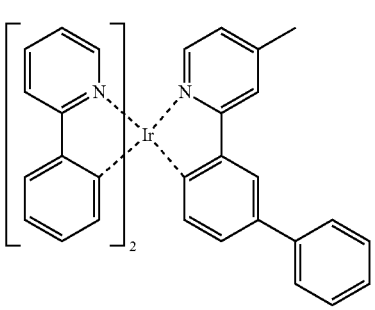
D-97
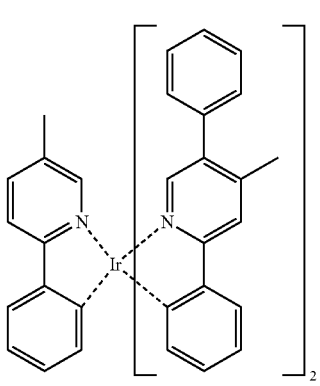

D-98
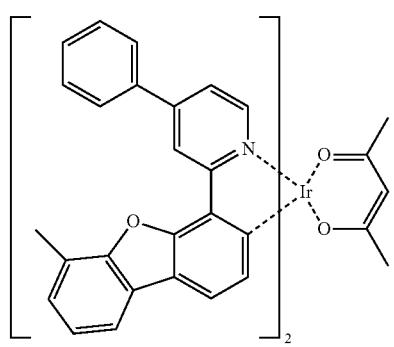
D-99
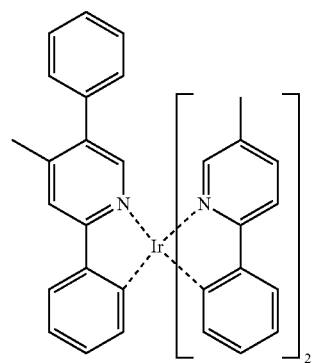
D-100
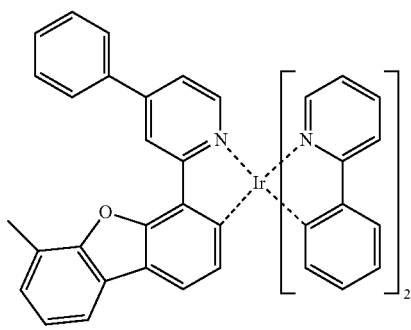
D-101
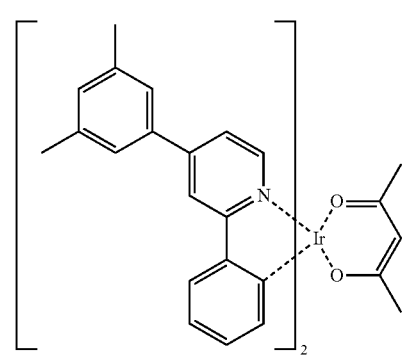
D-102
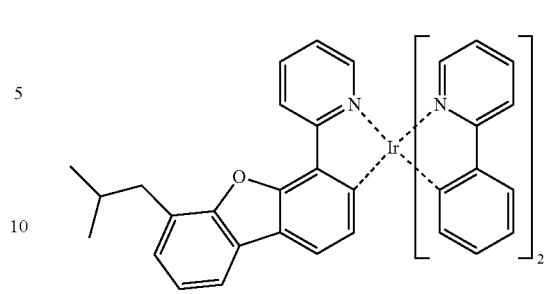
D-103
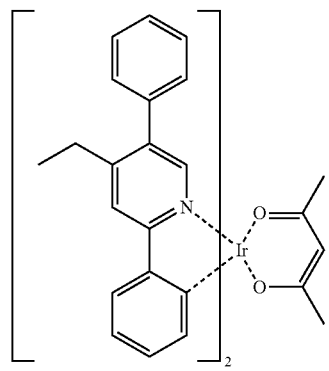
D-104
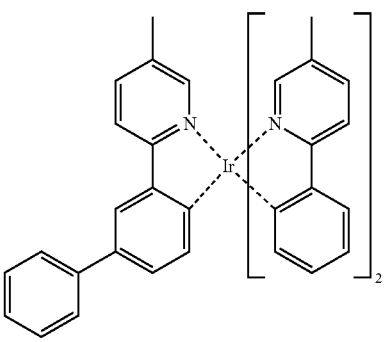
D-105
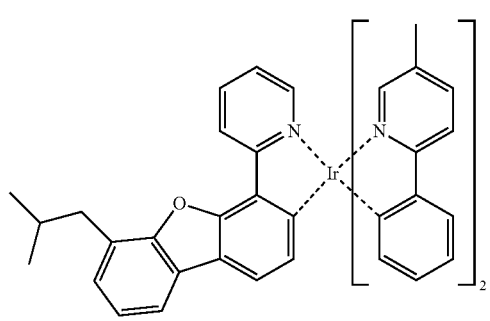
D-106
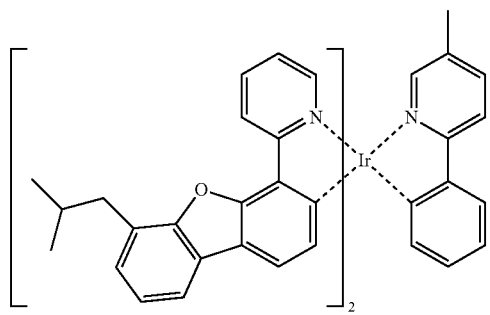

-continued
D-107
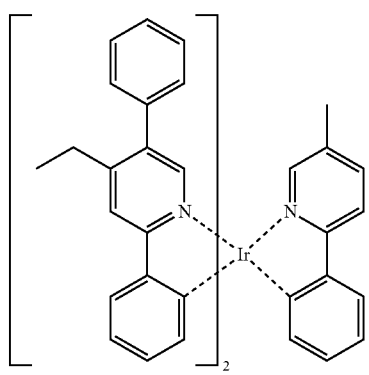
D-108
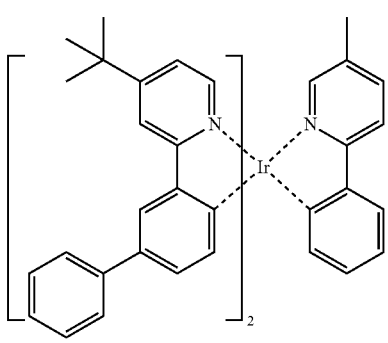
D-109
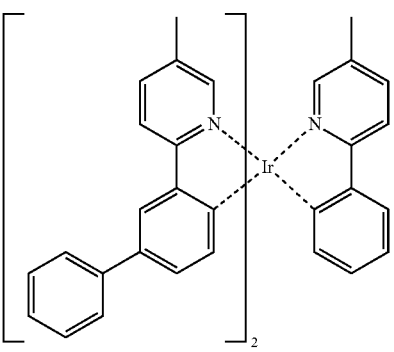
D-110
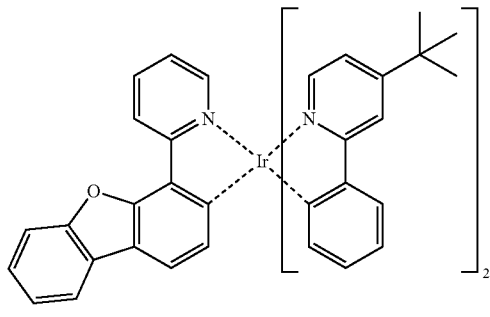
-continued
D-111
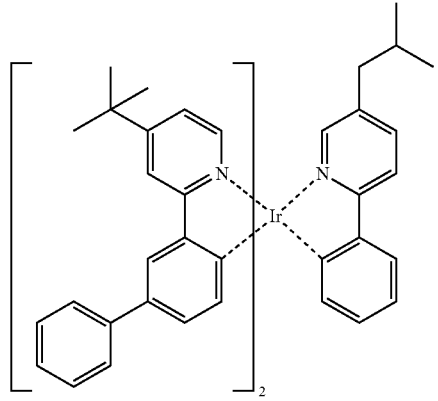
D-112
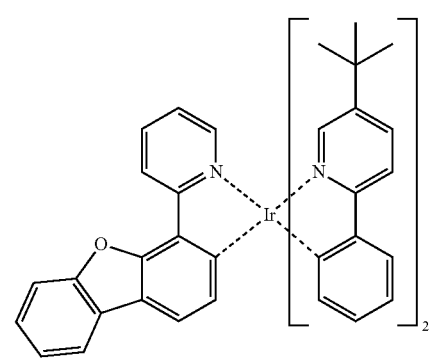
D-113
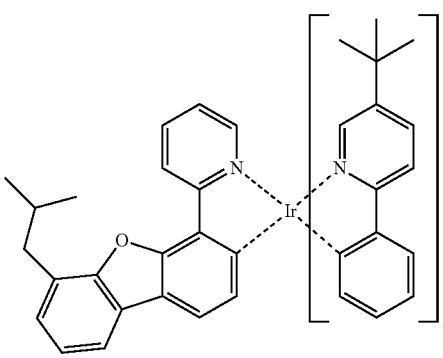
D-114
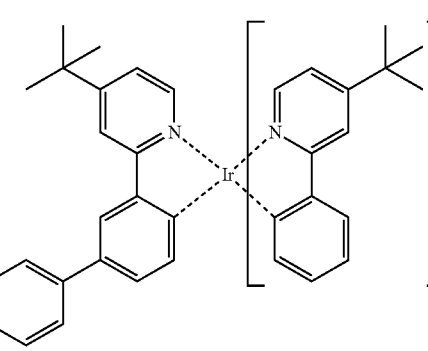

D-115
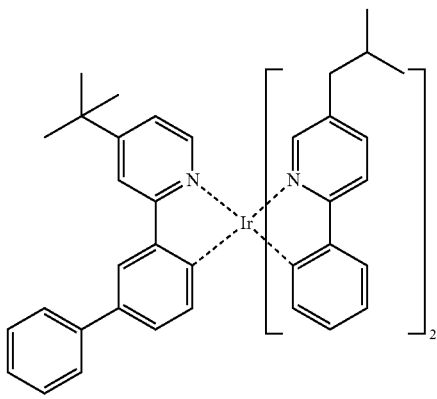
D-116
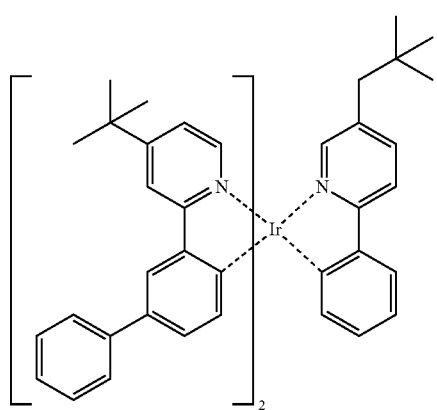
D-117
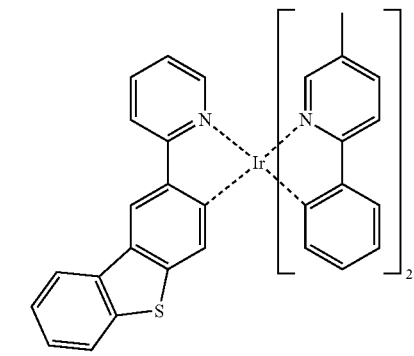
D-118
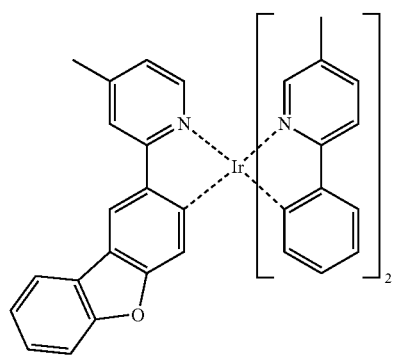
D-119
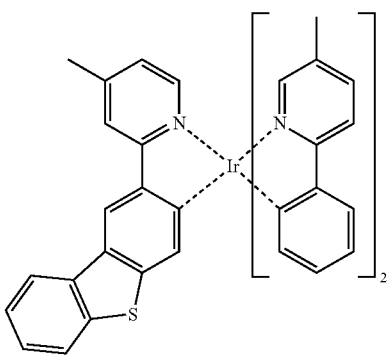
D-120
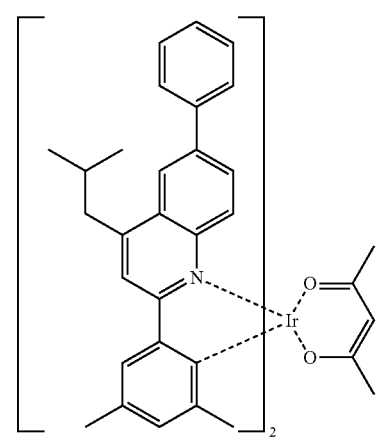
D-121
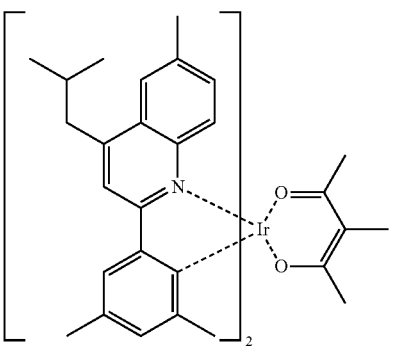
D-122
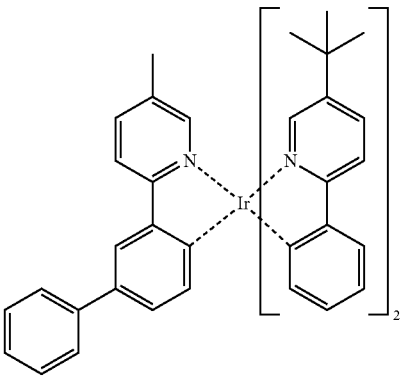

D-123
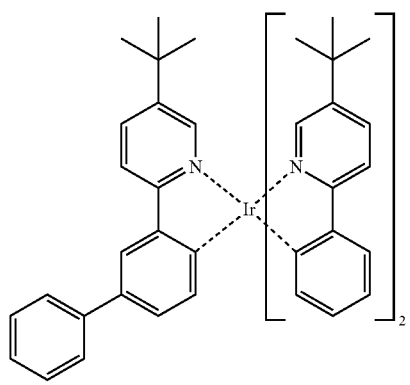
D-127
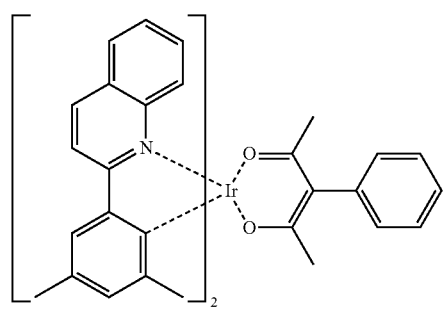
D-124
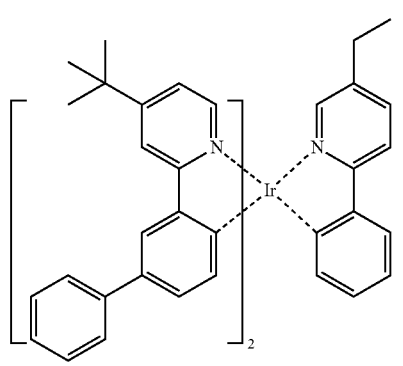
D-128
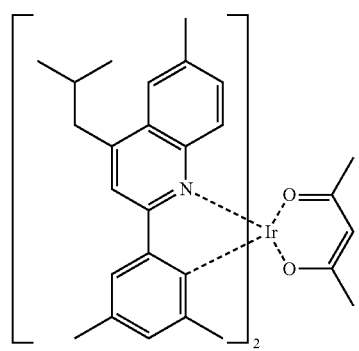
D-125
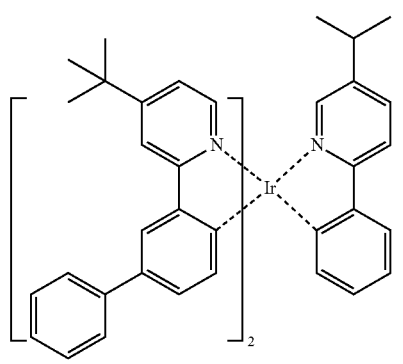
D-129
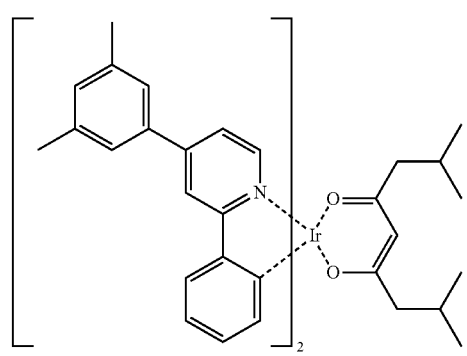
D-126
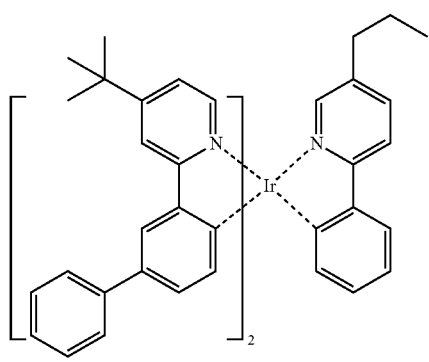
D-130
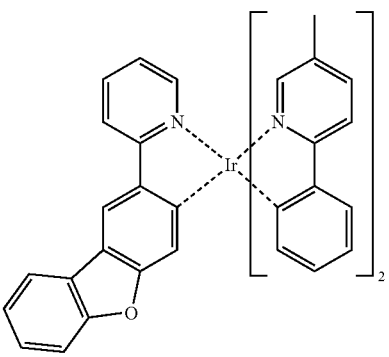

D-131
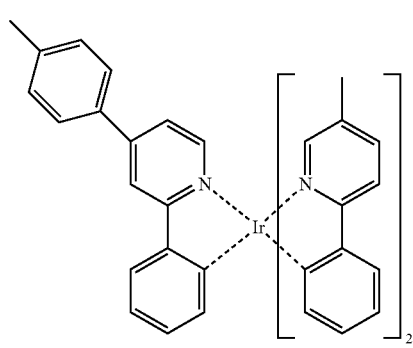
D-132
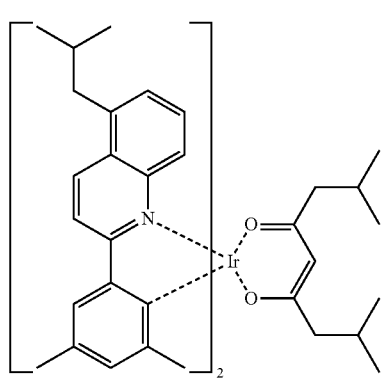
D-133
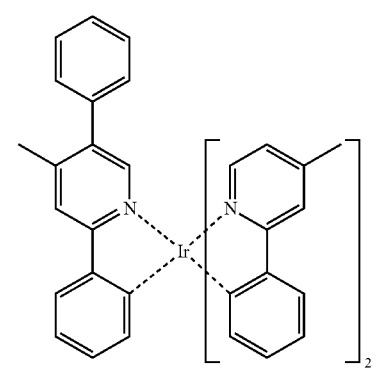
D-134
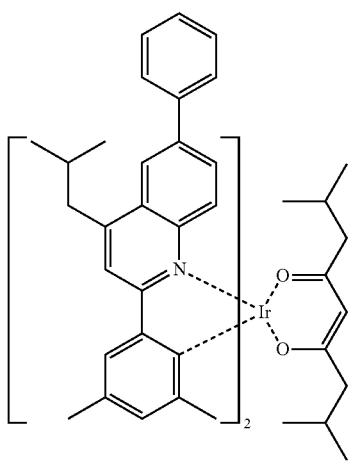
D-135
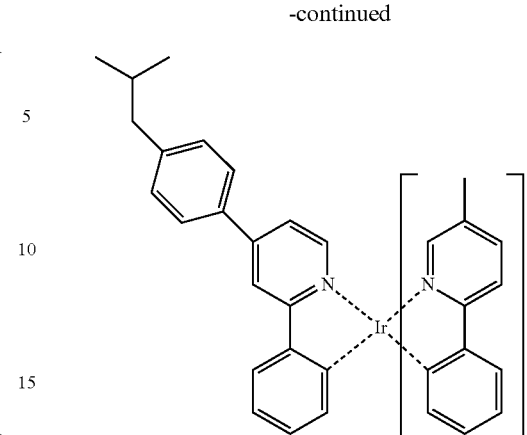
D-136
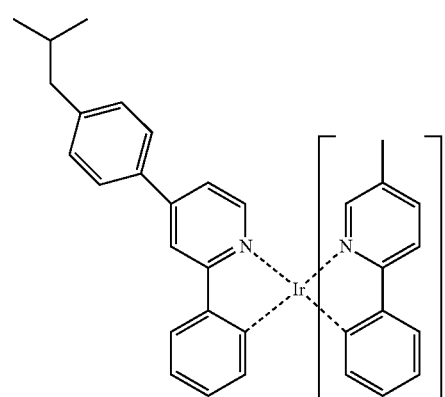
D-137
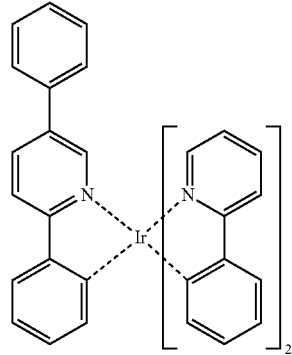
D-138
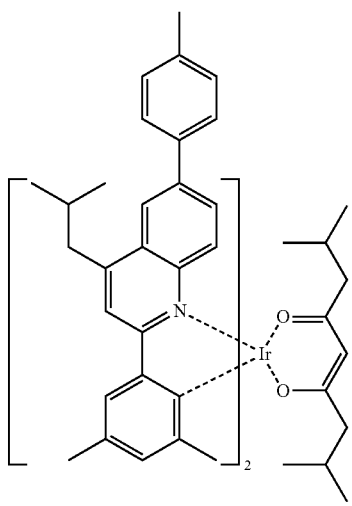

D-139 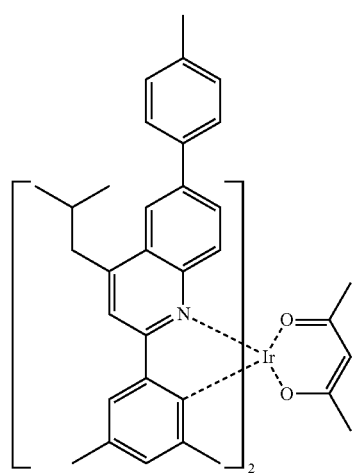
D-140 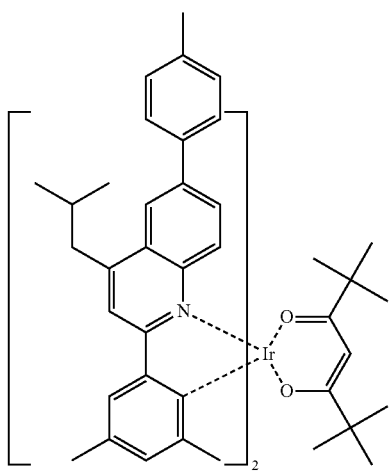
D-141 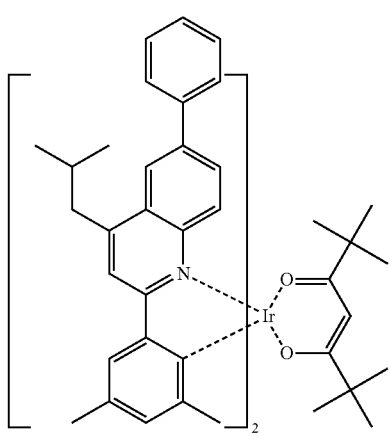
D-142 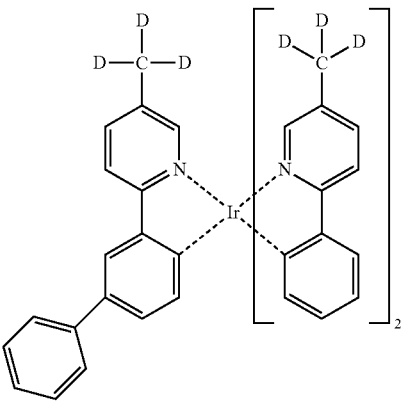
D-143 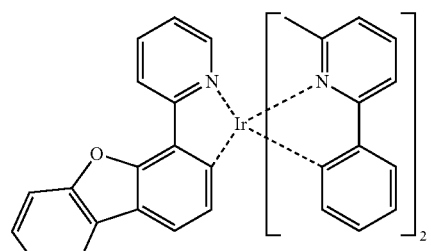
D-144 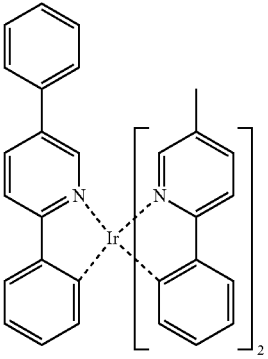
D-145 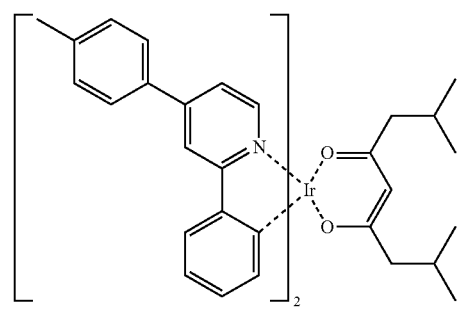
D-146 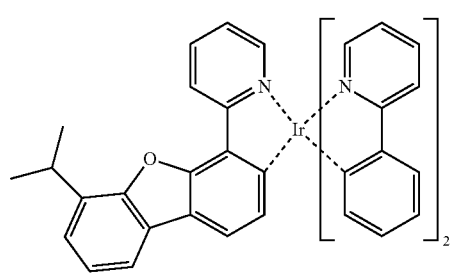

D-147
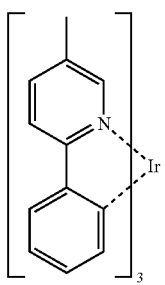
D-148
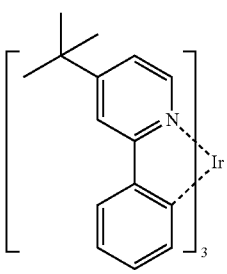
D-149
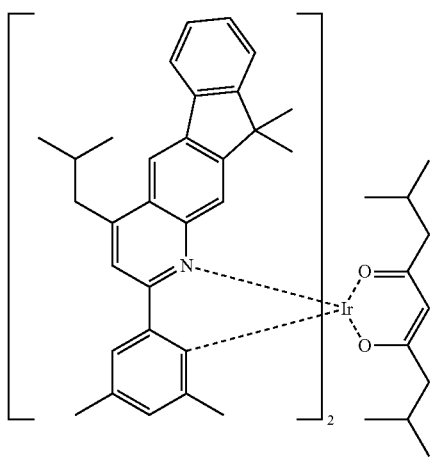
D-150
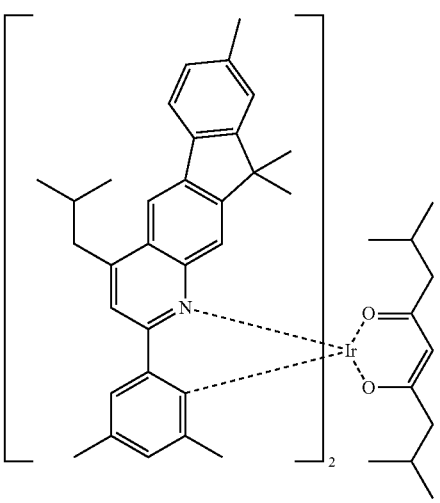
D-151
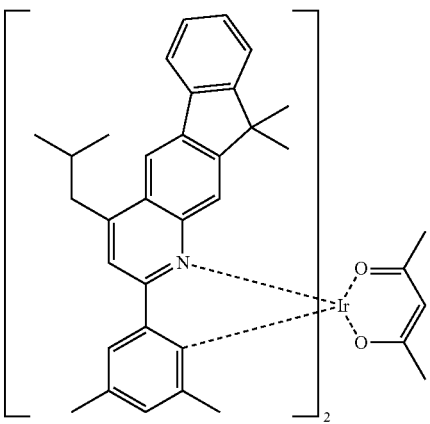
D-152
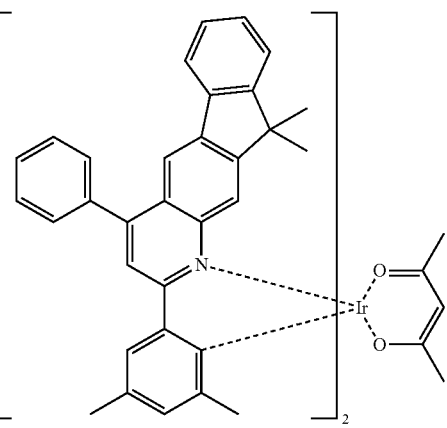
D-153
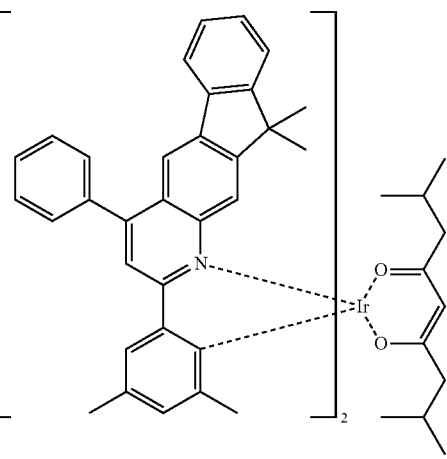

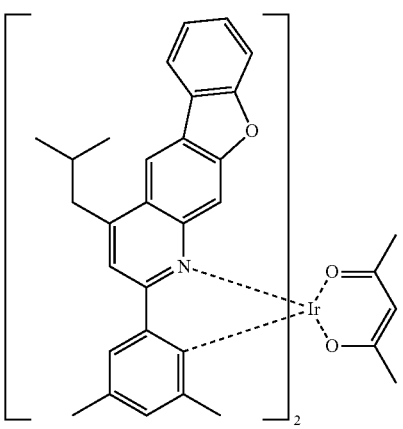

D-154

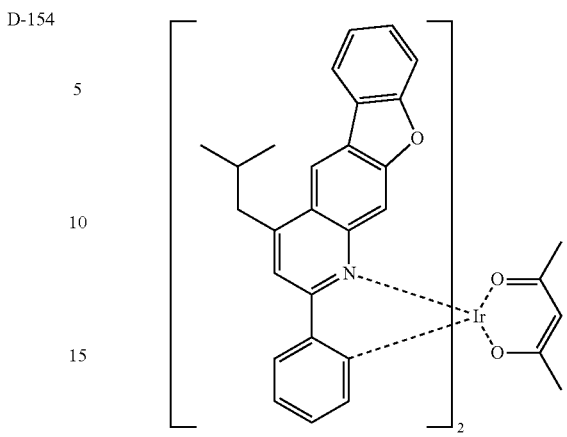

D-157

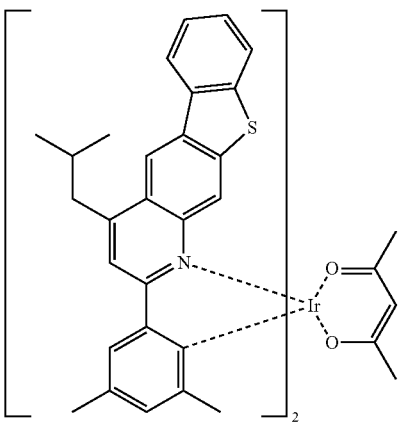

D-155

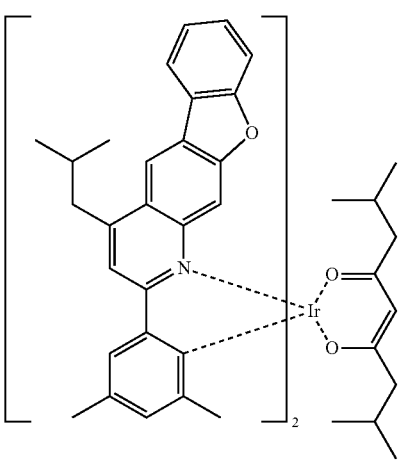

D-156

In another embodiment of the present disclosure, a composition for preparing an organic electroluminescent device, preferably a composition for preparing an organic electroluminescent device emitting red light is provided. The composition is preferably for preparing a light-emitting layer or a hole transport layer of an organic electroluminescent device and comprises the compound of the present disclosure. When there are two or more hole transport layers, the compound of the present disclosure may be comprised in the composition for preparing a hole transport layer adjacent to the light-emitting layer.

In addition, the organic electroluminescent device according to the present disclosure comprises a first electrode; a second electrode; and at least one organic layer between the first and second electrodes. The organic layer comprises a light-emitting layer, and the light-emitting layer may comprise the composition for preparing the organic electroluminescent device according to the present disclosure.

The organic electroluminescent device according to the present disclosure may further comprise, in addition to the organic electroluminescent compound represented by formula 1, at least one compound selected from the group consisting of arylamine-based compounds and styrylarylamine-based compounds.

In the organic electroluminescent device of the present disclosure, the organic layer may further comprise, besides the organic electroluminescent compound of formula 1, at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X(1≤X≤2)$, $AlO_X(1≤X≤1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a multi-component of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers and emitting white light.

In order to form each layer constituting the organic EL device of the present disclosure, dry film-forming methods such as vacuum deposition, sputtering, plasma, ion plating methods, etc., or wet film-forming methods such as spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

By using the organic electroluminescent device of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure.

EXAMPLE 1: PREPARATION OF COMPOUND C-4

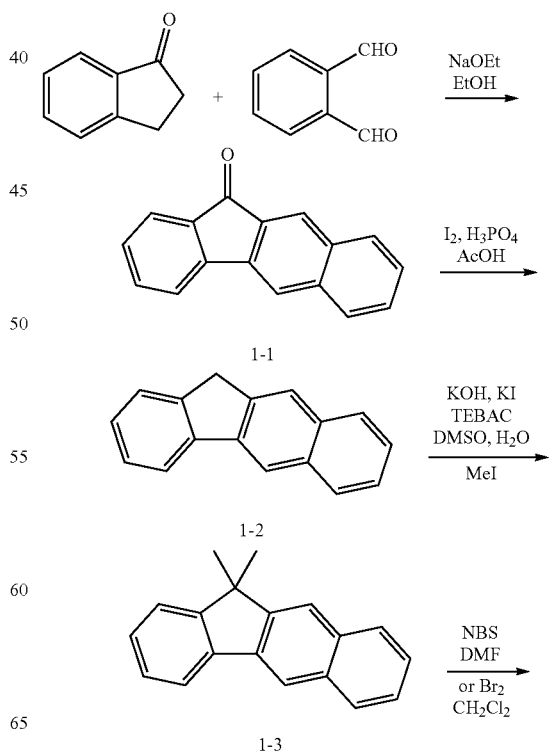

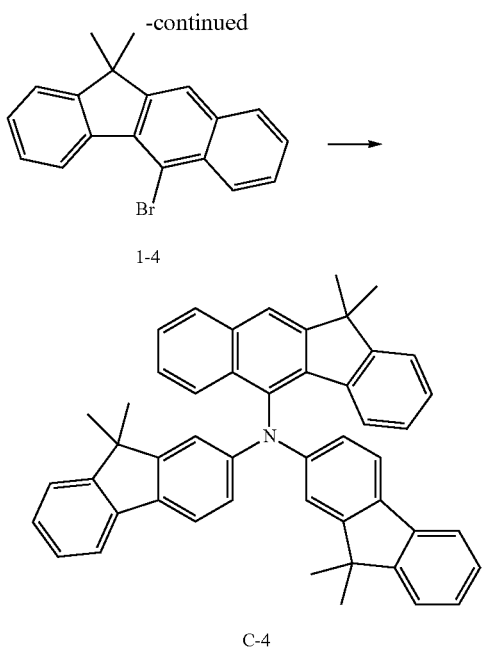

Preparation of Compound 1-1

100 g of indanone (757 mmol), 111.6 g of phthalaldehyde (832 mmol), 10.3 g of 20% sodium ethoxide ethyl alcohol solution (151 mmol), and 1300 mL of ethyl alcohol were introduced into a reaction vessel. After the mixture was refluxed for 2 hours, the mixture was cooled to room temperature and stirred overnight. The reaction solution was cooled to 0° C., and the separated solid was filtered and washed with cold methyl alcohol and hexane to obtain 95 g of compound 1-1 (yield: 55%).

Preparation of Compound 1-2

33.3 g of iodine (144 mmol), 44 g of hypophosphorous acid (660 mmol, 50% aqueous solution), and 2000 mL of acetic acid were introduced into a reaction vessel, and the mixture was stirred at 80° C. for 30 minutes. 95 g of compound 1-1 (413 mmol) was slowly added dropwise thereto and the mixture was stirred under reflux overnight. The reaction solution was cooled to room temperature, and the separated solid was filtered and washed with cold methyl alcohol and hexane to obtain 73 g of compound 1-2 (yield: 82%).

Preparation of Compound 1-3

30 g of compound 1-2 (139 mmol), 39 g of potassium hydroxide (694 mmol), 2.3 g of potassium iodide (14 mmol), 1.58 g of benzyltriethylammonium chloride (7 mmol), 70 mL of distilled water, and 700 mL of dimethylsulfoxide were introduced into a reaction vessel, and the mixture was stirred at room temperature for 30 minutes. 49 g of methyl iodide (347 mmol) was added thereto and the mixture was stirred at room temperature overnight. The reaction solution was diluted with ethylacetate and washed with distilled water. The extracted organic layer was then dried with magnesium sulfate. The solvent was removed with a rotary evaporator, and the resulting product was purified by column chromatography to obtain 34 g of compound 1-3 (yield: 68%).

Preparation of Compound 1-4

3 g of compound 1-3 (12 mmol) was dissolved in 50 mL of methylene chloride in a reaction vessel. 1.3 g of bromine (16 mmol) was dissolved in 10 mL of methylene chloride and added to the reaction solution. The mixture was then stirred at room temperature for 2 hours. The reaction solution was diluted with methylene chloride and washed with distilled water. The extracted organic layer was then dried with magnesium sulfate. The solvent was removed with a rotary evaporator, and the separated solid was filtered and washed with cold methyl alcohol to obtain 1.8 g of compound 1-4 (yield: 45%).

Compound 1-4 can also be obtained as follows:

1.3 g of compound 1-3 (5 mmol), 10 mL of dimethylformamide, and 1.23 g of N-bromosuccinimide (7 mmol) were introduced into a reaction vessel, and the mixture was stirred at room temperature overnight. The reaction solution was diluted with ethylacetate and washed with distilled water. The extracted organic layer was then dried with magnesium sulfate. The solvent was removed with a rotary evaporator, and the separated solid was filtered and washed with cold methyl alcohol to obtain 620 mg of compound 1-4 (yield: 36%).

Preparation of Compound C-4

10 g of compound 1-4 (31 mmol), 13.7 g of bis-9,9-dimethyl-9H-fluoren-2-ylamine (31 mmol), 1.46 g of tris(dibenzylideneacetone)dipalladium(0) (2 mmol), 2.2 mL of tri-t-butylphosphine (6 mmol, 50% toluene solution), 5.9 g of sodium t-butoxide (62 mmol), and 223 mL of toluene were introduced into a reaction vessel, and the mixture was refluxed for 4 hours. The reaction solution was cooled to room temperature. The solvent was removed with a rotary evaporator, and the resulting product was purified by column chromatography to obtain 10.5 g of compound C-4 (yield: 52%). The properties of compound C-4 are shown in Table 1.

EXAMPLE 2: PREPARATION OF COMPOUND C-5

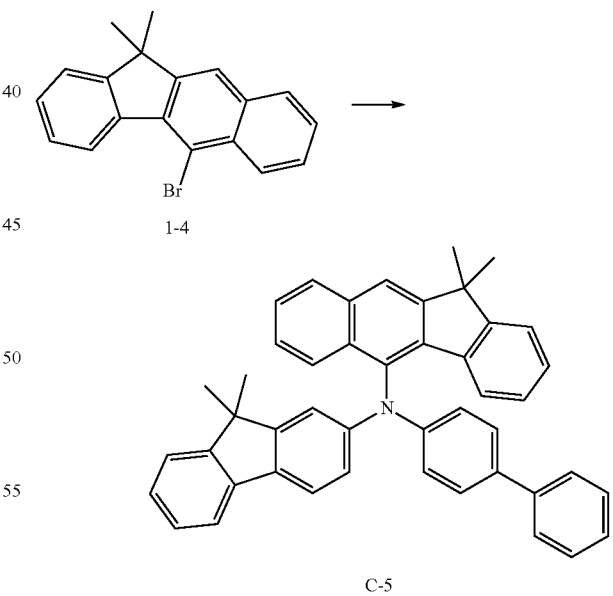

40 g of compound 1-4 (124 mmol), 44.7 g of N-1,1'-biphenyl-4-yl-9,9-dimethyl-9H-fluoren-2-amine (124 mmol), 3.4 g of tris(dibenzylideneacetone)dipalladium(0) (4 mmol), 3 mL of tri-t-butylphosphine (7 mmol, 50% toluene solution), 17.8 g of sodium t-butoxide (186 mmol), and 600 mL of toluene were introduced into a reaction vessel, and the mixture was refluxed for 3 hours. The reaction solution was cooled to room temperature. The solvent was removed with a rotary evaporator, and the resulting product was purified by column chromatography to obtain 37.8 g of compound C-5 (yield: 51%). The properties of compound C-5 are shown in Table 1.

EXAMPLE 3: PREPARATION OF COMPOUND C-7

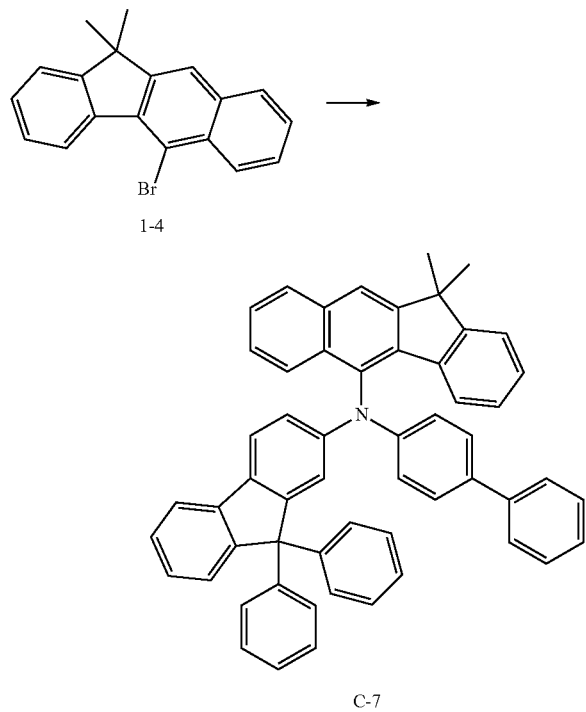

C-7

10 g of compound 1-4 (31 mmol), 16.5 g of N-1,1'-biphenyl-4-yl-9,9-dimethyl-9H-fluorene-2-amine (34 mmol), 1.4 g of tris(dibenzylideneacetone)dipalladium(0) (2 mmol), 1.2 mL of tri-t-butylphosphine (3 mmol, 50% toluene solution), 5.9 g of sodium t-butoxide (62 mmol), and 600 mL of toluene were introduced into a reaction vessel, and the mixture was refluxed for 3 hours. The reaction solution was cooled to room temperature. The solvent was removed with a rotary evaporator, and the resulting product was purified by column chromatography to obtain 11 g of compound C-7 (yield: 49%). The properties of compound C-7 are shown in Table 1.

EXAMPLE 4: PREPARATION OF COMPOUND C-73

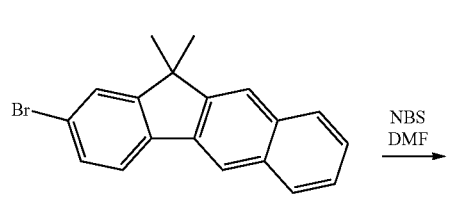

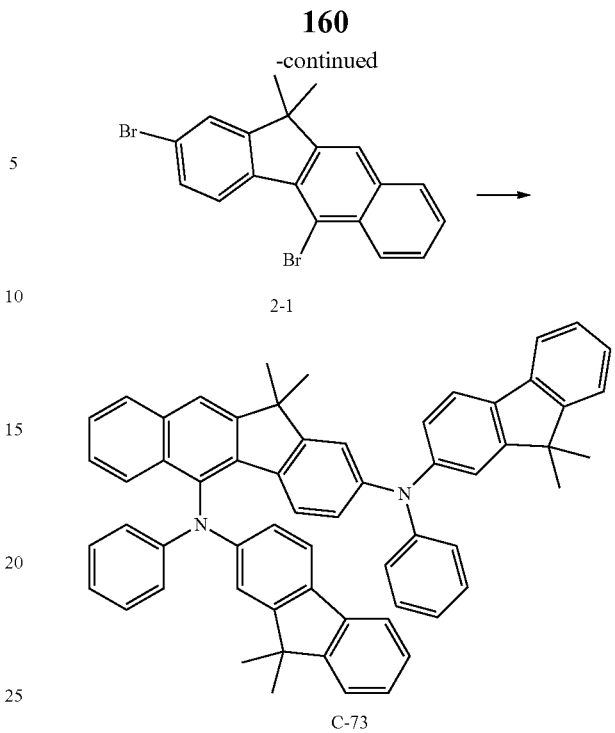

C-73

Preparation of Compound 2-1

10 g of 2-bromo-11,11-dimethyl-11H-benzo[b]fluorene (31 mmol), 10 mL of dimethylformamide, and 7.2 g of N-bromosuccinimide (40 mmol) were introduced into a reaction vessel, and the mixture was stirred at room temperature overnight. The reaction solution was diluted with ethylacetate and washed with distilled water. The extracted organic layer was then dried with magnesium sulfate. The solvent was removed with a rotary evaporator, and the separated solid was filtered and washed with cold methyl alcohol to obtain 10.5 mg of compound 2-1 (yield: 84%).

Preparation of Compound C-73

10 g of compound 2-1 (25 mmol), 15.6 g of N-1,1'-biphenyl-4-yl-9,9-diphenyl-9H-fluorene-2-amine (55 mmol), 2.3 g of tris(dibenzylideneacetone)dipalladium(0) (2.5 mmol), 2 mL of tri-t-butylphosphine (5 mmol, 50% toluene solution), 9.6 g of sodium t-butoxide (99 mmol), and 240 mL of toluene were introduced into a reaction vessel, and the mixture was refluxed for 3 hours. The reaction solution was cooled to room temperature. The solvent was removed with a rotary evaporator, and the resulting product was purified by column chromatography to obtain 9.6 g of compound C-73 (yield: 47%). The properties of compound C-73 are shown in Table 1.

EXAMPLE 5: PREPARATION OF COMPOUND C-10

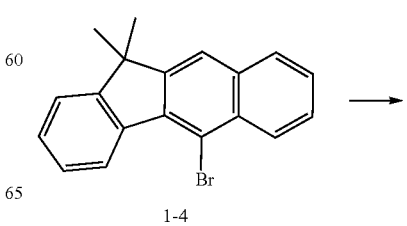

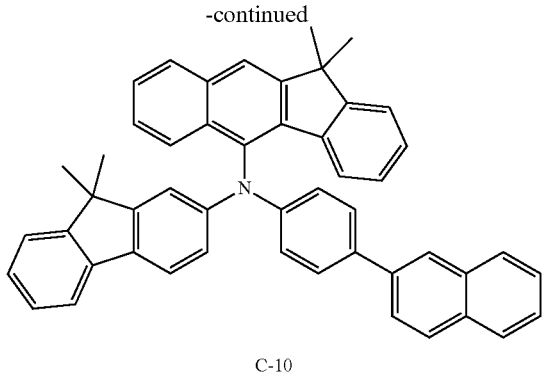

C-10

7.4 g of compound 1-4 (23 mmol), 9.4 g of 9,9-dimethyl-N-(4-(naphthalen-2-yl)phenyl)-9H-fluorene-2-amine (23 mmol), 1.05 g of tris(dibenzylideneacetone)dipalladium(0) (1.15 mmol), 1.2 mL of tri-t-butylphosphine (2.3 mmol, 50% toluene solution), 4.4 g of sodium t-butoxide (46 mmol), and 200 mL of toluene were introduced into a reaction vessel, and the mixture was refluxed for 3 hours at 80° C. The reaction solution was cooled to room temperature. The solvent was removed with a rotary evaporator, and the resulting product was purified by column chromatography to obtain 3.7 g of compound C-10 (yield: 25%). The properties of compound C-10 are shown in Table 1.

EXAMPLE 6: PREPARATION OF COMPOUND C-91

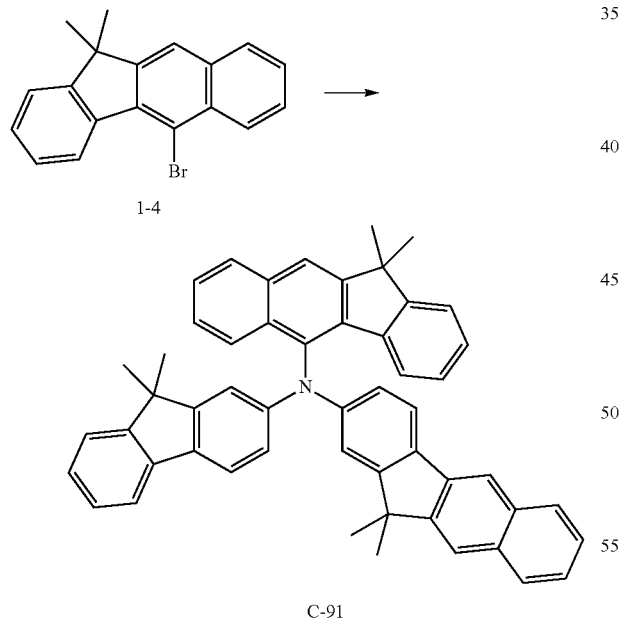

C-91

10 g of compound 1-4 (31 mmol), 14.0 g of N-(9,9-dimethyl-9H-fluoren-2-yl)-11,11'-dimethyl-11H-benzo[b]fluorene-2-amine (31 mmol), 1.42 g of tris(dibenzylideneacetone)dipalladium(0) (1.60 mmol), 1.6 mL of tri-t-butylphosphine (3.1 mmol, 50% toluene solution), 5.9 g of sodium t-butoxide (62 mmol), and 155 mL of toluene were introduced into a reaction vessel, and the mixture was refluxed for 16 hours at 80° C. The reaction solution was cooled to room temperature. The solvent was removed with a rotary evaporator, and the resulting product was purified by column chromatography to obtain 9.1 g of compound C-91 (yield: 42%). The properties of compound C-91 are shown in Table 1.

EXAMPLE 7: PREPARATION OF COMPOUND C-92

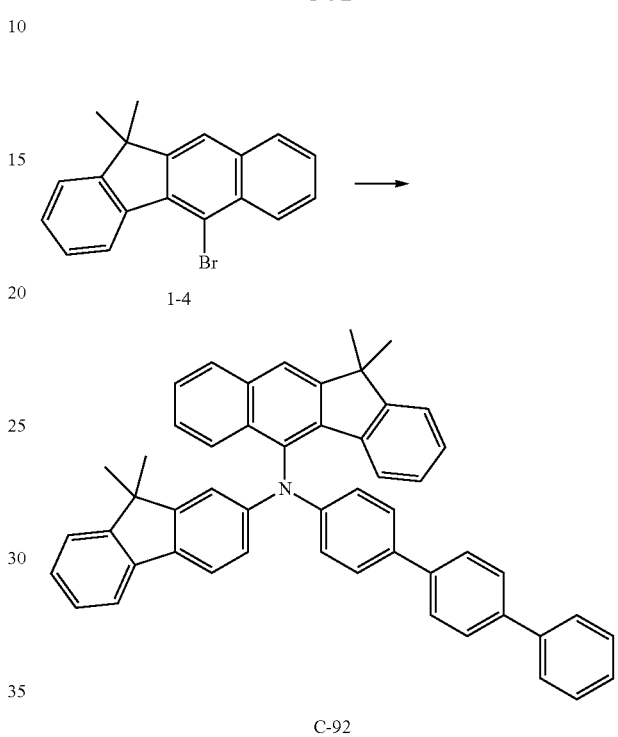

C-92

8 g of compound 1-4 (25 mmol), 11.9 g of N-([1,1':4',1''-terphenyl]-4-yl)-9,9-dimethyl-9H-fluorene-2-amine (27 mmol), 1.13 g of tris(dibenzylideneacetone)dipalladium(0) (1.35 mmol), 1.0 mL of tri-t-butylphosphine (2.7 mmol, 50% toluene solution), 4.8 g of sodium t-butoxide (50 mmol), and 125 mL of toluene were introduced into a reaction vessel, and the mixture was refluxed for 3 hours at 80° C. The reaction solution was cooled to room temperature. The solvent was removed with a rotary evaporator, and the resulting product was purified by column chromatography to obtain 5.7 g of compound C-92 (yield: 34%). The properties of compound C-92 are shown in Table 1.

EXAMPLE 8: PREPARATION OF COMPOUND C-71

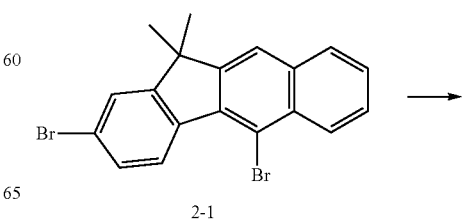

2-1

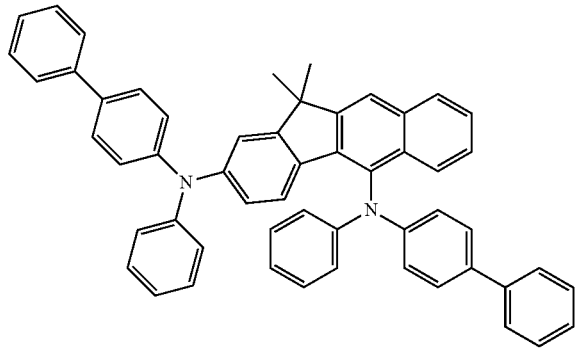

C-71

10 g of compound 2-1 (25 mmol), 13.4 g of N-phenyl-[1,1'-biphenyl]-4-amine (55 mmol), 2.3 g of tris(dibenzylideneacetone)dipalladium(0) (2.5 mmol), 2 mL of tri-t-butylphosphine (5 mmol, 50% toluene solution), 9.6 g of sodium t-butoxide (99 mmol), and 260 mL of toluene were introduced into a reaction vessel, and the mixture was refluxed for 3 hours at 80° C. The reaction solution was cooled to room temperature. The solvent was removed with a rotary evaporator, and the resulting product was purified by column chromatography to obtain 5.2 g of compound C-71 (yield: 18%). The properties of compound C-71 are shown in Table 1.

EXAMPLE 9: PREPARATION OF COMPOUND C-93

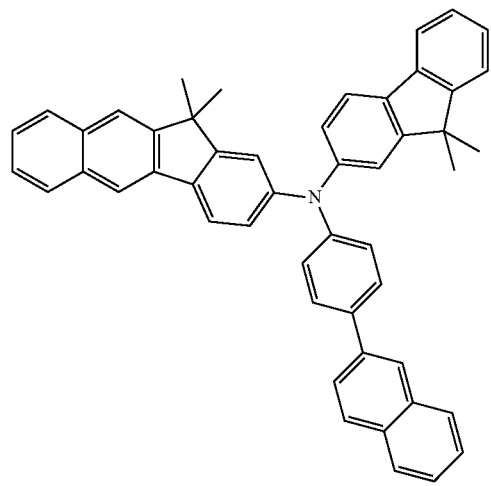

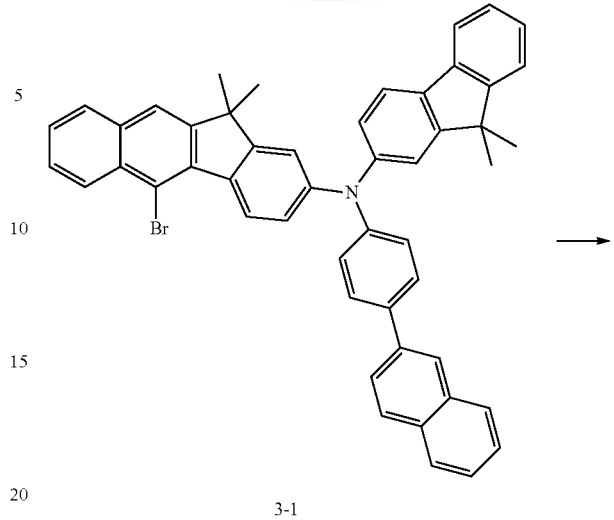

3-1

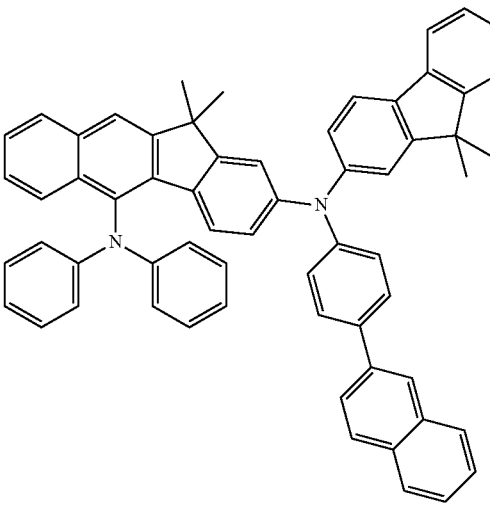

C-93

Preparation of Compound 3-1

15 g of N-(9,9-dimethyl-9H-fluoren-2-yl)-11,11-dimethyl-N-(4-(naphthalen-2-yl)phenyl)-1H-benzo[b]fluorene-2-amine (23 mmol), 120 mL of dimethylformamide, and 5.3 g of N-bromosuccinimide (30 mmol) were introduced into a reaction vessel, and the mixture was stirred at room temperature overnight. The reaction solution was diluted with ethylacetate and washed with distilled water. The extracted organic layer was then dried with magnesium sulfate. The solvent was removed with a rotary evaporator, and the resulting product was purified by column chromatography to obtain 15 g of compound 3-1 (yield: 89%).

Preparation of Compound C-93

10 g of compound 3-1 (14 mmol), 2.7 g of diphenylamine (16 mmol), 0.63 g of tris(dibenzylideneacetone)dipalladium(0) (0.68 mmol), 0.5 mL of tri-t-butylphosphine (1.4 mmol, 50% toluene solution), 2.6 g of sodium t-butoxide (28 mmol), and 260 mL of toluene were introduced into a reaction vessel, and the mixture was refluxed for 3 hours at 80° C. The reaction solution was cooled to room temperature. The solvent was removed with a rotary evaporator, and the resulting product was purified by column chromatography to obtain 3.1 g of compound C-93 (yield: 18%). The properties of compound C-93 are shown in Table 1.

EXAMPLE 10: PREPARATION OF COMPOUND C-94

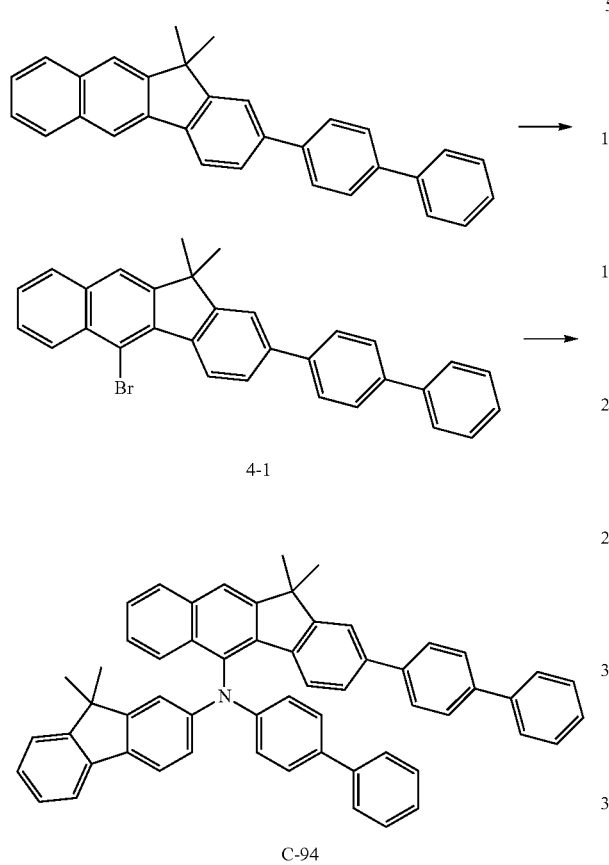

4-1

C-94

EXAMPLE 11: PREPARATION OF COMPOUND C-25

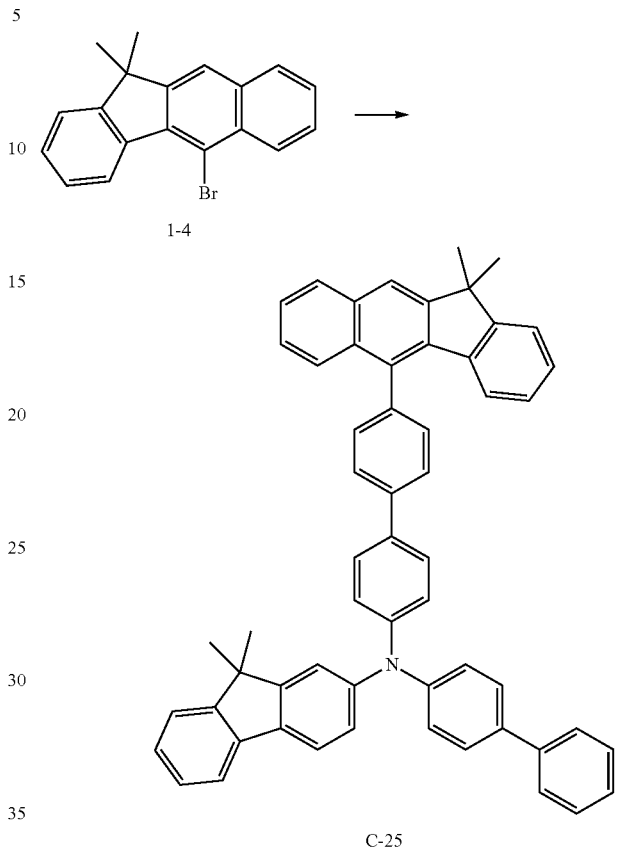

1-4

C-25

Preparation of Compound 4-1

26 g of 2-([1,1'-biphenyl]-4-yl)-11,11-dimethyl-11H-benzo[b]fluorene (66 mmol), 330 mL of dimethylformamide, 200 mL of methylene chloride, and 15.2 g of N-bromosuccinimide (85 mmol) were introduced into a reaction vessel, and the mixture was stirred at room temperature overnight. The reaction solution was diluted with ethylacetate and washed with distilled water. The extracted organic layer was then dried with magnesium sulfate. The solvent was removed with a rotary evaporator, and the resulting product was purified by column chromatography to obtain 26 g of compound 4-1 (yield: 83%).

Preparation of Compound C-94

13 g of compound 4-1 (27 mmol), 9.9 g of N-1,1'-biphenyl-4-yl-9,9-dimethyl-9H-fluorene-2-amine (27 mmol), 1.25 g of tris(dibenzylideneacetone)dipalladium(0) (1.4 mmol), 1.1 mL of tri-t-butylphosphine (2.7 mmol, 50% toluene solution), 5.3 g of sodium t-butoxide (54 mmol), and 136 mL of toluene were introduced into a reaction vessel, and the mixture was refluxed for 3 hours at 80° C. The reaction solution was cooled to room temperature. The solvent was removed with a rotary evaporator, and the resulting product was purified by column chromatography to obtain 4.5 g of compound C-94 (yield: 22%). The properties of compound C-94 are shown in Table 1.

4 g of compound 1-4 (12 mmol), 7.9 g of N-([1,1'-biphenyl]-4-yl)-9,9-dimethyl-N-(4'-(4,4,5,5-tetramethyl-1,3,2-dioxaborolan-2-yl)-[1,1'-biphenyl]-4-yl)-9H-fluorene-2-amine (12 mmol), 0.72 g of tetrakis(triphenylphosphine) palladium (0.6 mmol), 3.4 g of potassium carbonate (24 mmol), 30 mL of toluene, and 15 mL of ethyl alcohol were introduced into a reaction vessel, 15 mL of distilled water was added thereto, and the mixture was stirred at 80° C. for 18 hours. After completion of the reaction, ethyl alcohol and toluene were removed with a rotary evaporator, and an organic layer was extracted with methylene chloride and distilled water. The organic layer was then dried with magnesium sulfate. The solvent was removed with a rotary evaporator, and the resulting product was purified by column chromatography to obtain 3.1 g of compound C-25 (yield: 33%). The properties of compound C-25 are shown in Table 1.

TABLE 1

| Compound | Yield (%) | UV (nm) | PL (nm) | M.P. (° C.) | MS/EIMS (M + H) Found | Calculated |
|---|---|---|---|---|---|---|
| C-4 | 52 | 422 | 481 | 222 | 644.2 | 644.3 |
| C-5 | 51 | 384 | 473 | 250 | 604.2 | 604.3 |
| C-7 | 49 | 418 | 447 | 251 | 728.2 | 728.3 |
| C-73 | 47 | 418 | 445 | 286 | 811.3 | 811.4 |
| C-10 | 25 | 410 | 473 | 165 | 654.2 | 654.3 |
| C-91 | 42 | 418 | 479 | 173.5 | 694.2 | 694.4 |

TABLE 1-continued

| Compound | Yield (%) | UV (nm) | PL (nm) | M.P. (° C.) | MS/EIMS (M + H) Found | MS/EIMS (M + H) Calculated |
|---|---|---|---|---|---|---|
| C-92 | 34 | 394 | 449 | 258 | 680.2 | 680.3 |
| C-71 | 18 | 420 | 443 | 167 | 731.2 | 731.3 |
| C-93 | 28 | 415 | 461 | 295 | 821.2 | 821.4 |
| C-94 | 22 | 378 | 489 | 184 | 756.2 | 756.4 |
| C-25 | 33 | 392 | 459 | 179 | 756.2 | 756.4 |

DEVICE EXAMPLE 1: PRODUCTION OF AN OLED DEVICE COMPRISING THE ORGANIC ELECTROLUMINESCENT COMPOUND OF THE PRESENT DISCLOSURE

An OLED device comprising the organic electroluminescent compound of the present disclosure was produced as follows. A transparent electrode indium tin oxide (ITO) thin film (10 Ω/sq) on a glass substrate for an organic light-emitting diode (OLED) device (Geomatec, Japan) was subjected to an ultrasonic washing with acetone, ethanol, and distilled water, sequentially, and was then stored in isopropanol. Next, the ITO substrate was mounted on a substrate holder of a vacuum vapor depositing apparatus. $N^4,N^{4'}$-diphenyl-$N^4,N^{4'}$-bis(9-phenyl-9H-carbazol-3-yl)-[1,1'-biphenyl]-4,4'-diamine (compound HI-1) was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 90 nm on the ITO substrate. 1,4,5,8,9,12-hexaazatriphenylene-hexacarbonitrile (compound HI-2) was then introduced into another cell of said vacuum vapor depositing apparatus, and was evaporated by applying an electric current to the cell, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluoren-2-amine (compound HT-1) was introduced into another cell of said vacuum vapor depositing apparatus, and was evaporated by applying an electric current to the cell, thereby forming a first hole transport layer having a thickness of 10 nm on the second hole injection layer. Compound C-4 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. Compound B-198 as below was introduced into one cell of the vacuum vapor depositing apparatus as a host, and compound D-71 was introduced into another cell as a dopant. The two materials were evaporated at different rates and were deposited in a doping amount of 2 wt % (the amount of dopant) based on the total amount of the dopant and host to form a light-emitting layer having a thickness of 40 nm on the second hole transport layer. 2,4-bis(9,9-dimethyl-9H-fluoren-2-yl)-6-(naphthalen-2-yl)-1,3,5-triazine (compound ET-1) and lithium quinolate (compound EI-1) were then introduced into another two cells, evaporated at the rate of 1:1, and deposited to form an electron transport layer having a thickness of 35 nm on the light-emitting layer. Next, after depositing lithium quinolate (compound EI-1) as an electron injection layer having a thickness of 2 nm on the electron transport layer, an Al cathode having a thickness of 80 nm was deposited by another vacuum vapor deposition apparatus on the electron injection layer. Thus, an OLED device was produced.

The driving voltage, luminous efficiency, and CIE color coordinates at a luminance of 1,000 nit of the produced OLED device are provided in Table 2 below.

DEVICE EXAMPLES 2 AND 3: PRODUCTION OF AN OLED DEVICE COMPRISING THE ORGANIC ELECTROLUMINESCENT COMPOUND OF THE PRESENT DISCLOSURE

OLED devices were produced in the same manner as in Device Example 1, except for using the compounds shown in Table 2 for the second hole transport layer.

The driving voltage, luminous efficiency, and CIE color coordinates at a luminance of 1,000 nit of the produced OLED devices are provided in Table 2 below.

COMPARATIVE EXAMPLES 1 TO 3: PRODUCTION OF AN OLED DEVICE COMPRISING A CONVENTIONAL ORGANIC ELECTROLUMINESCENT COMPOUND

OLED devices were produced in the same manner as in Device Example 1, except for using the compounds shown in Table 2 for the second hole transport layer.

The driving voltage, luminous efficiency, and CIE color coordinates at a luminance of 1,000 nit of the produced OLED devices are provided in Table 2 below.

TABLE 2

| | Second hole transport layer | Voltage (V) | Efficiency (cd/A) | Color coordinate (x) | Color coordinate (y) |
|---|---|---|---|---|---|
| Device Example 1 | C-4 | 2.8 | 19.0 | 0.670 | 0.329 |
| Device Example 2 | C-5 | 2.7 | 24.7 | 0.671 | 0.329 |
| Device Example 3 | C-7 | 2.7 | 26.2 | 0.671 | 0.328 |
| Comparative Example 1 | R-1 | 2.9 | 12.2 | 0.667 | 0.331 |
| Comparative Example 2 | R-2 | 2.8 | 15.2 | 0.669 | 0.329 |
| Comparative Example 3 | R-3 | 2.9 | 15.8 | 0.670 | 0.329 |

DEVICE EXAMPLES 4 TO 11: PRODUCTION OF AN OLED DEVICE COMPRISING THE ORGANIC ELECTROLUMINESCENT COMPOUND OF THE PRESENT DISCLOSURE

OLED devices were produced in the same manner as in Device Example 1, except for using the compounds shown in Table 3 for the second hole transport layer, and using compound B-199 for the host.

The driving voltage, luminous efficiency, and CIE color coordinates at a luminance of 1,000 nit of the produced OLED devices are provided in Table 3 below.

COMPARATIVE EXAMPLES 4 AND 5: PRODUCTION OF AN OLED DEVICE COMPRISING A CONVENTIONAL ORGANIC ELECTROLUMINESCENT COMPOUND

OLED devices were produced in the same manner as in Device Example 4, except for using the compounds shown in Table 3 for the second hole transport layer.

The driving voltage, luminous efficiency, and CIE color coordinates at a luminance of 1,000 nit of the produced OLED devices are provided in Table 3 below.

TABLE 3

| | Second hole transport layer | Voltage (V) | Efficiency (cd/A) | Color coordinate (x) | Color coordinate (y) |
|---|---|---|---|---|---|
| Device Example 4 | C-8 | 2.7 | 25.1 | 0.667 | 0.332 |
| Device Example 5 | C-91 | 2.8 | 20.4 | 0.666 | 0.332 |
| Device Example 6 | C-92 | 2.8 | 23.7 | 0.669 | 0.331 |
| Device Example 7 | C-73 | 2.8 | 19.7 | 0.666 | 0.333 |
| Device Example 8 | C-71 | 2.8 | 20.6 | 0.668 | 0.331 |
| Device Example 9 | C-93 | 3.2 | 18.6 | 0.666 | 0.333 |
| Device Example 10 | C-94 | 2.9 | 26.0 | 0.669 | 0.331 |
| Device Example 11 | C-25 | 2.9 | 24.4 | 0.669 | 0.331 |
| Comparative Example 4 | R-1 | 3.0 | 14.3 | 0.663 | 0.334 |
| Comparative Example 5 | R-3 | 3.0 | 16.3 | 0.667 | 0.332 |

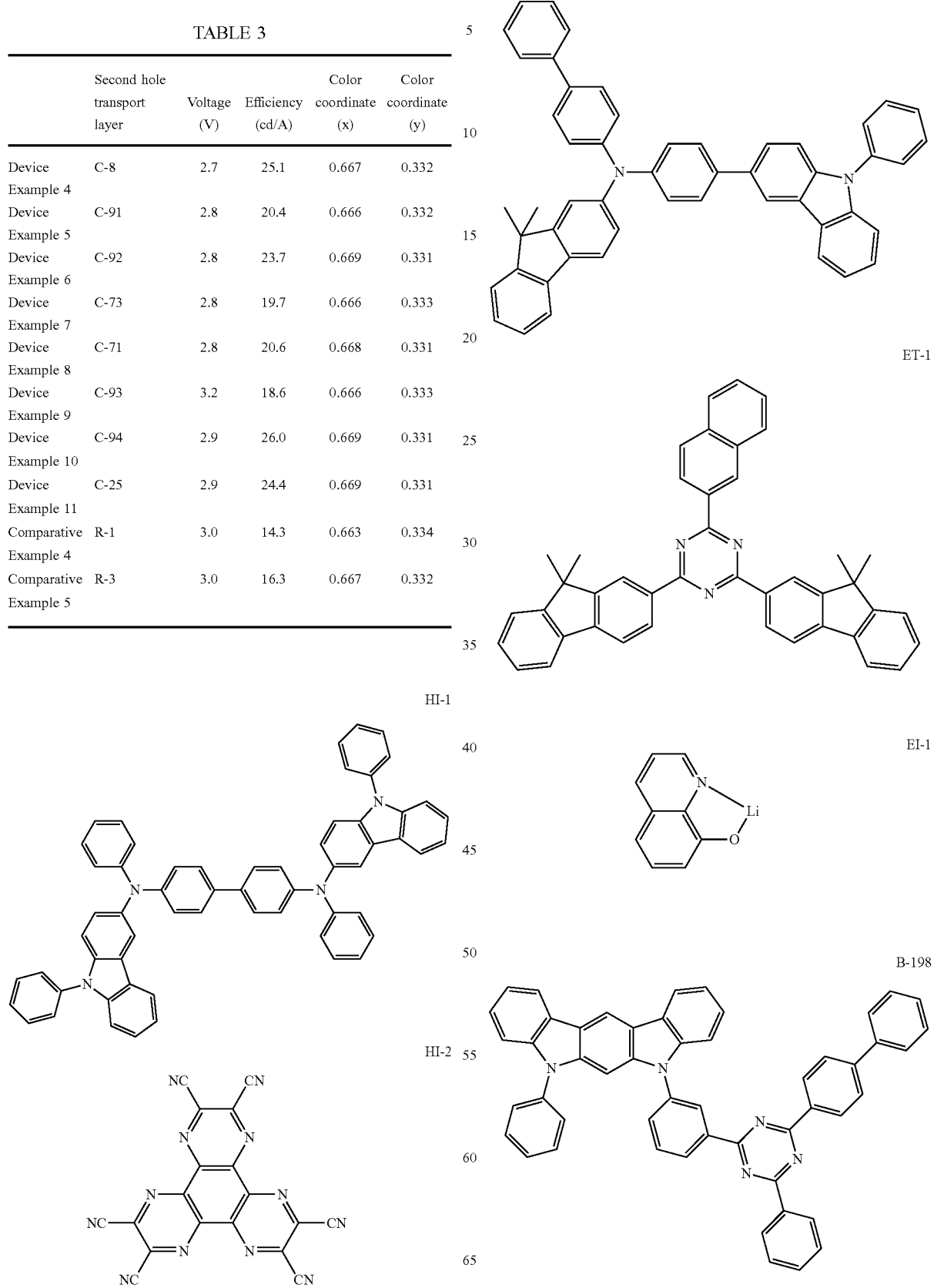

B-199
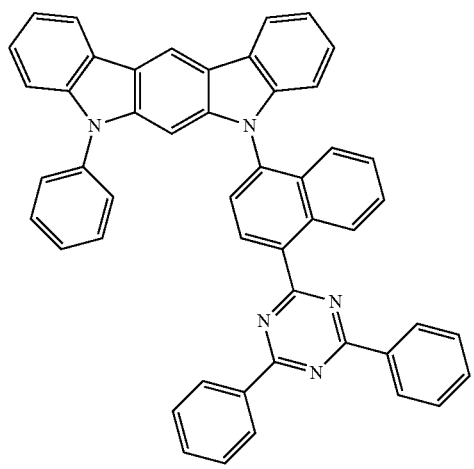
D-71
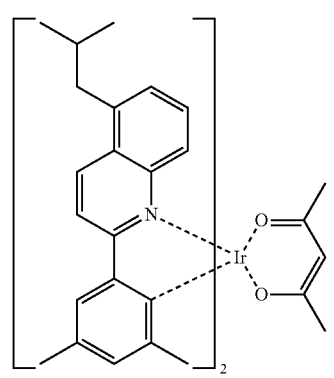
R-1
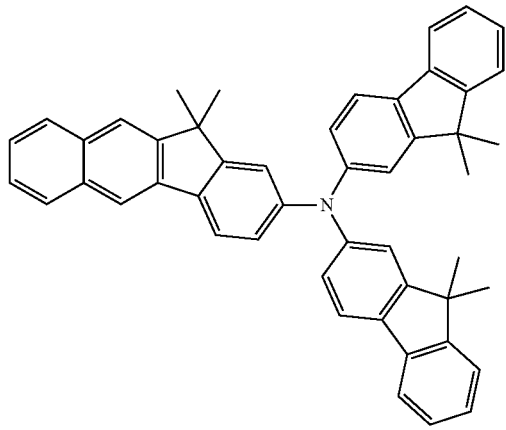
R-2
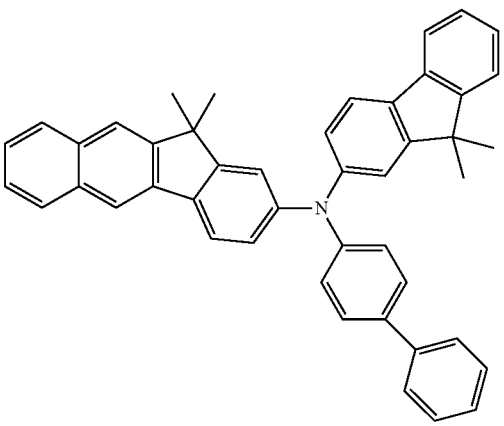
R-3
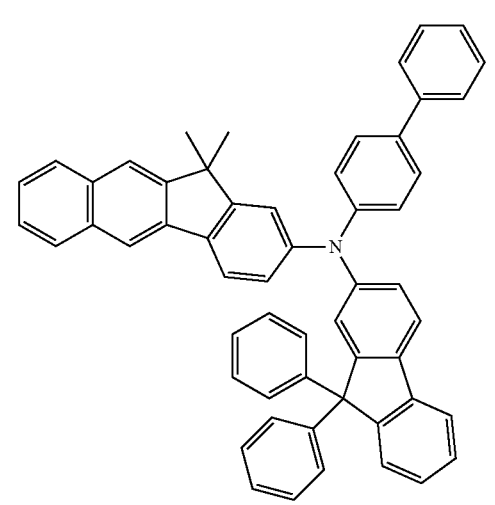
C-4
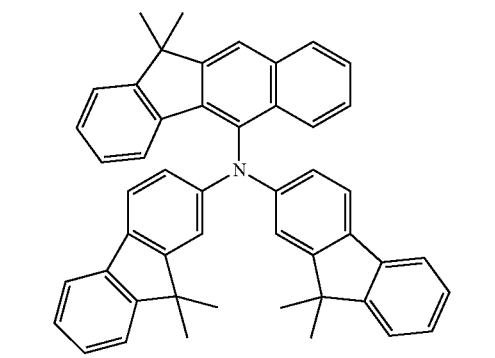
C-5
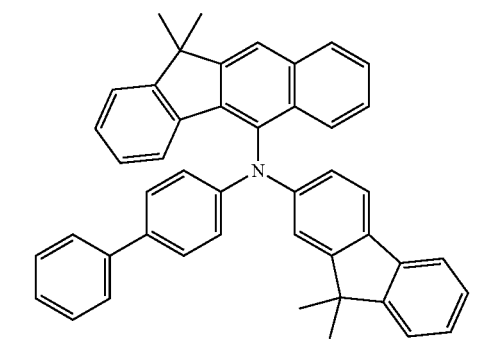

C-7
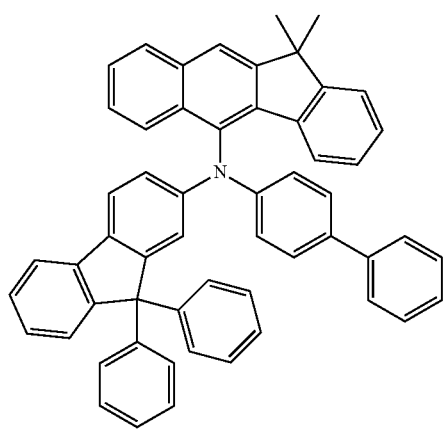
C-10
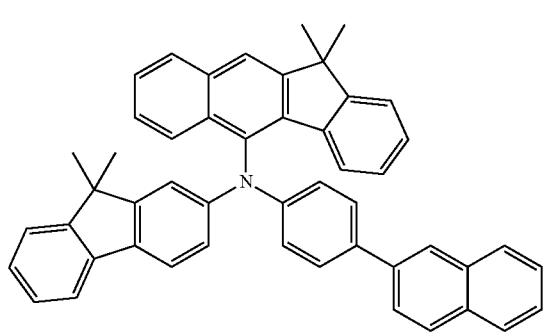
C-91
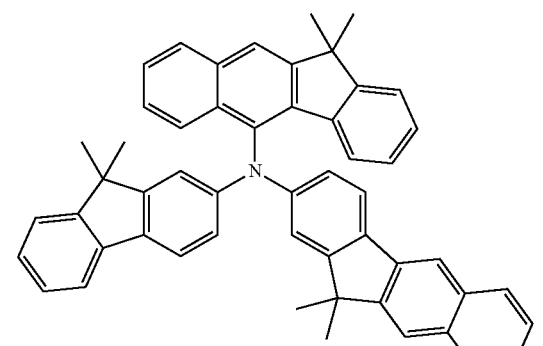
C-92
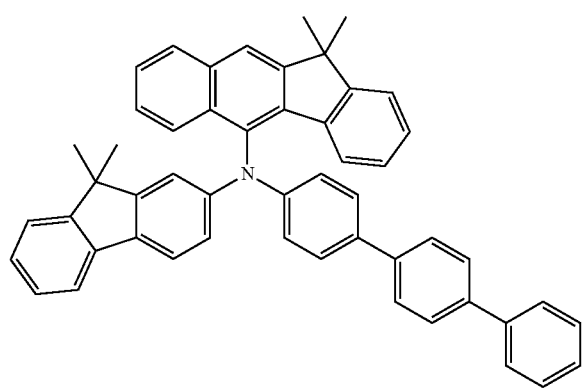
C-73
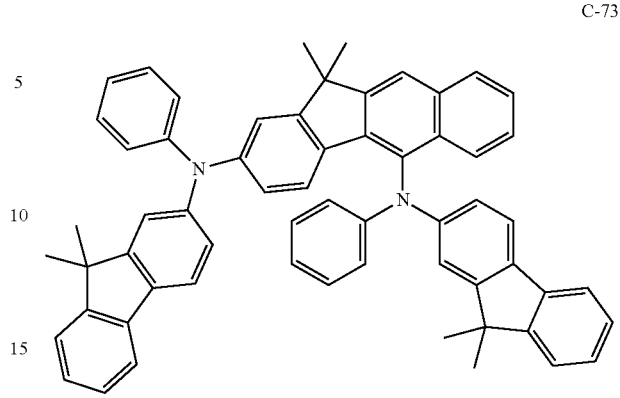
C-71
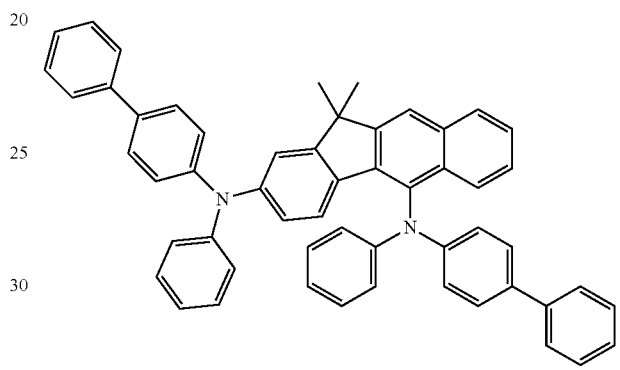
C-93
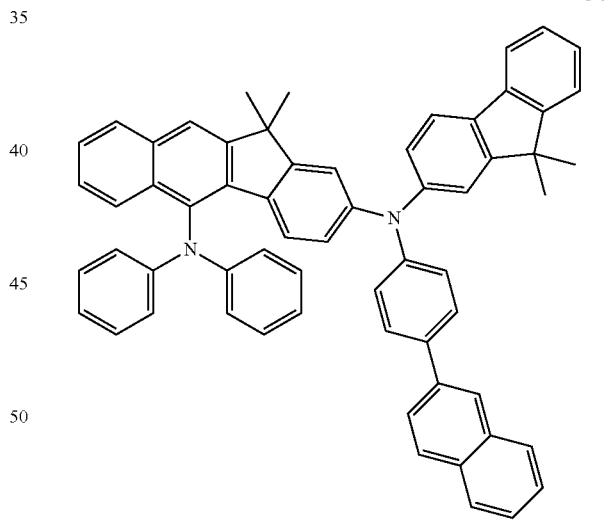
C-94
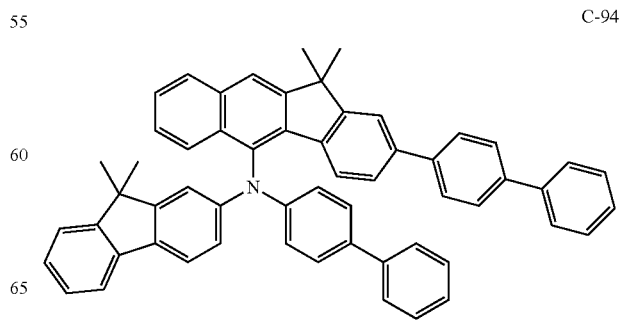

-continued

C-25

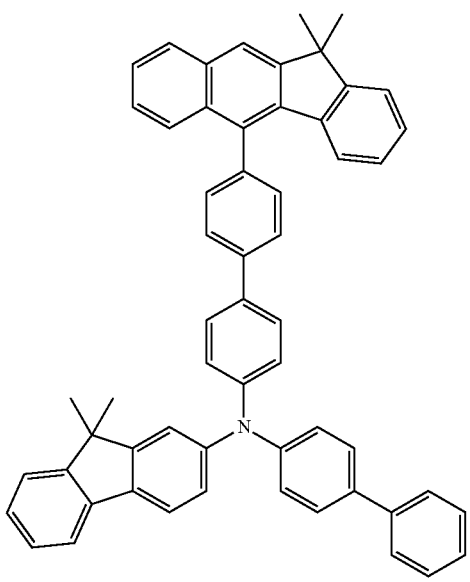

As shown in Tables 2 and 3, the devices using the organic electroluminescent compound according to the present disclosure in a second hole transport layer have excellent luminous efficiency. The second hole transport layer can also function as a hole auxiliary layer or a light-emitting auxiliary layer.

From the results, it can be seen that the characteristics of the device are varied depending on the substituent's position, i.e. whether it is bonded at the second carbon position or the fifth carbon position, of a benzo[b]fluorene structure even when the substituents are the same.

In addition, upon comparing Device Examples 1 to 3 and Comparative Examples 1 to 3, using compounds of structural isomer relation, the organic electroluminescent compound according to the present disclosure has a benzo[b]fluorene structure in which the substituent is bonded at the fifth carbon position. Accordingly, the luminous efficiency of the device increases due to the increase of triplet energy, and the thermal stability of the device is excellent due to the decrease of deposition temperature even when the molecular weight of the compounds are the same. This can be verified from Table 4 below.

TABLE 4

|  |  | HOMO (eV) | LUMO (eV) | Band gap (eV) | Triplet energy (eV) | Deposition temperature (° C.) |
|---|---|---|---|---|---|---|
| Device Example 1 | C-4 | −1.393 | −4.742 | 3.349 | 2.378 | 250 |
| Device Example 2 | C-5 | −1.397 | −4.831 | 3.434 | 2.400 | 250 |
| Device Example 3 | C-7 | −1.365 | −4.836 | 3.471 | 2.403 | 290 |
| Device Example 4 | C-8 | −1.412 | −4.826 | 3.415 | 2.398 | 280 |
| Device Example 5 | C-91 | −1.421 | −4.763 | 3.342 | 2.371 | 285 |
| Device Example 6 | C-92 | −1.411 | −4.828 | 3.417 | 2.397 | 290 |
| Device Example 7 | C-73 | −1.362 | −4.721 | 3.359 | 2.289 | 316 |
| Device Example 8 | C-71 | −1.377 | −4.803 | 3.426 | 2.310 | 315 |

TABLE 4-continued

|  |  | HOMO (eV) | LUMO (eV) | Band gap (eV) | Triplet energy (eV) | Deposition temperature (° C.) |
|---|---|---|---|---|---|---|
| Device Example 9 | C-93 | −1.385 | −4.741 | 3.356 | 2.296 | 328 |
| Device Example 10 | C-94 | −1.556 | −4.836 | 3.279 | 2.324 | 225 |
| Device Example 11 | C-25 | −1.175 | −4.826 | 3.651 | 2.520 | 360 |
| Comparative Example 1 | R-1 | −1.232 | −4.687 | 3.455 | 2.363 | 310 |
| Comparative Example 2 | R-2 | −1.242 | −4.752 | 3.510 | 2.377 | 280 |
| Comparative Example 3 | R-3 | −1.245 | −4.767 | 3.522 | 2.381 | 335 |

The invention claimed is:

1. An organic electroluminescent compound of the following formula 1:

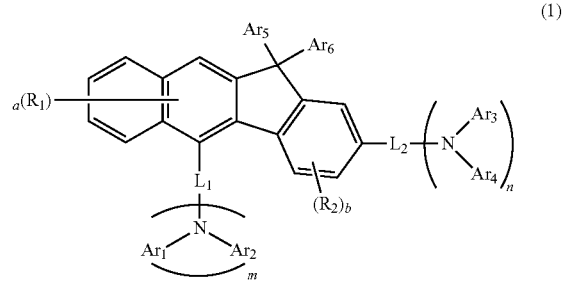

(1)

wherein

Ar$_1$ to Ar$_6$ each independently are selected from the group consisting of a substituted or unsubstituted (C1-C30) alkyl, a substituted or unsubstituted (C6-C30)aryl, a substituted or unsubstituted 5- to 30-membered heteroaryl, and a substituted or unsubstituted spiro[fluorene-(C3-C30)cycloalkane]yl; or Ar$_1$ and Ar$_2$, Ar$_3$ and Ar$_4$, and Ar$_5$ and Ar$_6$ may be linked to each other to form a mono- or polycyclic, 3- to 30-membered alicyclic or aromatic ring, whose carbon atom(s) may be replaced with at least one hetero atom selected from nitrogen, oxygen, and sulfur;

L$_1$ is selected from the group consisting of a single bond, a substituted or unsubstituted (C6-C30)arylene, and a substituted or unsubstituted 5- to 30-membered heteroarylene;

L$_2$ is selected from the group consisting of a single bond, a substituted or unsubstituted (C1-C30)alkylene, a substituted or unsubstituted (C6-C30)arylene, and a substituted or unsubstituted 5- to 30-membered heteroarylene, with a proviso that where n is 0, L$_2$ does not exist;

R$_1$ and R$_2$ each independently are selected from the group consisting of hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted 3- to 7-membered heterocycloalkyl, a substituted or unsubstituted (C6-C30)aryl(C1-C30) alkyl, —NR$_{11}$R$_{12}$, —SiR$_{13}$R$_{14}$R$_{15}$, —SR$_{16}$, —OR$_{17}$, a cyano, a nitro, and a hydroxyl; or are linked to an adjacent substituent(s) to form a mono- or polycyclic, 3- to 30-membered alicyclic or aromatic ring, whose carbon atom(s) may be replaced with at least one hetero atom selected from nitrogen, oxygen, and sulfur;

$R_{11}$ to $R_{17}$ each independently are selected from the group consisting of hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted 3- to 7-membered heterocycloalkyl, and a substituted or unsubstituted (C3-C30)cycloalkyl; or are linked to an adjacent substituent(s) to form a mono- or polycyclic, 3- to 30-membered alicyclic or aromatic ring, whose carbon atom(s) may be replaced with at least one hetero atom selected from nitrogen, oxygen, and sulfur;

m represents an integer of 1 to 2, where m is 2, each of $NAr_1Ar_2$ may be the same or different;

n represents an integer of 0 to 2, where n is 2, each of $NAr_3Ar_4$ may be the same or different;

a represents an integer of 1 to 5, where a is an integer of 2 or more, each of $R_1$ may be the same or different;

b represents an integer of 1 to 4, where b is an integer of 2 or more, each of $R_2$ may be the same or different;

the heteroaryl(ene) contains at least one hetero atom selected from B, N, O, S, Si, and P; and the heterocycloalkyl contains at least one hetero atom selected from O, S, and N.

2. The organic electroluminescent compound according to claim 1, wherein the compound of formula 1 is selected from the group consisting of formula 2 and formula 3:

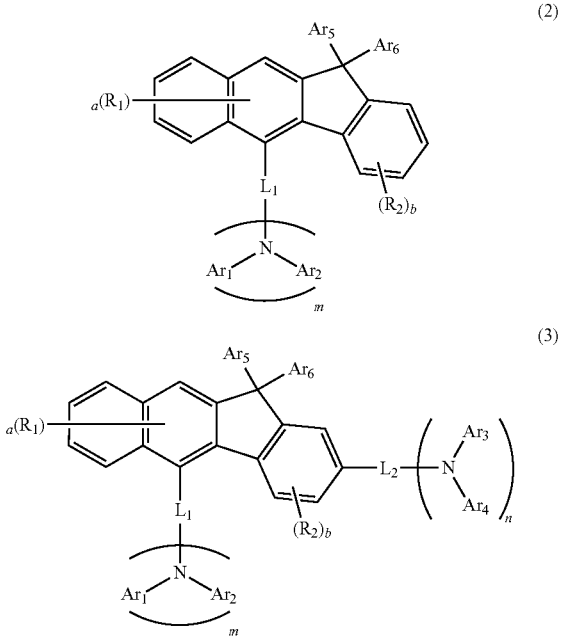

wherein $Ar_1$ to $Ar_6$, $L_1$, $L_2$, $R_1$, $R_2$, a, b, m, and n are as defined in claim 1.

3. The organic electroluminescent compound according to claim 1, wherein the substituents of the substituted alkyl(ene), the substituted aryl(ene), the substituted heteroaryl(ene), the substituted cycloalkyl, the substituted heterocycloalkyl, the substituted arylalkyl, and the substituted spiro[fluorene-(C3-C30)cycloalkane]yl in $Ar_1$ to $Ar_6$, $L_1$, $L_2$, $R_1$, $R_2$, and $R_{11}$ to $R_{17}$ each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

4. The organic electroluminescent compound according to claim 1, wherein $Ar_1$ to $Ar_4$ each independently are selected from the group consisting of a substituted or unsubstituted (C6-C25)aryl, a substituted or unsubstituted 5- to 15-membered heteroaryl, and a substituted or unsubstituted spiro[fluorene-(C5-C8)cycloalkane]yl;

$Ar_5$ and $Ar_6$ each independently are selected from the group consisting of a substituted or unsubstituted (C1-C6)alkyl, and a substituted or unsubstituted (C6-C12)aryl; or may be linked to each other to form a mono- or polycyclic, 5- to 15-membered alicyclic or aromatic ring;

$L_1$ is selected from the group consisting of a single bond, a substituted or unsubstituted (C6-C20)arylene, and a substituted or unsubstituted 5- to 15-membered heteroarylene;

$L_2$ is selected from the group consisting of a single bond, and a substituted or unsubstituted (C6-C12)arylene, with a proviso that where n is 0, $L_2$ does not exist; and $R_1$ and $R_2$ each independently represent hydrogen.

5. The organic electroluminescent compound according to claim 1, wherein $Ar_1$ to $Ar_4$ each independently are selected from the group consisting of a (C6-C25)aryl unsubstituted or substituted with a (C1-C6)alkyl or a (C6-C20)aryl; a 5- to 15-membered heteroaryl unsubstituted or substituted with a (C1-C6)alkyl or a (C6-C12)aryl; an unsubstituted spiro[fluorene-cyclopentane]yl; and an unsubstituted spiro[fluorene-cyclohexane]yl;

$Ar_5$ and $Ar_6$ each independently are selected from the group consisting of an unsubstituted (C1-C6)alkyl, and an unsubstituted (C6-C12)aryl; or may be linked to each other to form a monocyclic, 5- to 15-membered alicyclic ring;

$L_1$ is selected from the group consisting of a single bond, an unsubstituted (C6-C20)arylene, and an unsubstituted 5- to 15-membered heteroarylene;

$L_2$ is selected from the group consisting of a single bond, and an unsubstituted (C6-C12)arylene, with a proviso that where n is 0, $L_2$ does not exist; and $R_1$ and $R_2$ each independently represent hydrogen.

6. The organic electroluminescent compound according to claim 1, wherein the compound of formula 1 is selected from the group consisting of:

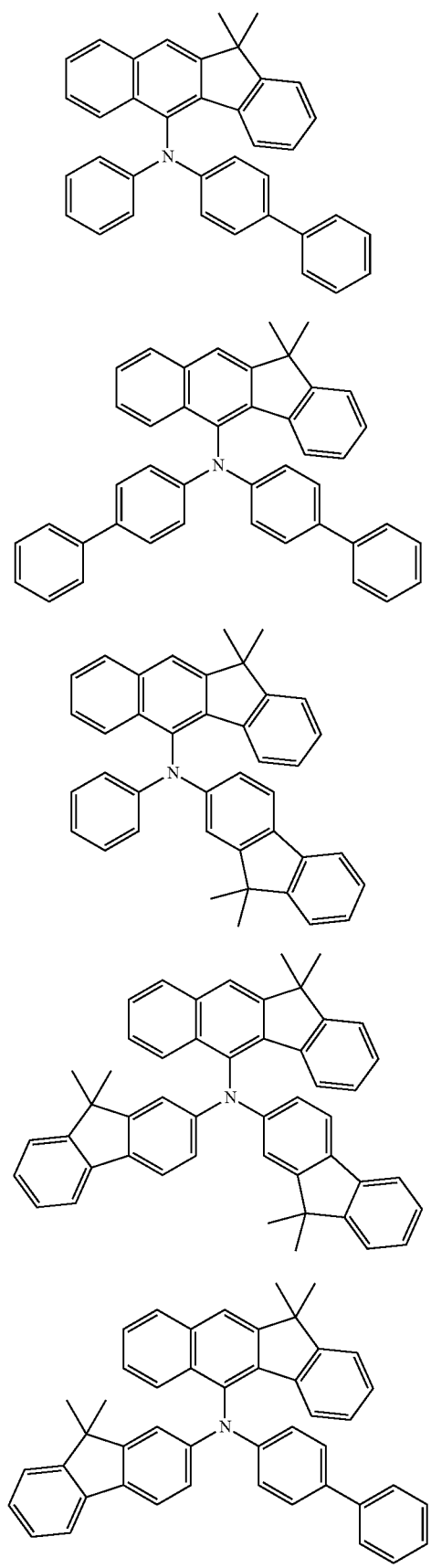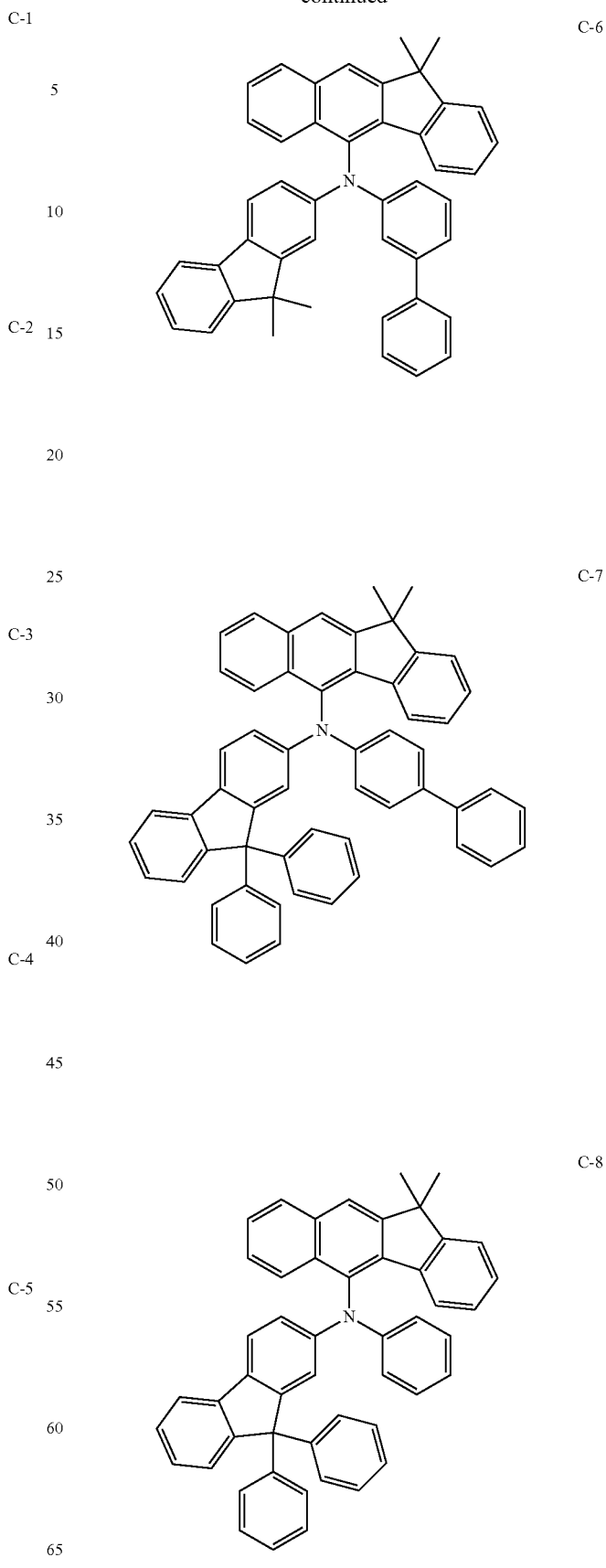

-continued
C-9
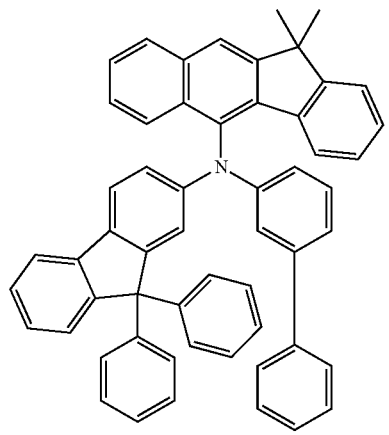
C-10
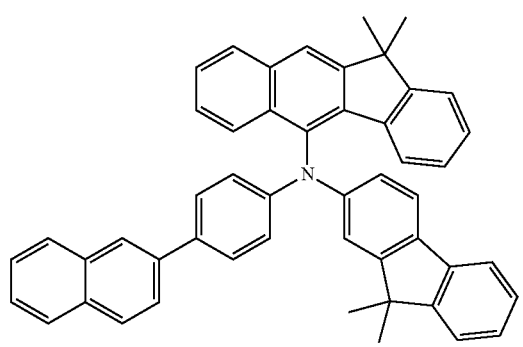
C-11
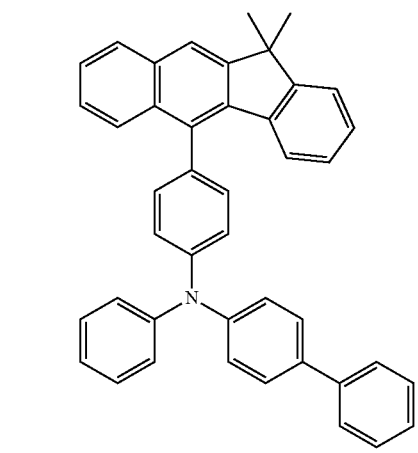
-continued
C-12
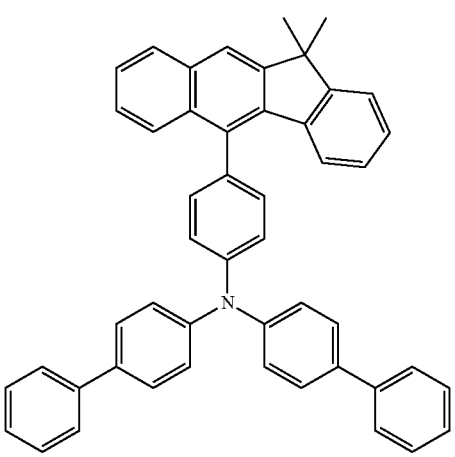
C-13
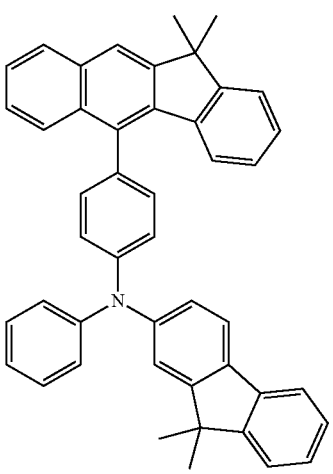
C-14
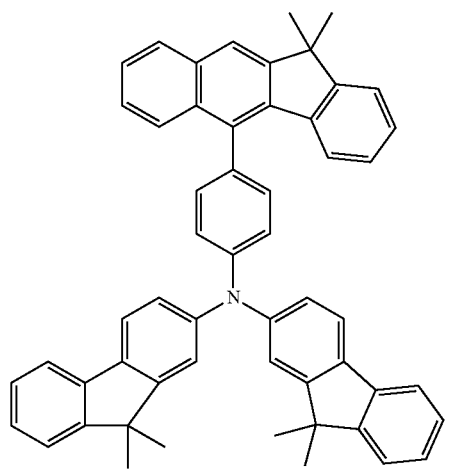

-continued
C-15
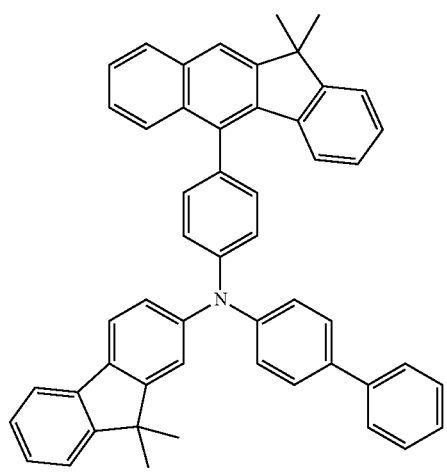
C-16
C-17
C-18
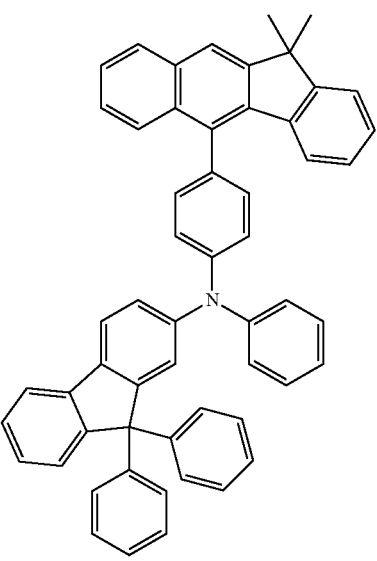
C-19
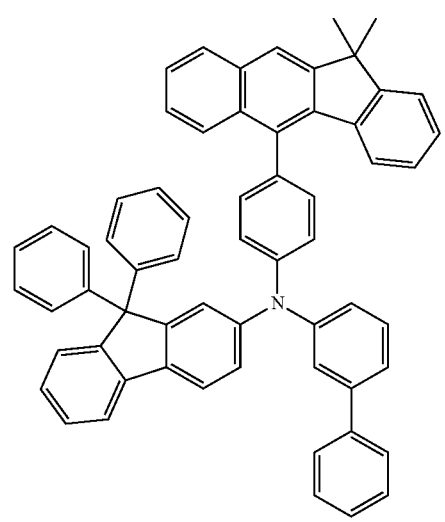
C-20
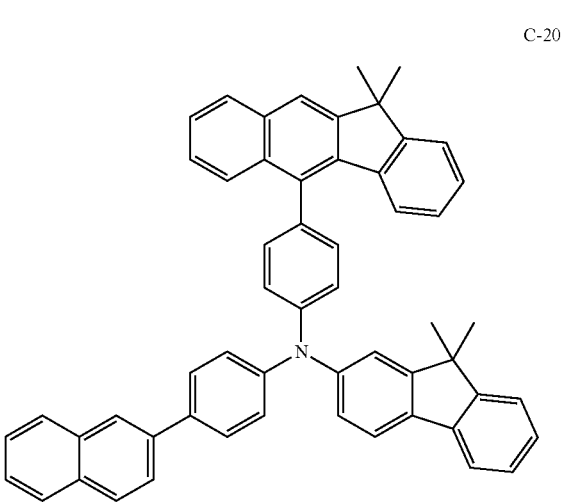

C-21
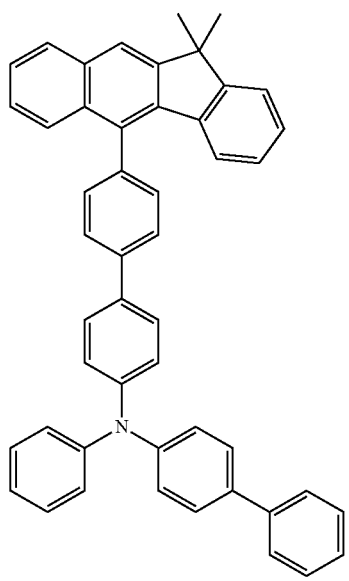
C-22
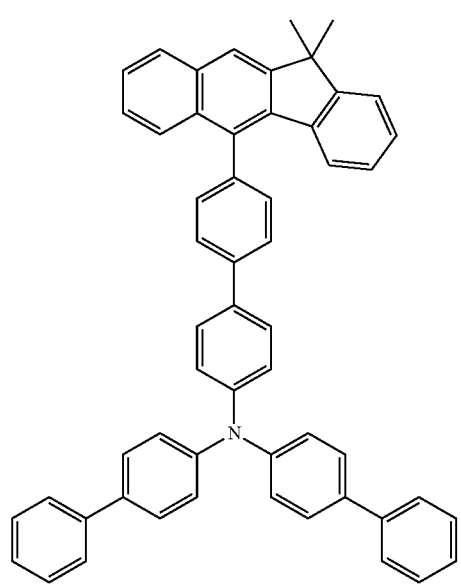
C-23
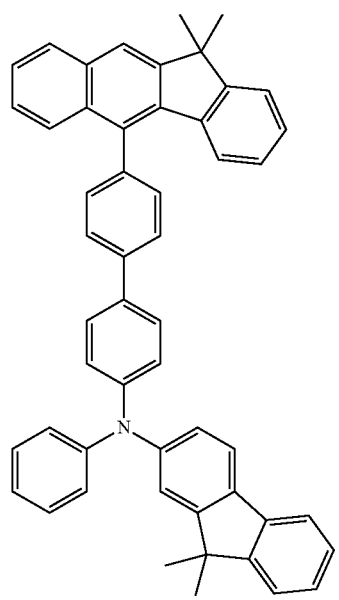
C-24
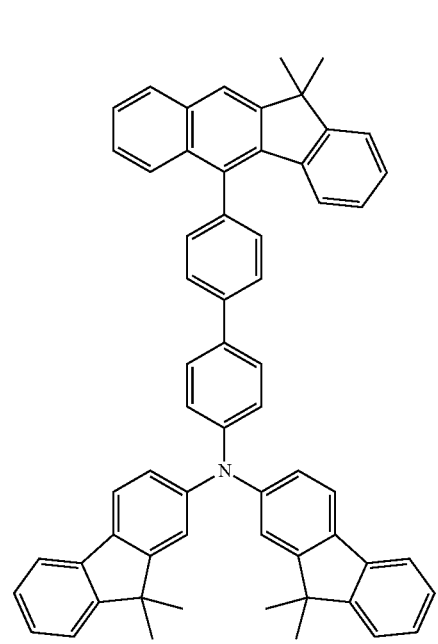

C-25
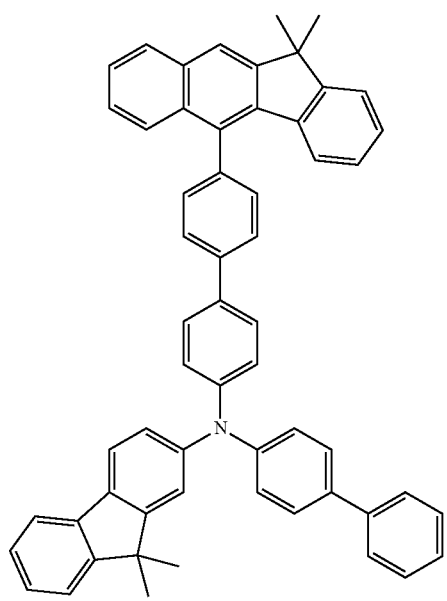
C-27
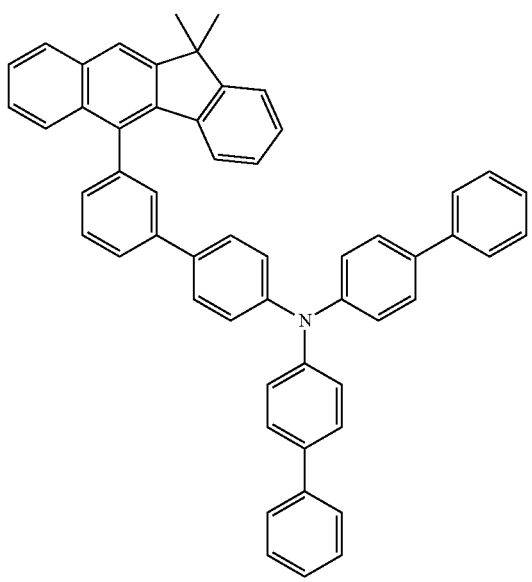
C-26
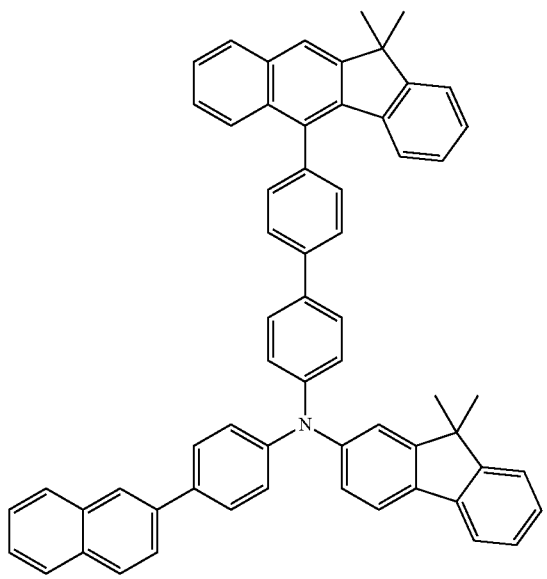
C-28
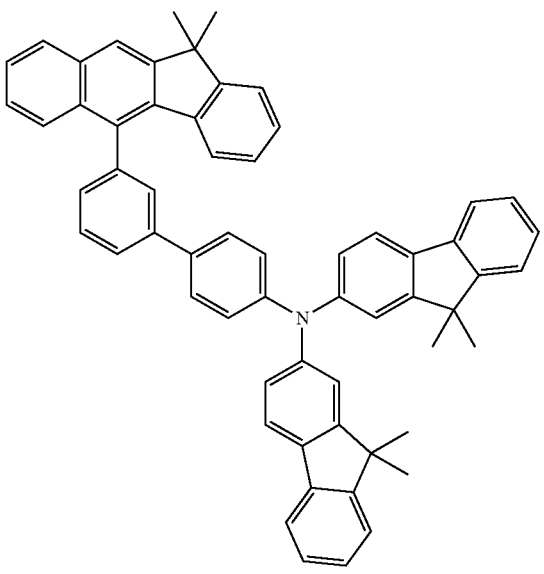

-continued
C-29
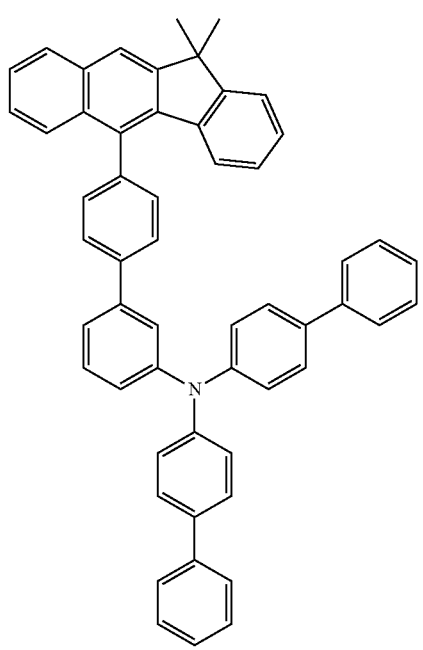
C-30
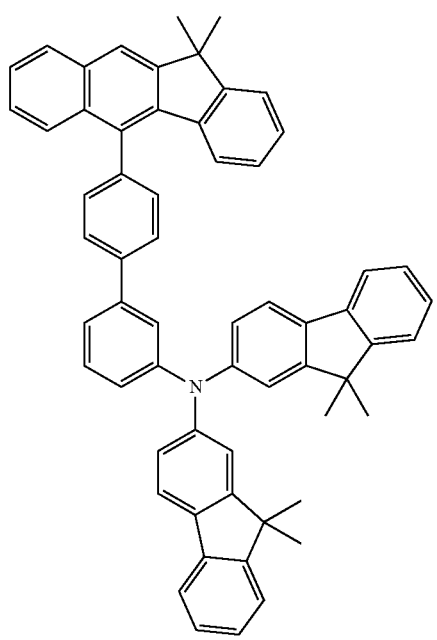
C-31
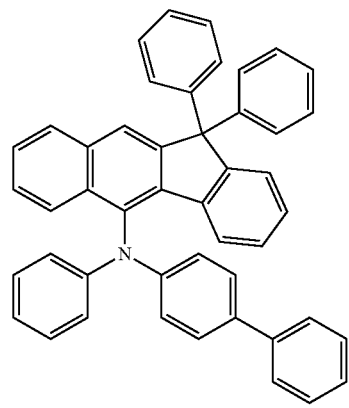
-continued
C-32
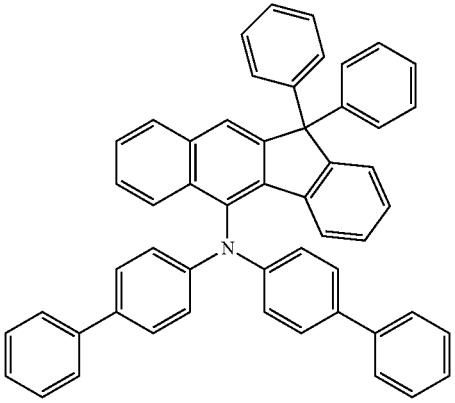
C-33
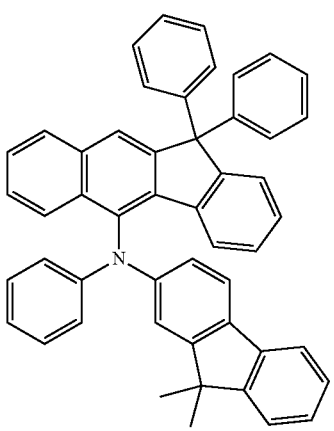
C-34
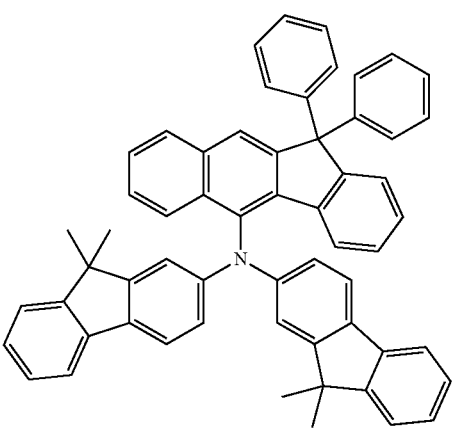

-continued
C-35
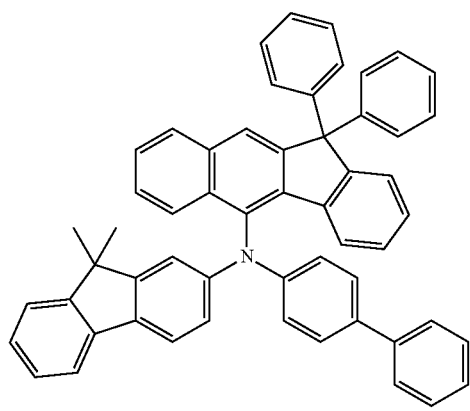
C-36
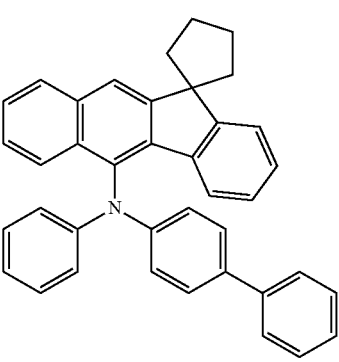
C-37
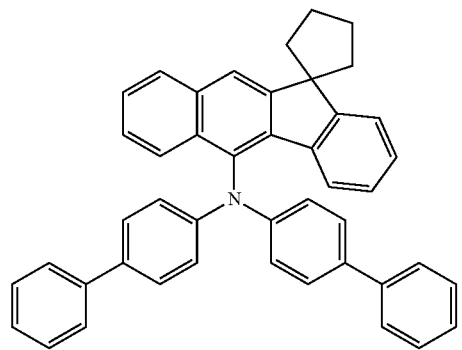
C-38
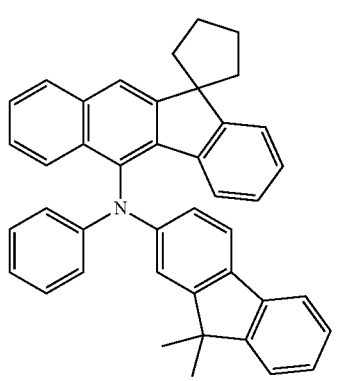
-continued
C-39
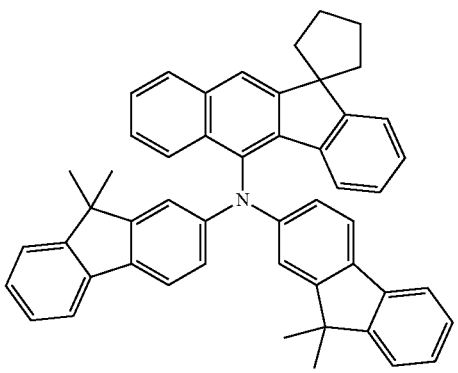
C-40
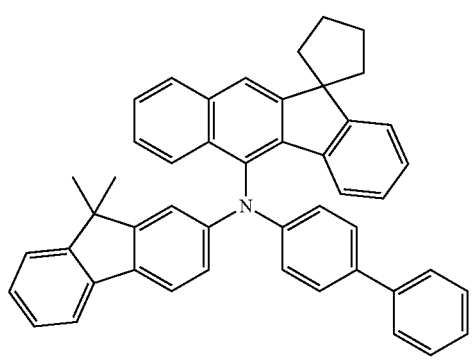
C-41
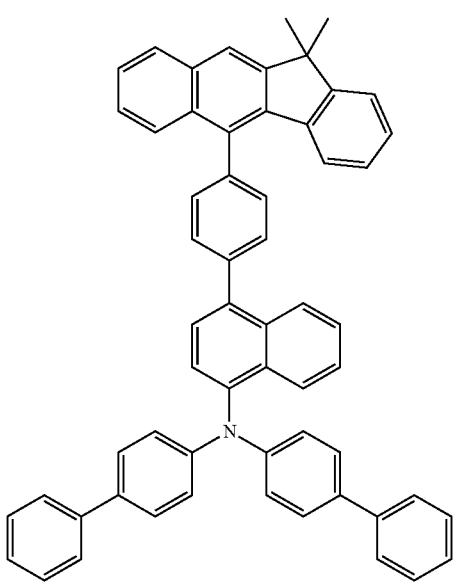

C-42
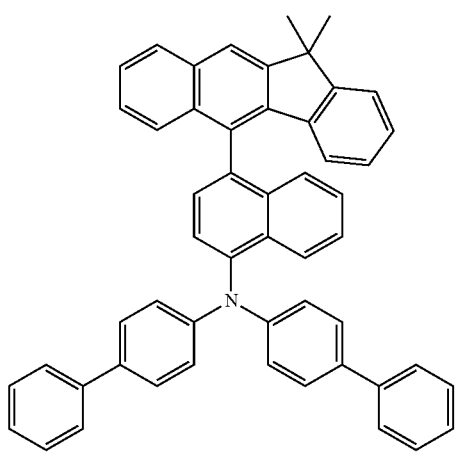
C-43
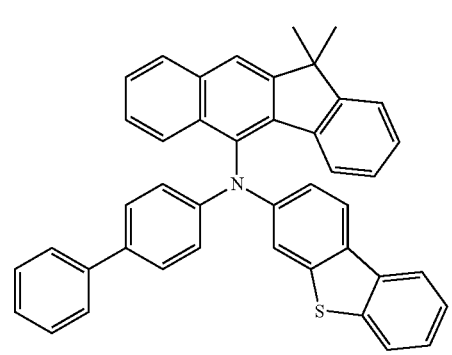
C-44
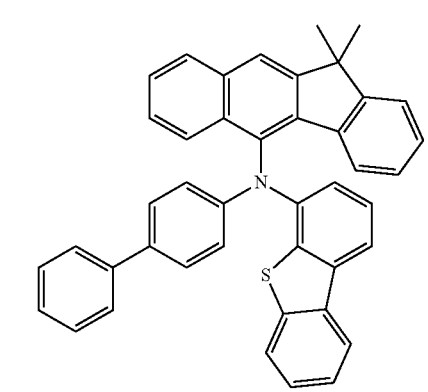
C-45
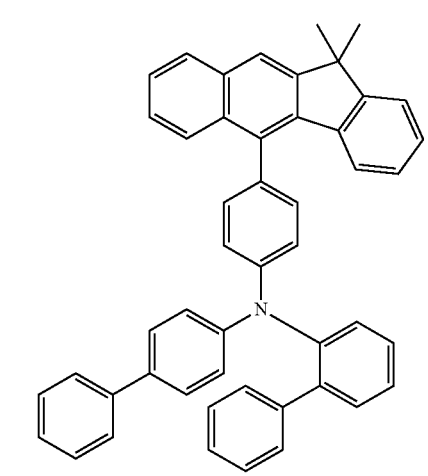
C-46
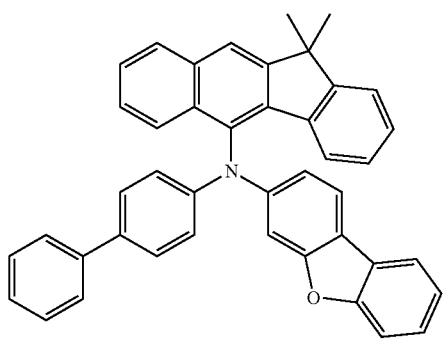
C-47
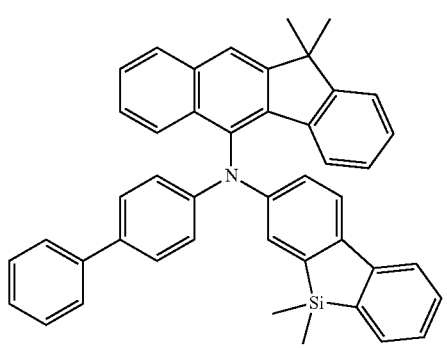
C-48
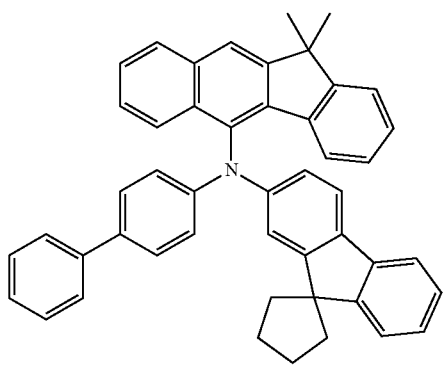
C-49
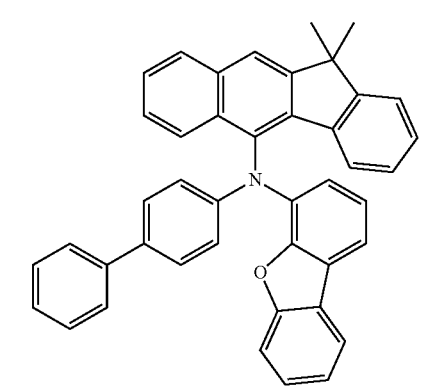

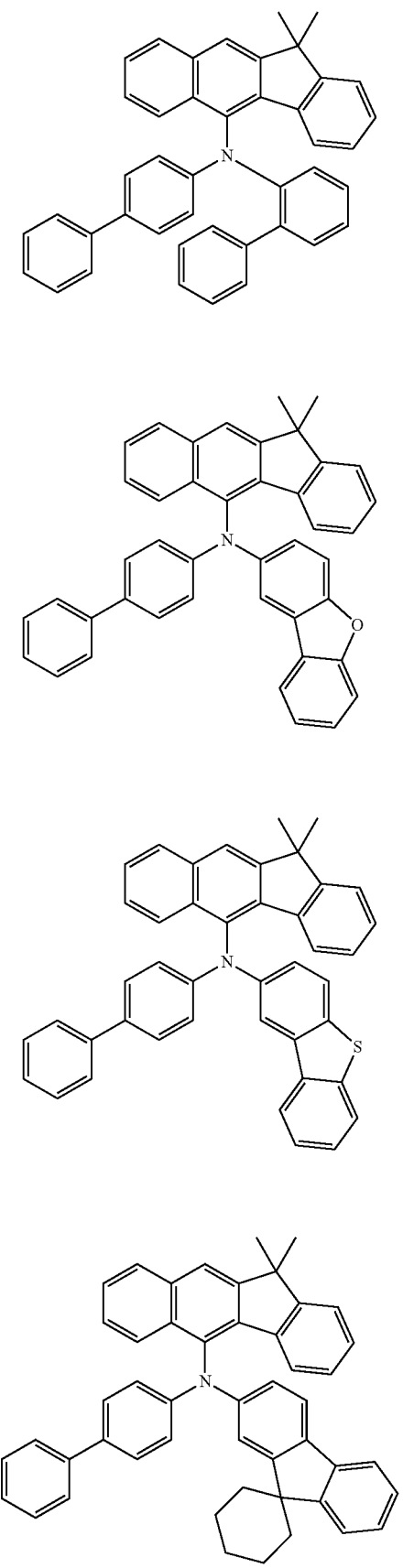
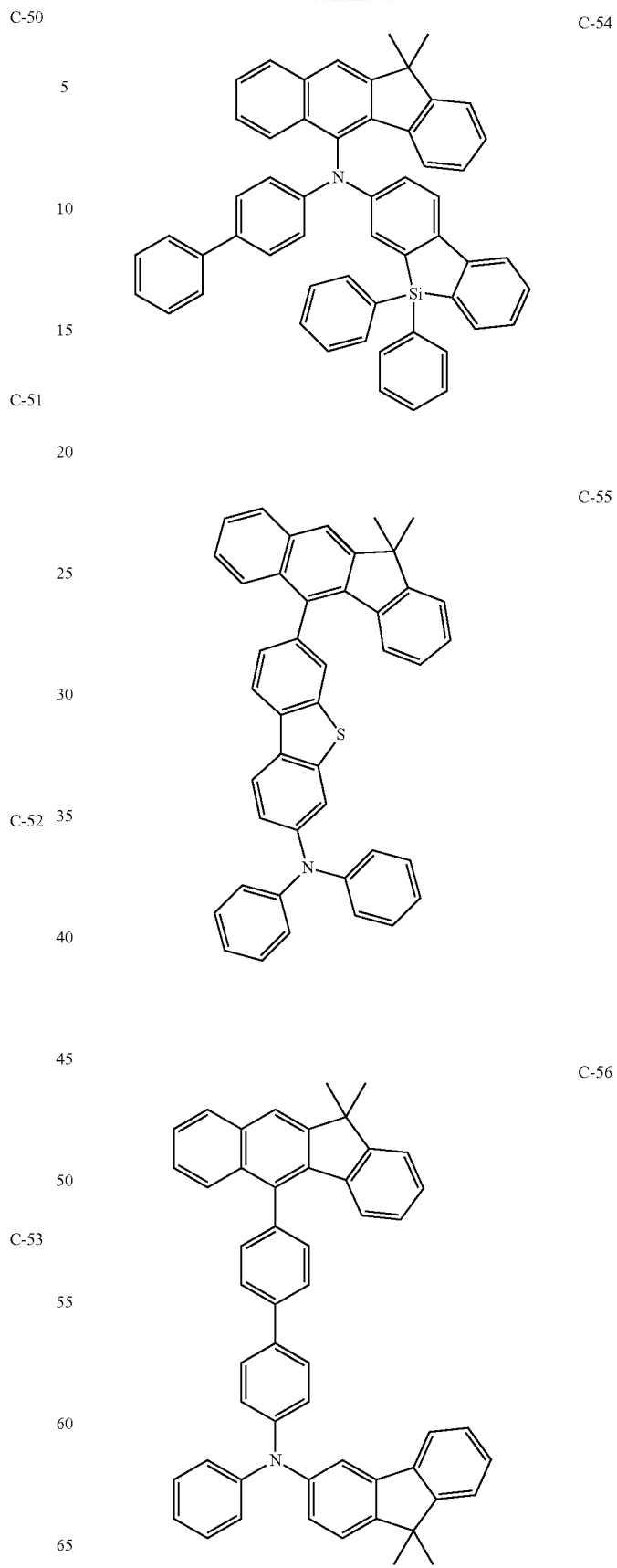

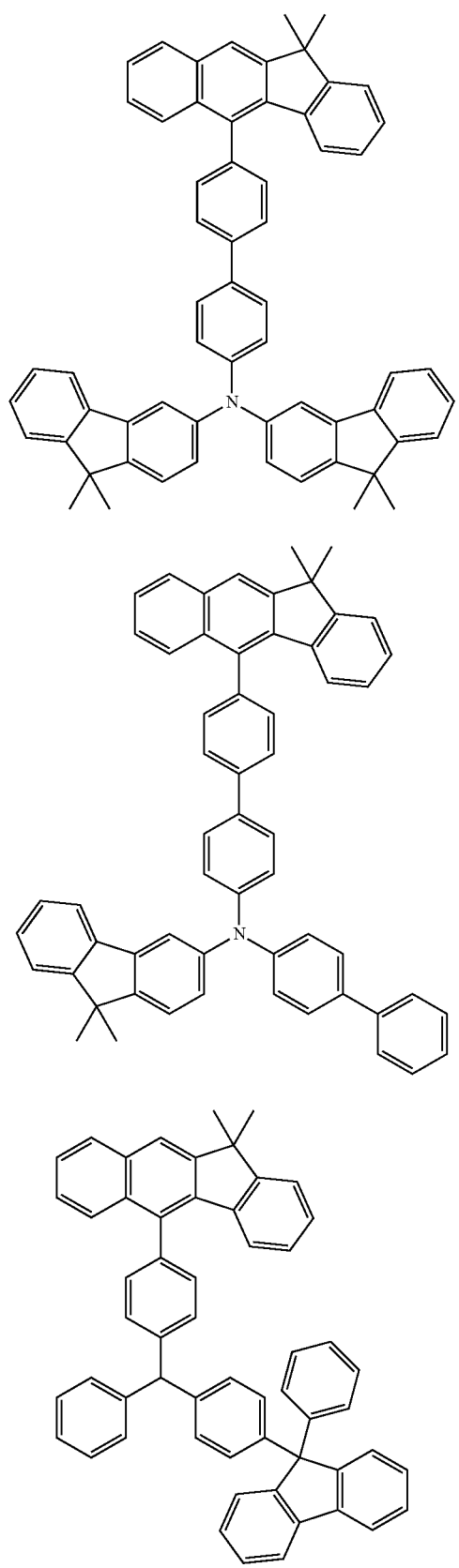
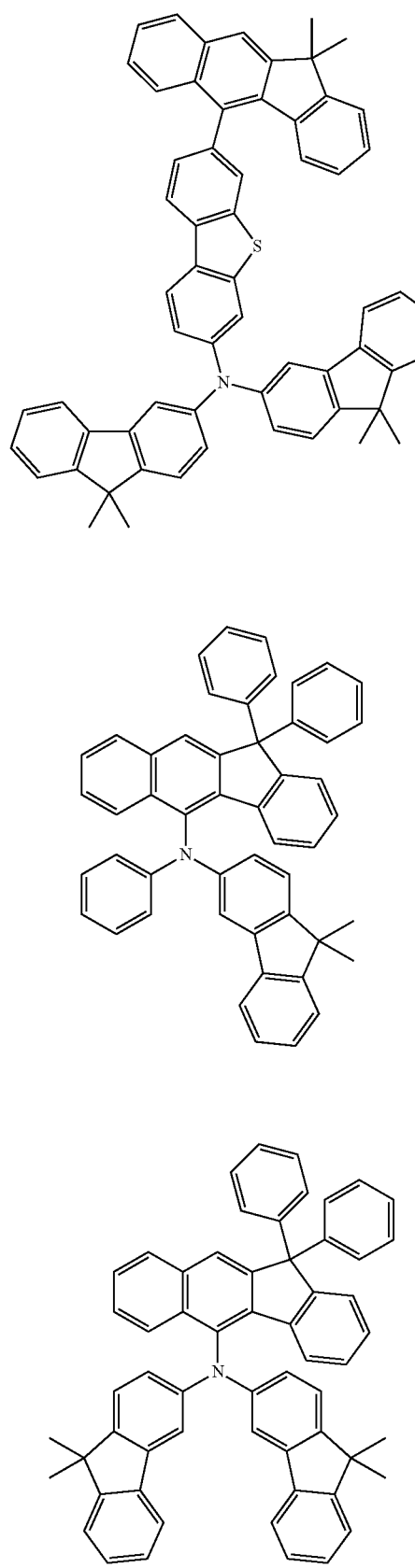

C-63
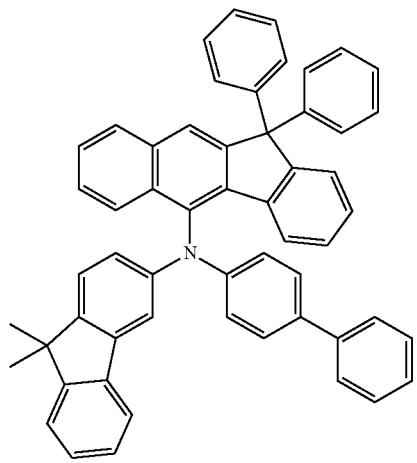
C-64
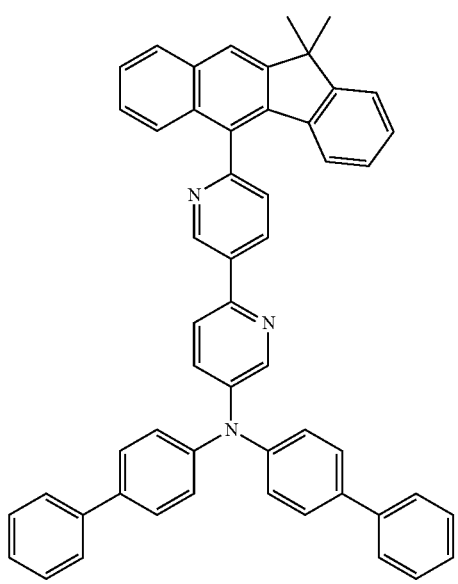
C-65
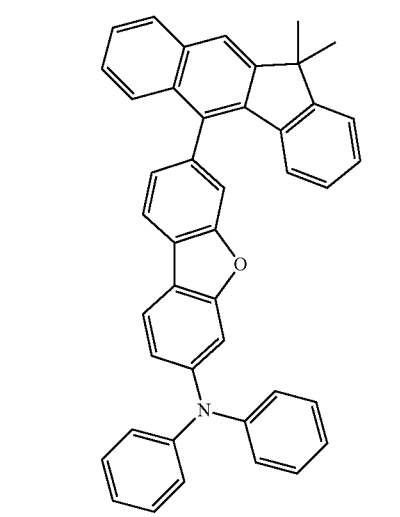
C-66
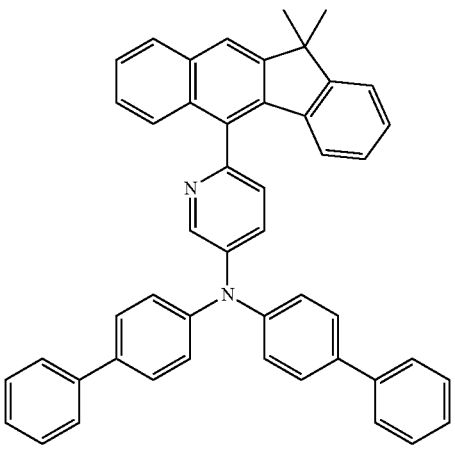
C-67
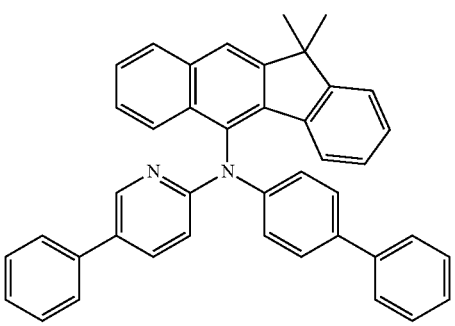
C-68
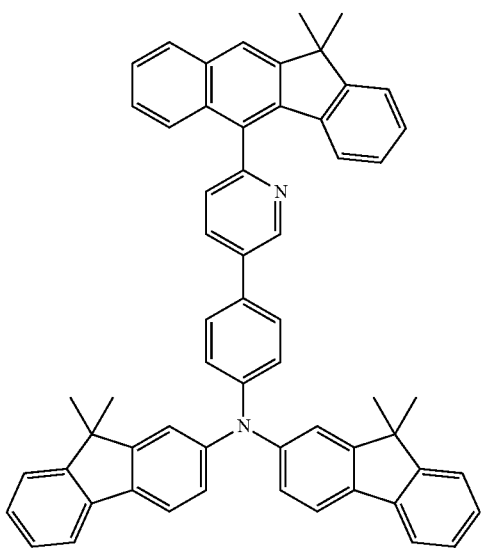

-continued
C-69
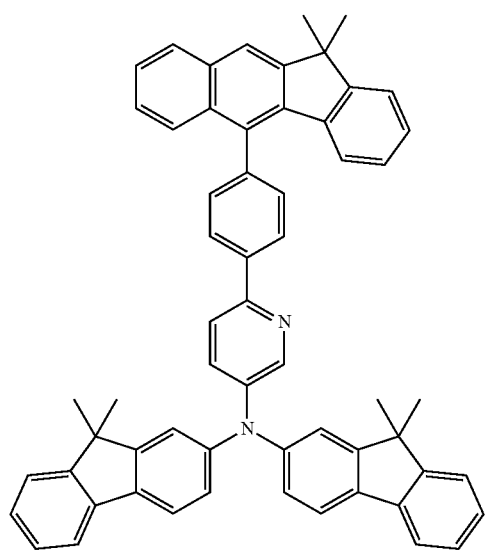
C-70
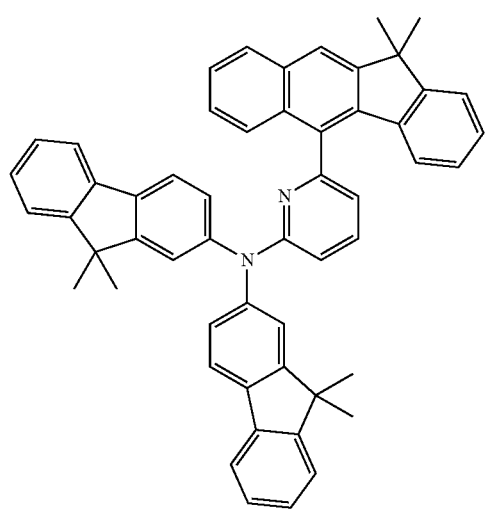
C-72
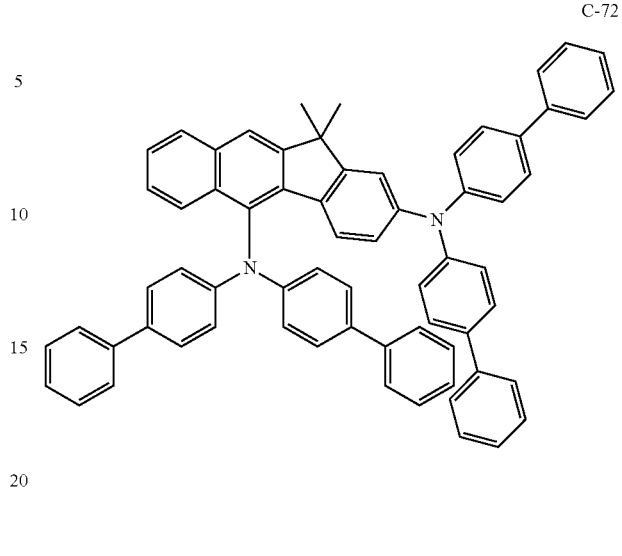
C-73
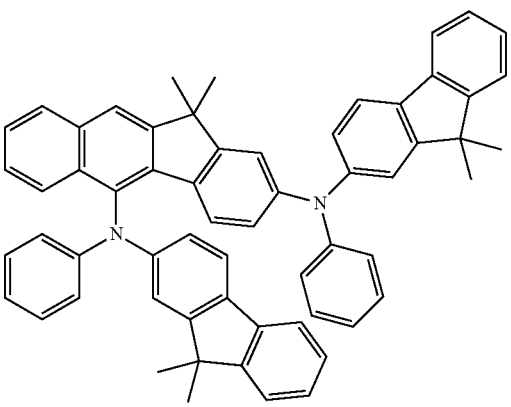
C-71
C-74
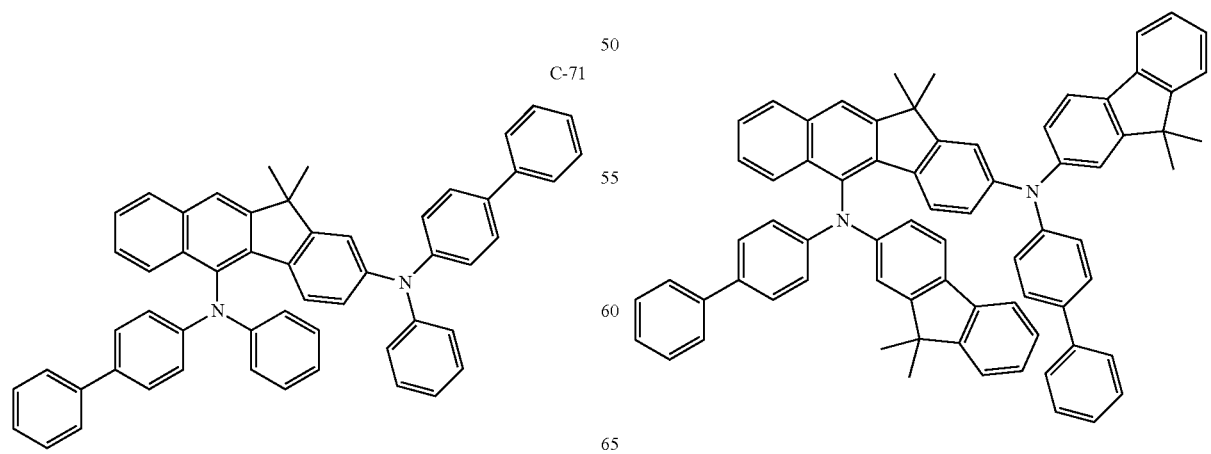

C-75
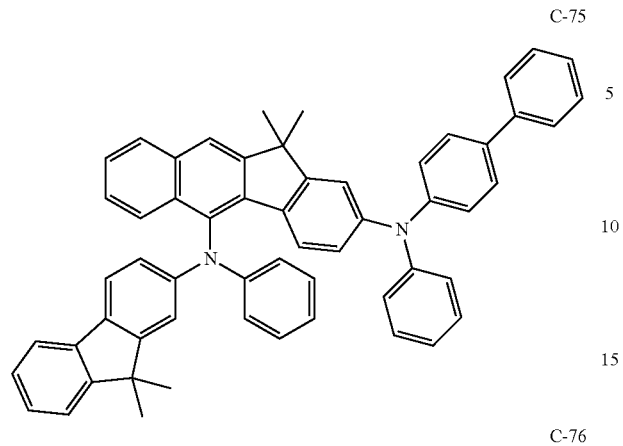
C-76
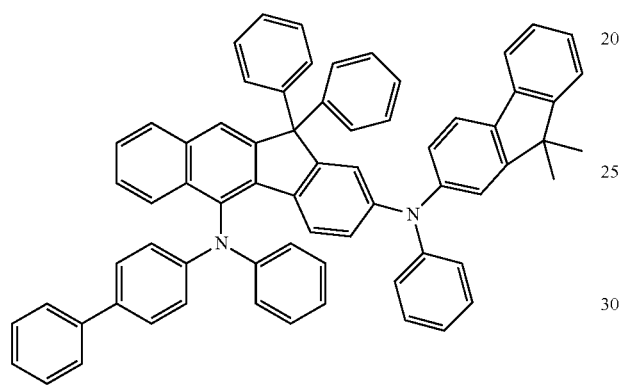
C-77
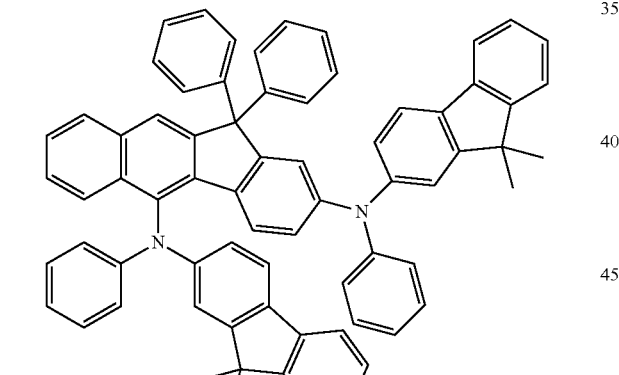
C-78
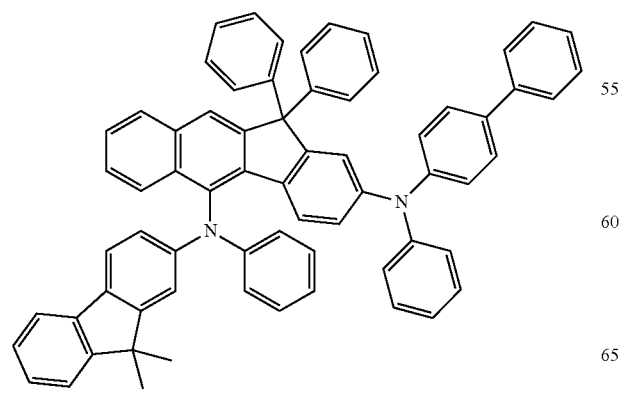
C-79
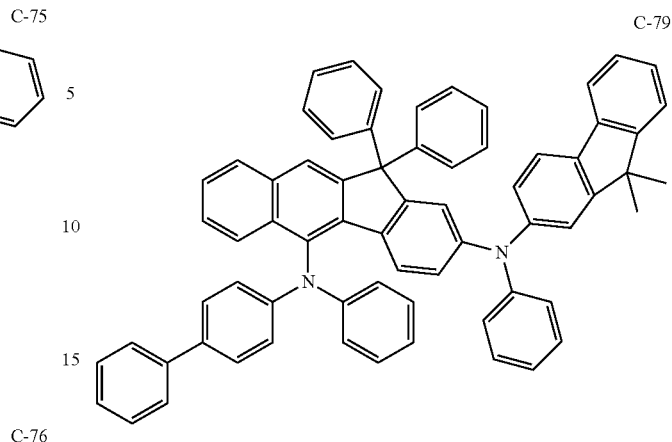
C-80
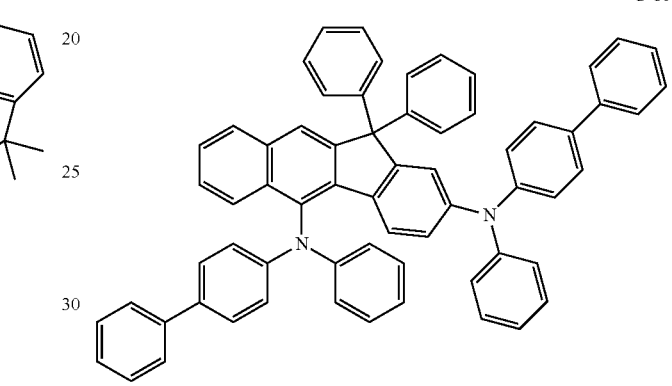
C-81
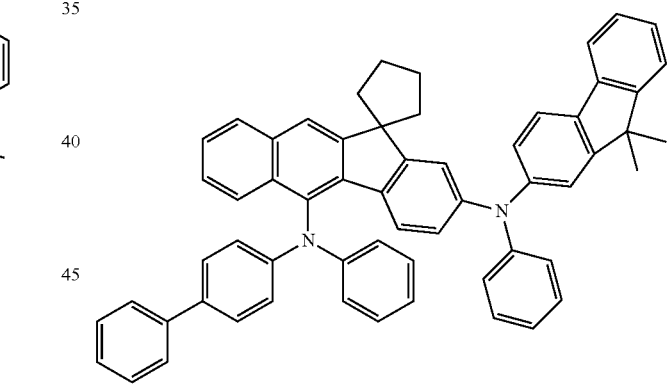
C-82
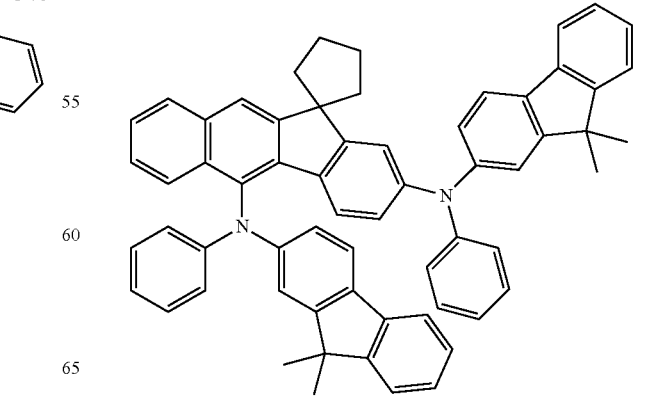

-continued
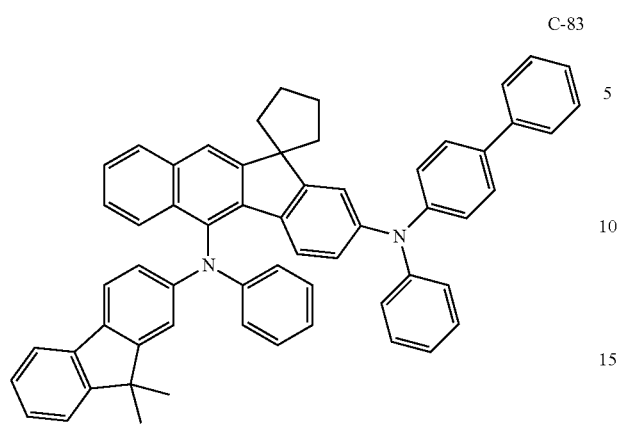
C-83
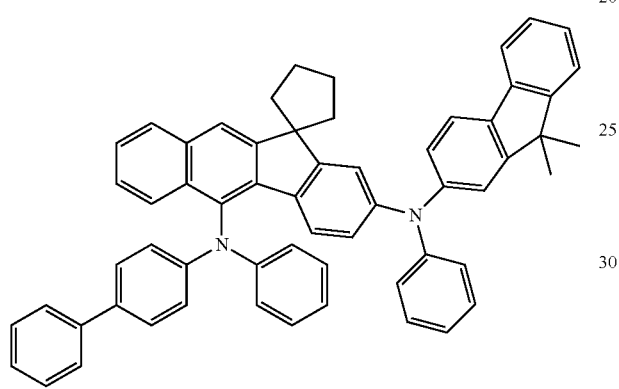
C-84
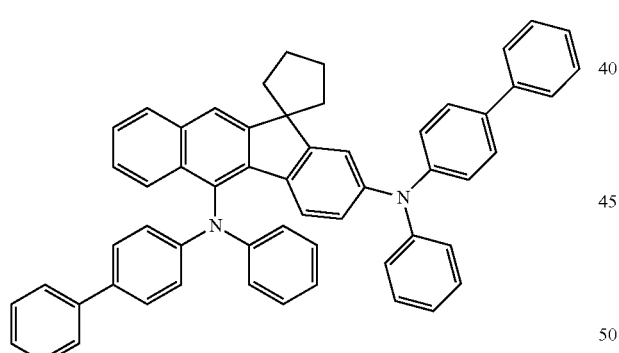
C-85
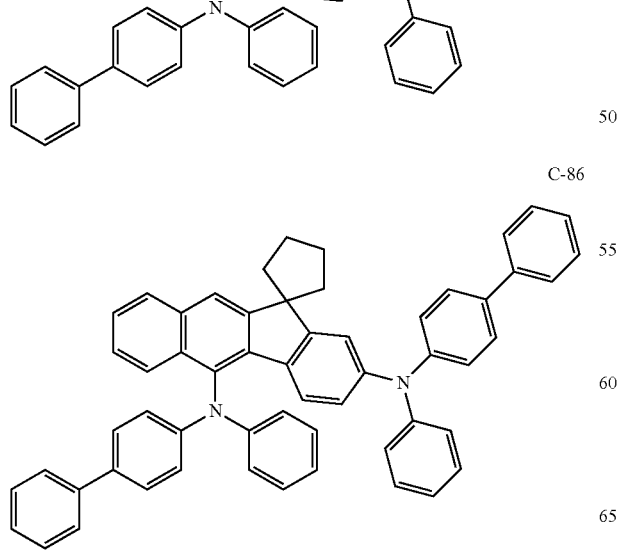
C-86
-continued
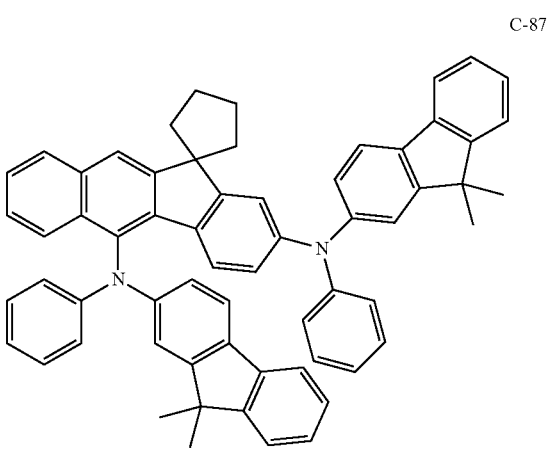
C-87
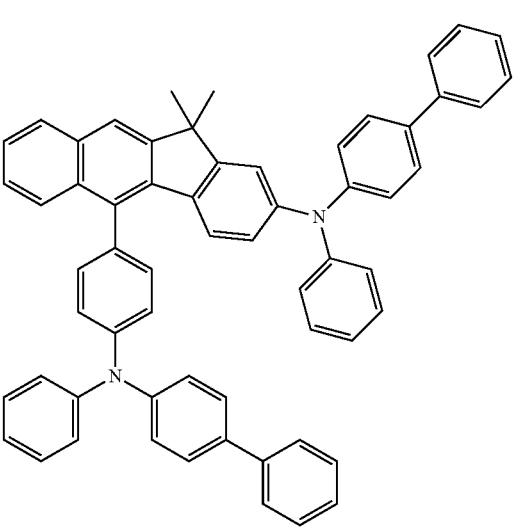
C-88
C-89

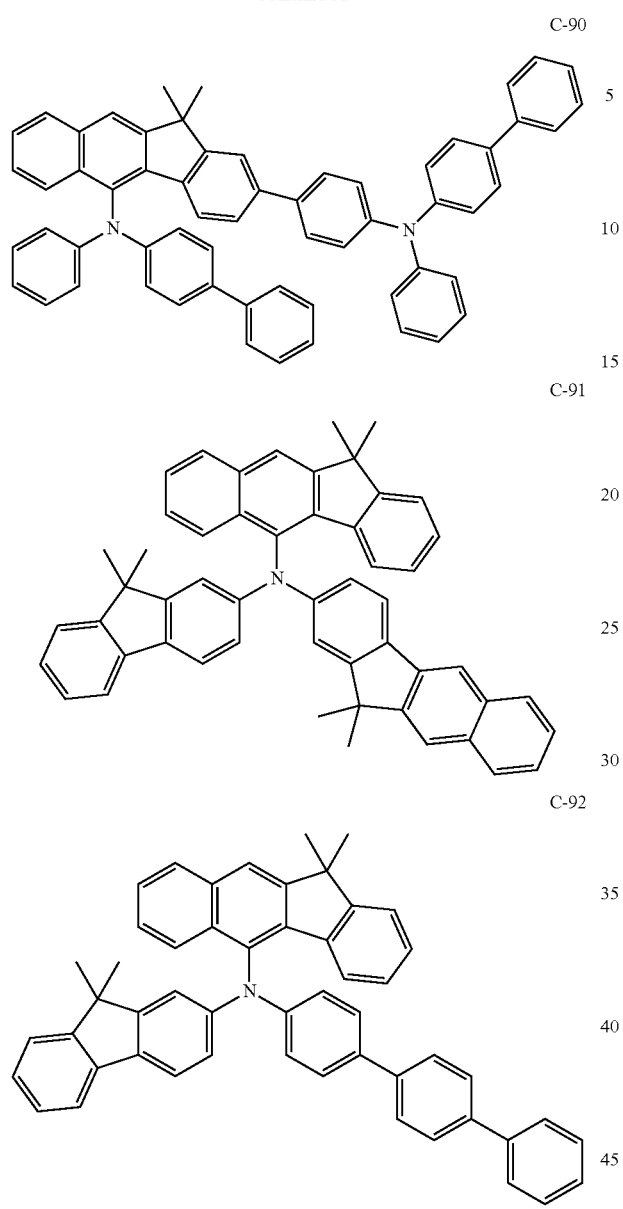

C-90

C-91

C-92

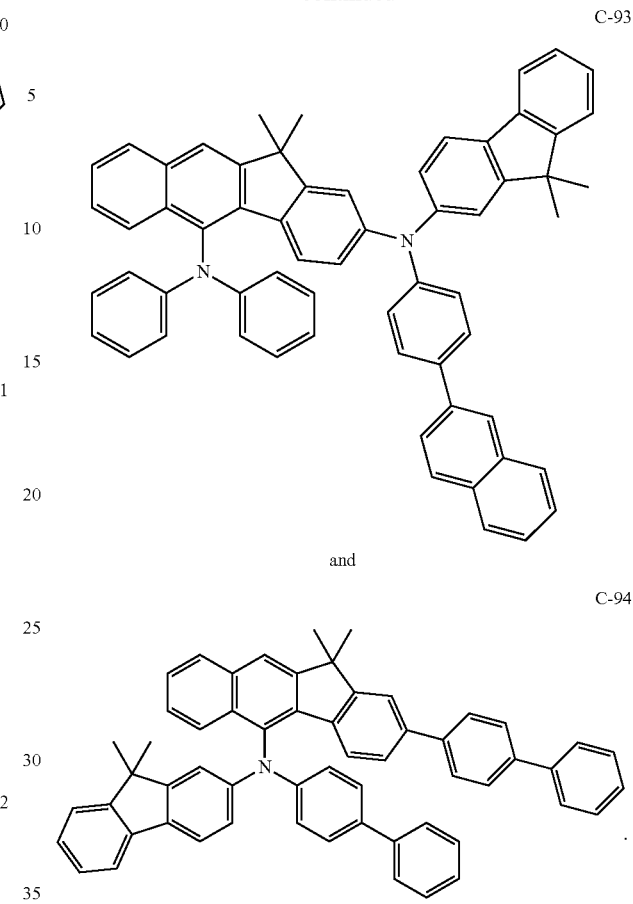

C-93 and

C-94

7. A hole transport material comprising the organic electroluminescent compound according to claim 1.

8. An organic electroluminescent device comprising the organic electroluminescent compound according to claim 1.

9. The organic electroluminescent device according to claim 8, wherein the organic electroluminescent compound is comprised in at least one layer of a light-emitting layer and a hole transport layer.

10. A display device comprising the organic electroluminescent compound according to claim 1.

* * * * *